US012612626B2

(12) United States Patent
Samarsky

(10) Patent No.: US 12,612,626 B2
(45) Date of Patent: Apr. 28, 2026

(54) siRNA COMPOUND THAT INHIBITS EXPRESSION OF APOC3

(71) Applicant: Sirnaomics, Inc., Gatithersburg, MD (US)

(72) Inventor: Dmitry Samarsky, Gaithersburg, MD (US)

(73) Assignee: SIRNAOMICS, INC., Gaithersburg, MD (US)

(*) Notice: Subject to any disclaimer, the term of this patent is extended or adjusted under 35 U.S.C. 154(b) by 0 days.

(21) Appl. No.: 17/849,382

(22) Filed: Jun. 24, 2022

(65) Prior Publication Data

US 2023/0089915 A1 Mar. 23, 2023

Related U.S. Application Data

(60) Provisional application No. 63/318,287, filed on Mar. 9, 2022, provisional application No. 63/214,608, filed on Jun. 24, 2021.

(51) Int. Cl.

| | |
|---|---|
| ***C12N 15/113*** | (2010.01) |
| ***A61K 31/232*** | (2006.01) |
| ***A61K 31/397*** | (2006.01) |
| ***A61K 31/713*** | (2006.01) |
| ***A61K 45/06*** | (2006.01) |

(52) U.S. Cl.

CPC .......... *C12N 15/113* (2013.01); *A61K 31/232* (2013.01); *A61K 31/397* (2013.01); *A61K 31/713* (2013.01); *A61K 45/06* (2013.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/3515* (2013.01); *C12N 2310/531* (2013.01); *C12N 2320/31* (2013.01)

(58) Field of Classification Search

CPC .............. C12N 15/113; C12N 2310/14; C12N 2310/315; C12N 2310/321; C12N 2310/322; C12N 2310/531; C12N 2310/351; A61K 31/713

See application file for complete search history.

(56) References Cited

U.S. PATENT DOCUMENTS

| | | | | |
|---|---|---|---|---|
| 9,023,820 | B2 * | 5/2015 | MacDonald | A61K 9/1617 536/23.1 |
| 9,957,517 | B2 | 5/2018 | Beigelman et al. | |
| 2015/0315584 | A1 | 11/2015 | MacDonald et al. | |
| 2017/0283816 | A1 * | 10/2017 | Beigelman | C12N 15/1137 |
| 2019/0078088 | A1 | 3/2019 | Li et al. | |
| 2020/0263176 | A1 | 8/2020 | Bettencourt et al. | |
| 2020/0303037 | A1 | 9/2020 | Hwang | |

FOREIGN PATENT DOCUMENTS

| | | | | |
|---|---|---|---|---|
| EP | 3719127 | A1 | 10/2020 | |
| WO | 2012/177947 | A2 | 12/2012 | |
| WO | WO-2016028649 | A1 * | 2/2016 | A61K 31/713 |
| WO | 2019/051402 | A1 | 3/2019 | |

OTHER PUBLICATIONS

Girard et al. A germline-specific class of small RNAs binds mammalian Piwi proteins, 2006, Nature, 442, 199-202 (Year: 2006).*
International Search Report and the Written Opinion in PCT/US2022/034965, Jan. 3, 2023, 12 pages.
EPO Communication pursuant to Rule 114(2) EPC dated Jun. 10, 2024 in corresponding European Patent Application No. 22829418. 7, 5 pages.

* cited by examiner

*Primary Examiner* — Jennifer Dunston
*Assistant Examiner* — Keyur A Vyas
(74) *Attorney, Agent, or Firm* — Edell, Shapiro & Finnan, LLC

(57) ABSTRACT

Nucleic acid products and compositions and their uses are provided. In particular, nucleic acid products are provided that modulate, interfere with, or inhibit APOC3 gene expression. The products can be oligomeric compounds that comprise at least a first region of linked nucleosides having at least a first nucleobase sequence that is at least partially complementary to at least a portion of RNA transcribed from a APOC3 gene, wherein said first nucleobase sequence is selected from the following sequences, or a portion thereof: SEQ ID NOs 1 to 39

18 Claims, 15 Drawing Sheets

Specification includes a Sequence Listing.

Dose Curves of APOC3 Leads for Candidates in Primary Human Hepatocytes

Dose Curves of APOC3 Leads for Humanized Mouse Study
in Primary Human Hepatocytes

Animal Model:
◦ Humanized liver mouse model

Test compounds:
• STP125G - A28(14-4)mF mxRNA

Dosing:
◦ 10 mg/kg

ROA:
◦ Subcutaneous

N:
◦ 4 mice/group

Terminal Endpoints:
◦ 2, 4, 6, 8 and 10-weeks

Readouts:
• qPCR (mRNA)
• ELISA (protein)
• Triglycerides

Treatment
All Groups

Day 0    Week 2    Week 4    Week 6    Week 8    Week 12

Terminal Timepoints
Liver tissue
Blood collection siRNA COMPOUND THAT INHIBITS EXPRESSION OF APOC3

CROSS REFERENCE TO RELATED PATENT APPLICATIONS

This application claims the benefit of and priority to two U.S. Provisional Patent Applications, Nos. 63/214,608, filed Jun. 24, 2021, and 63/318,287, filed Mar. 9, 2022, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 7, 2022, is named 4690_0050C_SL_ST.25.txt and is 373 kilobytes in size.

FIELD

Nucleic acid products and compositions, and their uses, that modulate, in particular interfere with, or inhibit, apolipoprotein C3 (APOC3) gene expression are provided. Specific embodiments provide methods, compounds, and compositions for reducing expression of APOC3 mRNA and protein in an animal. Such methods, compounds, and compositions are useful to treat, prevent, or ameliorate APOC3-associated disorders such as dyslipidemia, hypertriglyceridemia, hyperchylomicronemia, and atherosclerotic cardiovascular disease (ASCVD).

BACKGROUND

Triglycerides are esters of glycerol with three fatty acids. They serve as storage of fat and energy and are transported via the bloodstream. Excess level of blood triglycerides have been recognized early on as causative agents or bystanders of a range of disorders. More recent evidence suggests a causative role, partly in conjunction with elevated levels of cholesterol (in particular LDL cholesterol) in ASCVD and disorders subsumed under this term or associated therewith. A more comprehensive list of disorders associated with elevated levels of triglycerides is given in the embodiments disclosed further below. Apolipoprotein C3 is secreted by the liver and the small intestine. It can be found on triglyceride-rich lipoproteins including very low density lipoproteins (VLDL) and chylomicrons. It is involved in the negative regulation of lipid catabolism, especially triglyceride catabolism, and of the clearance of VLDL, LDL and HDL lipoproteins. A molecular function of APOC3 is the inhibition of lipoprotein lipase and of hepatic lipase.

Disease

Abnormal amounts of circulating triglycerides, also referred to as hypertriglyceridemia, is a recognized disorder in itself which is inter alia owed to the fact that such abnormal amounts, in particular if they persist over extended periods of time, may entail disorders of the cardiovascular system and/or inflammation.

Treatment

Established treatments include the administration of statins such as Rosuvastatin and Simvastatin as well as of fibrates such as fenofibrate. However, statins may cause side effects, and certain patients are statin-intolerant.

There therefore remains a need for therapies to treat APOC3-associated diseases. We, therefore, aim to provide compounds, methods, and pharmaceutical compositions for the treatment of such diseases. Double-stranded RNA (dsRNA) able to complementarily bind expressed mRNA has been shown to be able to block gene expression (Fire et al., 1998, Nature. 1998 Feb. 19; 391 (6669):806-1 1 and Elbashir et at., 2001, Nature. 2001 May 24; 41 1 (6836): 494-8) by a mechanism that has been termed RNA interference (RNAi). Short dsRNAs direct gene-specific, post-transcriptional silencing in many organisms, including vertebrates, and have become a useful tool for studying gene function. RNAi is mediated by the RNA-induced silencing complex (RISC), a sequence-specific, multi-component nuclease that destroys messenger RNAs homologous to the silencing trigger loaded into the RISC complex. Interfering RNA (iRNA) such as siRNAs, antisense RNA, and micro-RNA are oligonucleotides that prevent the formation of proteins by gene-silencing i.e. inhibiting gene translation of the protein through degradation of mRNA molecules. Gene-silencing agents are becoming increasingly important for therapeutic applications in medicine.

According to Watts and Corey in the Journal of Pathology (2012; Vol 226, p 365-379) there are algorithms that can be used to design nucleic acid silencing triggers, but all of these have severe limitations. It may take various experimental methods to identify potent siRNAs, as algorithms do not take into account factors such as tertiary structure of the target mRNA or the involvement of RNA binding proteins. Therefore the discovery of a potent nucleic acid silencing trigger with minimal off-target effects is a complex process. For the pharmaceutical development of these highly charged molecules it is necessary that they can be synthesised economically, distributed to target tissues, enter cells and function within acceptable limits of toxicity. An aim is to, therefore, provide compounds, methods, and pharmaceutical compositions for the treatment of thromboembolic diseases as described herein, which comprise oligomeric compounds that modulate, in particular inhibit, gene expression by RNAi.

SUMMARY

Nucleic acid products are provided that modulate, in particular, interfere with or inhibit, apolipoprotein C3 (APOC3) gene expression, and associated therapeutic uses. Specific oligomeric compounds and sequences are described herein. This summary provides a simplified form that is further described below in the detailed description. This summary is not intended to identify key features or essential features of the claimed subject matter, nor is it intended to be used to determine the scope of the claimed subject matter.

DETAILED DESCRIPTION AND EMBODIMENTS

Figure 1A:
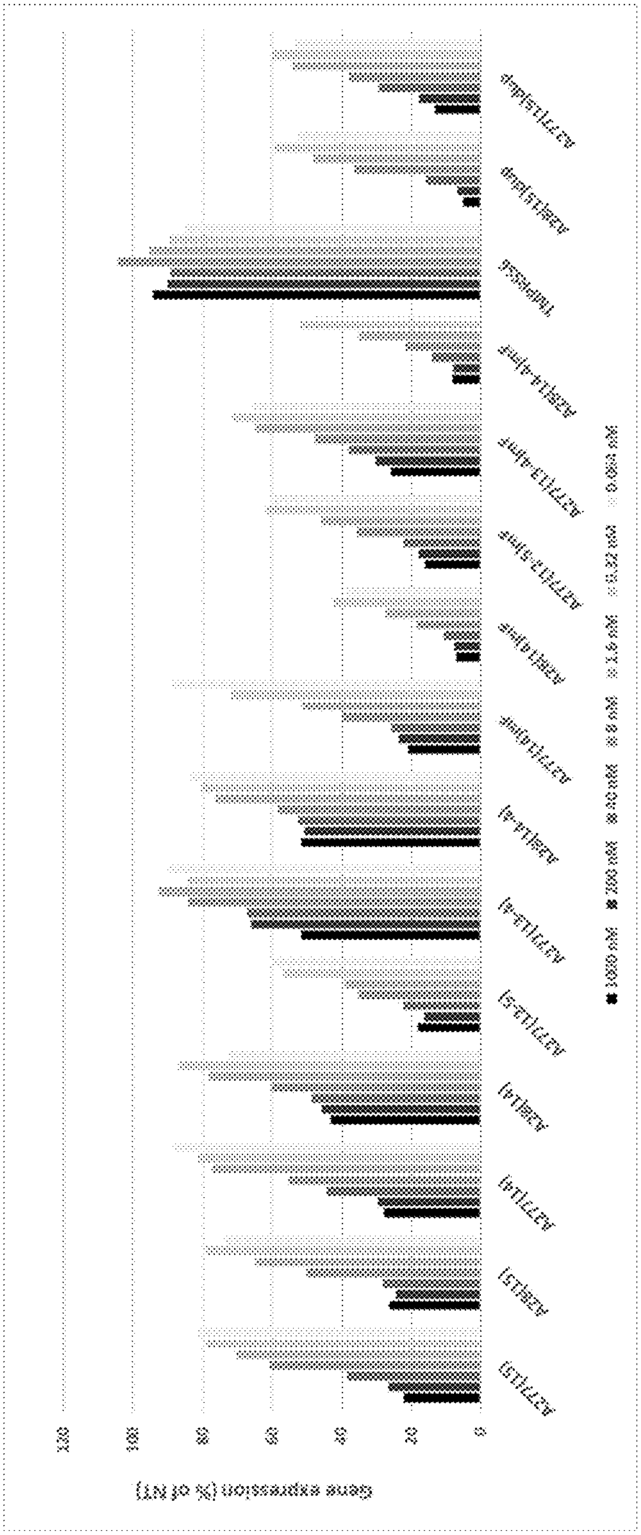
FIG. 1*a* shows dose curves of APOC3 leads for candidates in primary human hepatocytes.

The following are non-limiting aspects:

Aspect 1. An oligomeric compound capable of inhibiting expression of APOC3, wherein said compound comprises at least a first region of linked nucleosides having at least a first nucleobase sequence that is at least partially complementary to at least a portion of RNA transcribed from a APOC3 gene, wherein said first nucleobase sequence is selected from the following sequences, or a portion thereof: sequences of SEQ ID NOs 1 to 391, wherein said portion preferably has a length of at least 18 nucleotides.

Particularly preferred embodiments relate to mxRNAs: for further details see the embodiments and their discussion further below.

In addition, the antisense and sense regions disclosed herein may serve as building blocks for compounds which are directed to multiple targets. The general architecture of such compound ds is described in WO2020/065602.

Furthermore, and as disclosed further below, the disclosed embodiments also relate to double-stranded RNAs (dsRNAs). In contrast to an mxRNA, which has a hairpin-like structure connecting the sense and antisense RNA strands, a dsRNA lacks the hairpin loop and, therefore, dsRNA comprises two strands.

Aspect 2. A composition comprising an oligomeric compound according to aspect 1, and a physiologically acceptable excipient.

Aspect 3. A pharmaceutical composition comprising an oligomeric compound according to aspect 1.

Aspect 4. An oligomeric compound according to aspect 1, for use in human or veterinary medicine or therapy.

Aspect 5. An oligomeric compound according to aspect 1, for use in a method of treating a disease or disorder.

Aspect 6. A method of treating a disease or disorder comprising administration of an oligomeric compound according to aspect 1, to an individual in need of treatment.

Aspect 7. Use of an oligomeric compound according to aspect 1, for use in research as a gene function analysis tool.

Aspect 8. Use of an oligomeric compound according to aspect 1 in the manufacture of a medicament for a treatment of a disease or disorder.

Further embodiments are described below by way of example only. These examples represent the best ways of putting the disclosed embodiments into practice that are currently known to the applicant, although they are not the only ways in which this could be achieved.

It will be understood that the benefits and advantages described herein may relate to one embodiment or may relate to several embodiments. The embodiments are not limited to those that solve any or all of the stated problems or those that have any or all of the stated benefits and advantages.

Features of different aspects and embodiments as described herein may be combined as appropriate, as would be apparent to a skilled person, and may be combined with any other aspects.

Definitions

The following definitions pertain to the disclosed embodiments throughout. In many instances, the definitions, in addition to the respective definition as such, provide non-exhaustive listings of possible implementations, which amount to preferred embodiments.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21st edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "excipient" means any compound or mixture of compounds that is added to a composition as provided herein that is suitable for delivery of an oligomeric compound.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety, phosphate-linked nucleosides also being referred to as "nucleotides".

As used herein, "chemical modification" or "chemically modified" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA. A "naturally occurring sugar moiety" as referred to herein is also termed as an "unmodified sugar moiety". In particular, such a "naturally occurring sugar moiety" or an "unmodified sugar moiety" as referred to herein has a —H (DNA sugar moiety) or —OH(RNA sugar moiety) at the 2'-position of the sugar moiety, especially a —H (DNA sugar moiety) at the 2'-position of the sugar moiety.

As used herein, "sugar moiety" means a naturally occurring sugar moiety or a modified sugar moiety of a nucleoside. As used herein, "modified sugar moiety" means a substituted sugar moiety or a sugar surrogate.

As used herein, "substituted sugar moiety" means a furanosyl that has been substituted. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring).

As used herein, "MOE" means $—OCH_2CH_2OCH_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose). Duplexes of uniformly modified 2'-fluorinated (ribo) oligonucleotides hybridized to RNA strands are not RNase H substrates while the ara analogs retain RNase H activity.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2 '-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding, more specifically hydrogen bonding, with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides can comprise a modified sugar moiety and/or a modified nucleobase.

As used herein, "bicyclic nucleoside" or "BNA" means a nucleoside comprising a bicyclic sugar moiety. As used herein, "locked nucleic acid nucleoside" or "LNA" means a nucleoside comprising a bicyclic sugar moiety comprising a 4'—$CH_2$—O-2'bridge.

As used herein, "2 '-substituted nucleoside" means a nucleoside comprising a substituent at the 2'-position of the sugar moiety other than H or OH. Unless otherwise indicated, a 2 '-substituted nucleoside is not a bicyclic nucleoside.

As used herein, "deoxynucleoside" means a nucleoside comprising 2'—H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein, "modified oligonucleotide" means an oligonucleotide comprising at least one modified nucleoside and/or at least one modified internucleoside linkage.

Preferred modified internucleoside linkages are those which confer increased stability as compared to the naturally occurring phosphodiesters. "Stability" means, in particular, the stability against hydrolysis including enzyme-catalyzed hydrolysis, enzymes including exonucleases and endonucleases.

Preferred positions for such modified internucleoside linkages include the termini and the hairpin loop of single-stranded oligomeric compounds. For example, the internucleoside linkages connecting first and second nucleoside and second and third nucleoside counting from the 5' terminus, and/or the internucleoside linkages connecting first and second nucleoside and second and third nucleoside counting from the 3' terminus are modified. In addition, a linkage connecting the terminal nucleoside of the 3' terminus with a ligand, such as GalNAc, may be modified.

As discussed above, preferred positions are in the hairpin loop of said single-stranded oligomeric compounds. In particular, all linkages, all but one linkages or the majority of linkages in the hairpin loop are modified. As used herein, "linkages in the hairpin loop" designates the linkages between nucleosides which are not engaged in base pairing. For example, in a hairpin loop consisting of five nucleosides, there are four linkages between nucleosides which are not engaged in base pairing. Preferably, the term "linkages in the hairpin loop" also extends to the linkages connecting the stem to the loop, i.e., those linkages which connect a base-paired nucleoside to a non-based paired nucleoside. Generally, there are two such positions in hairpins and mxRNAs as described herein.

Most preferred is that modified internucleoside linkages are at both termini and in the hairpin loop. As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage. As used herein, "modified internucleoside linkage" means any internucleoside linkage other than a naturally occurring internucleoside linkage. In particular, a "modified internucleoside linkage" as referred to herein can include a modified phosphorous linking group such as a phosphorothioate or phosphorodithioate internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom and can include naturally occurring phosphorous linking groups as present in naturally occurring RNA or DNA, such as phosphodiester linking groups, or modified phosphorous linking groups that are not generally present in naturally occurring RNA or DNA, such as phosphorothioate or phosphorodithioate linking groups. Phosphorus linking groups can therefore include without limitation, phosphodiester, phosphorothioate, phosphorodithioate, phosphonate, methylphosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "oligomeric compound" means a polymeric structure comprising two or more substructures. In certain embodiments, an oligomeric compound comprises an oligonucleotide, such as a modified oligonucletide. In certain embodiments, an oligomeric compound further comprises one or more conjugate groups and/or terminal groups and/or ligands. In certain embodiments, an oligomeric compound consists of an oligonucleotide. In certain embodiments, an oligomeric compound comprises a backbone of one or more linked monomeric sugar moieties, where each linked monomeric sugar moiety is directly or indirectly attached to a heterocyclic base moiety. In certain embodiments, oligomeric compounds may also include monomeric sugar moieties that are not linked to a heterocyclic base moiety, thereby providing abasic sites. Oligomeric compounds may be defined in terms of a nucleobase sequence only, i.e., by specifying the sequence of A, G, C, U (or T). In such a case, the structure of the sugar-phosphate backbone is not particularly limited and may or may not comprise modified sugars and/or modified phosphates. On the other hand, oligomeric compounds may be more comprehensively defined, i.e, by specifying not only the nucleobase sequence, but also the structure of the backbone, in particular the modification status of the sugars (unmodified, 2'-0Me modified, 2'-F modified etc.) and/or of the phosphates.

As used herein, "terminal group" means one or more atom attached to either, or both, the 3' end or the 5' end of an oligonucleotide. In certain embodiments, a terminal group comprises one or more terminal group nucleosides.

As used herein, "conjugate" or "conjugate group" means an atom or group of atoms bound to an oligonucleotide or oligomeric compound. In certain embodiments, a conjugate group links a ligand to a modified oligonucleotide or oligomeric compound. In general, conjugate groups can modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link an oligonucleotide to another portion of the conjugate group. In certain embodiments, the point of attachment on the oligomeric compound is the 3 '-oxygen atom of the 3'-hydroxyl group of the 3' terminal nucleoside of the oligonucleotide. In certain embodiments the point of attachment on the oligomeric compound is the 5'-oxygen atom of the 5'-hydroxyl group of the 5' terminal nucleoside of the oligonucleotide. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and ligand portion that can comprise one or more ligands, such as a carbohydrate cluster portion, such as an N-Acetyl-Galactosamine, also referred to as "GalNAc", cluster portion. In certain embodiments, the carbohydrate cluster portion is identified by the number and identity of the ligand. For example, in certain embodiments, the carbohydrate cluster portion comprises 2 GalNAc groups. For example, in certain embodiments, the carbohydrate cluster portion comprises 3 GalNAc groups and this is particularly preferred. In certain embodiments, the carbohydrate cluster portion comprises 4 GalNAc groups. Such ligand portions are attached to an oligomeric compound via a cleavable moiety, such as a cleavable bond or cleavable nucleoside. The ligands can be arranged in a linear or branched configuration, such as a biantennary or triantennary configurations. A preferred carbohydrate cluster, also referred to as "toothbrush," has the following formula:

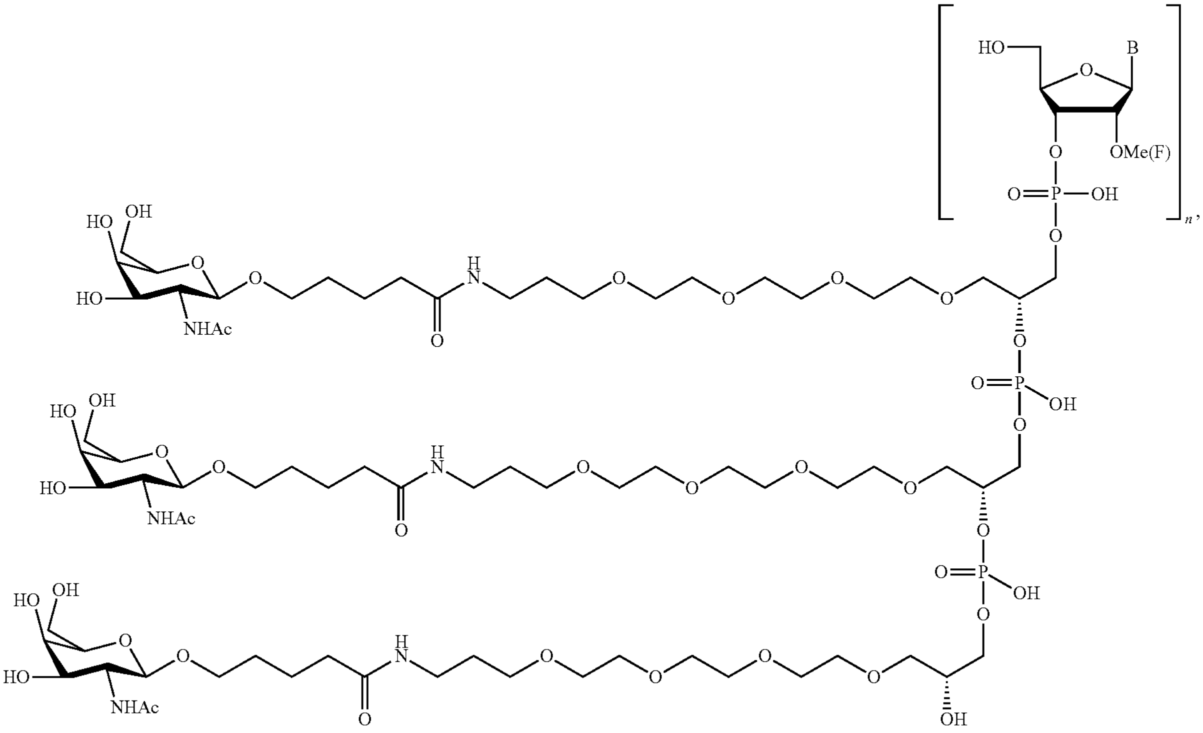

wherein in said structural formula one, two, or three phosphodiester linkages can also be substituted by phosphothionate linkages.

As used herein, "cleavable moiety" means a bond or group that is capable of being cleaved under physiological conditions. In certain embodiments, a cleavable moiety is cleaved inside a cell or sub-cellular compartments, such as an endosome or lysosome. In certain embodiments, a cleavable moiety is cleaved by endogenous enzymes, such as nucleases. In certain embodiments, a cleavable moiety comprises a group of atoms having one, two, three, four, or more than four cleavable bonds. In certain embodiments, a cleavable moiety is a phosphodiester linkage.

As used herein, "cleavable bond" means any chemical bond capable of being broken.

As used herein, "carbohydrate cluster" means a compound having one or more carbohydrate residues attached to a linker group.

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative. A carbohydrate is a biomolecule including carbon (C), hydrogen (H) and oxygen (O) atoms. Carbohydrates can include monosaccharide, disaccharides, trisaccharides, tetrasaccharides, oligosaccharides or polysaccharides, such as one or more galactose moieties, one or more lactose moieties, one or more N-Acetyl-Galactosamine moieties, and/or one or more mannose moieties. A particularly preferred carbohydrate is N-Acetyl-Galactosamine.

As used herein, "strand" means an oligomeric compound comprising linked nucleosides.

As used herein, "single strand" or "single-stranded" means an oligomeric compound comprising linked nucleosides that are connected in a continuous sequence without a break therebetween. Such single strands may include regions of sufficient self-complementarity so as to be capable of forming a stable self-duplex in a hairpin structure.

As used herein, "hairpin" means a single stranded oligomeric compound that includes a duplex formed by base pairing between sequences in the strand that are self-complementary and opposite in directionality.

As used herein, "hairpin loop" means an unpaired loop of linked nucleosides in a hairpin that is created as a result of hybridization of the self-complementary sequences. The resulting structure looks like a loop or a U-shape.

In particular, short hairpin RNA, also denoted as shRNA, comprises a duplex region and a loop connecting the regions forming the duplex. The end of the duplex region which does not carry the loop may be blunt-ended or carry (a) 3' and/or (a) 5' overhang(s). Preference is given to blunt-ended constructs.

As used herein, "directionality" means the end-to-end chemical orientation of an oligonucleotide based on the chemical convention of numbering of carbon atoms in the sugar moiety meaning that there will be a 5'-end defined by the 5' carbon of the sugar moiety, and a 3'-end defined by the 3' carbon of the sugar moiety. In a duplex or double stranded oligonucleotide, the respective strands run in opposite 5' to 3' directions to permit base pairing between them.

As used herein, "duplex" or also abbreviated as "dup" means two or more complementary strand regions, or strands, of an oligonucleotide or oligonucleotides, hybridized together by way of non-covalent, sequence-specific interaction therebetween. Most commonly, the hybridization in the duplex will be between nucleobases adenine (A) and thymine (T), and/or (A) adenine and uracil (U), and/or guanine (G) and cytosine (C). The duplex may be part of a single stranded structure, wherein self-complementarity leads to hybridization, or as a result of hybridization between respective strands in a double stranded construct.

As used herein, "double strand" or "double stranded" means a pair of oligomeric compounds that are hybridized to one another. In certain embodiments, a double-stranded oligomeric compound comprises a first and a second oligomeric compound.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "transcription" or "transcribed" means the first of several steps of DNA based gene expression in which a target sequence of DNA is copied into RNA (especially mRNA) by the enzyme RNA polymerase. During transcription, a DNA sequence is read by an RNA polymerase, which produces a complementary, antiparallel RNA sequence called a primary transcript.

As used herein, "target sequence" means a sequence to which an oligomeric compound is intended to hybridize to result in a desired activity with respect to APOC3 expression. Oligonucleotides have sufficient complementarity to their target sequences to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In both DNA and RNA, guanine (G) is complementary to cytosine (C). In certain embodiments, complementary nucleobase means a nucleobase of an oligomeric compound that is capable of base pairing with a nucleobase of its target sequence. For example, if a nucleobase at a certain position of an oligomeric compound is capable of hydrogen bonding with a nucleobase at a certain position of a target sequence, then the position of hydrogen bonding between the oligomeric compound and the target sequence is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides) means the capacity of such oligomeric compounds or regions thereof to hybridize to a target sequence, or to a region of the oligomeric compound itself, through nucleobase complementarity. Complementary oligomeric compounds need not have nucleobase complementarity at each nucleoside.

Rather, some mismatches are tolerated. In certain embodiments, complementary oligomeric compounds or regions are complementary at 70% of the nucleobases (70% complementary). In certain embodiments, complementary oligomeric compounds or regions are 80%>complementary. In certain embodiments, complementary oligomeric compounds or regions are 90%>complementary. In certain embodiments, complementary oligomeric compounds or regions are at least 95% complementary. In certain embodiments, complementary oligomeric compounds or regions are 100% complementary. As used herein, "self-complementarity" in reference to oligomeric compounds means a compound that may fold back on itself, creating a duplex as a result of nucleobase hybridization of internal complementary strand regions. Depending on how close together and/or how long the strand regions are, then the compound may form hairpin loops, junctions, bulges or internal loops.

As used herein, "mismatch" means a nucleobase of an oligomeric compound that is not capable of pairing with a nucleobase at a corresponding position of a target sequence, or at a corresponding position of the oligomeric compound itself when the oligomeric compound hybridizes as a result of self-complementarity, when the oligomeric compound and the target sequence and/or self-complementary regions of the oligomeric compound, are aligned.

As used herein, "hybridization" means the pairing of complementary oligomeric compounds (e.g., an oligomeric compound and its target sequence). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligomeric compound or region thereof means that each nucleobase of the oligomeric compound or region thereof is capable of pairing with a nucleobase of a complementary nucleic acid target sequence or a self-complementary region of the oligomeric compound. Thus, a fully complementary oligomeric compound or region thereof comprises no mismatches or unhybridized nucleobases with respect to its target sequence or a self-complementary region of the oligomeric compound.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" means chemical modifications or chemical substituents that are different from one another, including absence of modifications. Thus, for example, a MOE nucleoside and an unmodified naturally occurring RNA nucleoside are "differently modified," even though the naturally occurring nucleoside is unmodified.

Likewise, DNA and RNA oligonucleotides are "differently modified," even though both are naturally-occurring unmodified nucleosides. Nucleosides that are the same but for comprising different nucleobases are not differently modified. For example, a nucleoside comprising a 2'—OMe modified sugar moiety and an unmodified adenine nucleobase and a nucleoside comprising a 2'—OMe modified sugar moiety and an unmodified thymine nucleobase are not differently modified.

As used herein, "the same type of modifications" refers to modifications that are the same as one another, including absence of modifications. Thus, for example, two unmodified RNA nucleosides have "the same type of modification," even though the RNA nucleosides are unmodified. Such nucleosides having the same type modification may comprise different nucleobases.

As used herein, "region" or "regions", or "portion" or "portions", mean a plurality of linked nucleosides that have a function or character as defined herein, in particular with reference to the claims and definitions as provided herein. Typically such regions or portions comprise at least 10, at least 11, at least 12 or at least 13 linked nucleosides. For example, such regions can comprise 13 to 20 linked nucleosides, such as 13 to 16 or 18 to 20 linked nucleosides. Typically a first region as defined herein consists essentially of 18 to 20 nucleosides and a second region as defined herein consists essentially of 13 to 16 linked nucleosides.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as oxygen or an alkyl or hydrocarbyl group to a parent compound.

Such substituents can be present as the modification on the sugar moiety, in particular a substituent present at the 2'-position of the sugar moiety. Unless otherwise indicated, groups amenable for use as substituents include without limitation, one or more of halo, hydroxyl, alkyl, alkenyl, alkynyl, acyl, carboxyl, alkoxy, alkoxyalkylene and amino substituents. Certain substituents as described herein can represent modifications directly attached to a ring of a sugar moiety (such as a halo, such as fluoro, directly attached to a sugar ring), or a modification indirectly linked to a ring of a sugar moiety by way of an oxygen linking atom that itself is directly linked to the sugar moiety (such as an alkoxyalkylene, such as methoxyethylene, linked to an oxygen atom, overall providing an MOE substituent as described herein attached to the 2'-position of the sugar moiety).

As used herein, "alkyl," as used herein, means a saturated straight or branched monovalent $C_{1-6}$ hydrocarbon radical, with methyl being a most preferred alkyl as a substituent at the 2'-position of the sugar moiety. The alkyl group typically attaches to an oxygen linking atom at the 2'position of the sugar, therefore, overall providing a—Oalkyl substituent, such as an $—OCH_3$ substituent, on a sugar moiety of an oligomeric compound as described herein. This will be well understood be a person skilled in the art.

As used herein, "alkylene" means a saturated straight or branched divalent hydrocarbon radical of the general formula $—C_nH_{2n}—$ where n is 1-6. Methylene or ethylene are preferred alkylenes.

As used herein, "alkenyl" means a straight or branched unsaturated monovalent $C_{2-6}$ hydrocarbon radical, with ethenyl or propenyl being most preferred alkenyls as a substituent at the 2'-position of the sugar moiety. As will be well understood in the art, the degree of unsaturation that is present in an alkenyl radical is the presence of at least one carbon to carbon double bond. The alkenyl group typically attaches to an oxygen linking atom at the 2'-position of the sugar, therefore, overall providing a—Oalkenyl substituent, such as an $—OCH_2CH{=}CH_2$ substituent, on a sugar moiety of an oligomeric compound as described herein. This will be well understood be a person skilled in the art.

As used herein, "alkynyl" means a straight or branched unsaturated $C_{2-6}$ hydrocarbon radical, with ethynyl being a most preferred alkynyl as a substituent at the 2'-position of the sugar moiety. As will be well understood in the art, the degree of unsaturation that is present in an alkynyl radical is the presence of at least one carbon to carbon triple bond. The alkynyl group typically attaches to an oxygen linking atom at the 2'-position of the sugar, therefore, overall providing a—Oalkynyl substituent on a sugar moiety of an oligomeric compound as described herein. This will be well understood be a person skilled in the art.

As used herein, "carboxyl" is a radical having a general formula $—CO_2H$.

As used herein, "acyl" means a radical formed by removal of a hydroxyl group from a carboxyl radical as defined herein and has the general Formula —C(O)—X where X is typically Cis alkyl.

As used herein, "alkoxy" means a radical formed between an alkyl group, such as a $C_{1-6}$ alkyl group, and an oxygen atom wherein the oxygen atom is used to attach the alkoxy group either to a parent molecule (such as at the 2'-position of a sugar moiety), or to another group such as an alkylene group as defined herein. Examples of alkoxy groups include without limitation, methoxy, ethoxy, propoxy, isopropoxy, n-butoxy, sec-butoxy and tert-butoxy. Alkoxy groups as used herein may optionally include further substituent groups.

As used herein, alkoxyalkylene means an alkoxy group as defined herein that is attached to an alkylene group also as defined herein, and wherein the oxygen atom of the alkoxy group attaches to the alkylene group and the alkylene attaches to a parent molecule. The alkylene group typically attaches to an oxygen linking atom at the 2'-position of the sugar, therefore, overall providing a—Oalkylenealkoxy substituent, such as an $—OCH_2CH_2OCH_3$ substituent, on a sugar moiety of an oligomeric compound as described herein. This will be well understood by a person skilled in the art and is generally referred to as an MOE substituent as defined herein and as known in the art.

As used herein, "amino" includes primary, secondary and tertiary amino groups.

As used herein, "halo" and "halogen," mean an atom selected from fluorine, chlorine, bromine and iodine.

As used herein, the term "mxRNA" is in particular understood as defined in WO 2020/044186 A2 which is incorporated by reference herein in its entirety.

It will also be understood that oligomeric compounds as described herein may have one or more non-hybridizing nucleosides at one or both ends of one or both strands (overhangs) and/or one or more internal non-hybridizing nucleosides (mismatches) provided there is sufficient complementarity to maintain hybridization under physiologically relevant conditions. Alternatively, oligomeric compounds as described herein may be blunt ended at at least one end.

The term "comprising" is used herein to mean including the method steps or elements identified, but that such steps or elements do not comprise an exclusive list and as such there may be present additional steps or elements.

Further, to the extent that the term "includes" is used in either the detailed description or the claims, such term is intended to be inclusive in a manner similar to the term "comprising" as "comprising" is interpreted when employed as a transitional word in a claim.

The following exemplary embodiments (items) are provided:

1. An oligomeric compound capable of inhibiting expression of APOC3, wherein the compound comprises at least a first region of linked nucleosides having at least a first nucleobase sequence that is at least partially complementary to at least a portion of RNA transcribed from an APOC3 gene, wherein the first nucleobase sequence is selected from the following sequences, or a portion thereof: sequences of Tables 1a and 2a (SEQ ID NOs: 1 to 391), wherein the portion preferably has a length of at least 18 nucleotides.

Said first region is also referred to as the antisense region, and said second region is also referred to as the sense region. As disclosed in preferred embodiments below, said two regions may be located on the same strand, preferably in an adjacent manner. This gives rise to hairpin molecules, also referred to as mxRNAs. On the other hand, said two regions may be located on separate strands which gives rise to double-stranded RNAs (dsRNAs), wherein preferably each strand consists of the respective region. Moreover, said regions may serve as building blocks for muRNAs (see above at Aspect 1). In other words, said first and said second region as defined herein may be used, in accordance with the following definition of muRNAs as first and third regions, respectively:

A nucleic acid construct (muRNA) comprising at least:

(a) a first nucleic acid portion that is at least partially complementary to at least a first portion of an RNA which is transcribed from a APOC3 gene;

(b) a second nucleic acid portion that is at least partially complementary to at least a second portion of an RNA which is transcribed from another gene;

(c) a third nucleic acid portion that is at least partially complementary to said first nucleic acid portion of (a), so as to form a first nucleic acid duplex region therewith; and (d) a fourth nucleic acid portion that is at least partially complementary to said second nucleic acid portion of (b), so as to form a second nucleic acid duplex region therewith.

Preferred embodiments of and further aspects relating to muRNAs are disclosed in WO2020/065602.

2. The oligomeric compound according to item 1, which further comprises at least a second region of linked nucleosides having at least a second nucleobase sequence that is at least partially complementary to the first nucleobase sequence and is selected from the following sequences, or a portion thereof: sequences of Tables 1c and 2c (SEQ ID NOs: 401 to 791), wherein the portion preferably has a length of at least 11 nucleotides, or wherein the portion preferably has a length of at least 8, 9, 10 or 11 nucleotides, more preferably at least 10 nucleotides.

3. The oligomeric compound according to item 1 or 2, wherein the first nucleobase sequence is selected from the following sequences, or a portion thereof: SEQ ID NOs: 175, 293, 262, 297, 277, 366, 337, 254, 274, 286, 137, 149, 280, 343, 225, 221, 185, 373, 121, 281, 331, 367, 296, 28, 345, 328, 339, 278, 271, 212, 223, 369, 276, 332, 300, 341, 334, 138, 193, 340, 31, 167, 275, 191, 336, 90, 346, 219, 283, 213, 23, 24, 285, 347, 370, 206, 282, 342, 272, 303, 220, 209, 29, 89, 291, 117, 372, 218, 368, 148, 217, 128, 338, 171, 94, 324, and 299.

4. The oligomeric compound according to item 3, wherein the second nucleobase sequence is selected from the following sequences, or a portion thereof: SEQ ID NOs: 575, 693, 662, 697, 677, 766, 737, 654, 674, 686, 537, 549, 680, 743, 625, 621, 585, 773, 521, 681, 731, 767, 696, 428, 745, 728, 739, 678, 671, 612, 623, 769, 676, 732, 700, 741, 734, 538, 593, 740, 431, 567, 675, 591, 736, 490, 746, 619, 683, 613, 423, 424, 685, 747, 770, 606, 682, 742, 672, 703, 620, 609, 429, 489, 691, 517, 772, 618, 768, 548, 617, 528, 738, 571, 494, 724, and 699.

5. The oligomeric compound according to any of items 1 to 4, wherein the first nucleobase sequence is selected from the following sequences, or a portion thereof: SEQ ID NOs: 277, 337, 28, 343, 369, 366, 274, 367, 336, 332, 293, 373, 280, 221, 334, 286, 149, 193, 328, 175, 262, 254, 185, 328, 271, 137, 225, 167, 297, and 191.

6. The oligomeric compound according to item 5, wherein the second nucleobase sequence is selected from the following sequences, or a portion thereof: SEQ ID NOs: 677, 737, 428, 743, 769, 766, 674, 767, 736, 732, 693, 773, 680, 621, 734, 686, 549, 593, 728, 575, 662, 654, 585, 728, 671, 537, 625, 567, 697, and 591.

7. The oligomeric compound according to any of items 1 to 6, wherein the first nucleobase sequence is selected from the following sequences, or a portion thereof: SEQ ID NOs: 28, 277, 336, 337, 366, 367, and 369, preferably SEQ ID NO: 28 or 277, more preferably SEQ ID NO: 28.

These embodiments define antisense nucleobase sequences which provide for surprisingly outstanding performance. For evidence, reference is made to the Examples.

8. The oligomeric compound according to item 7, wherein the second nucleobase sequence is selected from the following sequences, or a portion thereof: SEQ ID NOs: 428, 677, 736, 737, 766, 767, and 769, preferably SEQ ID NO: 428 or 677, more preferably SEQ ID NO: 428.

9. The oligomeric compound according to any of items 1 to 8, wherein the first region of linked nucleosides consists essentially of 18 to 35, preferably 18 to 20, more preferably 18 or 19, and yet more preferably 19 linked nucleosides.

10. The oligomeric compound according to any of items 2 to 9, wherein the second region of linked nucleosides consists essentially of 11 to 35, preferably 11 to 20, more preferably 13 to 16, and yet more preferably 14 or 15, most preferably 14 linked nucleosides; or wherein the second region of linked nucleosides consists essentially of 10 to 35, preferably 10 to 20, more preferably 10 to 16, and yet more preferably 10 to 15 linked nucleosides.

11. The oligomeric compound according to any of items 2 to 10, which comprises at least one complementary duplex region that comprises at least a portion of the first nucleoside region directly or indirectly linked to at least a portion of the second nucleoside region, wherein preferably the duplex region has a length of 11 to 19, more preferably 14 to 19, and yet more preferably 14 or 15 base pairs, most preferably 14 base pairs, wherein optionally there is one mismatch within the duplex region; or which comprises at least one complementary duplex region that comprises at least a portion of the first nucleoside region directly or indirectly linked to at least a portion of the second nucleoside region, wherein preferably the duplex region has a length of 10 to 19, more preferably 12 to 19, and yet more preferably 12 to 15 base pairs, wherein optionally there is one mismatch within the duplex region.
12. The oligomeric compound according to item 11, wherein each of the first and second nucleoside regions has a 5' to 3' directionality thereby defining 5' and 3' regions respectively thereof.
13. The oligomeric compound according to item 12, wherein the 5' region of the first nucleoside region is directly or indirectly linked to the 3' region of the second nucleoside region, for example by complementary base pairing, and/or wherein the 3' region of the first nucleoside region is directly or indirectly linked to the 5' region of the second nucleoside region, wherein preferably the 5' terminal nucleoside of the first nucleoside region base pairs with the 3' terminal nucleoside of the second nucleoside region; or wherein the 5' region of the first nucleoside region is directly or indirectly linked to the 3' region of the second nucleoside region, for example by complementary base pairing, wherein preferably the 5' terminal nucleoside of the first nucleoside region base pairs with the 3' terminal nucleoside of the second nucleoside region.
14. The oligomeric compound according to item 12 or 13, wherein the 3' region of the first nucleoside region is directly or indirectly linked to the 5' region of the second nucleoside region, wherein preferably the first nucleoside region is directly and covalently linked to the second nucleoside region such as by a phosphate, a phosphorothioate, or a phosphorodithoate.
15. The oligomeric compound according to any of items 1 to 14, which further comprises one or more ligands.
16. The oligomeric compound according to item 15, wherein the one or more ligands are conjugated to the second nucleoside region and/or the first nucleoside region.
17. The oligomeric compound according to item 16, as dependent on claim 12, wherein the one or more ligands are conjugated at the 3' region, preferably to the 3' end of the second nucleoside region and/or of the first nucleoside region, and/or to the 5' end of the second nucleoside region.
18. The oligomeric compound according to any of item 15 to 17, wherein the one or more ligands are any cell directing moiety, such as lipids, carbohydrates, aptamers, vitamins and/or peptides that bind cellular membrane or a specific target on cellular surface.
19. The oligomeric compound according to item 18, wherein the one or more ligands comprise one or more carbohydrates.
20. The oligomeric compound according to item 19, wherein the one or more carbohydrates can be a monosaccharide, disaccharide, trisaccharide, tetrasaccharide, oligosaccharide or polysaccharide.
21. The oligomeric compound according to item 20, wherein the one or more carbohydrates comprise or consist of one or more hexose moieties.
22. The oligomeric compound according to item 21, wherein the one or more hexose moieties are one or more galactose moieties, one or more lactose moieties, one or more N-Acetyl-Galactosamine moieties, and/or one or more mannose moieties.
23. The oligomeric compound according to item 22, wherein the one or more carbohydrates comprise one or more N-Acetyl-Galactosamine moieties.
24. The oligomeric compound according to item 23, which comprises two or three N-Acetyl-Galactosamine moieties, preferably three.
25. The oligomeric compound according to any of items 15 to 24, wherein the one or more ligands are attached to the oligomeric compound, preferably to the second nucleoside region thereof, in a linear configuration, or in a branched configuration.
26. The oligomeric compound according to item 25, wherein the one or more ligands are attached to the oligomeric compound as a biantennary or triantennary configuration.
27. The oligomeric compound according to any one of items 1 to 26, wherein the compound consists of the first region of linked nucleosides and the second region of linked nucleosides.

Each of said regions may constitute a separate strand, thereby giving rise to a double-stranded RNA (dsRNA). Particularly preferred dsRNAs are those with a length of the first strand of 19 nucleosides and a length of the second region of 14 or 15, preferably 14 nucleosides. When used for defining the length of a region or strand, the terms “nucleoside” and “nucleotide” (sometimes abbreviated “nt”) are used equivalently.

28. The oligomeric compound according to item 12, wherein the oligomeric compound comprises a single strand comprising the first and second nucleoside regions, wherein the single strand dimerises whereby at least a portion of the first nucleoside region is directly or indirectly linked to at least a portion of the second nucleoside region so as to form the at least partially complementary duplex region.

In other words, the oligomeric compound comprises a single strand comprising the first and second nucleoside regions, wherein at least a portion of the first nucleoside region is directly or indirectly linked to at least a portion of the second nucleoside region so as to form the at least partially complementary duplex region.

29. The oligomeric compound according to item 28, wherein the first nucleoside region has a greater number of linked nucleosides compared to the second nucleoside region, whereby the additional number of linked nucleosides of the first nucleoside region form a hairpin loop linking the first and second nucleoside regions.

Such compounds are also referred to as hairpins or mxRNAs herein.

30. The oligomeric compound according to item 29, as dependent on claim 12, whereby the hairpin loop is present at the 3' region of the first nucleoside region.
31. The oligomeric compound according to item 29 or 30, wherein the hairpin loop comprises 4 or 5 linked nucleosides.

Particularly advantageous is a length of the first region of 19 nucleosides, of the second region of 14 nucleotides, and of the hairpin loop of five nucleotides, wherein the five nucleotides in the hairpin are the five 3'-terminal nucleosides of the first region. Such molecular architecture of a hairpin or mxRNA is also designated "14-5-14" herein.

32. The oligomeric compound according to any one of items 28 to 31, wherein the single strand has a nucleobase sequence selected from SEQ ID NOs: 792 to 803, preferably from SEQ ID NOs: 792, 793, 796, 800 and 803, most preferably from SEQ ID NOs: 796 and 803 particularly SEQ ID NO: 803.
33. The oligomeric compound according to item 32, wherein the single strand is selected from Table 3b, in particular from constructs A28(14-4)mF and A277(12-5_, A28(14-4)mF being especially advantageous.
34. The oligomeric compound according to any of items 1 to 33, which comprises internucleoside linkages and wherein at least one internucleoside linkage is a modified internucleoside linkage.

Specific modified internucleoside linkages are the subject of the embodiments which follow. Certain modified internucleoside linkages are known in the art and described in, for example, Hu et al., Signal Transduction and Targeted Therapy (2020)5:101.

35. The oligomeric compound according to item 34, wherein the modified internucleoside linkage is a phosphorothioate or phosphorodithioate internucleoside linkage.
36. The oligomeric compound according to item 35, which comprises 1 to 15 phosphorothioate or phosphorodithioate internucleoside linkages.
37. The oligomeric compound according to item 36, which comprises 7, 8, 9 or 10 phosphorothioate or phosphorodithioate internucleoside linkages.
38. The oligomeric compound according to any of items 35 to 37, as dependent on item 12, which comprises one or more phosphorothioate or phosphorodithioate internucleoside linkages at the 5' region of the first nucleoside region.
39. The oligomeric compound according to any of items 35 to 38, as dependent on item 12, which comprises one or more phosphorothioate or phosphorodithioate internucleoside linkages at the 5' region of the second nucleoside region.
40. The oligomeric compound according to any of items 35 to 39, as dependent on item 28, which comprises phosphorothioate or phosphorodithioate internucleoside linkages between at least two, preferably at least three, preferably at least four, preferably at least five, adjacent nucleosides of the hairpin loop, dependent on the number of nucleotides present in the hairpin loop.
41. The oligomeric compound according to item 40, which comprises a phosphorothioate or phosphorodithioate internucleoside linkage between each adjacent nucleoside that is present in the hairpin loop.
42. The oligomeric compound according to any of items 1 to 41, wherein at least one nucleoside comprises a modified sugar.

Preferred modified sugars are subject of the embodiments which follow. Certain modified sugars are known in the art and described in, for example, Hu et al., Signal Transduction and Targeted Therapy (2020)5:101.

43. The oligomeric compound according to item 42, wherein the modified sugar is selected from 2' modified sugars, locked nucleic acid (LNA) sugar, (S)—constrained ethyl bicyclic nucleic acid sugar, tricyclo-DNA sugar, morpholino, unlocked nucleic acid (UNA) sugar, and glycol nucleic acid (GNA) sugar.
44. The oligomeric compound according to item 43, wherein the 2' modified sugar is selected from 2'-O-methyl modified sugar, 2'-O-methoxyethyl modified sugar, 2'-F modified sugar, 2'-arabino-fluoro modified sugar, 2'-O-benzyl modified sugar, and 2'-O-methyl-4-pyridine modified sugar.
45. The oligomeric compound according to item 44, wherein at least one modified sugar is a 2'-O-methyl modified sugar.
46. The oligomeric compound according to item 44 or 45, wherein at least one modified sugar is a 2'-F modified sugar.
47. The oligomeric compound of item 45 or 46, wherein the sugar is ribose.
48. The oligomeric compound according to any of items 45 to 48, as dependent on item 12, wherein sugars of the nucleosides at any of positions 2 and 14 downstream from the first nucleoside of the 5' region of the first nucleoside region, do not contain 2'-O-methyl modifications.
49. The oligomeric compound according to any of items 45 to 48, as dependent on item 12, wherein sugars of the nucleosides of the second nucleoside region, that correspond in position to any of the nucleosides of the first nucleoside region at any of positions 9 to 11 downstream from the first nucleotide of the 5' region of the first nucleoside region, in particular from sequence A277(12-5) and A28(14-4)mF do not contain 2'-O-methyl modifications.
50. The oligomeric compound of any one of items 45 to 49, wherein the 3' terminal position of the second nucleoside region does not contain a 2'-O-methyl modification.
51. The oligomeric compound according to item 49 or 50, wherein sugars of the nucleosides at any of positions 2 and 14 downstream from the first nucleoside of the 5' region of the first nucleoside region, contain 2'-F modifications.
52. The oligomeric compound according to any of items 49 to 51, wherein sugars of the nucleosides of the second nucleoside region, that correspond in position to any of the nucleosides of the first nucleoside region at any of positions 9 to 11 downstream from the first nucleoside of the 5' region of the first nucleoside region, contain 2'-F modifications.
53. The oligomeric compound of item 51 or 52, wherein the 3' terminal position of the second nucleoside region contains a 2'-F modification.
54. The oligomeric compound according to any of items 47 to 53, as dependent on item 12, wherein one or more of the odd numbered nucleosides starting from the 5' region of the first nucleoside region are modified, and/or wherein one or more of the even numbered nucleotides starting from the 5' region of the first nucleoside region are modified, wherein typically the modification of the even numbered nucleotides is a second modification that is different from the modification of odd numbered nucleotides.
55. The oligomeric compound according to item 54, wherein one or more of the odd numbered nucleosides starting from the 3' region of the second nucleoside region are modified by a modification that is different from the modification of odd numbered nucleosides of the first nucleoside region.

56. The oligomeric compound according to item 54 or 55, wherein one or more of the even numbered nucleosides starting from the 3' region of the second nucleoside region are modified by a modification that is different from the modification of even numbered nucleosides of the first nucleoside region according to item 55.
57. The oligomeric compound according to any of items 54 to 56, wherein at least one or more of the modified even numbered nucleosides of the first nucleoside region is adjacent to at least one or more of the differently modified odd numbered nucleosides of the first nucleoside region.
58. The oligomeric compound according to any of items 54 to 57, wherein at least one or more of the modified even numbered nucleosides of the second nucleoside region is adjacent to at least one or more of the differently modified odd numbered nucleosides of the second nucleoside region.
59. The oligomeric compound according to any of items 54 to 58, wherein sugars of one or more of the odd numbered nucleosides starting from the 5' region of the first nucleoside region are 2'-O-methyl modified sugars.
60. The oligomeric compound according to any of items 54 to 59, wherein one or more of the even numbered nucleosides starting from the 5' region of the first nucleoside region are 2'-F modified sugars.
61. The oligomeric compound according to any of items 54 to 60, wherein sugars of one or more of the odd numbered nucleosides starting from the 3' region of the second nucleoside region are 2'-F modified sugars.
62. The oligomeric compound according to any of items 54 to 61, wherein one or more of the even numbered nucleosides starting from the 3' region of the second nucleoside region are 2'-O-methyl modified sugars.
63. The oligomeric compound according to any of items 42 to 62, wherein sugars of a plurality of adjacent nucleosides of the first nucleoside region are modified by a common modification.
64. The oligomeric compound according to any of items 42 to 63, wherein sugars of a plurality of adjacent nucleosides of the second nucleoside region are modified by a common modification.
65. The oligomeric compound according to any of items 54 to 64, as dependent on item 31, wherein sugars of a plurality of adjacent nucleosides of the hairpin loop are modified by a common modification.
66. The oligomeric compound according to any of items 63 to 65, wherein the common modification is a 2'-F modified sugar.
67. The oligomeric compound according to any of items 63 to 65, wherein the common modification is a 2'-O-methyl modified sugar.
68. The oligomeric compound according to item 67, wherein the plurality of adjacent 2'-O-methyl modified sugars are present in at least eight adjacent nucleosides of the first and/or second nucleoside regions.
69. The oligomeric compound according to item 67, wherein the plurality of adjacent 2'-O-methyl modified sugars are present in three or four adjacent nucleosides of the hairpin loop.
70. The oligomeric compound according to item 42, as dependent on item 29, wherein the hairpin loop comprises at least one nucleoside having a modified sugar.
71. The oligomeric compound according to item 70, wherein the at least one nucleoside is adjacent a nucleoside with a differently modified sugar.
72. The oligomeric compound according to item 71, wherein the modified sugar is a 2'-O-methyl modified sugar, and the differently modifies sugar is a 2'-F modified sugar.
73. The oligomeric compound according to any of items 1 to 72, which comprises one or more nucleosides having an un-modified sugar moiety.
74. The oligomeric compound according to item 73, wherein the unmodified sugar is present in the 5' region of the second nucleoside region.
75. The oligomeric compound according to item 73 or 74, as dependent on item 29, wherein the unmodified sugar is present in the hairpin loop.
76. The oligomeric compound according to any of items 1 to 75, wherein one or more nucleosides of the first nucleoside region and/or the second nucleoside region is an inverted nucleoside and is attached to an adjacent nucleoside via the 3' carbon of its sugar and the 3' carbon of the sugar of the adjacent nucleoside, and/or one or more nucleosides of the first nucleoside region and/or the second nucleoside region is an inverted nucleoside and is attached to an adjacent nucleoside via the 5' carbon of its sugar and the 5' carbon of the sugar of the adjacent nucleoside.
77. The oligomeric compound according to any of items 1 to 76, which is blunt ended.
78. The oligomeric compound according to any of items 1 to 76, wherein either the first or second nucleoside region has an overhang.
79. The oligomeric compound according to any one of the preceding items, wherein the first region of linked nucleotides is selected from Table 1 b or Table 2b, preferably from the entries in Table 1 b which have a nucleobase sequence as defined in any one of item 3, 5 or 7.
80. The oligomeric compound according to any one of the preceding items, wherein the second region of linked nucleotides is selected from Table 1d or Table 2d, preferably from the entries in Table 1b which have a nucleobase sequence as defined in any one of items 4, 6 or 8.
81. A composition comprising an oligomeric compound according to any of items 1 to 80, and a physiologically acceptable excipient.
82. A pharmaceutical composition comprising an oligomeric compound according to any of items 1 to 80.
83. The pharmaceutical composition of item 82, further comprising a pharmaceutically acceptable excipient, diluent, antioxidant, and/or preservative.
84. The pharmaceutical composition of item 82 or 83, wherein the oligomeric compound is the only pharmaceutically active agent.
85. The pharmaceutical composition of item 84, wherein the pharmaceutical composition is to be administered to patients or individuals which are statin-intolerant and/or for whom statins are contraindicated.
86. The pharmaceutical composition of item 82 or 83, wherein the pharmaceutical composition furthermore comprises one or more further pharmaceutically active agents.
87. The pharmaceutical composition of item 86, wherein the further pharmaceutically active agent(s) is/are a further oligomeric compound which is directed to a target different from APOC3, preferably PCSK9; Vascepa; Vupanorsen; statins such as Rosuvastatin and Simvastatin; fibrates such fenofibrate; and/or LDL-cholesterol lowering compounds such as statins and ezetimibe.

88. The pharmaceutical composition of item 86 or 87, wherein the oligomeric compound and the further pharmaceutically active agent(s) are to be administered concomitantly or in any order.
89. An oligomeric compound according to any of item 1 to 80, for use in human or veterinary medicine or therapy.
90. An oligomeric compound according to any of items 1 to 80, for use in a method of treating, ameliorating and/or preventing a disease or disorder.
91. The compound for use of item 90, wherein the disease or disorder is an APOC3-associated disease or disorder, or a disease or disorder requiring reduction of APOC3 expression levels, the disease or disorder preferably being selected from dyslipidemia including mixed dyslipidemia; hyperchylomicronemia including familial hyperchylomicronemia; hypertriglyceridemia, preferably severe hypertriglyceridemia and/or hypertriglyceridemia with blood triglyceride levels above 500 mg/dl;

inflammation including low-grade inflammation; atherosclerosis; atherosclerotic cardiovascular diseases (ASCVD) including major adverse cardiovascular events (MACE) such as myocardial infarction, stroke and peripheral arterial disease; and pancreatitis including acute pancreatitis.

92. A method of treating a disease or disorder comprising administration of an oligomeric compound according to any of item 1 to 80, to an individual in need of treatment.
93. The method according to item 92, wherein the oligomeric compound is administered subcutaneously or intravenously to the individual.
93. Use of an oligomeric compound according to any of item 1 to 80, for use in research as a gene function analysis tool.
94. Use of an oligomeric compound according to any of items 1 to 80 in the manufacture of a medicament for a treatment of a disease or disorder. The diseases and disorders are preferably the same as set forth under item 91 above.

Effects Achieved by the Oligomeric Compounds

Due to the use of the oligomeric compounds as described herein, a significant reduction of APOC3 mRNA, especially in vitro or in liver tissues consisting essentially of human hepatocytes, can be achieved as e.g. shown in the examples disclosed herein. In addition, a significant reduction of APCO3 proteins in the plasma level, e.g. of mice having a liver consisting essentially of human hepatocytes, can be achieved by using the oligomeric constructs as described herein. In particular these effects can last over an extended time period such as six weeks, e.g. in mice having a liver consisting essentially of human hepatocytes.

In addition, by using oligomeric compounds as described herein, significant degrees of reduction of triglyceride levels in the serum, in particular of mice having a liver essentially consisting of human hepatocytes, can be achieved, also over an extended period of time, such as six weeks. An unexpected and surprising finding is that, in addition to the reduction of triglycerides in the serum, in particular of the same mice, a significant reduction in the level of cholesterol in the serum is achieved at the same time over an extended time period, such as six weeks.

It has also been surprisingly found that, in certain embodiments, the aforementioned beneficial effects can be achieved by using oligomeric compounds as described herein in the form of shRNA constructs having a reduced number of fluorine substitutions, such as five fluorine substitutions in total, on the respective 2' positions of their ribose units compared to conventional shRNA molecules having an alternating series of 2'-fluoro and 2'-O-methyl modifications.

Furthermore, it was surprisingly found that, in certain embodiments, the mentioned effects are achieved by using oligomeric compounds as described herein in the form of shRNA constructs as described herein having a reduced length of e.g. 29 linked nucleosides compared to conventional shRNA molecules. The same effects can also surprisingly be achieved for such constructs having a length of the sense strand of about 10 nucleosides.

The aforementioned effects can be achieved by using a dosage of about 10 mg/kg body weight to 30 mg/kg body weight, in particular with respect to mice.

Constructs of the Oligomeric Compounds

The following Tables show nucleobase sequences of antisense and sense strands of oligomeric compounds as described herein, and definitions of antisense and sense strands of modified oligomeric compounds (the notation including nucleobase sequence, sugar modifications, and, where applicable, modified phosphates).

The notation used is common in the art and as the following meaning:

A represents adenine;
U represents uracil;
C represents cytosine;
G represents guanine.
P represents a terminal phosphate group which is preferred but not indispensable;
m represents a methyl modification at the 2' position of the sugar of the underlying nucleoside;
f represents a fluoro modification at the 2' position of the sugar of the underlying nucleoside.
r indicates an unmodified (2'-OH) ribonucleotide;
(ps) or #represents a phosphorothioate inter-nucleoside linkage;
i represents an inverted inter-nucleoside linkage, which can be either 3'-3', or 5'-5';
vp represents vinyl phosphonate;
mvp represents methyl vinyl phosphonate;
3xGalNAc represents a trivalent GalNAc.

Sometimes, nucleosides are shown in square brackets for ease of reading. This notation does not indicate structural elements or modifications.

To the extent displayed, the presence of a 5'-terminal phosphate ("P") is optional. Conversely, to the extent a 5'-terminal phosphate is not displayed, its presence is optional as well. Generally, there is no requirement for a 5'-terminal phosphate in compounds to be administered to mammalian cells, since a mammalian kinase adds a 5'-terminal phosphate in the case of its absence.

Furthermore when a notation like "A277(12-5)mF" is used, the term "A277" designates the sequence suitable for RNAi with APOC3, wherein the first number in the round brackets, i.e. 12 in the present case, designates the number of base pairs within a duplex region within a shRNA, and the second number in the round brackets, in this case 5, designates the number of nucleotides present in the hairpin loop of the shRNA. If there is no designation after the hyphen in the round brackets, it means that the loop consists of 5 nucleotides.

Tables 1a to 1d below show nucleobase sequences and sugar-phosphate backbone modifications of antisense and sense strands of the 376 constructs selected in accordance with the Examples. The above disclosed 30 preferred oligomeric compounds have been selected from these 376 constructs. The numbering in Table 1a coincides with the number of the corresponding entry in the sequence listing. For Table 1c the following applies: entry number in the sequence listing=entry number in the Table+400.

TABLE 1a

Nucleobase sequences of the antisense strands of 376 exemplary constructs

| SEQ ID NO: | Nucleobase sequence |
|---|---|
| 1 | UUCUAGGGAUGAACUGAGC |
| 2 | UCUCUAGGGAUGAACUGAG |
| 3 | UCCUCUAGGGAUGAACUGA |
| 4 | UGCCUCUAGGGAUGAACUG |
| 5 | UUGCCUCUAGGGAUGAACU |
| 6 | UCUGCCUCUAGGGAUGAAC |
| 7 | UGCUGCCUCUAGGGAUGAA |
| 8 | UAGCUGCCUCUAGGGAUGA |
| 9 | UGCAGCUGCCUCUAGGGAU |
| 10 | UAGCAGCUGCCUCUAGGGA |
| 11 | UGAGCAGCUGCCUCUAGGG |
| 12 | UGGAGCAGCUGCCUCUAGG |
| 13 | UUGUUCCUGGAGCAGCUGC |
| 14 | UCUGUUCCUGGAGCAGCUG |
| 15 | UCCUCUGUUCCUGGAGCAG |
| 16 | UACCUCUGUUCCUGGAGCA |
| 17 | UCACCUCUGUUCCUGGAGC |
| 18 | UGCACCUCUGUUCCUGGAG |
| 19 | UGGCACCUCUGUUCCUGGA |
| 20 | UUGGCACCUCUGUUCCUGG |
| 21 | UAUGGCACCUCUGUUCCUG |
| 22 | UCAUGGCACCUCUGUUCCU |
| 23 | UUGCAUGGCACCUCUGUUC |
| 24 | UCUGCAUGGCACCUCUGUU |
| 25 | UGCUGCAUGGCACCUCUGU |
| 26 | UGGCUGCAUGGCACCUCUG |
| 27 | UGGGCUGCAUGGCACCUCU |
| 28 | UCAACAAGGAGUACCCGGG |
| 29 | UACAACAAGGAGUACCCGG |
| 30 | UAACAACAAGGAGUACCCG |
| 31 | UCAACAACAAGGAGUACCC |
| 32 | UGCAACAACAAGGAGUACC |
| 33 | UGGCAACAACAAGGAGUAC |
| 34 | UGGGCAACAACAAGGAGUA |
| 35 | UAGGGCAACAACAAGGAGU |

TABLE 1a-continued

Nucleobase sequences of the antisense strands of 376 exemplary constructs

| SEQ ID NO: | Nucleobase sequence |
|---|---|
| 36 | UGAGGGCAACAACAAGGAG |
| 37 | UGGAGGGCAACAACAAGGA |
| 38 | UAGGAGGGCAACAACAAGG |
| 39 | UCAGGAGGGCAACAACAAG |
| 40 | UCCAGGAGGGCAACAACAA |
| 41 | UGCCAGGAGGGCAACAACA |
| 42 | UCGCCAGGAGGGCAACAAC |
| 43 | UGCGCCAGGAGGGCAACAA |
| 44 | UAGCGCCAGGAGGGCAACA |
| 45 | UGAGCGCCAGGAGGGCAAC |
| 46 | UGGAGCGCCAGGAGGGCAA |
| 47 | UAGGAGCGCCAGGAGGGCA |
| 48 | UGCCAGGAGCGCCAGGAGG |
| 49 | UAGAGGCCAGGAGCGCCAG |
| 50 | UCAGAGGCCAGGAGCGCCA |
| 51 | UGCAGAGGCCAGGAGCGCC |
| 52 | UGGCAGAGGCCAGGAGCGC |
| 53 | UGGGCAGAGGCCAGGAGCG |
| 54 | UUCGGGCAGAGGCCAGGAG |
| 55 | UCUCGGGCAGAGGCCAGGA |
| 56 | UGCUCGGGCAGAGGCCAGG |
| 57 | UAGCUCGGGCAGAGGCCAG |
| 58 | UAAGCUCGGGCAGAGGCCA |
| 59 | UGAAGCUCGGGCAGAGGCC |
| 60 | UUGAAGCUCGGGCAGAGGC |
| 61 | UCUGAAGCUCGGGCAGAGG |
| 62 | UUCUGAAGCUCGGGCAGAG |
| 63 | UCUCUGAAGCUCGGGCAGA |
| 64 | UCCUCUGAAGCUCGGGCAG |
| 65 | UGCCUCUGAAGCUCGGGCA |
| 66 | UGGCCUCUGAAGCUCGGGC |
| 67 | UCGGCCUCUGAAGCUCGGG |
| 68 | UUCGGCCUCUGAAGCUCGG |
| 69 | UCUCGGCCUCUGAAGCUCG |
| 70 | UCCUCGGCCUCUGAAGCUC |
| 71 | UUCCUCGGCCUCUGAAGCU |
| 72 | UAUCCUCGGCCUCUGAAGC |

TABLE 1a-continued

Nucleobase sequences of the antisense strands of 376 exemplary constructs

| SEQ ID NO: | Nucleobase sequence |
|---|---|
| 73 | UCAUCCUCGGCCUCUGAAG |
| 74 | UGCAUCCUCGGCCUCUGAA |
| 75 | UGGCAUCCUCGGCCUCUGA |
| 76 | UAGGCAUCCUCGGCCUCUG |
| 77 | UGAGGCAUCCUCGGCCUCU |
| 78 | UGGAGGCAUCCUCGGCCUC |
| 79 | UGGGAGGCAUCCUCGGCCU |
| 80 | UAGGGAGGCAUCCUCGGCC |
| 81 | UAAGGGAGGCAUCCUCGGC |
| 82 | UGAAGGGAGGCAUCCUCGG |
| 83 | UAGAAGGGAGGCAUCCUCG |
| 84 | UGAGAAGGGAGGCAUCCUC |
| 85 | UUGAGAAGGGAGGCAUCCU |
| 86 | UCUGAGAAGGGAGGCAUCC |
| 87 | UGCUGAGAAGGGAGGCAUC |
| 88 | UAGCUGAGAAGGGAGGCAU |
| 89 | UUGAAGCUGAGAAGGGAGG |
| 90 | UAUGAAGCUGAGAAGGGAG |
| 91 | UCAUGAAGCUGAGAAGGGA |
| 92 | UGCAUGAAGCUGAGAAGGG |
| 93 | UUGCAUGAAGCUGAGAAGG |
| 94 | UCUGCAUGAAGCUGAGAAG |
| 95 | UCCUGCAUGAAGCUGAGAA |
| 96 | UCCCUGCAUGAAGCUGAGA |
| 97 | UACCCUGCAUGAAGCUGAG |
| 98 | UAACCCUGCAUGAAGCUGA |
| 99 | UUAACCCUGCAUGAAGCUG |
| 100 | UGUAACCCUGCAUGAAGCU |
| 101 | UUGUAACCCUGCAUGAAGC |
| 102 | UAUGUAACCCUGCAUGAAG |
| 103 | UCAUGUAACCCUGCAUGAA |
| 104 | UUCAUGUAACCCUGCAUGA |
| 105 | UUUCAUGUAACCCUGCAUG |
| 106 | UCUUCAUGUAACCCUGCAU |
| 107 | UGCUUCAUGUAACCCUGCA |
| 108 | UUGCUUCAUGUAACCCUGC |
| 109 | UGUGCUUCAUGUAACCCUG |

TABLE 1a-continued

Nucleobase sequences of the antisense strands of 376 exemplary constructs

| SEQ ID NO: | Nucleobase sequence |
|---|---|
| 110 | UCGUGCUUCAUGUAACCCU |
| 111 | UGCGUGCUUCAUGUAACCC |
| 112 | UGGCGUGCUUCAUGUAACC |
| 113 | UUGGCGUGCUUCAUGUAAC |
| 114 | UGUGGCGUGCUUCAUGUAA |
| 115 | UGGUGGCGUGCUUCAUGUA |
| 116 | UUGGUGGCGUGCUUCAUGU |
| 117 | UUUGGUGGCGUGCUUCAUG |
| 118 | UCUUGGUGGCGUGCUUCAU |
| 119 | UUCUUGGUGGCGUGCUUCA |
| 120 | UGUCUUGGUGGCGUGCUUC |
| 121 | UGGUCUUGGUGGCGUGCUU |
| 122 | UCGGUCUUGGUGGCGUGCU |
| 123 | UGCGGUCUUGGUGGCGUGC |
| 124 | UGGCGGUCUUGGUGGCGUG |
| 125 | UUGGCGGUCUUGGUGGCGU |
| 126 | UUUGGCGGUCUUGGUGGCG |
| 127 | UCUUGGCGGUCUUGGUGGC |
| 128 | UCCUUGGCGGUCUUGGUGG |
| 129 | UUCCUUGGCGGUCUUGGUG |
| 130 | UAUCCUUGGCGGUCUUGGU |
| 131 | UCAUCCUUGGCGGUCUUGG |
| 132 | UGCAUCCUUGGCGGUCUUG |
| 133 | UUGCAUCCUUGGCGGUCUU |
| 134 | UGUGCAUCCUUGGCGGUCU |
| 135 | UAGUGCAUCCUUGGCGGUC |
| 136 | UCAGUGCAUCCUUGGCGGU |
| 137 | UUCAGUGCAUCCUUGGCGG |
| 138 | UCUCAGUGCAUCCUUGGCG |
| 139 | UGCUCAGUGCAUCCUUGGC |
| 140 | UUGCUCAGUGCAUCCUUGG |
| 141 | UCUGCUCAGUGCAUCCUUG |
| 142 | UGCUGCUCAGUGCAUCCUU |
| 143 | UCGCUGCUCAGUGCAUCCU |
| 144 | UACGCUGCUCAGUGCAUCC |
| 145 | UCACGCUGCUCAGUGCAUC |
| 146 | UGCACGCUGCUCAGUGCAU |

TABLE 1a-continued

Nucleobase sequences of the antisense strands of 376 exemplary constructs

| SEQ ID NO: | Nucleobase sequence |
|---|---|
| 147 | UUGCACGCUGCUCAGUGCA |
| 148 | UCUGCACGCUGCUCAGUGC |
| 149 | UCCUGCACGCUGCUCAGUG |
| 150 | UUCCUGCACGCUGCUCAGU |
| 151 | UACUCCUGCACGCUGCUCA |
| 152 | UGGGACUCCUGCACGCUGC |
| 153 | UUGGGACUCCUGCACGCUG |
| 154 | UCUGGGACUCCUGCACGCU |
| 155 | UCCUGGGACUCCUGCACGC |
| 156 | UACCUGGGACUCCUGCACG |
| 157 | UCACCUGGGACUCCUGCAC |
| 158 | UCCACCUGGGACUCCUGCA |
| 159 | UGGGCCACCUGGGACUCCU |
| 160 | UUGGGCCACCUGGGACUCC |
| 161 | UUGCUGGGCCACCUGGGAC |
| 162 | UCUGCUGGGCCACCUGGGA |
| 163 | UGGCCUGCUGGGCCACCUG |
| 164 | UCCUGGCCUGCUGGGCCAC |
| 165 | UCCAUCGGUCACCCAGCCC |
| 166 | UGCCAUCGGUCACCCAGCC |
| 167 | UAGCCAUCGGUCACCCAGC |
| 168 | UAAGCCAUCGGUCACCCAG |
| 169 | UGAAGCCAUCGGUCACCCA |
| 170 | UUGAAGCCAUCGGUCACCC |
| 171 | UCUGAAGCCAUCGGUCACC |
| 172 | UACUGAAGCCAUCGGUCAC |
| 173 | UAACUGAAGCCAUCGGUCA |
| 174 | UGAACUGAAGCCAUCGGUC |
| 175 | UGGAACUGAAGCCAUCGGU |
| 176 | UGGGAACUGAAGCCAUCGG |
| 177 | UAGGGAACUGAAGCCAUCG |
| 178 | UCAGGGAACUGAAGCCAUC |
| 179 | UUCAGGGAACUGAAGCCAU |
| 180 | UUUCAGGGAACUGAAGCCA |
| 181 | UUUUCAGGGAACUGAAGCC |
| 182 | UCUUUCAGGGAACUGAAGC |
| 183 | UUCUUUCAGGGAACUGAAG |

TABLE 1a-continued

Nucleobase sequences of the antisense strands of 376 exemplary constructs

| SEQ ID NO: | Nucleobase sequence |
|---|---|
| 184 | UGUCUUUCAGGGAACUGAA |
| 185 | UAGUCUUUCAGGGAACUGA |
| 186 | UUAGUCUUUCAGGGAACUG |
| 187 | UGUAGUCUUUCAGGGAACU |
| 188 | UAGUAGUCUUUCAGGGAAC |
| 189 | UCAGUAGUCUUUCAGGGAA |
| 190 | UCCAGUAGUCUUUCAGGGA |
| 191 | UUCCAGUAGUCUUUCAGGG |
| 192 | UCUCCAGUAGUCUUUCAGG |
| 193 | UGCUCCAGUAGUCUUUCAG |
| 194 | UUGCUCCAGUAGUCUUUCA |
| 195 | UGUGCUCCAGUAGUCUUUC |
| 196 | UGGUGCUCCAGUAGUCUUU |
| 197 | UCGGUGCUCCAGUAGUCUU |
| 198 | UACGGUGCUCCAGUAGUCU |
| 199 | UAACGGUGCUCCAGUAGUC |
| 200 | UUAACGGUGCUCCAGUAGU |
| 201 | UUUAACGGUGCUCCAGUAG |
| 202 | UCUUAACGGUGCUCCAGUA |
| 203 | UCCUUAACGGUGCUCCAGU |
| 204 | UUCCUUAACGGUGCUCCAG |
| 205 | UGUCCUUAACGGUGCUCCA |
| 206 | UUGUCCUUAACGGUGCUCC |
| 207 | UUUGUCCUUAACGGUGCUC |
| 208 | UCUUGUCCUUAACGGUGCU |
| 209 | UACUUGUCCUUAACGGUGC |
| 210 | UAACUUGUCCUUAACGGUG |
| 211 | UGAACUUGUCCUUAACGGU |
| 212 | UAGAACUUGUCCUUAACGG |
| 213 | UGAGAACUUGUCCUUAACG |
| 214 | UAGAGAACUUGUCCUUAAC |
| 215 | UCAGAGAACUUGUCCUUAA |
| 216 | UUCAGAGAACUUGUCCUUA |
| 217 | UCUCAGAGAACUUGUCCUU |
| 218 | UACUCAGAGAACUUGUCCU |
| 219 | UAACUCAGAGAACUUGUCC |
| 220 | UGAACUCAGAGAACUUGUC |

TABLE 1a-continued

| Nucleobase sequences of the antisense strands of 376 exemplary constructs | |
|---|---|
| SEQ ID NO: | Nucleobase sequence |
| 221 | UCAGAACUCAGAGAACUUG |
| 222 | UCCAGAACUCAGAGAACUU |
| 223 | UCCCAGAACUCAGAGAACU |
| 224 | UUCCCAGAACUCAGAGAAC |
| 225 | UAUCCCAGAACUCAGAGAA |
| 226 | UAAUCCCAGAACUCAGAGA |
| 227 | UAAAUCCCAGAACUCAGAG |
| 228 | UCAAAUCCCAGAACUCAGA |
| 229 | UCCAAAUCCCAGAACUCAG |
| 230 | UUCCAAAUCCCAGAACUCA |
| 231 | UGUCCAAAUCCCAGAACUC |
| 232 | UGGUCCAAAUCCCAGAACU |
| 233 | UGGGUCCAAAUCCCAGAAC |
| 234 | UAGGGUCCAAAUCCCAGAA |
| 235 | UCAGGGUCCAAAUCCCAGA |
| 236 | UUCAGGGUCCAAAUCCCAG |
| 237 | UGACCUCAGGGUCCAAAUC |
| 238 | UUGACCUCAGGGUCCAAAU |
| 239 | UCUGACCUCAGGGUCCAAA |
| 240 | UUCUGACCUCAGGGUCCAA |
| 241 | UGUCUGACCUCAGGGUCCA |
| 242 | UGGUCUGACCUCAGGGUCC |
| 243 | UUGGUCUGACCUCAGGGUC |
| 244 | UUUGGUCUGACCUCAGGGU |
| 245 | UGUUGGUCUGACCUCAGGG |
| 246 | UAGUUGGUCUGACCUCAGG |
| 247 | UAAGUUGGUCUGACCUCAG |
| 248 | UGAAGUUGGUCUGACCUCA |
| 249 | UUGAAGUUGGUCUGACCUC |
| 250 | UCUGAAGUUGGUCUGACCU |
| 251 | UGGCUGAAGUUGGUCUGAC |
| 252 | UCGGCUGAAGUUGGUCUGA |
| 253 | UACGGCUGAAGUUGGUCUG |
| 254 | UCACGGCUGAAGUUGGUCU |
| 255 | UCCACGGCUGAAGUUGGUC |
| 256 | UGCCACGGCUGAAGUUGGU |
| 257 | UCAGCCACGGCUGAAGUUG |

TABLE 1a-continued

| Nucleobase sequences of the antisense strands of 376 exemplary constructs | |
|---|---|
| SEQ ID NO: | Nucleobase sequence |
| 258 | UGCAGCCACGGCUGAAGUU |
| 259 | UGGCAGCCACGGCUGAAGU |
| 260 | UAGGCAGCCACGGCUGAAG |
| 261 | UCAGGCAGCCACGGCUGAA |
| 262 | UUCUCAGGCAGCCACGGCU |
| 263 | UGUCUCAGGCAGCCACGGC |
| 264 | UGGUCUCAGGCAGCCACGG |
| 265 | UAGGUCUCAGGCAGCCACG |
| 266 | UUGAGGUCUCAGGCAGCCA |
| 267 | UUUGAGGUCUCAGGCAGCC |
| 268 | UAUUGAGGUCUCAGGCAGC |
| 269 | UUAUUGAGGUCUCAGGCAG |
| 270 | UGUAUUGAGGUCUCAGGCA |
| 271 | UGGUAUUGAGGUCUCAGGC |
| 272 | UGGGUAUUGAGGUCUCAGG |
| 273 | UUAGGCAGGUGGACUUGGG |
| 274 | UAUAGGCAGGUGGACUUGG |
| 275 | UGAUAGGCAGGUGGACUUG |
| 276 | UGGAUAGGCAGGUGGACUU |
| 277 | UUGGAUAGGCAGGUGGACU |
| 278 | UAUGGAUAGGCAGGUGGAC |
| 279 | UGAUGGAUAGGCAGGUGGA |
| 280 | UGGAUGGAUAGGCAGGUGG |
| 281 | UAGGAUGGAUAGGCAGGUG |
| 282 | UCAGGAUGGAUAGGCAGGU |
| 283 | UGCAGGAUGGAUAGGCAGG |
| 284 | UCGCAGGAUGGAUAGGCAG |
| 285 | UUCGCAGGAUGGAUAGGCA |
| 286 | UCUCGCAGGAUGGAUAGGC |
| 287 | UGCUCGCAGGAUGGAUAGG |
| 288 | UAGCUCGCAGGAUGGAUAG |
| 289 | UGAGCUCGCAGGAUGGAUA |
| 290 | UGGAGCUCGCAGGAUGGAU |
| 291 | UAGGAGCUCGCAGGAUGGA |
| 292 | UAAGGAGCUCGCAGGAUGG |
| 293 | UCAAGGAGCUCGCAGGAUG |
| 294 | UCCAAGGAGCUCGCAGGAU |

TABLE 1a-continued

Nucleobase sequences of the antisense strands of 376 exemplary constructs

| SEQ ID NO: | Nucleobase sequence |
|---|---|
| 295 | UCCCAAGGAGCUCGCAGGA |
| 296 | UACCCAAGGAGCUCGCAGG |
| 297 | UGACCCAAGGAGCUCGCAG |
| 298 | UGGACCCAAGGAGCUCGCA |
| 299 | UAGGACCCAAGGAGCUCGC |
| 300 | UCAGGACCCAAGGAGCUCG |
| 301 | UGCAGGACCCAAGGAGCUC |
| 302 | UUGCAGGACCCAAGGAGCU |
| 303 | UUUGCAGGACCCAAGGAGC |
| 304 | UAUUGCAGGACCCAAGGAG |
| 305 | UGAUUGCAGGACCCAAGGA |
| 306 | UAGAUUGCAGGACCCAAGG |
| 307 | UGAGAUUGCAGGACCCAAG |
| 308 | UGGAGAUUGCAGGACCCAA |
| 309 | UUGGAGAUUGCAGGACCCA |
| 310 | UCUGGAGAUUGCAGGACCC |
| 311 | UCCUGGAGAUUGCAGGACC |
| 312 | UCCCUGGAGAUUGCAGGAC |
| 313 | UGCCCUGGAGAUUGCAGGA |
| 314 | UAGCCCUGGAGAUUGCAGG |
| 315 | UCAGCCCUGGAGAUUGCAG |
| 316 | UGCAGCCCUGGAGAUUGCA |
| 317 | UGGCAGCCCUGGAGAUUGC |
| 318 | UGGGCAGCCCUGGAGAUUG |
| 319 | UUUUAAGCAACCUACAGGG |
| 320 | UUUUUAAGCAACCUACAGG |
| 321 | UCUUUUAAGCAACCUACAG |
| 322 | UCCUUUUAAGCAACCUACA |
| 323 | UCCCUUUUAAGCAACCUAC |
| 324 | UUCCCUUUUAAGCAACCUA |
| 325 | UGUCCCUUUUAAGCAACCU |
| 326 | UACUGUCCCUUUUAAGCAA |
| 327 | UUACUGUCCCUUUUAAGCA |
| 328 | UAUACUGUCCCUUUUAAGC |
| 329 | UAAUACUGUCCCUUUUAAG |
| 330 | UGAAUACUGUCCCUUUUAA |
| 331 | UAGAAUACUGUCCCUUUUA |

TABLE 1a-continued

Nucleobase sequences of the antisense strands of 376 exemplary constructs

| SEQ ID NO: | Nucleobase sequence |
|---|---|
| 332 | UGAGAAUACUGUCCCUUUU |
| 333 | UUGAGAAUACUGUCCCUUU |
| 334 | UCUGAGAAUACUGUCCCUU |
| 335 | UACUGAGAAUACUGUCCCU |
| 336 | UCACUGAGAAUACUGUCCC |
| 337 | UGCACUGAGAAUACUGUCC |
| 338 | UAGCACUGAGAAUACUGUC |
| 339 | UGAGCACUGAGAAUACUGU |
| 340 | UAGAGCACUGAGAAUACUG |
| 341 | UGAGAGCACUGAGAAUACU |
| 342 | UGGAGAGCACUGAGAAUAC |
| 343 | UAGGAGAGCACUGAGAAUA |
| 344 | UUAGGAGAGCACUGAGAAU |
| 345 | UGUAGGAGAGCACUGAGAA |
| 346 | UGGUAGGAGAGCACUGAGA |
| 347 | UGGGUAGGAGAGCACUGAG |
| 348 | UGGCCAGGCAUGAGGUGGG |
| 349 | UGGGCCAGGCAUGAGGUGG |
| 350 | UGCCAGCAUGCCUGGAGGG |
| 351 | UGGCCAGCAUGCCUGGAGG |
| 352 | UAGGCCAGCAUGCCUGGAG |
| 353 | UGAGGCCAGCAUGCCUGGA |
| 354 | UGGAGGCCAGCAUGCCUGG |
| 355 | UGGGAGGCCAGCAUGCCUG |
| 356 | UUGGGAGGCCAGCAUGCCU |
| 357 | UAUUGGGAGGCCAGCAUGC |
| 358 | UUAUUGGGAGGCCAGCAUG |
| 359 | UUUAUUGGGAGGCCAGCAU |
| 360 | UUUUAUUGGGAGGCCAGCA |
| 361 | UCUUUAUUGGGAGGCCAGC |
| 362 | UGCUUUAUUGGGAGGCCAG |
| 363 | UAGCUUUAUUGGGAGGCCA |
| 364 | UCAGCUUUAUUGGGAGGCC |
| 365 | UCCAGCUUUAUUGGGAGGC |
| 366 | UUCCAGCUUUAUUGGGAGG |
| 367 | UGUCCAGCUUUAUUGGGAG |
| 368 | UUUGUCCAGCUUUAUUGGG |

TABLE 1a-continued

| Nucleobase sequences of the antisense strands of 376 exemplary constructs | |
|---|---|
| SEQ ID NO: | Nucleobase sequence |
| 369 | UCUUGUCCAGCUUUAUUGG |
| 370 | UUCUUGUCCAGCUUUAUUG |
| 371 | UUUCUUGUCCAGCUUUAUU |
| 372 | UCUUCUUGUCCAGCUUUAU |
| 373 | UGCUUCUUGUCCAGCUUUA |
| 374 | UGCAGCUUCUUGUCCAGCU |
| 375 | UUAGCAGCUUCUUGUCCAG |
| 376 | UAUAGCAGCUUCUUGUCCA |

TABLE 1b

Nucleobase sequences and sugar-phosphate backbone modifications of the antisense strands of 376 exemplary constructs:

| # | SEQ ID NO: | Oligo Sequence (5' to 3') and backbone modifications |
|---|---|---|
| 1 | 804 | PmU•fU•mC•fU•mA•fG•mG•fG•mA•fU•mG•fA•mA•fC•mU•fG•mA•fG•mC |
| 2 | 805 | PmU•fC•mU•fC•mU•fA•mG•fG•mG•fA•mU•fG•mA•fA•mC•fU•mG•fA•mG |
| 3 | 806 | PmU•fC•mC•fU•mC•fU•mA•fG•mG•fG•mA•fU•mG•fA•mA•fC•mU•fG•mA |
| 4 | 807 | PmU•fG•mC•fC•mU•fC•mU•fA•mG•fG•mG•fA•mU•fG•mA•fA•mC•fU•mG |
| 5 | 808 | PmU•fU•mG•fC•mC•fU•mC•fU•mA•fG•mG•fG•mA•fU•mG•fA•mA•fC•mU |
| 6 | 809 | PmU•fC•mU•fG•mC•fC•mU•fC•mU•fA•mG•fG•mG•fA•mU•fG•mA•fA•mC |
| 7 | 810 | PmU•fG•mC•fU•mG•fC•mC•fU•mC•fU•mA•fG•mG•fG•mA•fU•mG•fA•mA |
| 8 | 811 | PmU•fA•mG•fC•mU•fG•mC•fC•mU•fC•mU•fA•mG•fG•mG•fA•mU•fG•mA |
| 9 | 812 | PmU•fG•mC•fA•mG•fC•mU•fG•mC•fC•mU•fC•mU•fA•mG•fG•mG•fA•mU |
| 10 | 813 | PmU•fA•mG•fC•mA•fG•mC•fU•mG•fC•mC•fU•mC•fU•mA•fG•mG•fG•mA |
| 11 | 814 | PmU•fG•mA•fG•mC•fA•mG•fC•mU•fG•mC•fC•mU•fC•mU•fA•mG•fG•mG |
| 12 | 815 | PmU•fG•mG•fA•mG•fC•mA•fG•mC•fU•mG•fC•mC•fU•mC•fU•mA•fG•mG |
| 13 | 816 | PmU•fU•mG•fU•mU•fC•mC•fU•mG•fG•mA•fG•mC•fA•mG•fC•mU•fG•mC |
| 14 | 817 | PmU•fC•mU•fG•mU•fU•mC•fC•mU•fG•mG•fA•mG•fC•mA•fG•mC•fU•mG |
| 15 | 818 | PmU•fC•mC•fU•mC•fU•mG•fU•mU•fC•mC•fU•mG•fG•mA•fG•mC•fA•mG |
| 16 | 819 | PmU•fA•mC•fC•mU•fC•mU•fG•mU•fU•mC•fC•mU•fG•mG•fA•mG•fC•mA |
| 17 | 820 | PmU•fC•mA•fC•mC•fU•mC•fU•mG•fU•mU•fC•mC•fU•mG•fG•mA•fG•mC |
| 18 | 821 | PmU•fG•mC•fA•mC•fC•mU•fC•mU•fG•mU•fU•mC•fC•mU•fG•mG•fA•mG |
| 19 | 822 | PmU•fG•mG•fC•mA•fC•mC•fU•mC•fU•mG•fU•mU•fC•mC•fU•mG•fG•mA |
| 20 | 823 | PmU•fU•mG•fG•mC•fA•mC•fC•mU•fC•mU•fG•mU•fU•mC•fC•mU•fG•mG |
| 21 | 824 | PmU•fA•mU•fG•mG•fC•mA•fC•mC•fU•mC•fU•mG•fU•mU•fC•mC•fU•mG |
| 22 | 825 | PmU•fC•mA•fU•mG•fG•mC•fA•mC•fC•mU•fC•mU•fG•mU•fU•mC•fC•mU |
| 23 | 826 | PmU•fU•mG•fC•mA•fU•mG•fG•mC•fA•mC•fC•mU•fC•mU•fG•mU•fU•mC |
| 24 | 827 | PmU•fC•mU•fG•mC•fA•mU•fG•mG•fC•mA•fC•mC•fU•mC•fU•mG•fU•mU |
| 25 | 828 | PmU•fG•mC•fU•mG•fC•mA•fU•mG•fG•mC•fA•mC•fC•mU•fC•mU•fG•mU |
| 26 | 829 | PmU•fG•mG•fC•mU•fG•mC•fA•mU•fG•mG•fC•mA•fC•mC•fU•mC•fU•mG |
| 27 | 830 | PmU•fG•mG•fG•mC•fU•mG•fC•mA•fU•mG•fG•mC•fA•mC•fC•mU•fC•mU |
| 28 | 831 | PmU•fC•mA•fA•mC•fA•mA•fG•mG•fA•mG•fU•mA•fC•mC•fC•mG•fG•mG |
| 29 | 832 | PmU•fA•mC•fA•mA•fC•mA•fA•mG•fG•mA•fG•mU•fA•mC•fC•mC•fG•mG |
| 30 | 833 | PmU•fA•mA•fC•mA•fA•mC•fA•mA•fG•mG•fA•mG•fU•mA•fC•mC•fC•mG |
| 31 | 834 | PmU•fC•mA•fA•mC•fA•mA•fC•mA•fA•mG•fG•mA•fG•mU•fA•mC•fC•mC |
| 32 | 835 | PmU•fG•mC•fA•mA•fC•mA•fA•mC•fA•mA•fG•mG•fA•mG•fU•mA•fC•mC |
| 33 | 836 | PmU•fG•mG•fC•mA•fA•mC•fA•mA•fC•mA•fA•mG•fG•mA•fG•mU•fA•mC |
| 34 | 837 | PmU•fG•mG•fG•mC•fA•mA•fC•mA•fA•mC•fA•mA•fG•mG•fA•mG•fU•mA |
| 35 | 838 | PmU•fA•mG•fG•mG•fC•mA•fA•mC•fA•mA•fC•mA•fA•mG•fG•mA•fG•mU |
| 36 | 839 | PmU•fG•mA•fG•mG•fG•mC•fA•mA•fC•mA•fA•mC•fA•mA•fG•mG•fA•mG |
| 37 | 840 | PmU•fG•mG•fA•mG•fG•mG•fC•mA•fA•mC•fA•mA•fC•mA•fA•mG•fG•mA |
| 38 | 841 | PmU•fA•mG•fG•mA•fG•mG•fG•mC•fA•mA•fC•mA•fA•mC•fA•mA•fG•mG |
| 39 | 842 | PmU•fC•mA•fG•mG•fA•mG•fG•mG•fC•mA•fA•mC•fA•mA•fC•mA•fA•mG |
| 40 | 843 | PmU•fC•mC•fA•mG•fG•mA•fG•mG•fG•mC•fA•mA•fC•mA•fA•mC•fA•mA |
| 41 | 844 | PmU•fG•mC•fC•mA•fG•mG•fA•mG•fG•mG•fC•mA•fA•mC•fA•mA•fC•mA |
| 42 | 845 | PmU•fC•mG•fC•mC•fA•mG•fG•mA•fG•mG•fG•mC•fA•mA•fC•mA•fA•mC |
| 43 | 846 | PmU•fG•mC•fG•mC•fC•mA•fG•mG•fA•mG•fG•mG•fC•mA•fA•mC•fA•mA |
| 44 | 847 | PmU•fA•mG•fC•mG•fC•mC•fA•mG•fG•mA•fG•mG•fG•mC•fA•mA•fC•mA |
| 45 | 848 | PmU•fG•mA•fG•mC•fG•mC•fC•mA•fG•mG•fA•mG•fG•mG•fC•mA•fA•mC |
| 46 | 849 | PmU•fG•mG•fA•mG•fC•mG•fC•mC•fA•mG•fG•mA•fG•mG•fG•mC•fA•mA |
| 47 | 850 | PmU•fA•mG•fG•mA•fG•mC•fG•mC•fC•mA•fG•mG•fA•mG•fG•mG•fC•mA |
| 48 | 851 | PmU•fG•mC•fC•mA•fG•mG•fA•mG•fC•mG•fC•mC•fA•mG•fG•mA•fG•mG |
| 49 | 852 | PmU•fA•mG•fA•mG•fG•mC•fC•mA•fG•mG•fA•mG•fC•mG•fC•mC•fA•mG |
| 50 | 853 | PmU•fC•mA•fG•mA•fG•mG•fC•mC•fA•mG•fG•mA•fG•mC•fG•mC•fC•mA |
| 51 | 854 | PmU•fG•mC•fA•mG•fA•mG•fG•mC•fC•mA•fG•mG•fA•mG•fC•mG•fC•mC |
| 52 | 855 | PmU•fG•mG•fC•mA•fG•mA•fG•mG•fC•mC•fA•mG•fG•mA•fG•mC•fG•mC |
| 53 | 856 | PmU•fG•mG•fG•mC•fA•mG•fA•mG•fG•mC•fC•mA•fG•mG•fA•mG•fC•mG |

TABLE 1b-continued

Nucleobase sequences and sugar-phosphate backbone modifications of the antisense strands of 376 exemplary constructs:

| # | SEQ ID NO: | Oligo Sequence (5' to 3') and backbone modifications |
|---|---|---|
| 54 | 857 | PmU•fU•mC•fG•mG•fG•mC•fA•mG•fA•mG•fG•mC•fC•mA•fG•mG•fA•mG |
| 55 | 858 | PmU•fC•mU•fC•mG•fG•mG•fC•mA•fG•mA•fG•mG•fC•mC•fA•mG•fG•mA |
| 56 | 859 | PmU•fG•mC•fU•mC•fG•mG•fG•mC•fA•mG•fA•mG•fG•mC•fC•mA•fG•mG |
| 57 | 860 | PmU•fA•mG•fC•mU•fC•mG•fG•mG•fC•mA•fG•mA•fG•mG•fC•mC•fA•mG |
| 58 | 861 | PmU•fA•mA•fG•mC•fU•mC•fG•mG•fG•mC•fA•mG•fA•mG•fG•mC•fC•mA |
| 59 | 862 | PmU•fG•mA•fA•mG•fC•mU•fC•mG•fG•mG•fC•mA•fG•mA•fG•mG•fC•mC |
| 60 | 863 | PmU•fU•mG•fA•mA•fG•mC•fU•mC•fG•mG•fG•mC•fA•mG•fA•mG•fG•mC |
| 61 | 864 | PmU•fC•mU•fG•mA•fA•mG•fC•mU•fC•mG•fG•mG•fC•mA•fG•mA•fG•mG |
| 62 | 865 | PmU•fU•mC•fU•mG•fA•mA•fG•mC•fU•mC•fG•mG•fG•mC•fA•mG•fA•mG |
| 63 | 866 | PmU•fC•mU•fC•mU•fG•mA•fA•mG•fC•mU•fC•mG•fG•mG•fC•mA•fG•mA |
| 64 | 867 | PmU•fC•mC•fU•mC•fU•mG•fA•mA•fG•mC•fU•mC•fG•mG•fG•mC•fA•mG |
| 65 | 868 | PmU•fG•mC•fC•mU•fC•mU•fG•mA•fA•mG•fC•mU•fC•mG•fG•mG•fC•mA |
| 66 | 869 | PmU•fG•mG•fC•mC•fU•mC•fU•mG•fA•mA•fG•mC•fU•mC•fG•mG•fG•mC |
| 67 | 870 | PmU•fC•mG•fG•mC•fC•mU•fC•mU•fG•mA•fA•mG•fC•mU•fC•mG•fG•mG |
| 68 | 871 | PmU•fU•mC•fG•mG•fC•mC•fU•mC•fU•mG•fA•mA•fG•mC•fU•mC•fG•mG |
| 69 | 872 | PmU•fC•mU•fC•mG•fG•mC•fC•mU•fC•mU•fG•mA•fA•mG•fC•mU•fC•mG |
| 70 | 873 | PmU•fC•mC•fU•mC•fG•mG•fC•mC•fU•mC•fU•mG•fA•mA•fG•mC•fU•mC |
| 71 | 874 | PmU•fU•mC•fC•mU•fC•mG•fG•mC•fC•mU•fC•mU•fG•mA•fA•mG•fC•mU |
| 72 | 875 | PmU•fA•mU•fC•mC•fU•mC•fG•mG•fC•mC•fU•mC•fU•mG•fA•mA•fG•mC |
| 73 | 876 | PmU•fC•mA•fU•mC•fC•mU•fC•mG•fG•mC•fC•mU•fC•mU•fG•mA•fA•mG |
| 74 | 877 | PmU•fG•mC•fA•mU•fC•mC•fU•mC•fG•mG•fC•mC•fU•mC•fU•mG•fA•mA |
| 75 | 878 | PmU•fG•mG•fC•mA•fU•mC•fC•mU•fC•mG•fG•mC•fC•mU•fC•mU•fG•mA |
| 76 | 879 | PmU•fA•mG•fG•mC•fA•mU•fC•mC•fU•mC•fG•mG•fC•mC•fU•mC•fU•mG |
| 77 | 880 | PmU•fG•mA•fG•mG•fC•mA•fU•mC•fC•mU•fC•mG•fG•mC•fC•mU•fC•mU |
| 78 | 881 | PmU•fG•mG•fA•mG•fG•mC•fA•mU•fC•mC•fU•mC•fG•mG•fC•mC•fU•mC |
| 79 | 882 | PmU•fG•mG•fG•mA•fG•mG•fC•mA•fU•mC•fC•mU•fC•mG•fG•mC•fC•mU |
| 80 | 883 | PmU•fA•mG•fG•mG•fA•mG•fG•mC•fA•mU•fC•mC•fU•mC•fG•mG•fC•mC |
| 81 | 884 | PmU•fA•mA•fG•mG•fG•mA•fG•mG•fC•mA•fU•mC•fC•mU•fC•mG•fG•mC |
| 82 | 885 | PmU•fG•mA•fA•mG•fG•mG•fA•mG•fG•mC•fA•mU•fC•mC•fU•mC•fG•mG |
| 83 | 886 | PmU•fA•mG•fA•mA•fG•mG•fG•mA•fG•mG•fC•mA•fU•mC•fC•mU•fC•mG |
| 84 | 887 | PmU•fG•mA•fG•mA•fA•mG•fG•mG•fA•mG•fG•mC•fA•mU•fC•mC•fU•mC |
| 85 | 888 | PmU•fU•mG•fA•mG•fA•mA•fG•mG•fG•mA•fG•mG•fC•mA•fU•mC•fC•mU |
| 86 | 889 | PmU•fC•mU•fG•mA•fG•mA•fA•mG•fG•mG•fA•mG•fG•mC•fA•mU•fC•mC |
| 87 | 890 | PmU•fG•mC•fU•mG•fA•mG•fA•mA•fG•mG•fG•mA•fG•mG•fC•mA•fU•mC |
| 88 | 891 | PmU•fA•mG•fC•mU•fG•mA•fG•mA•fA•mG•fG•mG•fA•mG•fG•mC•fA•mU |
| 89 | 892 | PmU•fU•mG•fA•mA•fG•mC•fU•mG•fA•mG•fA•mA•fG•mG•fG•mA•fG•mG |
| 90 | 893 | PmU•fA•mU•fG•mA•fA•mG•fC•mU•fG•mA•fG•mA•fA•mG•fG•mG•fA•mG |
| 91 | 894 | PmU•fC•mA•fU•mG•fA•mA•fG•mC•fU•mG•fA•mG•fA•mA•fG•mG•fG•mA |
| 92 | 895 | PmU•fG•mC•fA•mU•fG•mA•fA•mG•fC•mU•fG•mA•fG•mA•fA•mG•fG•mG |
| 93 | 896 | PmU•fU•mG•fC•mA•fU•mG•fA•mA•fG•mC•fU•mG•fA•mG•fA•mA•fG•mG |
| 94 | 897 | PmU•fC•mU•fG•mC•fA•mU•fG•mA•fA•mG•fC•mU•fG•mA•fG•mA•fA•mG |
| 95 | 898 | PmU•fC•mC•fU•mG•fC•mA•fU•mG•fA•mA•fG•mC•fU•mG•fA•mG•fA•mA |
| 96 | 899 | PmU•fC•mC•fC•mU•fG•mC•fA•mU•fG•mA•fA•mG•fC•mU•fG•mA•fG•mA |
| 97 | 900 | PmU•fA•mC•fC•mC•fU•mG•fC•mA•fU•mG•fA•mA•fG•mC•fU•mG•fA•mG |
| 98 | 901 | PmU•fA•mA•fC•mC•fC•mU•fG•mC•fA•mU•fG•mA•fA•mG•fC•mU•fG•mA |
| 99 | 902 | PmU•fU•mA•fA•mC•fC•mC•fU•mG•fC•mA•fU•mG•fA•mA•fG•mC•fU•mG |
| 100 | 903 | PmU•fG•mU•fA•mA•fC•mC•fC•mU•fG•mC•fA•mU•fG•mA•fA•mG•fC•mU |
| 101 | 904 | PmU•fU•mG•fU•mA•fA•mC•fC•mC•fU•mG•fC•mA•fU•mG•fA•mA•fG•mC |
| 102 | 905 | PmU•fA•mU•fG•mU•fA•mA•fC•mC•fC•mU•fG•mC•fA•mU•fG•mA•fA•mG |
| 103 | 906 | PmU•fC•mA•fU•mG•fU•mA•fA•mC•fC•mC•fU•mG•fC•mA•fU•mG•fA•mA |
| 104 | 907 | PmU•fU•mC•fA•mU•fG•mU•fA•mA•fC•mC•fC•mU•fG•mC•fA•mU•fG•mA |
| 105 | 908 | PmU•fU•mU•fC•mA•fU•mG•fU•mA•fA•mC•fC•mC•fU•mG•fC•mA•fU•mG |
| 106 | 909 | PmU•fC•mU•fU•mC•fA•mU•fG•mU•fA•mA•fC•mC•fC•mU•G•mC•fA•mU |
| 107 | 910 | PmU•fG•mC•fU•mU•fC•mA•fU•mG•fU•mA•fA•mC•fC•mC•fU•mG•fC•mA |
| 108 | 911 | PmU•fU•mG•fC•mU•fU•mC•fA•mU•fG•mU•fA•mA•fC•mC•fC•mU•fG•mC |
| 109 | 912 | PmU•fG•mU•fG•mC•fU•mU•fC•mA•fU•mG•fU•mA•fA•mC•fC•mC•fU•mG |
| 110 | 913 | PmU•fC•mG•fU•mG•fC•mU•fU•mC•fA•mU•fG•mU•fA•mA•fC•mC•fC•mU |
| 111 | 914 | PmU•fG•mC•fG•mU•fG•mC•fU•mU•fC•mA•fU•mG•fU•mA•fA•mC•fC•mC |
| 112 | 915 | PmU•fG•mG•fC•mG•fU•mG•fC•mU•fU•mC•fA•mU•fG•mU•fA•mA•fC•mC |
| 113 | 916 | PmU•fU•mG•fG•mC•fG•mU•fG•mC•fU•mU•fC•mA•fU•mG•fU•mA•fA•mC |
| 114 | 917 | PmU•fG•mU•fG•mG•fC•mG•fU•mG•fC•mU•fU•mC•fA•mU•fG•mU•fA•mA |
| 115 | 918 | PmU•fG•mG•fU•mG•fG•mC•fG•mU•fG•mC•fU•mU•fC•mA•fU•mG•fU•mA |
| 116 | 919 | PmU•fU•mG•fG•mU•fG•mG•fC•mG•fU•mG•fC•mU•fU•mC•fA•mU•fG•mU |
| 117 | 920 | PmU•fU•mU•fG•mG•fU•mG•fG•mC•fG•mU•fG•mC•fU•mU•fC•mA•fU•mG |
| 118 | 921 | PmU•fC•mU•fU•mG•fG•mU•fG•mG•fC•mG•fU•mG•fC•mU•fU•mC•fA•mU |
| 119 | 922 | PmU•fU•mC•fU•mU•fG•mG•fU•mG•fG•mC•fG•mU•fG•mC•fU•mU•fC•mA |
| 120 | 923 | PmU•fG•mU•fC•mU•fU•mG•fG•mU•fG•mG•fC•mG•fU•mG•fC•mU•fU•mC |
| 121 | 924 | PmU•fG•mG•fU•mC•fU•mU•fG•mG•fU•mG•fG•mC•fG•mU•fG•mC•fU•mU |
| 122 | 925 | PmU•fC•mG•fG•mU•fC•mU•fU•mG•fG•mU•fG•mG•fC•mG•fU•mG•fC•mU |
| 123 | 926 | PmU•fG•mC•fG•mG•fU•mC•fU•mU•fG•mG•fU•mG•fG•mC•fG•mU•fG•mC |
| 124 | 927 | PmU•fG•mG•fC•mG•fG•mU•fC•mU•fU•mG•fG•mU•fG•mG•fC•mG•fU•mG |
| 125 | 928 | PmU•fU•mG•fG•mC•fG•mG•fU•mC•fU•mU•fG•mG•fU•mG•fG•mC•fG•mU |
| 126 | 929 | PmU•fU•mU•fG•mG•fC•mG•fG•mU•fC•mU•fU•mG•fG•mU•fG•mG•fC•mG |

TABLE 1b-continued

Nucleobase sequences and sugar-phosphate backbone modifications of the antisense strands of 376 exemplary constructs:

| # | SEQ ID NO: | Oligo Sequence (5' to 3') and backbone modifications |
|---|---|---|
| 127 | 930 | PmU•fC•mU•fU•mG•fG•mC•fG•mG•fU•mC•fU•mU•fG•mG•fU•mG•fG•mC |
| 128 | 931 | PmU•fC•mC•fU•mU•fG•mG•fC•mG•fG•mU•fC•mU•fU•mG•fG•mU•fG•mG |
| 129 | 932 | PmU•fU•mC•fC•mU•fU•mG•fG•mC•fG•mG•fU•mC•fU•mU•fG•mG•fU•mG |
| 130 | 933 | PmU•fA•mU•fC•mC•fU•mU•fG•mG•fC•mG•fG•mU•fC•mU•fU•mG•fG•mU |
| 131 | 934 | PmU•fC•mA•fU•mC•fC•mU•fU•mG•fG•mC•fG•mG•fU•mC•fU•mU•fG•mG |
| 132 | 935 | PmU•fG•mC•fA•mU•fC•mC•fU•mU•fG•mG•fC•mG•fG•mU•fC•mU•fU•mG |
| 133 | 936 | PmU•fU•mG•fC•mA•fU•mC•fC•mU•fU•mG•fG•mC•fG•mG•fU•mC•fU•mU |
| 134 | 937 | PmU•fG•mU•fG•mC•fA•mU•fC•mC•fU•mU•fG•mG•fC•mG•fG•mU•fC•mU |
| 135 | 938 | PmU•fA•mG•fU•mG•fC•mA•fU•mC•fC•mU•fU•mG•fG•mC•fG•mG•fU•mC |
| 136 | 939 | PmU•fC•mA•fG•mU•fG•mC•fA•mU•fC•mC•fU•mU•fG•mG•fC•mG•fG•mU |
| 137 | 940 | PmU•fU•mC•fA•mG•fU•mG•fC•mA•fU•mC•fC•mU•fU•mG•fG•mC•fG•mG |
| 138 | 941 | PmU•fC•mU•fC•mA•fG•mU•fG•mC•fA•mU•fC•mC•fU•mU•fG•mG•fC•mG |
| 139 | 942 | PmU•fG•mC•fU•mC•fA•mG•fU•mG•fC•mA•fU•mC•fC•mU•fU•mG•fG•mC |
| 140 | 943 | PmU•fU•mG•fC•mU•fC•mA•fG•mU•fG•mC•fA•mU•fC•mC•fU•mU•fG•mG |
| 141 | 944 | PmU•fC•mU•fG•mC•fU•mC•fA•mG•fU•mG•fC•mA•fU•mC•fC•mU•fU•mG |
| 142 | 945 | PmU•fG•mC•fU•mG•fC•mU•fC•mA•fG•mU•fG•mC•fA•mU•fC•mC•fU•mU |
| 143 | 946 | PmU•fC•mG•fC•mU•fG•mC•fU•mC•fA•mG•fU•mG•fC•mA•fU•mC•fC•mU |
| 144 | 947 | PmU•fA•mC•fG•mC•fU•mG•fC•mU•fC•mA•fG•mU•fG•mC•fA•mU•fC•mC |
| 145 | 948 | PmU•fC•mA•fC•mG•fC•mU•fG•mC•fU•mC•fA•mG•fU•mG•fC•mA•fU•mC |
| 146 | 949 | PmU•fG•mC•fA•mC•fG•mC•fU•mG•fC•mU•fC•mA•fG•mU•fG•mC•fA•mU |
| 147 | 950 | PmU•fU•mG•fC•mA•fC•mG•fC•mU•fG•mC•fU•mC•fA•mG•fU•mG•fC•mA |
| 148 | 951 | PmU•fC•mU•fG•mC•fA•mC•fG•mC•fU•mG•fC•mU•fC•mA•fG•mU•fG•mC |
| 149 | 952 | PmU•fC•mC•fU•mG•fC•mA•fC•mG•fC•mU•fG•mC•fU•mC•fA•mG•fU•mG |
| 150 | 953 | PmU•fU•mC•fC•mU•fG•mC•fA•mC•fG•mC•fU•mG•fC•mU•fC•mA•fG•mU |
| 151 | 954 | PmU•fA•mC•fU•mC•fC•mU•fG•mC•fA•mC•fG•mC•fU•mG•fC•mU•fC•mA |
| 152 | 955 | PmU•fG•mG•fG•mA•fC•mU•fC•mC•fU•mG•fC•mA•fC•mG•fC•mU•fG•mC |
| 153 | 956 | PmU•fU•mG•fG•mG•fA•mC•fU•mC•fC•mU•fG•mC•fA•mC•fG•mC•fU•mG |
| 154 | 957 | PmU•fC•mU•fG•mG•fG•mA•fC•mU•fC•mC•fU•mG•fC•mA•fC•mG•fC•mU |
| 155 | 958 | PmU•fC•mC•fU•mG•fG•mG•fA•mC•fU•mC•fC•mU•fG•mC•fA•mC•fG•mC |
| 156 | 959 | PmU•fA•mC•fC•mU•fG•mG•fG•mA•fC•mU•fC•mC•fU•mG•fC•mA•fC•mG |
| 157 | 960 | PmU•fC•mA•fC•mC•fU•mG•fG•mG•fA•mC•fU•mC•fC•mU•fG•mC•fA•mC |
| 158 | 961 | PmU•fC•mC•fA•mC•fC•mU•fG•mG•fG•mA•fC•mU•fC•mC•fU•mG•fC•mA |
| 159 | 962 | PmU•fG•mG•fG•mC•fC•mA•fC•mC•fU•mG•fG•mG•fA•mC•fU•mC•fC•mU |
| 160 | 963 | PmU•fU•mG•fG•mG•fC•mC•fA•mC•fC•mU•fG•mG•fG•mA•fC•mU•fC•mC |
| 161 | 964 | PmU•fU•mG•fC•mU•fG•mG•fG•mC•fC•mA•fC•mC•fU•mG•fG•mG•fA•mC |
| 162 | 965 | PmU•fC•mU•fG•mC•fU•mG•fG•mG•fC•mC•fA•mC•fC•mU•fG•mG•fG•mA |
| 163 | 966 | PmU•fG•mG•fC•mC•fU•mG•fC•mU•fG•mG•fG•mC•fC•mA•fC•mC•fU•mG |
| 164 | 967 | PmU•fC•mC•fU•mG•fG•mC•fC•mU•fG•mC•fU•mG•fG•mG•fC•mC•fA•mC |
| 165 | 968 | PmU•fC•mC•fA•mU•fC•mG•fG•mU•fC•mA•fC•mC•fC•mA•fG•mC•fC•mC |
| 166 | 969 | PmU•fG•mC•fC•mA•fU•mC•fG•mG•fU•mC•fA•mC•fC•mC•fA•mG•fC•mC |
| 167 | 970 | PmU•fA•mG•fC•mC•fA•mU•fC•mG•fG•mU•fC•mA•fC•mC•fC•mA•fG•mC |
| 168 | 971 | PmU•fA•mA•fG•mC•fC•mA•fU•mC•fG•mG•fU•mC•fA•mC•fC•mC•fA•mG |
| 169 | 972 | PmU•fG•mA•fA•mG•fC•mC•fA•mU•fC•mG•fG•mU•fC•mA•fC•mC•fC•mA |
| 170 | 973 | PmU•fU•mG•fA•mA•fG•mC•fC•mA•fU•mC•fG•mG•fU•mC•fA•mC•fC•mC |
| 171 | 974 | PmU•fC•mU•fG•mA•fA•mG•fC•mC•fA•mU•fC•mG•fG•mU•fC•mA•fC•mC |
| 172 | 975 | PmU•fA•mC•fU•mG•fA•mA•fG•mC•fC•mA•fU•mC•fG•mG•fU•mC•fA•mC |
| 173 | 976 | PmU•fA•mA•fC•mU•fG•mA•fA•mG•fC•mC•fA•mU•fC•mG•fG•mU•fC•mA |
| 174 | 977 | PmU•fG•mA•fA•mC•fU•mG•fA•mA•fG•mC•fC•mA•fU•mC•fG•mG•fU•mC |
| 175 | 978 | PmU•fG•mG•fA•mA•fC•mU•fG•mA•fA•mG•fC•mC•fA•mU•fC•mG•fG•mU |
| 176 | 979 | PmU•fG•mG•fG•mA•fA•mC•fU•mG•fA•mA•fG•mC•fC•mA•fU•mC•fG•mG |
| 177 | 980 | PmU•fA•mG•fG•mG•fA•mA•fC•mU•fG•mA•fA•mG•fC•mC•fA•mU•fC•mG |
| 178 | 981 | PmU•fC•mA•fG•mG•fG•mA•fA•mC•fU•mG•fA•mA•fG•mC•fC•mA•fU•mC |
| 179 | 982 | PmU•fU•mC•fA•mG•fG•mG•fA•mA•fC•mU•fG•mA•fA•mG•fC•mC•fA•mU |
| 180 | 983 | PmU•fU•mU•fC•mA•fG•mG•fG•mA•fA•mC•fU•mG•fA•mA•fG•mC•fC•mA |
| 181 | 984 | PmU•fU•mU•fU•mC•fA•mG•fG•mG•fA•mA•fC•mU•fG•mA•fA•mG•fC•mC |
| 182 | 985 | PmU•fC•mU•fU•mU•fC•mA•fG•mG•fG•mA•fA•mC•fU•mG•fA•mA•fG•mC |
| 183 | 986 | PmU•fU•mC•fU•mU•fU•mC•fA•mG•fG•mG•fA•mA•fC•mU•fG•mA•fA•mG |
| 184 | 987 | PmU•fG•mU•fC•mU•fU•mU•fC•mA•fG•mG•fG•mA•fA•mC•fU•mG•fA•mA |
| 185 | 988 | PmU•fA•mG•fU•mC•fU•mU•fU•mC•fA•mG•fG•mG•fA•mA•fC•mU•fG•mA |
| 186 | 989 | PmU•fU•mA•fG•mU•fC•mU•fU•mU•fC•mA•fG•mG•fG•mA•fA•mC•fU•mG |
| 187 | 990 | PmU•fG•mU•fA•mG•fU•mC•fU•mU•fU•mC•fA•mG•fG•mG•fA•mA•fC•mU |
| 188 | 991 | PmU•fA•mG•fU•mA•fG•mU•fC•mU•fU•mU•fC•mA•fG•mG•fG•mA•fA•mC |
| 189 | 992 | PmU•fC•mA•fG•mU•fA•mG•fU•mC•fU•mU•fU•mC•fA•mG•fG•mG•fA•mA |
| 190 | 993 | PmU•fC•mC•fA•mG•fU•mA•fG•mU•fC•mU•fU•mU•fC•mA•fG•mG•fG•mA |
| 191 | 994 | PmU•fU•mC•fC•mA•fG•mU•fA•mG•fU•mC•fU•mU•fU•mC•fA•mG•fG•mG |
| 192 | 995 | PmU•fC•mU•fC•mC•fA•mG•fU•mA•fG•mU•fC•mU•fU•mU•fC•mA•fG•mG |
| 193 | 996 | PmU•fG•mC•fU•mC•fC•mA•fG•mU•fA•mG•fU•mC•fU•mU•fU•mC•fA•mG |
| 194 | 997 | PmU•fU•mG•fC•mU•fC•mC•fA•mG•fU•mA•fG•mU•fC•mU•fU•mU•fC•mA |
| 195 | 998 | PmU•fG•mU•fG•mC•fU•mC•fC•mA•fG•mU•fA•mG•fU•mC•fU•mU•fU•mC |
| 196 | 999 | PmU•fG•mG•fU•mG•fC•mU•fC•mC•fA•mG•fU•mA•fG•mU•fC•mU•fU•mU |
| 197 | 1000 | PmU•fC•mG•fG•mU•fG•mC•fU•mC•fC•mA•fG•mU•fA•mG•fU•mC•fU•mU |
| 198 | 1001 | PmU•fA•mC•fG•mG•fU•mG•fC•mU•fC•mC•fA•mG•fU•mA•fG•mU•fC•mU |
| 199 | 1002 | PmU•fA•mA•fC•mG•fG•mU•fG•mC•fU•mC•fC•mA•fG•mU•fA•mG•fU•mC |

TABLE 1b-continued

Nucleobase sequences and sugar-phosphate backbone modifications of the antisense strands of 376 exemplary constructs:

| # | SEQ ID NO: | Oligo Sequence (5' to 3') and backbone modifications |
|---|---|---|
| 200 | 1003 | PmU•fU•mA•fA•mC•fG•mG•fU•mG•fC•mU•fC•mC•fA•mG•fU•mA•fG•mU |
| 201 | 1004 | PmU•fU•mU•fA•mA•fC•mG•fG•mU•fG•mC•fU•mC•fC•mA•fG•mU•fA•mG |
| 202 | 1005 | PmU•fC•mU•fU•mA•fA•mC•fG•mG•fU•mG•fC•mU•fC•mC•fA•mG•fU•mA |
| 203 | 1006 | PmU•fC•mC•fU•mU•fA•mA•fC•mG•fG•mU•fG•mC•fU•mC•fC•mA•fG•mU |
| 204 | 1007 | PmU•fU•mC•fC•mU•fU•mA•fA•mC•fG•mG•fU•mG•fC•mU•fC•mC•fA•mG |
| 205 | 1008 | PmU•fG•mU•fC•mC•fU•mU•fA•mA•fC•mG•fG•mU•fG•mC•fU•mC•fC•mA |
| 206 | 1009 | PmU•fU•mG•fU•mC•fC•mU•fU•mA•fA•mC•fG•mG•fU•mG•fC•mU•fC•mC |
| 207 | 1010 | PmU•fU•mU•fG•mU•fC•mC•fU•mU•fA•mA•fC•mG•fG•mU•fG•mC•fU•mC |
| 208 | 1011 | PmU•fC•mU•fU•mG•fU•mC•fC•mU•fU•mA•fA•mC•fG•mG•fU•mG•fC•mU |
| 209 | 1012 | PmU•fA•mC•fU•mU•fG•mU•fC•mC•fU•mU•fA•mA•fC•mG•fG•mU•fG•mC |
| 210 | 1013 | PmU•fA•mA•fC•mU•fU•mG•fU•mC•fC•mU•fU•mA•fA•mC•fG•mG•fU•mG |
| 211 | 1014 | PmU•fG•mA•fA•mC•fU•mU•fG•mU•fC•mC•fU•mU•fA•mA•fC•mG•fG•mU |
| 212 | 1015 | PmU•fA•mG•fA•mA•fC•mU•fU•mG•fU•mC•fC•mU•fU•mA•fA•mC•fG•mG |
| 213 | 1016 | PmU•fG•mA•fG•mA•fA•mC•fU•mU•fG•mU•fC•mC•fU•mU•fA•mA•fC•mG |
| 214 | 1017 | PmU•fA•mG•fA•mG•fA•mA•fC•mU•fU•mG•fU•mC•fC•mU•fU•mA•fA•mC |
| 215 | 1018 | PmU•fC•mA•fG•mA•fG•mA•fA•mC•fU•mU•fG•mU•fC•mC•fU•mU•fA•mA |
| 216 | 1019 | PmU•fU•mC•fA•mG•fA•mG•fA•mA•fC•mU•fU•mG•fU•mC•fC•mU•fU•mA |
| 217 | 1020 | PmU•fC•mU•fC•mA•fG•mA•fG•mA•fA•mC•fU•mU•fG•mU•fC•mC•fU•mU |
| 218 | 1021 | PmU•fA•mC•fU•mC•fA•mG•fA•mG•fA•mA•fC•mU•fU•mG•fU•mC•fC•mU |
| 219 | 1022 | PmU•fA•mA•fC•mU•fC•mA•fG•mA•fG•mA•fA•mC•fU•mU•fG•mU•fC•mC |
| 220 | 1023 | PmU•fG•mA•fA•mC•fU•mC•fA•mG•fA•mG•fA•mA•fC•mU•fU•mG•fU•mC |
| 221 | 1024 | PmU•fC•mA•fG•mA•fA•mC•fU•mC•fA•mG•fA•mG•fA•mA•fC•mU•fU•mG |
| 222 | 1025 | PmU•fC•mC•fA•mG•fA•mA•fC•mU•fC•mA•fG•mA•fG•mA•fA•mC•fU•mU |
| 223 | 1026 | PmU•fC•mC•fC•mA•fG•mA•fA•mC•fU•mC•fA•mG•fA•mG•fA•mA•fC•mU |
| 224 | 1027 | PmU•fU•mC•fC•mC•fA•mG•fA•mA•fC•mU•fC•mA•fG•mA•fG•mA•fA•mC |
| 225 | 1028 | PmU•fA•mU•fC•mC•fC•mA•fG•mA•fA•mC•fU•mC•fA•mG•fA•mG•fA•mA |
| 226 | 1029 | PmU•fA•mA•fU•mC•fC•mC•fA•mG•fA•mA•fC•mU•fC•mA•fG•mA•fG•mA |
| 227 | 1030 | PmU•fA•mA•fA•mU•fC•mC•fC•mA•fG•mA•fA•mC•fU•mC•fA•mG•fA•mG |
| 228 | 1031 | PmU•fC•mA•fA•mA•fU•mC•fC•mC•fA•mG•fA•mA•fC•mU•fC•mA•fG•mA |
| 229 | 1032 | PmU•fC•mC•fA•mA•fA•mU•fC•mC•fC•mA•fG•mA•fA•mC•fU•mC•fA•mG |
| 230 | 1033 | PmU•fU•mC•fC•mA•fA•mA•fU•mC•fC•mC•fA•mG•fA•mA•fC•mU•fC•mA |
| 231 | 1034 | PmU•fG•mU•fC•mC•fA•mA•fA•mU•fC•mC•fC•mA•fG•mA•fA•mC•fU•mC |
| 232 | 1035 | PmU•fG•mG•fU•mC•fC•mA•fA•mA•fU•mC•fC•mC•fA•mG•fA•mA•fC•mU |
| 233 | 1036 | PmU•fG•mG•fG•mU•fC•mC•fA•mA•fA•mU•fC•mC•fC•mA•fG•mA•fA•mC |
| 234 | 1037 | PmU•fA•mG•fG•mG•fU•mC•fC•mA•fA•mA•fU•mC•fC•mC•fA•mG•fA•mA |
| 235 | 1038 | PmU•fC•mA•fG•mG•fG•mU•fC•mC•fA•mA•fA•mU•fC•mC•fC•mA•fG•mA |
| 236 | 1039 | PmU•fU•mC•fA•mG•fG•mG•fU•mC•fC•mA•fA•mA•fU•mC•fC•mC•fA•mG |
| 237 | 1040 | PmU•fG•mA•fC•mC•fU•mC•fA•mG•fG•mG•fU•mC•fC•mA•fA•mA•fU•mC |
| 238 | 1041 | PmU•fU•mG•fA•mC•fC•mU•fC•mA•fG•mG•fG•mU•fC•mC•fA•mA•fA•mU |
| 239 | 1042 | PmU•fC•mU•fG•mA•fC•mC•fU•mC•fA•mG•fG•mG•fU•mC•fC•mA•fA•mA |
| 240 | 1043 | PmU•fU•mC•fU•mG•fA•mC•fC•mU•fC•mA•fG•mG•fG•mU•fC•mC•fA•mA |
| 241 | 1044 | PmU•fG•mU•fC•mU•fG•mA•fC•mC•fU•mC•fA•mG•fG•mG•fU•mC•fC•mA |
| 242 | 1045 | PmU•fG•mG•fU•mC•fU•mG•fA•mC•fC•mU•fC•mA•fG•mG•fG•mU•fC•mC |
| 243 | 1046 | PmU•fU•mG•fG•mU•fC•mU•fG•mA•fC•mC•fU•mC•fA•mG•fG•mG•fU•mC |
| 244 | 1047 | PmU•fU•mU•fG•mG•fU•mC•fU•mG•fA•mC•fC•mU•fC•mA•fG•mG•fG•mU |
| 245 | 1048 | PmU•fG•mU•fU•mG•fG•mU•fC•mU•fG•mA•fC•mC•fU•mC•fA•mG•fG•mG |
| 246 | 1049 | PmU•fA•mG•fU•mU•fG•mG•fU•mC•fU•mG•fA•mC•fC•mU•fC•mA•fG•mG |
| 247 | 1050 | PmU•fA•mA•fG•mU•fU•mG•fG•mU•fC•mU•fG•mA•fC•mC•fU•mC•fA•mG |
| 248 | 1051 | PmU•fG•mA•fA•mG•fU•mU•fG•mG•fU•mC•fU•mG•fA•mC•fC•mU•fC•mA |
| 249 | 1052 | PmU•fU•mG•fA•mA•fG•mU•fU•mG•fG•mU•fC•mU•fG•mA•fC•mC•fU•mC |
| 250 | 1053 | PmU•fC•mU•fG•mA•fA•mG•fU•mU•fG•mG•fU•mC•fU•mG•fA•mC•fC•mU |
| 251 | 1054 | PmU•fG•mG•fC•mU•fG•mA•fA•mG•fU•mU•fG•mG•fU•mC•fU•mG•fA•mC |
| 252 | 1055 | PmU•fC•mG•fG•mC•fU•mG•fA•mA•fG•mU•fU•mG•fG•mU•fC•mU•fG•mA |
| 253 | 1056 | PmU•fA•mC•fG•mG•fC•mU•fG•mA•fA•mG•fU•mU•fG•mG•fU•mC•fU•mG |
| 254 | 1057 | PmU•fC•mA•fC•mG•fG•mC•fU•mG•fA•mA•fG•mU•fU•mG•fG•mU•fC•mU |
| 255 | 1058 | PmU•fC•mC•fA•mC•fG•mG•fC•mU•fG•mA•fA•mG•fU•mU•fG•mG•fU•mC |
| 256 | 1059 | PmU•fG•mC•fC•mA•fC•mG•fG•mC•fU•mG•fA•mA•fG•mU•fU•mG•fG•mU |
| 257 | 1060 | PmU•fC•mA•fG•mC•fC•mA•fC•mG•fG•mC•fU•mG•fA•mA•fG•mU•fU•mG |
| 258 | 1061 | PmU•fG•mC•fA•mG•fC•mC•fA•mC•fG•mG•fC•mU•fG•mA•fA•mG•fU•mU |
| 259 | 1062 | PmU•fG•mG•fC•mA•fG•mC•fC•mA•fC•mG•fG•mC•fU•mG•fA•mA•fG•mU |
| 260 | 1063 | PmU•fA•mG•fG•mC•fA•mG•fC•mC•fA•mC•fG•mG•fC•mU•fG•mA•fA•mG |
| 261 | 1064 | PmU•fC•mA•fG•mG•fC•mA•fG•mC•fC•mA•fC•mG•fG•mC•fU•mG•fA•mA |
| 262 | 1065 | PmU•fU•mC•fU•mC•fA•mG•fG•mC•fA•mG•fC•mC•fA•mC•fG•mG•fC•mU |
| 263 | 1066 | PmU•fG•mU•fC•mU•fC•mA•fG•mG•fC•mA•fG•mC•fC•mA•fC•mG•fG•mC |
| 264 | 1067 | PmU•fG•mG•fU•mC•fU•mC•fA•mG•fG•mC•fA•mG•fC•mC•fA•mC•fG•mG |
| 265 | 1068 | PmU•fA•mG•fG•mU•fC•mU•fC•mA•fG•mG•fC•mA•fG•mC•fC•mA•fC•mG |
| 266 | 1069 | PmU•fU•mG•fA•mG•fG•mU•fC•mU•fC•mA•fG•mG•fC•mA•fG•mC•fC•mA |
| 267 | 1070 | PmU•fU•mU•fG•mA•fG•mG•fU•mC•fU•mC•fA•mG•fG•mC•fA•mG•fC•mC |
| 268 | 1071 | PmU•fA•mU•fU•mG•fA•mG•fG•mU•fC•mU•fC•mA•fG•mG•fC•mA•fG•mC |
| 269 | 1072 | PmU•fU•mA•fU•mU•fG•mA•fG•mG•fU•mC•fU•mC•fA•mG•fG•mC•fA•mG |
| 270 | 1073 | PmU•fG•mU•fA•mU•fU•mG•fA•mG•fG•mU•fC•mU•fC•mA•fG•mG•fC•mA |
| 271 | 1074 | PmU•fG•mG•fU•mA•fU•mU•fG•mA•fG•mG•fU•mC•fU•mC•fA•mG•fG•mC |
| 272 | 1075 | PmU•fG•mG•fG•mU•fA•mU•fU•mG•fA•mG•fG•mU•fC•mU•fC•mA•fG•mG |

TABLE 1b-continued

Nucleobase sequences and sugar-phosphate backbone modifications of the antisense strands of 376 exemplary constructs:

| # | SEQ ID NO: | Oligo Sequence (5' to 3') and backbone modifications |
|---|---|---|
| 273 | 1076 | PmU•fU•mA•fG•mG•fC•mA•fG•mG•fU•mG•fG•mA•fC•mU•fU•mG•fG•mG |
| 274 | 1077 | PmU•fA•mU•fA•mG•fG•mC•fA•mG•fG•mU•fG•mG•fA•mC•fU•mU•fG•mG |
| 275 | 1078 | PmU•fG•mA•fU•mA•fG•mG•fC•mA•fG•mG•fU•mG•fG•mA•fC•mU•fU•mG |
| 276 | 1079 | PmU•fG•mG•fA•mU•fA•mG•fG•mC•fA•mG•fG•mU•fG•mG•fA•mC•fU•mU |
| 277 | 1080 | PmU•fU•mG•fG•mA•fU•mA•fG•mG•fC•mA•fG•mG•fU•mG•fG•mA•fC•mU |
| 278 | 1081 | PmU•fA•mU•fG•mG•fA•mU•fA•mG•fG•mC•fA•mG•fG•mU•fG•mG•fA•mC |
| 279 | 1082 | PmU•fG•mA•fU•mG•fG•mA•fU•mA•fG•mG•fC•mA•fG•mG•fU•mG•fG•mA |
| 280 | 1083 | PmU•fG•mG•fA•mU•fG•mG•fA•mU•fA•mG•fG•mC•fA•mG•fG•mU•fG•mG |
| 281 | 1084 | PmU•fA•mG•fG•mA•fU•mG•fG•mA•fU•mA•fG•mG•fC•mA•fG•mG•fU•mG |
| 282 | 1085 | PmU•fC•mA•fG•mG•fA•mU•fG•mG•fA•mU•fA•mG•fG•mC•fA•mG•fG•mU |
| 283 | 1086 | PmU•fG•mC•fA•mG•fG•mA•fU•mG•fG•mA•fU•mA•fG•mG•fC•mA•fG•mG |
| 284 | 1087 | PmU•fC•mG•fC•mA•fG•mG•fA•mU•fG•mG•fA•mU•fA•mG•fG•mC•fA•mG |
| 285 | 1088 | PmU•fU•mC•fG•mC•fA•mG•fG•mA•fU•mG•fG•mA•fU•mA•fG•mG•fC•mA |
| 286 | 1089 | PmU•fC•mU•fC•mG•fC•mA•fG•mG•fA•mU•fG•mG•fA•mU•fA•mG•fG•mC |
| 287 | 1090 | PmU•fG•mC•fU•mC•fG•mC•fA•mG•fG•mA•fU•mG•fG•mA•fU•mA•fG•mG |
| 288 | 1091 | PmU•fA•mG•fC•mU•fC•mG•fC•mA•fG•mG•fA•mU•fG•mG•fA•mU•fA•mG |
| 289 | 1092 | PmU•fG•mA•fG•mC•fU•mC•fG•mC•fA•mG•fG•mA•fU•mG•fG•mA•fU•mA |
| 290 | 1093 | PmU•fG•mG•fA•mG•fC•mU•fC•mG•fC•mA•fG•mG•fA•mU•fG•mG•fA•mU |
| 291 | 1094 | PmU•fA•mG•fG•mA•fG•mC•fU•mC•fG•mC•fA•mG•fG•mA•fU•mG•fG•mA |
| 292 | 1095 | PmU•fA•mA•fG•mG•fA•mG•fC•mU•fC•mG•fC•mA•fG•mG•fA•mU•fG•mG |
| 293 | 1096 | PmU•fC•mA•fA•mG•fG•mA•fG•mC•fU•mC•fG•mC•fA•mG•fG•mA•fU•mG |
| 294 | 1097 | PmU•fC•mC•fA•mA•fG•mG•fA•mG•fC•mU•fC•mG•fC•mA•fG•mG•fA•mU |
| 295 | 1098 | PmU•fC•mC•fC•mA•fA•mG•fG•mA•fG•mC•fU•mC•fG•mC•fA•mG•fG•mA |
| 296 | 1099 | PmU•fA•mC•fC•mC•fA•mA•fG•mG•fA•mG•fC•mU•fC•mG•fC•mA•fG•mG |
| 297 | 1100 | PmU•fG•mA•fC•mC•fC•mA•fA•mG•fG•mA•fG•mC•fU•mC•fG•mC•fA•mG |
| 298 | 1101 | PmU•fG•mG•fA•mC•fC•mC•fA•mA•fG•mG•fA•mG•fC•mU•fC•mG•fC•mA |
| 299 | 1102 | PmU•fA•mG•fG•mA•fC•mC•fC•mA•fA•mG•fG•mA•fG•mC•fU•mC•fG•mC |
| 300 | 1103 | PmU•fC•mA•fG•mG•fA•mC•fC•mC•fA•mA•fG•mG•fA•mG•fC•mU•fC•mG |
| 301 | 1104 | PmU•fG•mC•fA•mG•fG•mA•fC•mC•fC•mA•fA•mG•fG•mA•fG•mC•fU•mC |
| 302 | 1105 | PmU•fU•mG•fC•mA•fG•mG•fA•mC•fC•mC•fA•mA•fG•mG•fA•mG•fC•mU |
| 303 | 1106 | PmU•fU•mU•fG•mC•fA•mG•fG•mA•fC•mC•fC•mA•fA•mG•fG•mA•fG•mC |
| 304 | 1107 | PmU•fA•mU•fU•mG•fC•mA•fG•mG•fA•mC•fC•mC•fA•mA•fG•mG•fA•mG |
| 305 | 1108 | PmU•fG•mA•fU•mU•fG•mC•fA•mG•fG•mA•fC•mC•fC•mA•fA•mG•fG•mA |
| 306 | 1109 | PmU•fA•mG•fA•mU•fU•mG•fC•mA•fG•mG•fA•mC•fC•mC•fA•mA•fG•mG |
| 307 | 1110 | PmU•fG•mA•fG•mA•fU•mU•fG•mC•fA•mG•fG•mA•fC•mC•fC•mA•fA•mG |
| 308 | 1111 | PmU•fG•mG•fA•mG•fA•mU•fU•mG•fC•mA•fG•mG•fA•mC•fC•mC•fA•mA |
| 309 | 1112 | PmU•fU•mG•fG•mA•fG•mA•fU•mU•fG•mC•fA•mG•fG•mA•fC•mC•fC•mA |
| 310 | 1113 | PmU•fC•mU•fG•mG•fA•mG•fA•mU•fU•mG•fC•mA•fG•mG•fA•mC•fC•mC |
| 311 | 1114 | PmU•fC•mC•fU•mG•fG•mA•fG•mA•fU•mU•fG•mC•fA•mG•fG•mA•fC•mC |
| 312 | 1115 | PmU•fC•mC•fC•mU•fG•mG•fA•mG•fA•mU•fU•mG•fC•mA•fG•mG•fA•mC |
| 313 | 1116 | PmU•fG•mC•fC•mC•fU•mG•fG•mA•fG•mA•fU•mU•fG•mC•fA•mG•fG•mA |
| 314 | 1117 | PmU•fA•mG•fC•mC•fC•mU•fG•mG•fA•mG•fA•mU•fU•mG•fC•mA•fG•mG |
| 315 | 1118 | PmU•fC•mA•fG•mC•fC•mC•fU•mG•fG•mA•fG•mA•fU•mU•fG•mC•fA•mG |
| 316 | 1119 | PmU•fG•mC•fA•mG•fC•mC•fC•mU•fG•mG•fA•mG•fA•mU•fU•mG•fC•mA |
| 317 | 1120 | PmU•fG•mG•fC•mA•fG•mC•fC•mC•fU•mG•fG•mA•fG•mA•fU•mU•fG•mC |
| 318 | 1121 | PmU•fG•mG•fG•mC•fA•mG•fC•mC•fC•mU•fG•mG•fA•mG•fA•mU•fU•mG |
| 319 | 1122 | PmU•fU•mU•fU•mA•fA•mG•fC•mA•fA•mC•fC•mU•fA•mC•fA•mG•fG•mG |
| 320 | 1123 | PmU•fU•mU•fU•mU•fA•mA•fG•mC•fA•mA•fC•mC•fU•mA•fC•mA•fG•mG |
| 321 | 1124 | PmU•fC•mU•fU•mU•fU•mA•fA•mG•fC•mA•fA•mC•fC•mU•fA•mC•fA•mG |
| 322 | 1125 | PmU•fC•mC•fU•mU•fU•mU•fA•mA•fG•mC•fA•mA•fC•mC•fU•mA•fC•mA |
| 323 | 1126 | PmU•fC•mC•fC•mU•fU•mU•fU•mA•fA•mG•fC•mA•fA•mC•fC•mU•fA•mC |
| 324 | 1127 | PmU•fU•mC•fC•mC•fU•mU•fU•mU•fA•mA•fG•mC•fA•mA•fC•mC•fU•mA |
| 325 | 1128 | PmU•fG•mU•fC•mC•fC•mU•fU•mU•fU•mA•fA•mG•fC•mA•fA•mC•fC•mU |
| 326 | 1129 | PmU•fA•mC•fU•mG•fU•mC•fC•mC•fU•mU•fU•mU•fA•mA•fG•mC•fA•mA |
| 327 | 1130 | PmU•fU•mA•fC•mU•fG•mU•fC•mC•fC•mU•fU•mU•fU•mA•fA•mG•fC•mA |
| 328 | 1131 | PmU•fA•mU•fA•mC•fU•mG•fU•mC•fC•mC•fU•mU•fU•mU•fA•mA•fG•mC |
| 329 | 1132 | PmU•fA•mA•fU•mA•fC•mU•fG•mU•fC•mC•fC•mU•fU•mU•fU•mA•fA•mG |
| 330 | 1133 | PmU•fG•mA•fA•mU•fA•mC•fU•mG•fU•mC•fC•mC•fU•mU•fU•mU•fA•mA |
| 331 | 1134 | PmU•fA•mG•fA•mA•fU•mA•fC•mU•fG•mU•fC•mC•fC•mU•fU•mU•fU•mA |
| 332 | 1135 | PmU•fG•mA•fG•mA•fA•mU•fA•mC•fU•mG•fU•mC•fC•mC•fU•mU•fU•mU |
| 333 | 1136 | PmU•fU•mG•fA•mG•fA•mA•fU•mA•fC•mU•fG•mU•fC•mC•fC•mU•fU•mU |
| 334 | 1137 | PmU•fC•mU•fG•mA•fG•mA•fA•mU•fA•mC•fU•mG•fU•mC•fC•mC•fU•mU |
| 335 | 1138 | PmU•fA•mC•fU•mG•fA•mG•fA•mA•fU•mA•fC•mU•fG•mU•fC•mC•fC•mU |
| 336 | 1139 | PmU•fC•mA•fC•mU•fG•mA•fG•mA•fA•mU•fA•mC•fU•mG•fU•mC•fC•mC |
| 337 | 1140 | PmU•fG•mC•fA•mC•fU•mG•fA•mG•fA•mA•fU•mA•fC•mU•fG•mU•fC•mC |
| 338 | 1141 | PmU•fA•mG•fC•mA•fC•mU•fG•mA•fG•mA•fA•mU•fA•mC•fU•mG•fU•mC |
| 339 | 1142 | PmU•fG•mA•fG•mC•fA•mC•fU•mG•fA•mG•fA•mA•fU•mA•fC•mU•fG•mU |
| 340 | 1143 | PmU•fA•mG•fA•mG•fC•mA•fC•mU•fG•mA•fG•mA•fA•mU•fA•mC•fU•mG |
| 341 | 1144 | PmU•fG•mA•fG•mA•fG•mC•fA•mC•fU•mG•fA•mG•fA•mA•fU•mA•fC•mU |
| 342 | 1145 | PmU•fG•mG•fA•mG•fA•mG•fC•mA•fC•mU•fG•mA•fG•mA•fA•mU•fA•mC |
| 343 | 1146 | PmU•fA•mG•fG•mA•fG•mA•fG•mC•fA•mC•fU•mG•fA•mG•fA•mA•fU•mA |
| 344 | 1147 | PmU•fU•mA•fG•mG•fA•mG•fA•mG•fC•mA•fC•mU•fG•mA•fG•mA•fA•mU |
| 345 | 1148 | PmU•fG•mU•fA•mG•fG•mA•fG•mA•fG•mC•fA•mC•fU•mG•fA•mG•fA•mA |

TABLE 1b-continued

Nucleobase sequences and sugar-phosphate backbone modifications of the antisense strands of 376 exemplary constructs:

| # | SEQ ID NO: | Oligo Sequence (5' to 3') and backbone modifications |
|---|---|---|
| 346 | 1149 | PmU•fG•mG•fU•mA•fG•mG•fA•mG•fA•mG•fC•mA•fC•mU•fG•mA•fG•mA |
| 347 | 1150 | PmU•fG•mG•fG•mU•fA•mG•fG•mA•fG•mA•fG•mC•fA•mC•fU•mG•fA•mG |
| 348 | 1151 | PmU•fG•mG•fC•mC•fA•mG•fG•mC•fA•mU•fG•mA•fG•mG•fU•mG•fG•mG |
| 349 | 1152 | PmU•fG•mG•fG•mC•fC•mA•fG•mG•fC•mA•fU•mG•fA•mG•fG•mU•fG•mG |
| 350 | 1153 | PmU•fG•mC•fC•mA•fG•mC•fA•mU•fG•mC•fC•mU•fG•mG•fA•mG•fG•mG |
| 351 | 1154 | PmU•fG•mG•fC•mC•fA•mG•fC•mA•fU•mG•fC•mC•fU•mG•fG•mA•fG•mG |
| 352 | 1155 | PmU•fA•mG•fG•mC•fC•mA•fG•mC•fA•mU•fG•mC•fC•mU•fG•mG•fA•mG |
| 353 | 1156 | PmU•fG•mA•fG•mG•fC•mC•fA•mG•fC•mA•fU•mG•fC•mC•fU•mG•fG•mA |
| 354 | 1157 | PmU•fG•mG•fA•mG•fG•mC•fC•mA•fG•mC•fA•mU•fG•mC•fC•mU•fG•mG |
| 355 | 1158 | PmU•fG•mG•fG•mA•fG•mG•fC•mC•fA•mG•fC•mA•fU•mG•fC•mC•fU•mG |
| 356 | 1159 | PmU•fU•mG•fG•mG•fA•mG•fG•mC•fC•mA•fG•mC•fA•mU•fG•mC•fC•mU |
| 357 | 1160 | PmU•fA•mU•fU•mG•fG•mG•fA•mG•fG•mC•fC•mA•fG•mC•fA•mU•fG•mC |
| 358 | 1161 | PmU•fU•mA•fU•mU•fG•mG•fG•mA•fG•mG•fC•mC•fA•mG•fC•mA•fU•mG |
| 359 | 1162 | PmU•fU•mU•fA•mU•fU•mG•fG•mG•fA•mG•fG•mC•fC•mA•fG•mC•fA•mU |
| 360 | 1163 | PmU•fU•mU•fU•mA•fU•mU•fG•mG•fG•mA•fG•mG•fC•mC•fA•mG•fC•mA |
| 361 | 1164 | PmU•fC•mU•fU•mU•fA•mU•fU•mG•fG•mG•fA•mG•fG•mC•fC•mA•fG•mC |
| 362 | 1165 | PmU•fG•mC•fU•mU•fU•mA•fU•mU•fG•mG•fG•mA•fG•mG•fC•mC•fA•mG |
| 363 | 1166 | PmU•fA•mG•fC•mU•fU•mU•fA•mU•fU•mG•fG•mG•fA•mG•fG•mC•fC•mA |
| 364 | 1167 | PmU•fC•mA•fG•mC•fU•mU•fU•mA•fU•mU•fG•mG•fG•mA•fG•mG•fC•mC |
| 365 | 1168 | PmU•fC•mC•fA•mG•fC•mU•fU•mU•fA•mU•fU•mG•fG•mG•fA•mG•fG•mC |
| 366 | 1169 | PmU•fU•mC•fC•mA•fG•mC•fU•mU•fU•mA•fU•mU•fG•mG•fG•mA•fG•mG |
| 367 | 1170 | PmU•fG•mU•fC•mC•fA•mG•fC•mU•fU•mU•fA•mU•fU•mG•fG•mG•fA•mG |
| 368 | 1171 | PmU•fU•mU•fG•mU•fC•mC•fA•mG•fC•mU•fU•mU•fA•mU•fU•mG•fG•mG |
| 369 | 1172 | PmU•fC•mU•fU•mG•fU•mC•fC•mA•fG•mC•fU•mU•fU•mA•fU•mU•fG•mG |
| 370 | 1173 | PmU•fU•mC•fU•mU•fG•mU•fC•mC•fA•mG•fC•mU•fU•mU•fA•mU•fU•mG |
| 371 | 1174 | PmU•fU•mU•fC•mU•fU•mG•fU•mC•fC•mA•fG•mC•fU•mU•fU•mA•fU•mU |
| 372 | 1175 | PmU•fC•mU•fU•mC•fU•mU•fG•mU•fC•mC•fA•mG•fC•mU•fU•mU•fA•mU |
| 373 | 1176 | PmU•fG•mC•fU•mU•fC•mU•fU•mG•fU•mC•fC•mA•fG•mC•fU•mU•fU•mA |
| 374 | 1177 | PmU•fG•mC•fA•mG•fC•mU•fU•mC•fU•mU•fG•mU•fC•mC•fA•mG•fC•mU |
| 375 | 1178 | PmU•fU•mA•fG•mC•fA•mG•fC•mU•fU•mC•fU•mU•fG•mU•fC•mC•fA•mG |
| 376 | 1179 | PmU•fA•mU•fA•mG•fC•mA•fG•mC•fU•mU•fC•mU•fU•mG•fU•mC•fC•mA |

TABLE 1c

Nucleobase sequences of the sense strands of 376 exemplary constructs

| # | SEQ ID NO: | Nucleobase sequence |
|---|---|---|
| 1 | 401 | AGUUCAUCCCUAGAA |
| 2 | 402 | GUUCAUCCCUAGAGA |
| 3 | 403 | UUCAUCCCUAGAGGA |
| 4 | 404 | UCAUCCCUAGAGGCA |
| 5 | 405 | CAUCCCUAGAGGCAA |
| 6 | 406 | AUCCCUAGAGGCAGA |
| 7 | 407 | UCCCUAGAGGCAGCA |
| 8 | 408 | CCCUAGAGGCAGCUA |
| 9 | 409 | CUAGAGGCAGCUGCA |
| 10 | 410 | UAGAGGCAGCUGCUA |
| 11 | 411 | AGAGGCAGCUGCUCA |
| 12 | 412 | GAGGCAGCUGCUCCA |
| 13 | 413 | CUGCUCCAGGAACAA |
| 14 | 414 | UGCUCCAGGAACAGA |
| 15 | 415 | UCCAGGAACAGAGGA |

TABLE 1c-continued

Nucleobase sequences of the sense strands of 376 exemplary constructs

| # | SEQ ID NO: | Nucleobase sequence |
|---|---|---|
| 16 | 416 | CCAGGAACAGAGGUA |
| 17 | 417 | CAGGAACAGAGGUGA |
| 18 | 418 | AGGAACAGAGGUGCA |
| 19 | 419 | GGAACAGAGGUGCCA |
| 20 | 420 | GAACAGAGGUGCCAA |
| 21 | 421 | AACAGAGGUGCCAUA |
| 22 | 422 | ACAGAGGUGCCAUGA |
| 23 | 423 | AGAGGUGCCAUGCAA |
| 24 | 424 | GAGGUGCCAUGCAGA |
| 25 | 425 | AGGUGCCAUGCAGCA |
| 26 | 426 | GGUGCCAUGCAGCCA |
| 27 | 427 | GUGCCAUGCAGCCCA |
| 28 | 428 | GGUACUCCUUGUUGA |
| 29 | 429 | GUACUCCUUGUUGUA |
| 30 | 430 | UACUCCUUGUUGUUA |

TABLE 1c-continued

Nucleobase sequences of the sense strands of 376 exemplary constructs

| # | SEQ ID NO: | Nucleobase sequence |
|---|---|---|
| 31 | 431 | ACUCCUUGUUGUUGA |
| 32 | 432 | CUCCUUGUUGUUGCA |
| 33 | 433 | UCCUUGUUGUUGCCA |
| 34 | 434 | CCUUGUUGUUGCCCA |
| 35 | 435 | CUUGUUGUUGCCCUA |
| 36 | 436 | UUGUUGUUGCCCUCA |
| 37 | 437 | UGUUGUUGCCCUCCA |
| 38 | 438 | GUUGUUGCCCUCCUA |
| 39 | 439 | UUGUUGCCCUCCUGA |
| 40 | 440 | UGUUGCCCUCCUGGA |
| 41 | 441 | GUUGCCCUCCUGGCA |
| 42 | 442 | UUGCCCUCCUGGCGA |
| 43 | 443 | UGCCCUCCUGGCGCA |
| 44 | 444 | GCCCUCCUGGCGCUA |
| 45 | 445 | CCCUCCUGGCGCUCA |
| 46 | 446 | CCUCCUGGCGCUCCA |
| 47 | 447 | CUCCUGGCGCUCCUA |
| 48 | 448 | CUGGCGCUCCUGGCA |
| 49 | 449 | CGCUCCUGGCCUCUA |
| 50 | 450 | GCUCCUGGCCUCUGA |
| 51 | 451 | CUCCUGGCCUCUGCA |
| 52 | 452 | UCCUGGCCUCUGCCA |
| 53 | 453 | CCUGGCCUCUGCCCA |
| 54 | 454 | UGGCCUCUGCCCGAA |
| 55 | 455 | GGCCUCUGCCCGAGA |
| 56 | 456 | GCCUCUGCCCGAGCA |
| 57 | 457 | CCUCUGCCCGAGCUA |
| 58 | 458 | CUCUGCCCGAGCUUA |
| 59 | 459 | UCUGCCCGAGCUUCA |
| 60 | 460 | CUGCCCGAGCUUCAA |
| 61 | 461 | UGCCCGAGCUUCAGA |
| 62 | 462 | GCCCGAGCUUCAGAA |
| 63 | 463 | CCCGAGCUUCAGAGA |
| 64 | 464 | CCGAGCUUCAGAGGA |
| 65 | 465 | CGAGCUUCAGAGGCA |
| 66 | 466 | GAGCUUCAGAGGCCA |
| 67 | 467 | AGCUUCAGAGGCCGA |
| 68 | 468 | GCUUCAGAGGCCGAA |
| 69 | 469 | CUUCAGAGGCCGAGA |
| 70 | 470 | UUCAGAGGCCGAGGA |
| 71 | 471 | UCAGAGGCCGAGGAA |
| 72 | 472 | CAGAGGCCGAGGAUA |
| 73 | 473 | AGAGGCCGAGGAUGA |
| 74 | 474 | GAGGCCGAGGAUGCA |
| 75 | 475 | AGGCCGAGGAUGCCA |
| 76 | 476 | GGCCGAGGAUGCCUA |
| 77 | 477 | GCCGAGGAUGCCUCA |
| 78 | 478 | CCGAGGAUGCCUCCA |
| 79 | 479 | CGAGGAUGCCUCCCA |
| 80 | 480 | GAGGAUGCCUCCCUA |
| 81 | 481 | AGGAUGCCUCCCUUA |
| 82 | 482 | GGAUGCCUCCCUUCA |
| 83 | 483 | GAUGCCUCCCUUCUA |
| 84 | 484 | AUGCCUCCCUUCUCA |
| 85 | 485 | UGCCUCCCUUCUCAA |
| 86 | 486 | GCCUCCCUUCUCAGA |
| 87 | 487 | CCUCCCUUCUCAGCA |
| 88 | 488 | CUCCCUUCUCAGCUA |
| 89 | 489 | CCUUCUCAGCUUCAA |
| 90 | 490 | CUUCUCAGCUUCAUA |
| 91 | 491 | UUCUCAGCUUCAUGA |
| 92 | 492 | UCUCAGCUUCAUGCA |
| 93 | 493 | CUCAGCUUCAUGCAA |
| 94 | 494 | UCAGCUUCAUGCAGA |
| 95 | 495 | CAGCUUCAUGCAGGA |
| 96 | 496 | AGCUUCAUGCAGGGA |
| 97 | 497 | GCUUCAUGCAGGGUA |
| 98 | 498 | CUUCAUGCAGGGUUA |
| 99 | 499 | UUCAUGCAGGGUUAA |
| 100 | 500 | UCAUGCAGGGUUACA |
| 101 | 501 | CAUGCAGGGUUACAA |
| 102 | 502 | AUGCAGGGUUACAUA |
| 103 | 503 | UGCAGGGUUACAUGA |
| 104 | 504 | GCAGGGUUACAUGAA |

TABLE 1c-continued

Nucleobase sequences of the sense strands of 376 exemplary constructs

| # | SEQ ID NO: | Nucleobase sequence |
|---|---|---|
| 105 | 505 | CAGGGUUACAUGAAA |
| 106 | 506 | AGGGUUACAUGAAGA |
| 107 | 507 | GGGUUACAUGAAGCA |
| 108 | 508 | GGUUACAUGAAGCAA |
| 109 | 509 | GUUACAUGAAGCACA |
| 110 | 510 | UUACAUGAAGCACGA |
| 111 | 511 | UACAUGAAGCACGCA |
| 112 | 512 | ACAUGAAGCACGCCA |
| 113 | 513 | CAUGAAGCACGCCAA |
| 114 | 514 | AUGAAGCACGCCACA |
| 115 | 515 | UGAAGCACGCCACCA |
| 116 | 516 | GAAGCACGCCACCAA |
| 117 | 517 | AAGCACGCCACCAAA |
| 118 | 518 | AGCACGCCACCAAGA |
| 119 | 519 | GCACGCCACCAAGAA |
| 120 | 520 | CACGCCACCAAGACA |
| 121 | 521 | ACGCCACCAAGACCA |
| 122 | 522 | CGCCACCAAGACCGA |
| 123 | 523 | GCCACCAAGACCGCA |
| 124 | 524 | CCACCAAGACCGCCA |
| 125 | 525 | CACCAAGACCGCCAA |
| 126 | 526 | ACCAAGACCGCCAAA |
| 127 | 527 | CCAAGACCGCCAAGA |
| 128 | 528 | CAAGACCGCCAAGGA |
| 129 | 529 | AAGACCGCCAAGGAA |
| 130 | 530 | AGACCGCCAAGGAUA |
| 131 | 531 | GACCGCCAAGGAUGA |
| 132 | 532 | ACCGCCAAGGAUGCA |
| 133 | 533 | CCGCCAAGGAUGCAA |
| 134 | 534 | CGCCAAGGAUGCACA |
| 135 | 535 | GCCAAGGAUGCACUA |
| 136 | 536 | CCAAGGAUGCACUGA |
| 137 | 537 | CAAGGAUGCACUGAA |
| 138 | 538 | AAGGAUGCACUGAGA |
| 139 | 539 | AGGAUGCACUGAGCA |
| 140 | 540 | GGAUGCACUGAGCAA |
| 141 | 541 | GAUGCACUGAGCAGA |

TABLE 1c-continued

Nucleobase sequences of the sense strands of 376 exemplary constructs

| # | SEQ ID NO: | Nucleobase sequence |
|---|---|---|
| 142 | 542 | AUGCACUGAGCAGCA |
| 143 | 543 | UGCACUGAGCAGCGA |
| 144 | 544 | GCACUGAGCAGCGUA |
| 145 | 545 | CACUGAGCAGCGUGA |
| 146 | 546 | ACUGAGCAGCGUGCA |
| 147 | 547 | CUGAGCAGCGUGCAA |
| 148 | 548 | UGAGCAGCGUGCAGA |
| 149 | 549 | GAGCAGCGUGCAGGA |
| 150 | 550 | AGCAGCGUGCAGGAA |
| 151 | 551 | CAGCGUGCAGGAGUA |
| 152 | 552 | CGUGCAGGAGUCCCA |
| 153 | 553 | GUGCAGGAGUCCCAA |
| 154 | 554 | UGCAGGAGUCCCAGA |
| 155 | 555 | GCAGGAGUCCCAGGA |
| 156 | 556 | CAGGAGUCCCAGGUA |
| 157 | 557 | AGGAGUCCCAGGUGA |
| 158 | 558 | GGAGUCCCAGGUGGA |
| 159 | 559 | GUCCCAGGUGGCCCA |
| 160 | 560 | UCCCAGGUGGCCCAA |
| 161 | 561 | CAGGUGGCCCAGCAA |
| 162 | 562 | AGGUGGCCCAGCAGA |
| 163 | 563 | UGGCCCAGCAGGCCA |
| 164 | 564 | CCCAGCAGGCCAGGA |
| 165 | 565 | UGGGUGACCGAUGGA |
| 166 | 566 | GGGUGACCGAUGGCA |
| 167 | 567 | GGUGACCGAUGGCUA |
| 168 | 568 | GUGACCGAUGGCUUA |
| 169 | 569 | UGACCGAUGGCUUCA |
| 170 | 570 | GACCGAUGGCUUCAA |
| 171 | 571 | ACCGAUGGCUUCAGA |
| 172 | 572 | CCGAUGGCUUCAGUA |
| 173 | 573 | CGAUGGCUUCAGUUA |
| 174 | 574 | GAUGGCUUCAGUUCA |
| 175 | 575 | AUGGCUUCAGUUCCA |
| 176 | 576 | UGGCUUCAGUUCCCA |
| 177 | 577 | GGCUUCAGUUCCCUA |
| 178 | 578 | GCUUCAGUUCCCUGA |

TABLE 1c-continued

| Nucleobase sequences of the sense strands of 376 exemplary constructs | | |
|---|---|---|
| # | SEQ ID NO: | Nucleobase sequence |
| 179 | 579 | CUUCAGUUCCCUGAA |
| 180 | 580 | UUCAGUUCCCUGAAA |
| 181 | 581 | UCAGUUCCCUGAAAA |
| 182 | 582 | CAGUUCCCUGAAAGA |
| 183 | 583 | AGUUCCCUGAAAGAA |
| 184 | 584 | GUUCCCUGAAAGACA |
| 185 | 585 | UUCCCUGAAAGACUA |
| 186 | 586 | UCCCUGAAAGACUAA |
| 187 | 587 | CCCUGAAAGACUACA |
| 188 | 588 | CCUGAAAGACUACUA |
| 189 | 589 | CUGAAAGACUACUGA |
| 190 | 590 | UGAAAGACUACUGGA |
| 191 | 591 | GAAAGACUACUGGAA |
| 192 | 592 | AAAGACUACUGGAGA |
| 193 | 593 | AAGACUACUGGAGCA |
| 194 | 594 | AGACUACUGGAGCAA |
| 195 | 595 | GACUACUGGAGCACA |
| 196 | 596 | ACUACUGGAGCACCA |
| 197 | 597 | CUACUGGAGCACCGA |
| 198 | 598 | UACUGGAGCACCGUA |
| 199 | 599 | ACUGGAGCACCGUUA |
| 200 | 600 | CUGGAGCACCGUUAA |
| 201 | 601 | UGGAGCACCGUUAAA |
| 202 | 602 | GGAGCACCGUUAAGA |
| 203 | 603 | GAGCACCGUUAAGGA |
| 204 | 604 | AGCACCGUUAAGGAA |
| 205 | 605 | GCACCGUUAAGGACA |
| 206 | 606 | CACCGUUAAGGACAA |
| 207 | 607 | ACCGUUAAGGACAAA |
| 208 | 608 | CCGUUAAGGACAAGA |
| 209 | 609 | CGUUAAGGACAAGUA |
| 210 | 610 | GUUAAGGACAAGUUA |
| 211 | 611 | UUAAGGACAAGUUCA |
| 212 | 612 | UAAGGACAAGUUCUA |
| 213 | 613 | AAGGACAAGUUCUCA |
| 214 | 614 | AGGACAAGUUCUCUA |
| 215 | 615 | GGACAAGUUCUCUGA |

TABLE 1c-continued

| Nucleobase sequences of the sense strands of 376 exemplary constructs | | |
|---|---|---|
| # | SEQ ID NO: | Nucleobase sequence |
| 216 | 616 | GACAAGUUCUCUGAA |
| 217 | 617 | ACAAGUUCUCUGAGA |
| 218 | 618 | CAAGUUCUCUGAGUA |
| 219 | 619 | AAGUUCUCUGAGUUA |
| 220 | 620 | AGUUCUCUGAGUUCA |
| 221 | 621 | UUCUCUGAGUUCUGA |
| 222 | 622 | UCUCUGAGUUCUGGA |
| 223 | 623 | CUCUGAGUUCUGGGA |
| 224 | 624 | UCUGAGUUCUGGGAA |
| 225 | 625 | CUGAGUUCUGGGAUA |
| 226 | 626 | UGAGUUCUGGGAUUA |
| 227 | 627 | GAGUUCUGGGAUUUA |
| 228 | 628 | AGUUCUGGGAUUUGA |
| 229 | 629 | GUUCUGGGAUUUGGA |
| 230 | 630 | UUCUGGGAUUUGGAA |
| 231 | 631 | UCUGGGAUUUGGACA |
| 232 | 632 | CUGGGAUUUGGACCA |
| 233 | 633 | UGGGAUUUGGACCCA |
| 234 | 634 | GGGAUUUGGACCCUA |
| 235 | 635 | GGAUUUGGACCCUGA |
| 236 | 636 | GAUUUGGACCCUGAA |
| 237 | 637 | UGGACCCUGAGGUCA |
| 238 | 638 | GGACCCUGAGGUCAA |
| 239 | 639 | GACCCUGAGGUCAGA |
| 240 | 640 | ACCCUGAGGUCAGAA |
| 241 | 641 | CCCUGAGGUCAGACA |
| 242 | 642 | CCUGAGGUCAGACCA |
| 243 | 643 | CUGAGGUCAGACCAA |
| 244 | 644 | UGAGGUCAGACCAAA |
| 245 | 645 | GAGGUCAGACCAACA |
| 246 | 646 | AGGUCAGACCAACUA |
| 247 | 647 | GGUCAGACCAACUUA |
| 248 | 648 | GUCAGACCAACUUCA |
| 249 | 649 | UCAGACCAACUUCAA |
| 250 | 650 | CAGACCAACUUCAGA |
| 251 | 651 | GACCAACUUCAGCCA |
| 252 | 652 | ACCAACUUCAGCCGA |

TABLE 1c-continued

Nucleobase sequences of the sense strands of 376 exemplary constructs

| # | SEQ ID NO: | Nucleobase sequence |
|---|---|---|
| 253 | 653 | CCAACUUCAGCCGUA |
| 254 | 654 | CAACUUCAGCCGUGA |
| 255 | 655 | AACUUCAGCCGUGGA |
| 256 | 656 | ACUUCAGCCGUGGCA |
| 257 | 657 | UUCAGCCGUGGCUGA |
| 258 | 658 | UCAGCCGUGGCUGCA |
| 259 | 659 | CAGCCGUGGCUGCCA |
| 260 | 660 | AGCCGUGGCUGCCUA |
| 261 | 661 | GCCGUGGCUGCCUGA |
| 262 | 662 | GUGGCUGCCUGAGAA |
| 263 | 663 | UGGCUGCCUGAGACA |
| 264 | 664 | GGCUGCCUGAGACCA |
| 265 | 665 | GCUGCCUGAGACCUA |
| 266 | 666 | UGCCUGAGACCUCAA |
| 267 | 667 | GCCUGAGACCUCAAA |
| 268 | 668 | CCUGAGACCUCAAUA |
| 269 | 669 | CUGAGACCUCAAUAA |
| 270 | 670 | UGAGACCUCAAUACA |
| 271 | 671 | GAGACCUCAAUACCA |
| 272 | 672 | AGACCUCAAUACCCA |
| 273 | 673 | AGUCCACCUGCCUAA |
| 274 | 674 | GUCCACCUGCCUAUA |
| 275 | 675 | UCCACCUGCCUAUCA |
| 276 | 676 | CCACCUGCCUAUCCA |
| 277 | 677 | CACCUGCCUAUCCAA |
| 278 | 678 | ACCUGCCUAUCCAUA |
| 279 | 679 | CCUGCCUAUCCAUCA |
| 280 | 680 | CUGCCUAUCCAUCCA |
| 281 | 681 | UGCCUAUCCAUCCUA |
| 282 | 682 | GCCUAUCCAUCCUGA |
| 283 | 683 | CCUAUCCAUCCUGCA |
| 284 | 684 | CUAUCCAUCCUGCGA |
| 285 | 685 | UAUCCAUCCUGCGAA |
| 286 | 686 | AUCCAUCCUGCGAGA |
| 287 | 687 | UCCAUCCUGCGAGCA |
| 288 | 688 | CCAUCCUGCGAGCUA |
| 289 | 689 | CAUCCUGCGAGCUCA |

TABLE 1c-continued

Nucleobase sequences of the sense strands of 376 exemplary constructs

| # | SEQ ID NO: | Nucleobase sequence |
|---|---|---|
| 290 | 690 | AUCCUGCGAGCUCCA |
| 291 | 691 | UCCUGCGAGCUCCUA |
| 292 | 692 | CCUGCGAGCUCCUUA |
| 293 | 693 | CUGCGAGCUCCUUGA |
| 294 | 694 | UGCGAGCUCCUUGGA |
| 295 | 695 | GCGAGCUCCUUGGGA |
| 296 | 696 | CGAGCUCCUUGGGUA |
| 297 | 697 | GAGCUCCUUGGGUCA |
| 298 | 698 | AGCUCCUUGGGUCCA |
| 299 | 699 | GCUCCUUGGGUCCUA |
| 300 | 700 | CUCCUUGGGUCCUGA |
| 301 | 701 | UCCUUGGGUCCUGCA |
| 302 | 702 | CCUUGGGUCCUGCAA |
| 303 | 703 | CUUGGGUCCUGCAAA |
| 304 | 704 | UUGGGUCCUGCAAUA |
| 305 | 705 | UGGGUCCUGCAAUCA |
| 306 | 706 | GGGUCCUGCAAUCUA |
| 307 | 707 | GGUCCUGCAAUCUCA |
| 308 | 708 | GUCCUGCAAUCUCCA |
| 309 | 709 | UCCUGCAAUCUCCAA |
| 310 | 710 | CCUGCAAUCUCCAGA |
| 311 | 711 | CUGCAAUCUCCAGGA |
| 312 | 712 | UGCAAUCUCCAGGGA |
| 313 | 713 | GCAAUCUCCAGGGCA |
| 314 | 714 | CAAUCUCCAGGGCUA |
| 315 | 715 | AAUCUCCAGGGCUGA |
| 316 | 716 | AUCUCCAGGGCUGCA |
| 317 | 717 | UCUCCAGGGCUGCCA |
| 318 | 718 | CUCCAGGGCUGCCCA |
| 319 | 719 | GUAGGUUGCUUAAAA |
| 320 | 720 | UAGGUUGCUUAAAAA |
| 321 | 721 | AGGUUGCUUAAAAGA |
| 322 | 722 | GGUUGCUUAAAAGGA |
| 323 | 723 | GUUGCUUAAAAGGGA |
| 324 | 724 | UUGCUUAAAAGGGAA |
| 325 | 725 | UGCUUAAAAGGGACA |
| 326 | 726 | UUAAAAGGGACAGUA |

TABLE 1c-continued

Nucleobase sequences of the sense strands of 376 exemplary constructs

| # | SEQ ID NO: | Nucleobase sequence |
|---|---|---|
| 327 | 727 | UAAAAGGGACAGUAA |
| 328 | 728 | AAAAGGGACAGUAUA |
| 329 | 729 | AAAGGGACAGUAUUA |
| 330 | 730 | AAGGGACAGUAUUCA |
| 331 | 731 | AGGGACAGUAUUCUA |
| 332 | 732 | GGGACAGUAUUCUCA |
| 333 | 733 | GGACAGUAUUCUCAA |
| 334 | 734 | GACAGUAUUCUCAGA |
| 335 | 735 | ACAGUAUUCUCAGUA |
| 336 | 736 | CAGUAUUCUCAGUGA |
| 337 | 737 | AGUAUUCUCAGUGCA |
| 338 | 738 | GUAUUCUCAGUGCUA |
| 339 | 739 | UAUUCUCAGUGCUCA |
| 340 | 740 | AUUCUCAGUGCUCUA |
| 341 | 741 | UUCUCAGUGCUCUCA |
| 342 | 742 | UCUCAGUGCUCUCCA |
| 343 | 743 | CUCAGUGCUCUCCUA |
| 344 | 744 | UCAGUGCUCUCCUAA |
| 345 | 745 | CAGUGCUCUCCUACA |
| 346 | 746 | AGUGCUCUCCUACCA |
| 347 | 747 | GUGCUCUCCUACCCA |
| 348 | 748 | CCUCAUGCCUGGCCA |
| 349 | 749 | CUCAUGCCUGGCCCA |
| 350 | 750 | CCAGGCAUGCUGGCA |
| 351 | 751 | CAGGCAUGCUGGCCA |
| 352 | 752 | AGGCAUGCUGGCCUA |
| 353 | 753 | GGCAUGCUGGCCUCA |
| 354 | 754 | GCAUGCUGGCCUCCA |
| 355 | 755 | CAUGCUGGCCUCCCA |
| 356 | 756 | AUGCUGGCCUCCCAA |
| 357 | 757 | GCUGGCCUCCCAAUA |
| 358 | 758 | CUGGCCUCCCAAUAA |
| 359 | 759 | UGGCCUCCCAAUAAA |
| 360 | 760 | GGCCUCCCAAUAAAA |
| 361 | 761 | GCCUCCCAAUAAAGA |
| 362 | 762 | CCUCCCAAUAAAGCA |
| 363 | 763 | CUCCCAAUAAAGCUA |
| 364 | 764 | UCCCAAUAAAGCUGA |
| 365 | 765 | CCCAAUAAAGCUGGA |
| 366 | 766 | CCAAUAAAGCUGGAA |
| 367 | 767 | CAAUAAAGCUGGACA |
| 368 | 768 | AUAAAGCUGGACAAA |
| 369 | 769 | UAAAGCUGGACAAGA |
| 370 | 770 | AAAGCUGGACAAGAA |
| 371 | 771 | AAGCUGGACAAGAAA |
| 372 | 772 | AGCUGGACAAGAAGA |
| 373 | 773 | GCUGGACAAGAAGCA |
| 374 | 774 | GGACAAGAAGCUGCA |
| 375 | 775 | ACAAGAAGCUGCUAA |
| 376 | 776 | CAAGAAGCUGCUAUA |

TABLE 1d

Nucleobase sequences and sugar-phosphate backbone modifications of the sense strands of 376 exemplary constructs:

| # | SEQ ID NO: | Nucleobase sequence and backbone modification |
|---|---|---|
| 1 | 1180 | fA•mG•fU•mU•fC•mA•fU•mC•fC•mC•fU•mA•fG•mA•fA |
| 2 | 1181 | fG•mU•fU•mC•fA•mU•fC•mC•fC•mU•fA•mG•fA•mG•fA |
| 3 | 1182 | fU•mU•fC•mA•fU•mC•fC•mC•fU•mA•fG•mA•fG•mG•fA |
| 4 | 1183 | fU•mC•fA•mU•fC•mC•fC•mU•fA•mG•fA•mG•fG•mC•fA |
| 5 | 1184 | fC•mA•fU•mC•fC•mC•fU•mA•fG•mA•fG•mG•fC•mA•fA |
| 6 | 1185 | fA•mU•fC•mC•fC•mU•fA•mG•fA•mG•fG•mC•fA•mG•fA |
| 7 | 1186 | fU•mC•fC•mC•fU•mA•fG•mA•fG•mG•fC•mA•fG•mC•fA |
| 8 | 1187 | fC•mC•fC•mU•fA•mG•fA•mG•fG•mC•fA•mG•fC•mU•fA |
| 9 | 1188 | fC•mU•fA•mG•fA•mG•fG•mC•fA•mG•fC•mU•fG•mC•fA |
| 10 | 1189 | fU•mA•fG•mA•fG•mG•fC•mA•fG•mC•fU•mG•fC•mU•fA |
| 11 | 1190 | fA•mG•fA•mG•fG•mC•fA•mG•fC•mU•fG•mC•fU•mC•fA |
| 12 | 1191 | fG•mA•fG•mG•fC•mA•fG•mC•fU•mG•fC•mU•fC•mC•fA |
| 13 | 1192 | fC•mU•fG•mC•fU•mC•fC•mA•fG•mG•fA•mA•fC•mA•fA |
| 14 | 1193 | fU•mG•fC•mU•fC•mC•fA•mG•fG•mA•fA•mC•fA•mG•fA |
| 15 | 1194 | fU•mC•fC•mA•fG•mG•fA•mA•fC•mA•fG•mA•fG•mG•fA |
| 16 | 1195 | fC•mC•fA•mG•fG•mA•fA•mC•fA•mG•fA•mG•fG•mU•fA |
| 17 | 1196 | fC•mA•fG•mG•fA•mA•fC•mA•fG•mA•fG•mG•fU•mG•fA |
| 18 | 1197 | fA•mG•fG•mA•fA•mC•fA•mG•fA•mG•fG•mU•fG•mC•fA |
| 19 | 1198 | fG•mG•fA•mA•fC•mA•fG•mA•fG•mG•fU•mG•fC•mC•fA |
| 20 | 1199 | fG•mA•fA•mC•fA•mG•fA•mG•fG•mU•fG•mC•fC•mA•fA |
| 21 | 1200 | fA•mA•fC•mA•fG•mA•fG•mG•fU•mG•fC•mC•fA•mU•fA |
| 22 | 1201 | fA•mC•fA•mG•fA•mG•fG•mU•fG•mC•fC•mA•fU•mG•fA |
| 23 | 1202 | fA•mG•fA•mG•fG•mU•fG•mC•fC•mA•fU•mG•fC•mA•fA |
| 24 | 1203 | fG•mA•fG•mG•fU•mG•fC•mC•fA•mU•fG•mC•fA•mG•fA |
| 25 | 1204 | fA•mG•fG•mU•fG•mC•fC•mA•fU•mG•fC•mA•fG•mC•fA |
| 26 | 1205 | fG•mG•fU•mG•fC•mC•fA•mU•fG•mC•fA•mG•fC•mC•fA |
| 27 | 1206 | fG•mU•fG•mC•fC•mA•fU•mG•fC•mA•fG•mC•fC•mC•fA |
| 28 | 1207 | fG•mG•fU•mA•fC•mU•fC•mC•fU•mU•fG•mU•fU•mG•fA |
| 29 | 1208 | fG•mU•fA•mC•fU•mC•fC•mU•fU•mG•fU•mU•fG•mU•fA |
| 30 | 1209 | fU•mA•fC•mU•fC•mC•fU•mU•fG•mU•fU•mG•fU•mU•fA |
| 31 | 1210 | fA•mC•fU•mC•fC•mU•fU•mG•fU•mU•fG•mU•fU•mG•fA |
| 32 | 1211 | fC•mU•fC•mC•fU•mU•fG•mU•fU•mG•fU•mU•fG•mC•fA |
| 33 | 1212 | fU•mC•fC•mU•fU•mG•fU•mU•fG•mU•fU•mG•fC•mC•fA |
| 34 | 1213 | fC•mC•fU•mU•fG•mU•fU•mG•fU•mU•fG•mC•fC•mC•fA |
| 35 | 1214 | fC•mU•fU•mG•fU•mU•fG•mU•fU•mG•fC•mC•fC•mU•fA |
| 36 | 1215 | fU•mU•fG•mU•fU•mG•fU•mU•fG•mC•fC•mC•fU•mC•fA |

TABLE 1d-continued

Nucleobase sequences and sugar-phosphate backbone modifications of the sense strands of 376 exemplary constructs:

| # | SEQ ID NO: | Nucleobase sequence and backbone modification |
|---|---|---|
| 37 | 1216 | fU•mG•fU•mU•fG•mU•fU•mG•fC•mC•fC•mU•fC•mC•fA |
| 38 | 1217 | fG•mU•fU•mG•fU•mU•fG•mC•fC•mC•fU•mC•fC•mU•fA |
| 39 | 1218 | fU•mU•fG•mU•fU•mG•fC•mC•fC•mU•fC•mC•fU•mG•fA |
| 40 | 1219 | fU•mG•fU•mU•fG•mC•fC•mC•fU•mC•fC•mU•fG•mG•fA |
| 41 | 1220 | fG•mU•fU•mG•fC•mC•fC•mU•fC•mC•fU•mG•fG•mC•fA |
| 42 | 1221 | fU•mU•fG•mC•fC•mC•fU•mC•fC•mU•fG•mG•fC•mG•fA |
| 43 | 1222 | fU•mG•fC•mC•fC•mU•fC•mC•fU•mG•fG•mC•fG•mC•fA |
| 44 | 1223 | fG•mC•fC•mC•fU•mC•fC•mU•fG•mG•fC•mG•fC•mU•fA |
| 45 | 1224 | fC•mC•fC•mU•fC•mC•fU•mG•fG•mC•fG•mC•fU•mC•fA |
| 46 | 1225 | fC•mC•fU•mC•fC•mU•fG•mG•fC•mG•fC•mU•fC•mC•fA |
| 47 | 1226 | fC•mU•fC•mC•fU•mG•fG•mC•fG•mC•fU•mC•fC•mU•fA |
| 48 | 1227 | fC•mU•fG•mG•fC•mG•fC•mU•fC•mC•fU•mG•fG•mC•fA |
| 49 | 1228 | fC•mG•fC•mU•fC•mC•fU•mG•fG•mC•fC•mU•fC•mU•fA |
| 50 | 1229 | fG•mC•fU•mC•fC•mU•fG•mG•fC•mC•fU•mC•fU•mG•fA |
| 51 | 1230 | fC•mU•fC•mC•fU•mG•fG•mC•fC•mU•fC•mU•fG•mC•fA |
| 52 | 1231 | fU•mC•fC•mU•fG•mG•fC•mC•fU•mC•fU•mG•fC•mC•fA |
| 53 | 1232 | fC•mC•fU•mG•fG•mC•fC•mU•fC•mU•fG•mC•fC•mC•fA |
| 54 | 1233 | fU•mG•fG•mC•fC•mU•fC•mU•fG•mC•fC•mC•fG•mA•fA |
| 55 | 1234 | fG•mG•fC•mC•fU•mC•fU•mG•fC•mC•fC•mG•fA•mG•fA |
| 56 | 1235 | fG•mC•fC•mU•fC•mU•fG•mC•fC•mC•fG•mA•fG•mC•fA |
| 57 | 1236 | fC•mC•fU•mC•fU•mG•fC•mC•fC•mG•fA•mG•fC•mU•fA |
| 58 | 1237 | fC•mU•fC•mU•fG•mC•fC•mC•fG•mA•fG•mC•fU•mU•fA |
| 59 | 1238 | fU•mC•fU•mG•fC•mC•fC•mG•fA•mG•fC•mU•fU•mC•fA |
| 60 | 1239 | fC•mU•fG•mC•fC•mC•fG•mA•fG•mC•fU•mU•fC•mA•fA |
| 61 | 1240 | fU•mG•fC•mC•fC•mG•fA•mG•fC•mU•fU•mC•fA•mG•fA |
| 62 | 1241 | fG•mC•fC•mC•fG•mA•fG•mC•fU•mU•fC•mA•fG•mA•fA |
| 63 | 1242 | fC•mC•fC•mG•fA•mG•fC•mU•fU•mC•fA•mG•fA•mG•fA |
| 64 | 1243 | fC•mC•fG•mA•fG•mC•fU•mU•fC•mA•fG•mA•fG•mG•fA |
| 65 | 1244 | fC•mG•fA•mG•fC•mU•fU•mC•fA•mG•fA•mG•fG•mC•fA |
| 66 | 1245 | fG•mA•fG•mC•fU•mU•fC•mA•fG•mA•fG•mG•fC•mC•fA |
| 67 | 1246 | fA•mG•fC•mU•fU•mC•fA•mG•fA•mG•fG•mC•fC•mG•fA |
| 68 | 1247 | fG•mC•fU•mU•fC•mA•fG•mA•fG•mG•fC•mC•fG•mA•fA |
| 69 | 1248 | fC•mU•fU•mC•fA•mG•fA•mG•fG•mC•fC•mG•fA•mG•fA |
| 70 | 1249 | fU•mU•fC•mA•fG•mA•fG•mG•fC•mC•fG•mA•fG•mG•fA |
| 71 | 1250 | fU•mC•fA•mG•fA•mG•fG•mC•fC•mG•fA•mG•fG•mA•fA |
| 72 | 1251 | fC•mA•fG•mA•fG•mG•fC•mC•fG•mA•fG•mG•fA•mU•fA |
| 73 | 1252 | fA•mG•fA•mG•fG•mC•fC•mG•fA•mG•fG•mA•fU•mG•fA |
| 74 | 1253 | fG•mA•fG•mG•fC•mC•fG•mA•fG•mG•fA•mU•fG•mC•fA |
| 75 | 1254 | fA•mG•fG•mC•fC•mG•fA•mG•fG•mA•fU•mG•fC•mC•fA |
| 76 | 1255 | fG•mG•fC•mC•fG•mA•fG•mG•fA•mU•fG•mC•fC•mU•fA |
| 77 | 1256 | fG•mC•fC•mG•fA•mG•fG•mA•fU•mG•fC•mC•fU•mC•fA |
| 78 | 1257 | fC•mC•fG•mA•fG•mG•fA•mU•fG•mC•fC•mU•fC•mC•fA |
| 79 | 1258 | fC•mG•fA•mG•fG•mA•fU•mG•fC•mC•fU•mC•fC•mC•fA |
| 80 | 1259 | fG•mA•fG•mG•fA•mU•fG•mC•fC•mU•fC•mC•fC•mU•fA |
| 81 | 1260 | fA•mG•fG•mA•fU•mG•fC•mC•fU•mC•fC•mC•fU•mU•fA |
| 82 | 1261 | fG•mG•fA•mU•fG•mC•fC•mU•fC•mC•fC•mU•fU•mC•fA |
| 83 | 1262 | fG•mA•fU•mG•fC•mC•fU•mC•fC•mC•fU•mU•fC•mU•fA |
| 84 | 1263 | fA•mU•fG•mC•fC•mU•fC•mC•fC•mU•fU•mC•fU•mC•fA |
| 85 | 1264 | fU•mG•fC•mC•fU•mC•fC•mC•fU•mU•fC•mU•fC•mA•fA |
| 86 | 1265 | fG•mC•fC•mU•fC•mC•fC•mU•fU•mC•fU•mC•fA•mG•fA |
| 87 | 1266 | fC•mC•fU•mC•fC•mC•fU•mU•fC•mU•fC•mA•fG•mC•fA |
| 88 | 1267 | fC•mU•fC•mC•fC•mU•fU•mC•fU•mC•fA•mG•fC•mU•fA |
| 89 | 1268 | fC•mC•fU•mU•fC•mU•fC•mA•fG•mC•fU•mU•fC•mA•fA |
| 90 | 1269 | fC•mU•fU•mC•fU•mC•fA•mG•fC•mU•fU•mC•fA•mU•fA |
| 91 | 1270 | fU•mU•fC•mU•fC•mA•fG•mC•fU•mU•fC•mA•fU•mG•fA |
| 92 | 1271 | fU•mC•fU•mC•fA•mG•fC•mU•fU•mC•fA•mU•fG•mC•fA |
| 93 | 1272 | fC•mU•fC•mA•fG•mC•fU•mU•fC•mA•fU•mG•fC•mA•fA |
| 94 | 1273 | fU•mC•fA•mG•fC•mU•fU•mC•fA•mU•fG•mC•fA•mG•fA |
| 95 | 1274 | fC•mA•fG•mC•fU•mU•fC•mA•fU•mG•fC•mA•fG•mG•fA |
| 96 | 1275 | fA•mG•fC•mU•fU•mC•fA•mU•fG•mC•fA•mG•fG•mG•fA |
| 97 | 1276 | fG•mC•fU•mU•fC•mA•fU•mG•fC•mA•fG•mG•fG•mU•fA |
| 98 | 1277 | fC•mU•fU•mC•fA•mU•fG•mC•fA•mG•fG•mG•fU•mU•fA |
| 99 | 1278 | fU•mU•fC•mA•fU•mG•fC•mA•fG•mG•fG•mU•fU•mA•fA |
| 100 | 1279 | fU•mC•fA•mU•fG•mC•fA•mG•fG•mG•fU•mU•fA•mC•fA |
| 101 | 1280 | fC•mA•fU•mG•fC•mA•fG•mG•fG•mU•fU•mA•fC•mA•fA |
| 102 | 1281 | fA•mU•fG•mC•fA•mG•fG•mG•fU•mU•fA•mC•fA•mU•fA |
| 103 | 1282 | fU•mG•fC•mA•fG•mG•fG•mU•fU•mA•fC•mA•fU•mG•fA |
| 104 | 1283 | fG•mC•fA•mG•fG•mG•fU•mU•fA•mC•fA•mU•fG•mA•fA |
| 105 | 1284 | fC•mA•fG•mG•fG•mU•fU•mA•fC•mA•fU•mG•fA•mA•fA |
| 106 | 1285 | fA•mG•fG•mG•fU•mU•fA•mC•fA•mU•fG•mA•fA•mG•fA |
| 107 | 1286 | fG•mG•fG•mU•fU•mA•fC•mA•fU•mG•fA•mA•fG•mC•fA |
| 108 | 1287 | fG•mG•fU•mU•fA•mC•fA•mU•fG•mA•fA•mG•fC•mA•fA |
| 109 | 1288 | fG•mU•fU•mA•fC•mA•fU•mG•fA•mA•fG•mC•fA•mC•fA |
| 110 | 1289 | fU•mU•fA•mC•fA•mU•fG•mA•fA•mG•fC•mA•fC•mG•fA |
| 111 | 1290 | fU•mA•fC•mA•fU•mG•fA•mA•fG•mC•fA•mC•fG•mC•fA |
| 112 | 1291 | fA•mC•fA•mU•fG•mA•fA•mG•fC•mA•fC•mG•fC•mC•fA |
| 113 | 1292 | fC•mA•fU•mG•fA•mA•fG•mC•fA•mC•fG•mC•fC•mA•fA |
| 114 | 1293 | fA•mU•fG•mA•fA•mG•fC•mA•fC•mG•fC•mC•fA•mC•fA |
| 115 | 1294 | fU•mG•fA•mA•fG•mC•fA•mC•fG•mC•fC•mA•fC•mC•fA |
| 116 | 1295 | fG•mA•fA•mG•fC•mA•fC•mG•fC•mC•fA•mC•fC•mA•fA |
| 117 | 1296 | fA•mA•fG•mC•fA•mC•fG•mC•fC•mA•fC•mC•fA•mA•fA |
| 118 | 1297 | fA•mG•fC•mA•fC•mG•fC•mC•fA•mC•fC•mA•fA•mG•fA |
| 119 | 1298 | fG•mC•fA•mC•fG•mC•fC•mA•fC•mC•fA•mA•fG•mA•fA |
| 120 | 1299 | fC•mA•fC•mG•fC•mC•fA•mC•fC•mA•fA•mG•fA•mC•fA |
| 121 | 1300 | fA•mC•fG•mC•fC•mA•fC•mC•fA•mA•fG•mA•fC•mC•fA |
| 122 | 1301 | fC•mG•fC•mC•fA•mC•fC•mA•fA•mG•fA•mC•fC•mG•fA |
| 123 | 1302 | fG•mC•fC•mA•fC•mC•fA•mA•fG•mA•fC•mC•fG•mC•fA |
| 124 | 1303 | fC•mC•fA•mC•fC•mA•fA•mG•fA•mC•fC•mG•fC•mC•fA |
| 125 | 1304 | fC•mA•fC•mC•fA•mA•fG•mA•fC•mC•fG•mC•fC•mA•fA |
| 126 | 1305 | fA•mC•fC•mA•fA•mG•fA•mC•fC•mG•fC•mC•fA•mA•fA |
| 127 | 1306 | fC•mC•fA•mA•fG•mA•fC•mC•fG•mC•fC•mA•fA•mG•fA |
| 128 | 1307 | fC•mA•fA•mG•fA•mC•fC•mG•fC•mC•fA•mA•fG•mG•fA |
| 129 | 1308 | fA•mA•fG•mA•fC•mC•fG•mC•fC•mA•fA•mG•fG•mA•fA |
| 130 | 1309 | fA•mG•fA•mC•fC•mG•fC•mC•fA•mA•fG•mG•fA•mU•fA |
| 131 | 1310 | fG•mA•fC•mC•fG•mC•fC•mA•fA•mG•fG•mA•fU•mG•fA |
| 132 | 1311 | fA•mC•fC•mG•fC•mC•fA•mA•fG•mG•fA•mU•fG•mC•fA |
| 133 | 1312 | fC•mC•fG•mC•fC•mA•fA•mG•fG•mA•fU•mG•fC•mA•fA |
| 134 | 1313 | fC•mG•fC•mC•fA•mA•fG•mG•fA•mU•fG•mC•fA•mC•fA |
| 135 | 1314 | fG•mC•fC•mA•fA•mG•fG•mA•fU•mG•fC•mA•fC•mU•fA |
| 136 | 1315 | fC•mC•fA•mA•fG•mG•fA•mU•fG•mC•fA•mC•fU•mG•fA |
| 137 | 1316 | fC•mA•fA•mG•fG•mA•fU•mG•fC•mA•fC•mU•fG•mA•fA |
| 138 | 1317 | fA•mA•fG•mG•fA•mU•fG•mC•fA•mC•fU•mG•fA•mG•fA |
| 139 | 1318 | fA•mG•fG•mA•fU•mG•fC•mA•fC•mU•fG•mA•fG•mC•fA |
| 140 | 1319 | fG•mG•fA•mU•fG•mC•fA•mC•fU•mG•fA•mG•fC•mA•fA |
| 141 | 1320 | fG•mA•fU•mG•fC•mA•fC•mU•fG•mA•fG•mC•fA•mG•fA |
| 142 | 1321 | fA•mU•fG•mC•fA•mC•fU•mG•fA•mG•fC•mA•fG•mC•fA |
| 143 | 1322 | fU•mG•fC•mA•fC•mU•fG•mA•fG•mC•fA•mG•fC•mG•fA |
| 144 | 1323 | fG•mC•fA•mC•fU•mG•fA•mG•fC•mA•fG•mC•fG•mU•fA |
| 145 | 1324 | fC•mA•fC•mU•fG•mA•fG•mC•fA•mG•fC•mG•fU•mG•fA |
| 146 | 1325 | fA•mC•fU•mG•fA•mG•fC•mA•fG•mC•fG•mU•fG•mC•fA |
| 147 | 1326 | fC•mU•fG•mA•fG•mC•fA•mG•fC•mG•fU•mG•fC•mA•fA |
| 148 | 1327 | fU•mG•fA•mG•fC•mA•fG•mC•fG•mU•fG•mC•fA•mG•fA |
| 149 | 1328 | fG•mA•fG•mC•fA•mG•fC•mG•fU•mG•fC•mA•fG•mG•fA |
| 150 | 1329 | fA•mG•fC•mA•fG•mC•fG•mU•fG•mC•fA•mG•fG•mA•fA |
| 151 | 1330 | fC•mA•fG•mC•fG•mU•fG•mC•fA•mG•fG•mA•fG•mU•fA |
| 152 | 1331 | fC•mG•fU•mG•fC•mA•fG•mG•fA•mG•fU•mC•fC•mC•fA |
| 153 | 1332 | fG•mU•fG•mC•fA•mG•fG•mA•fG•mU•fC•mC•fC•mA•fA |
| 154 | 1333 | fU•mG•fC•mA•fG•mG•fA•mG•fU•mC•fC•mC•fA•mG•fA |
| 155 | 1334 | fG•mC•fA•mG•fG•mA•fG•mU•fC•mC•fC•mA•fG•mG•fA |
| 156 | 1335 | fC•mA•fG•mG•fA•mG•fU•mC•fC•mC•fA•mG•fG•mU•fA |
| 157 | 1336 | fA•mG•fG•mA•fG•mU•fC•mC•fC•mA•fG•mG•fU•mG•fA |
| 158 | 1337 | fG•mG•fA•mG•fU•mC•fC•mC•fA•mG•fG•mU•fG•mG•fA |
| 159 | 1338 | fG•mU•fC•mC•fC•mA•fG•mG•fU•mG•fG•mC•fC•mC•fA |
| 160 | 1339 | fU•mC•fC•mC•fA•mG•fG•mU•fG•mG•fC•mC•fC•mA•fA |
| 161 | 1340 | fC•mA•fG•mG•fU•mG•fG•mC•fC•mC•fA•mG•fC•mA•fA |
| 162 | 1341 | fA•mG•fG•mU•fG•mG•fC•mC•fC•mA•fG•mC•fA•mG•fA |
| 163 | 1342 | fU•mG•fG•mC•fC•mC•fA•mG•fC•mA•fG•mG•fC•mC•fA |
| 164 | 1343 | fC•mC•fC•mA•fG•mC•fA•mG•fG•mC•fC•mA•fG•mG•fA |
| 165 | 1344 | fU•mG•fG•mG•fU•mG•fA•mC•fC•mG•fA•mU•fG•mG•fA |
| 166 | 1345 | fG•mG•fG•mU•fG•mA•fC•mC•fG•mA•fU•mG•fG•mC•fA |
| 167 | 1346 | fG•mG•fU•mG•fA•mC•fC•mG•fA•mU•fG•mG•fC•mU•fA |
| 168 | 1347 | fG•mU•fG•mA•fC•mC•fG•mA•fU•mG•fG•mC•fU•mU•fA |
| 169 | 1348 | fU•mG•fA•mC•fC•mG•fA•mU•fG•mG•fC•mU•fU•mC•fA |
| 170 | 1349 | fG•mA•fC•mC•fG•mA•fU•mG•fG•mC•fU•mU•fC•mA•fA |
| 171 | 1350 | fA•mC•fC•mG•fA•mU•fG•mG•fC•mU•fU•mC•fA•mG•fA |
| 172 | 1351 | fC•mC•fG•mA•fU•mG•fG•mC•fU•mU•fC•mA•fG•mU•fA |
| 173 | 1352 | fC•mG•fA•mU•fG•mG•fC•mU•fU•mC•fA•mG•fU•mU•fA |
| 174 | 1353 | fG•mA•fU•mG•fG•mC•fU•mU•fC•mA•fG•mU•fU•mC•fA |
| 175 | 1354 | fA•mU•fG•mG•fC•mU•fU•mC•fA•mG•fU•mU•fC•mC•fA |
| 176 | 1355 | fU•mG•fG•mC•fU•mU•fC•mA•fG•mU•fU•mC•fC•mC•fA |
| 177 | 1356 | fG•mG•fC•mU•fU•mC•fA•mG•fU•mU•fC•mC•fC•mU•fA |
| 178 | 1357 | fG•mC•fU•mU•fC•mA•fG•mU•fU•mC•fC•mC•fU•mG•fA |
| 179 | 1358 | fC•mU•fU•mC•fA•mG•fU•mU•fC•mC•fC•mU•fG•mA•fA |
| 180 | 1359 | fU•mU•fC•mA•fG•mU•fU•mC•fC•mC•fU•mG•fA•mA•fA |
| 181 | 1360 | fU•mC•fA•mG•fU•mU•fC•mC•fC•mU•fG•mA•fA•mA•fA |
| 182 | 1361 | fC•mA•fG•mU•fU•mC•fC•mC•fU•mG•fA•mA•fA•mG•fA |

TABLE 1d-continued

Nucleobase sequences and sugar-phosphate backbone modifications of the sense strands of 376 exemplary constructs:

| # | SEQ ID NO: | Nucleobase sequence and backbone modification |
|---|---|---|
| 183 | 1362 | fA•mG•fU•mU•fC•mC•fC•mU•fG•mA•fA•mA•fG•mA•fA |
| 184 | 1363 | fG•mU•fU•mC•fC•mC•fU•mG•fA•mA•fA•mG•fA•mC•fA |
| 185 | 1364 | fU•mU•fC•mC•fC•mU•fG•mA•fA•mA•fG•mA•fC•mU•fA |
| 186 | 1365 | fU•mC•fC•mC•fU•mG•fA•mA•fA•mG•fA•mC•fU•mA•fA |
| 187 | 1366 | fC•mC•fC•mU•fG•mA•fA•mA•fG•mA•fC•mU•fA•mC•fA |
| 188 | 1367 | fC•mC•fU•mG•fA•mA•fA•mG•fA•mC•fU•mA•fC•mU•fA |
| 189 | 1368 | fC•mU•fG•mA•fA•mA•fG•mA•fC•mU•fA•mC•fU•mG•fA |
| 190 | 1369 | fU•mG•fA•mA•fA•mG•fA•mC•fU•mA•fC•mU•fG•mG•fA |
| 191 | 1370 | fG•mA•fA•mA•fG•mA•fC•mU•fA•mC•fU•mG•fG•mA•fA |
| 192 | 1371 | fA•mA•fA•mG•fA•mC•fU•mA•fC•mU•fG•mG•fA•mG•fA |
| 193 | 1372 | fA•mA•fG•mA•fC•mU•fA•mC•fU•mG•fG•mA•fG•mC•fA |
| 194 | 1373 | fA•mG•fA•mC•fU•mA•fC•mU•fG•mG•fA•mG•fC•mA•fA |
| 195 | 1374 | fG•mA•fC•mU•fA•mC•fU•mG•fG•mA•fG•mC•fA•mC•fA |
| 196 | 1375 | fA•mC•fU•mA•fC•mU•fG•mG•fA•mG•fC•mA•fC•mC•fA |
| 197 | 1376 | fC•mU•fA•mC•fU•mG•fG•mA•fG•mC•fA•mC•fC•mG•fA |
| 198 | 1377 | fU•mA•fC•mU•fG•mG•fA•mG•fC•mA•fC•mC•fG•mU•fA |
| 199 | 1378 | fA•mC•fU•mG•fG•mA•fG•mC•fA•mC•fC•mG•fU•mU•fA |
| 200 | 1379 | fC•mU•fG•mG•fA•mG•fC•mA•fC•mC•fG•mU•fU•mA•fA |
| 201 | 1380 | fU•mG•fG•mA•fG•mC•fA•mC•fC•mG•fU•mU•fA•mA•fA |
| 202 | 1381 | fG•mG•fA•mG•fC•mA•fC•mC•fG•mU•fU•mA•fA•mG•fA |
| 203 | 1382 | fG•mA•fG•mC•fA•mC•fC•mG•fU•mU•fA•mA•fG•mG•fA |
| 204 | 1383 | fA•mG•fC•mA•fC•mC•fG•mU•fU•mA•fA•mG•fG•mA•fA |
| 205 | 1384 | fG•mC•fA•mC•fC•mG•fU•mU•fA•mA•fG•mG•fA•mC•fA |
| 206 | 1385 | fC•mA•fC•mC•fG•mU•fU•mA•fA•mG•fG•mA•fC•mA•fA |
| 207 | 1386 | fA•mC•fC•mG•fU•mU•fA•mA•fG•mG•fA•mC•fA•mA•fA |
| 208 | 1387 | fC•mC•fG•mU•fU•mA•fA•mG•fG•mA•fC•mA•fA•mG•fA |
| 209 | 1388 | fC•mG•fU•mU•fA•mA•fG•mG•fA•mC•fA•mA•fG•mU•fA |
| 210 | 1389 | fG•mU•fU•mA•fA•mG•fG•mA•fC•mA•fA•mG•fU•mU•fA |
| 211 | 1390 | fU•mU•fA•mA•fG•mG•fA•mC•fA•mA•fG•mU•fU•mC•fA |
| 212 | 1391 | fU•mA•fA•mG•fG•mA•fC•mA•fA•mG•fU•mU•fC•mU•fA |
| 213 | 1392 | fA•mA•fG•mG•fA•mC•fA•mA•fG•mU•fU•mC•fU•mC•fA |
| 214 | 1393 | fA•mG•fG•mA•fC•mA•fA•mG•fU•mU•fC•mU•fC•mU•fA |
| 215 | 1394 | fG•mG•fA•mC•fA•mA•fG•mU•fU•mC•fU•mC•fU•mG•fA |
| 216 | 1395 | fG•mA•fC•mA•fA•mG•fU•mU•fC•mU•fC•mU•fG•mA•fA |
| 217 | 1396 | fA•mC•fA•mA•fG•mU•fU•mC•fU•mC•fU•mG•fA•mG•fA |
| 218 | 1397 | fC•mA•fA•mG•fU•mU•fC•mU•fC•mU•fG•mA•fG•mU•fA |
| 219 | 1398 | fA•mA•fG•mU•fU•mC•fU•mC•fU•mG•fA•mG•fU•mU•fA |
| 220 | 1399 | fA•mG•fU•mU•fC•mU•fC•mU•fG•mA•fG•mU•fU•mC•fA |
| 221 | 1400 | fU•mU•fC•mU•fC•mU•fG•mA•fG•mU•fU•mC•fU•mG•fA |
| 222 | 1401 | fU•mC•fU•mC•fU•mG•fA•mG•fU•mU•fC•mU•fG•mG•fA |
| 223 | 1402 | fC•mU•fC•mU•fG•mA•fG•mU•fU•mC•fU•mG•fG•mG•fA |
| 224 | 1403 | fU•mC•fU•mG•fA•mG•fU•mU•fC•mU•fG•mG•fG•mA•fA |
| 225 | 1404 | fC•mU•fG•mA•fG•mU•fU•mC•fU•mG•fG•mG•fA•mU•fA |
| 226 | 1405 | fU•mG•fA•mG•fU•mU•fC•mU•fG•mG•fG•mA•fU•mU•fA |
| 227 | 1406 | fG•mA•fG•mU•fU•mC•fU•mG•fG•mG•fA•mU•fU•mU•fA |
| 228 | 1407 | fA•mG•fU•mU•fC•mU•fG•mG•fG•mA•fU•mU•fU•mG•fA |
| 229 | 1408 | fG•mU•fU•mC•fU•mG•fG•mG•fA•mU•fU•mU•fG•mG•fA |
| 230 | 1409 | fU•mU•fC•mU•fG•mG•fG•mA•fU•mU•fU•mG•fG•mA•fA |
| 231 | 1410 | fU•mC•fU•mG•fG•mG•fA•mU•fU•mU•fG•mG•fA•mC•fA |
| 232 | 1411 | fC•mU•fG•mG•fG•mA•fU•mU•fU•mG•fG•mA•fC•mC•fA |
| 233 | 1412 | fU•mG•fG•mG•fA•mU•fU•mU•fG•mG•fA•mC•fC•mC•fA |
| 234 | 1413 | fG•mG•fG•mA•fU•mU•fU•mG•fG•mA•fC•mC•fC•mU•fA |
| 235 | 1414 | fG•mG•fA•mU•fU•mU•fG•mG•fA•mC•fC•mC•fU•mG•fA |
| 236 | 1415 | fG•mA•fU•mU•fU•mG•fG•mA•fC•mC•fC•mU•fG•mA•fA |
| 237 | 1416 | fU•mG•fG•mA•fC•mC•fC•mU•fG•mA•fG•mG•fU•mC•fA |
| 238 | 1417 | fG•mG•fA•mC•fC•mC•fU•mG•fA•mG•fG•mU•fC•mA•fA |
| 239 | 1418 | fG•mA•fC•mC•fC•mU•fG•mA•fG•mG•fU•mC•fA•mG•fA |
| 240 | 1419 | fA•mC•fC•mC•fU•mG•fA•mG•fG•mU•fC•mA•fG•mA•fA |
| 241 | 1420 | fC•mC•fC•mU•fG•mA•fG•mG•fU•mC•fA•mG•fA•mC•fA |
| 242 | 1421 | fC•mC•fU•mG•fA•mG•fG•mU•fC•mA•fG•mA•fC•mC•fA |
| 243 | 1422 | fC•mU•fG•mA•fG•mG•fU•mC•fA•mG•fA•mC•fC•mA•fA |
| 244 | 1423 | fU•mG•fA•mG•fG•mU•fC•mA•fG•mA•fC•mC•fA•mA•fA |
| 245 | 1424 | fG•mA•fG•mG•fU•mC•fA•mG•fA•mC•fC•mA•fA•mC•fA |
| 246 | 1425 | fA•mG•fG•mU•fC•mA•fG•mA•fC•mC•fA•mA•fC•mU•fA |
| 247 | 1426 | fG•mG•fU•mC•fA•mG•fA•mC•fC•mA•fA•mC•fU•mU•fA |
| 248 | 1427 | fG•mU•fC•mA•fG•mA•fC•mC•fA•mA•fC•mU•fU•mC•fA |
| 249 | 1428 | fU•mC•fA•mG•fA•mC•fC•mA•fA•mC•fU•mU•fC•mA•fA |
| 250 | 1429 | fC•mA•fG•mA•fC•mC•fA•mA•fC•mU•fU•mC•fA•mG•fA |
| 251 | 1430 | fG•mA•fC•mC•fA•mA•fC•mU•fU•mC•fA•mG•fC•mC•fA |
| 252 | 1431 | fA•mC•fC•mA•fA•mC•fU•mU•fC•mA•fG•mC•fC•mG•fA |
| 253 | 1432 | fC•mC•fA•mA•fC•mU•fU•mC•fA•mG•fC•mC•fG•mU•fA |
| 254 | 1433 | fC•mA•fA•mC•fU•mU•fC•mA•fG•mC•fC•mG•fU•mG•fA |
| 255 | 1434 | fA•mA•fC•mU•fU•mC•fA•mG•fC•mC•fG•mU•fG•mG•fA |
| 256 | 1435 | fA•mC•fU•mU•fC•mA•fG•mC•fC•mG•fU•mG•fG•mC•fA |
| 257 | 1436 | fU•mU•fC•mA•fG•mC•fC•mG•fU•mG•fG•mC•fU•mG•fA |
| 258 | 1437 | fU•mC•fA•mG•fC•mC•fG•mU•fG•mG•fC•mU•fG•mC•fA |
| 259 | 1438 | fC•mA•fG•mC•fC•mG•fU•mG•fG•mC•fU•mG•fC•mC•fA |
| 260 | 1439 | fA•mG•fC•mC•fG•mU•fG•mG•fC•mU•fG•mC•fC•mU•fA |
| 261 | 1440 | fG•mC•fC•mG•fU•mG•fG•mC•fU•mG•fC•mC•fU•mG•fA |
| 262 | 1441 | fG•mU•fG•mG•fC•mU•fG•mC•fC•mU•fG•mA•fG•mA•fA |
| 263 | 1442 | fU•mG•fG•mC•fU•mG•fC•mC•fU•mG•fA•mG•fA•mC•fA |
| 264 | 1443 | fG•mG•fC•mU•fG•mC•fC•mU•fG•mA•fG•mA•fC•mC•fA |
| 265 | 1444 | fG•mC•fU•mG•fC•mC•fU•mG•fA•mG•fA•mC•fC•mU•fA |
| 266 | 1445 | fU•mG•fC•mC•fU•mG•fA•mG•fA•mC•fC•mU•fC•mA•fA |
| 267 | 1446 | fG•mC•fC•mU•fG•mA•fG•mA•fC•mC•fU•mC•fA•mA•fA |
| 268 | 1447 | fC•mC•fU•mG•fA•mG•fA•mC•fC•mU•fC•mA•fA•mU•fA |
| 269 | 1448 | fC•mU•fG•mA•fG•mA•fC•mC•fU•mC•fA•mA•fU•mA•fA |
| 270 | 1449 | fU•mG•fA•mG•fA•mC•fC•mU•fC•mA•fA•mU•fA•mC•fA |
| 271 | 1450 | fG•mA•fG•mA•fC•mC•fU•mC•fA•mA•fU•mA•fC•mC•fA |
| 272 | 1451 | fA•mG•fA•mC•fC•mU•fC•mA•fA•mU•fA•mC•fC•mC•fA |
| 273 | 1452 | fA•mG•fU•mC•fC•mA•fC•mC•fU•mG•fC•mC•fU•mA•fA |
| 274 | 1453 | fG•mU•fC•mC•fA•mC•fC•mU•fG•mC•fC•mU•fA•mU•fA |
| 275 | 1454 | fU•mC•fC•mA•fC•mC•fU•mG•fC•mC•fU•mA•fU•mC•fA |
| 276 | 1455 | fC•mC•fA•mC•fC•mU•fG•mC•fC•mU•fA•mU•fC•mC•fA |
| 277 | 1456 | fC•mA•fC•mC•fU•mG•fC•mC•fU•mA•fU•mC•fC•mA•fA |
| 278 | 1457 | fA•mC•fC•mU•fG•mC•fC•mU•fA•mU•fC•mC•fA•mU•fA |
| 279 | 1458 | fC•mC•fU•mG•fC•mC•fU•mA•fU•mC•fC•mA•fU•mC•fA |
| 280 | 1459 | fC•mU•fG•mC•fC•mU•fA•mU•fC•mC•fA•mU•fC•mC•fA |
| 281 | 1460 | fU•mG•fC•mC•fU•mA•fU•mC•fC•mA•fU•mC•fC•mU•fA |
| 282 | 1461 | fG•mC•fC•mU•fA•mU•fC•mC•fA•mU•fC•mC•fU•mG•fA |
| 283 | 1462 | fC•mC•fU•mA•fU•mC•fC•mA•fU•mC•fC•mU•fG•mC•fA |
| 284 | 1463 | fC•mU•fA•mU•fC•mC•fA•mU•fC•mC•fU•mG•fC•mG•fA |
| 285 | 1464 | fU•mA•fU•mC•fC•mA•fU•mC•fC•mU•fG•mC•fG•mA•fA |
| 286 | 1465 | fA•mU•fC•mC•fA•mU•fC•mC•fU•mG•fC•mG•fA•mG•fA |
| 287 | 1466 | fU•mC•fC•mA•fU•mC•fC•mU•fG•mC•fG•mA•fG•mC•fA |
| 288 | 1467 | fC•mC•fA•mU•fC•mC•fU•mG•fC•mG•fA•mG•fC•mU•fA |
| 289 | 1468 | fC•mA•fU•mC•fC•mU•fG•mC•fG•mA•fG•mC•fU•mC•fA |
| 290 | 1469 | fA•mU•fC•mC•fU•mG•fC•mG•fA•mG•fC•mU•fC•mC•fA |
| 291 | 1470 | fU•mC•fC•mU•fG•mC•fG•mA•fG•mC•fU•mC•fC•mU•fA |
| 292 | 1471 | fC•mC•fU•mG•fC•mG•fA•mG•fC•mU•fC•mC•fU•mU•fA |
| 293 | 1472 | fC•mU•fG•mC•fG•mA•fG•mC•fU•mC•fC•mU•fU•mG•fA |
| 294 | 1473 | fU•mG•fC•mG•fA•mG•fC•mU•fC•mC•fU•mU•fG•mG•fA |
| 295 | 1474 | fG•mC•fG•mA•fG•mC•fU•mC•fC•mU•fU•mG•fG•mG•fA |
| 296 | 1475 | fC•mG•fA•mG•fC•mU•fC•mC•fU•mU•fG•mG•fG•mU•fA |
| 297 | 1476 | fG•mA•fG•mC•fU•mC•fC•mU•fU•mG•fG•mG•fU•mC•fA |
| 298 | 1477 | fA•mG•fC•mU•fC•mC•fU•mU•fG•mG•fG•mU•fC•mC•fA |
| 299 | 1478 | fG•mC•fU•mC•fC•mU•fU•mG•fG•mG•fU•mC•fC•mU•fA |
| 300 | 1479 | fC•mU•fC•mC•fU•mU•fG•mG•fG•mU•fC•mC•fU•mG•fA |
| 301 | 1480 | fU•mC•fC•mU•fU•mG•fG•mG•fU•mC•fC•mU•fG•mC•fA |
| 302 | 1481 | fC•mC•fU•mU•fG•mG•fG•mU•fC•mC•fU•mG•fC•mA•fA |
| 303 | 1482 | fC•mU•fU•mG•fG•mG•fU•mC•fC•mU•fG•mC•fA•mA•fA |
| 304 | 1483 | fU•mU•fG•mG•fG•mU•fC•mC•fU•mG•fC•mA•fA•mU•fA |
| 305 | 1484 | fU•mG•fG•mG•fU•mC•fC•mU•fG•mC•fA•mA•fU•mC•fA |
| 306 | 1485 | fG•mG•fG•mU•fC•mC•fU•mG•fC•mA•fA•mU•fC•mU•fA |
| 307 | 1486 | fG•mG•fU•mC•fC•mU•fG•mC•fA•mA•fU•mC•fU•mC•fA |
| 308 | 1487 | fG•mU•fC•mC•fU•mG•fC•mA•fA•mU•fC•mU•fC•mC•fA |
| 309 | 1488 | fU•mC•fC•mU•fG•mC•fA•mA•fU•mC•fU•mC•fC•mA•fA |
| 310 | 1489 | fC•mC•fU•mG•fC•mA•fA•mU•fC•mU•fC•mC•fA•mG•fA |
| 311 | 1490 | fC•mU•fG•mC•fA•mA•fU•mC•fU•mC•fC•mA•fG•mG•fA |
| 312 | 1491 | fU•mG•fC•mA•fA•mU•fC•mU•fC•mC•fA•mG•fG•mG•fA |
| 313 | 1492 | fG•mC•fA•mA•fU•mC•fU•mC•fC•mA•fG•mG•fG•mC•fA |
| 314 | 1493 | fC•mA•fA•mU•fC•mU•fC•mC•fA•mG•fG•mG•fC•mU•fA |
| 315 | 1494 | fA•mA•fU•mC•fU•mC•fC•mA•fG•mG•fG•mC•fU•mG•fA |
| 316 | 1495 | fA•mU•fC•mU•fC•mC•fA•mG•fG•mG•fC•mU•fG•mC•fA |
| 317 | 1496 | fU•mC•fU•mC•fC•mA•fG•mG•fG•mC•fU•mG•fC•mC•fA |
| 318 | 1497 | fC•mU•fC•mC•fA•mG•fG•mG•fC•mU•fG•mC•fC•mC•fA |
| 319 | 1498 | fG•mU•fA•mG•fG•mU•fU•mG•fC•mU•fU•mA•fA•mA•fA |
| 320 | 1499 | fU•mA•fG•mG•fU•mU•fG•mC•fU•mU•fA•mA•fA•mA•fA |
| 321 | 1500 | fA•mG•fG•mU•fU•mG•fC•mU•fU•mA•fA•mA•fA•mG•fA |
| 322 | 1501 | fG•mG•fU•mU•fG•mC•fU•mU•fA•mA•fA•mA•fG•mG•fA |
| 323 | 1502 | fG•mU•fU•mG•fC•mU•fU•mA•fA•mA•fA•mG•fG•mG•fA |
| 324 | 1503 | fU•mU•fG•mC•fU•mU•fA•mA•fA•mA•fG•mG•fG•mA•fA |
| 325 | 1504 | fU•mG•fC•mU•fU•mA•fA•mA•fA•mG•fG•mG•fA•mC•fA |
| 326 | 1505 | fU•mU•fA•mA•fA•mA•fG•mG•fG•mA•fC•mA•fG•mU•fA |
| 327 | 1506 | fU•mA•fA•mA•fA•mG•fG•mG•fA•mC•fA•mG•fU•mA•fA |
| 328 | 1507 | fA•mA•fA•mA•fG•mG•fG•mA•fC•mA•fG•mU•fA•mU•fA |

TABLE 1d-continued

| Nucleobase sequences and sugar-phosphate backbone modifications of the sense strands of 376 exemplary constructs: | | |
|---|---|---|
| # | SEQ ID NO: | Nucleobase sequence and backbone modification |
| 329 | 1508 | fA•mA•fA•mG•fG•mG•fA•mC•fA•mG•fU•mA•fU•mU•fA |
| 330 | 1509 | fA•mA•fG•mG•fG•mA•fC•mA•fG•mU•fA•mU•fU•mC•fA |
| 331 | 1510 | fA•mG•fG•mG•fA•mC•fA•mG•fU•mA•fU•mU•fC•mU•fA |
| 332 | 1511 | fG•mG•fG•mA•fC•mA•fG•mU•fA•mU•fU•mC•fU•mC•fA |
| 333 | 1512 | fG•mG•fA•mC•fA•mG•fU•mA•fU•mU•fC•mU•fC•mA•fA |
| 334 | 1513 | fG•mA•fC•mA•fG•mU•fA•mU•fU•mC•fU•mC•fA•mG•fA |
| 335 | 1514 | fA•mC•fA•mG•fU•mA•fU•mU•fC•mU•fC•mA•fG•mU•fA |
| 336 | 1515 | fC•mA•fG•mU•fA•mU•fU•mC•fU•mC•fA•mG•fU•mG•fA |
| 337 | 1516 | fA•mG•fU•mA•fU•mU•fC•mU•fC•mA•fG•mU•fG•mC•fA |
| 338 | 1517 | fG•mU•fA•mU•fU•mC•fU•mC•fA•mG•fU•mG•fC•mU•fA |
| 339 | 1518 | fU•mA•fU•mU•fC•mU•fC•mA•fG•mU•fG•mC•fU•mC•fA |
| 340 | 1519 | fA•mU•fU•mC•fU•mC•fA•mG•fU•mG•fC•mU•fC•mU•fA |
| 341 | 1520 | fU•mU•fC•mU•fC•mA•fG•mU•fG•mC•fU•mC•fU•mC•fA |
| 342 | 1521 | fU•mC•fU•mC•fA•mG•fU•mG•fC•mU•fC•mU•fC•mC•fA |
| 343 | 1522 | fC•mU•fC•mA•fG•mU•fG•mC•fU•mC•fU•mC•fC•mU•fA |
| 344 | 1523 | fU•mC•fA•mG•fU•mG•fC•mU•fC•mU•fC•mC•fU•mA•fA |
| 345 | 1524 | fC•mA•fG•mU•fG•mC•fU•mC•fU•mC•fC•mU•fA•mC•fA |
| 346 | 1525 | fA•mG•fU•mG•fC•mU•fC•mU•fC•mC•fU•mA•fC•mC•fA |
| 347 | 1526 | fG•mU•fG•mC•fU•mC•fU•mC•fC•mU•fA•mC•fC•mC•fA |
| 348 | 1527 | fC•mC•fU•mC•fA•mU•fG•mC•fC•mU•fG•mG•fC•mC•fA |
| 349 | 1528 | fC•mU•fC•mA•fU•mG•fC•mC•fU•mG•fG•mC•fC•mC•fA |
| 350 | 1529 | fC•mC•fA•mG•fG•mC•fA•mU•fG•mC•fU•mG•fG•mC•fA |
| 351 | 1530 | fC•mA•fG•mG•fC•mA•fU•mG•fC•mU•fG•mG•fC•mC•fA |
| 352 | 1531 | fA•mG•fG•mC•fA•mU•fG•mC•fU•mG•fG•mC•fC•mU•fA |
| 353 | 1532 | fG•mG•fC•mA•fU•mG•fC•mU•fG•mG•fC•mC•fU•mC•fA |
| 354 | 1533 | fG•mC•fA•mU•fG•mC•fU•mG•fG•mC•fC•mU•fC•mC•fA |
| 355 | 1534 | fC•mA•fU•mG•fC•mU•fG•mG•fC•mC•fU•mC•fC•mC•fA |
| 356 | 1535 | fA•mU•fG•mC•fU•mG•fG•mC•fC•mU•fC•mC•fC•mA•fA |
| 357 | 1536 | fG•mC•fU•mG•fG•mC•fC•mU•fC•mC•fC•mA•fA•mU•fA |
| 358 | 1537 | fC•mU•fG•mG•fC•mC•fU•mC•fC•mC•fA•mA•fU•mA•fA |
| 359 | 1538 | fU•mG•fG•mC•fC•mU•fC•mC•fC•mA•fA•mU•fA•mA•fA |
| 360 | 1539 | fG•mG•fC•mC•fU•mC•fC•mC•fA•mA•fU•mA•fA•mA•fA |
| 361 | 1540 | fG•mC•fC•mU•fC•mC•fC•mA•fA•mU•fA•mA•fA•mG•fA |
| 362 | 1541 | fC•mC•fU•mC•fC•mC•fA•mA•fU•mA•fA•mA•fG•mC•fA |
| 363 | 1542 | fC•mU•fC•mC•fC•mA•fA•mU•fA•mA•fA•mG•fC•mU•fA |
| 364 | 1543 | fU•mC•fC•mC•fA•mA•fU•mA•fA•mA•fG•mC•fU•mG•fA |
| 365 | 1544 | fC•mC•fC•mA•fA•mU•fA•mA•fA•mG•fC•mU•fG•mG•fA |
| 366 | 1545 | fC•mC•fA•mA•fU•mA•fA•mA•fG•mC•fU•mG•fG•mA•fA |
| 367 | 1546 | fC•mA•fA•mU•fA•mA•fA•mG•fC•mU•fG•mG•fA•mC•fA |
| 368 | 1547 | fA•mU•fA•mA•fA•mG•fC•mU•fG•mG•fA•mC•fA•mA•fA |
| 369 | 1548 | fU•mA•fA•mA•fG•mC•fU•mG•fG•mA•fC•mA•fA•mG•fA |
| 370 | 1549 | fA•mA•fA•mG•fC•mU•fG•mG•fA•mC•fA•mA•fG•mA•fA |
| 371 | 1550 | fA•mA•fG•mC•fU•mG•fG•mA•fC•mA•fA•mG•fA•mA•fA |
| 372 | 1551 | fA•mG•fC•mU•fG•mG•fA•mC•fA•mA•fG•mA•fA•mG•fA |
| 373 | 1552 | fG•mC•fU•mG•fG•mA•fC•mA•fA•mG•fA•mA•fG•mC•fA |
| 374 | 1553 | fG•mG•fA•mC•fA•mA•fG•mA•fA•mG•fC•mU•fG•mC•fA |
| 375 | 1554 | fA•mC•fA•mA•fG•mA•fA•mG•fC•mU•fG•mC•fU•mA•fA |
| 376 | 1555 | fC•mA•fA•mG•fA•mA•fG•mC•fU•mG•fC•mU•fA•mU•fA |

Tables 2a to 2d below show nucleobase sequences and sugar-phosphate backbone modifications of antisense and sense strands of a further 15 exemplary constructs. For corresponding entries in the sequence listing, the following applies: entry number in Table 2a+376=entry number in the sequence listing; entry number in Table 2c+776=entry number in the sequence listing.

TABLE 2a

| Nucleobase sequences of the antisense strands of 15 further exemplary constructs | | |
|---|---|---|
| # | SEQ ID NO: | AS unmodified |
| 1 | 377 | UAACUCAGAGAACUUGUCC |
| 2 | 378 | UUGUCCUUAACGGUGCUCC |
| 3 | 379 | UAAUCCCAGAACUCAGAGA |
| 4 | 380 | UCCUUGGCGGUCUUGGUGG |
| 5 | 381 | UCUGAAGCCAUCGGUCACC |
| 6 | 382 | UCAGAGAACUUGUCCUUAA |
| 7 | 383 | UACUCAGAGAACUUGUCCU |
| 8 | 384 | UGAACUCAGAGAACUUGUC |
| 9 | 385 | UACUUGUCCUUAACGGUGC |
| 10 | 386 | UCUCAGAGAACUUGUCCUU |
| 11 | 387 | UUUGUCCUUAACGGUGCUC |
| 12 | 388 | UUCCUUGGCGGUCUUGGUG |
| 13 | 389 | UGCUCCAGUAGUCUUUCAG |
| 14 | 390 | UCAUCCUCGGCCUCUGAAG |
| 15 | 391 | UUGGUGGCGUGCUUCAUGU |

TABLE 2b

| Nucleobase sequences and sugar-phosphate backbone modifications of the antisense strands of 15 further exemplary constructs: | | |
|---|---|---|
| # | SEQ ID NO: | Antisense strand modified |
| 1 | 1556 | [mU][#][fA][#][mA][#][fC][mU][fC][mA][fG][mA][fG][mA][fA][mC][fU][#][mU][#][fG][#][mU][#][fC][#]rC |
| 2 | 1557 | [mU][#][fU][#][mG][#][fU][mC][fC][mU][fU][mA][fA][mC][fG][mG][fU][#][mG][#][fC][#][mU][#][fC][#]rC |
| 3 | 1558 | [mU][#][fA][#][mA][#][fU][mC][fC][mC][fA][mG][fA][mA][fC][mU][fC][#][mA][#][fG][#][mA][#][fG][#]rA |
| 4 | 1559 | [mU][#][fC][#][mC][#][fU][mU][fG][mG][fC][mG][fG][mU][fC][mU][fU][#][mG][#][fG][#][mU][#][fG][#]rG |
| 5 | 1560 | [mU][#][fC][#][mU][#][fG][mA][fA][mG][fC][mC][fA][mU][fC][mG][fG][#][mU][#][fC][#][mA][#][fC][#]rC |
| 6 | 1561 | [mU][#][fC][#][mA][#][fG][mA][fG][mA][fA][mC][fU][mU][fG][mU][fC][#][mC][#][fU][#][mU][#][fA][#]rA |
| 7 | 1562 | [mU][#][fA][#][mC][#][fU][mC][fA][mG][fA][mG][fA][mA][fC][mU][fU][#][mG][#][fU][#][mC][#][fC][#]rU |
| 8 | 1563 | [mU][#][fG][#][mA][#][fA][mC][fU][mC][fA][mG][fA][mG][fA][mA][fC][#][mU][#][fU][#][mG][#][fU][#]rC |
| 9 | 1564 | [mU][#][fA][#][mC][#][fU][mU][fG][mU][fC][mC][fU][mU][fA][mA][fC][#][mG][#][fG][#][mU][#][fG][#]rC |

TABLE 2b-continued

Nucleobase sequences and sugar-phosphate backbone modifications of the antisense strands of 15 further exemplary constructs:

| # | SEQ ID NO: | Antisense strand modified |
|---|---|---|
| 10 | 1565 | [mU][#][fC][#][mU][#][fC][mA][fG][mA][fG][mA][fA][mC][fU][mU][fG][#][mU][#][fC][#][mC][#][fU][#]rU |
| 11 | 1566 | [mU][#][fU][#][mU][#][fG][mU][fC][mC][fU][mU][fA][mA][fC][mG][fG][#][mU][#][fG][#][mC][#][fU][#]rC |
| 12 | 1567 | [mU][#][fU][#][mC][#][fC][mU][fU][mG][fG][mC][fG][mG][fU][mC][fU][#][mU][#][fG][#][mG][#][fU][#]rG |
| 13 | 1568 | [mU][#][fG][#][mC][#][fU][mC][fC][mA][fG][mU][fA][mG][fU][mC][fU][#][mU][#][fU][#][mC][#][fA][#]rG |
| 14 | 1569 | [mU][#][fC][#][mA][#][fU][mC][fC][mU][fC][mG][fG][mC][fC][mU][fC][#][mU][#][fG][#][mA][#][fA][#]rG |
| 15 | 1570 | [mU][#][fU][#][mG][#][fG][mU][fG][mG][fC][mG][fU][mG][fC][mU][fU][#][mC][#][fA][#][mU][#][fG][#]rU |

TABLE 2c

Nucleobase sequences of the sense strands of 15 further exemplary constructs

| # | SEQ ID NO: | SS unmodified |
|---|---|---|
| 1 | 777 | AGUUCUCUGAGUUA |
| 2 | 778 | ACCGUUAAGGACAA |
| 3 | 779 | GAGUUCUGGGAUUA |
| 4 | 780 | AAGACCGCCAAGGA |
| 5 | 781 | CCGAUGGCUUCAGA |
| 6 | 782 | GACAAGUUCUCUGA |
| 7 | 783 | AAGUUCUCUGAGUA |
| 8 | 784 | GUUCUCUGAGUUCA |

TABLE 2c-continued

Nucleobase sequences of the sense strands of 15 further exemplary constructs

| # | SEQ ID NO: | SS unmodified |
|---|---|---|
| 9 | 785 | GUUAAGGACAAGUA |
| 10 | 786 | CAAGUUCUCUGAGA |
| 11 | 787 | CCGUUAAGGACAAA |
| 12 | 788 | AGACCGCCAAGGAA |
| 13 | 789 | AGACUACUGGAGCA |
| 14 | 790 | GAGGCCGAGGAUGA |
| 15 | 791 | AAGCACGCCACCAA |

TABLE 2d

Nucleobase sequences and sugar-phosphate backbone modifications of the sense strands of 15 further exemplary constructs:

| # | SEQ ID NO: | Sense strand modified |
|---|---|---|
| 1 | 1571 | [mA][#][fG][#][mU][fU][mC][fU][mC][fU][mG][fA][mG][fU][#][mU][#][fA][#][3 × GalNac] |
| 2 | 1572 | [mA][#][fC][#][mC][fG][mU][fU][mA][fA][mG][fG][mA][fC][#][mA][#][fA][#][3 × GalNac] |
| 3 | 1573 | [mG][#][fA][#][mG][fU][mU][fC][mU][fG][mG][fG][mA][fU][#][mU][#][fA][#][3 × GalNac] |
| 4 | 1574 | [mA][#][fA][#][mG][fA][mC][fC][mG][fC][mC][fA][mA][fG][#][mG][#][fA][#][3 × GalNac] |
| 5 | 1575 | [mC][#][fC][#][mG][fA][mU][fG][mG][fC][mU][fU][mC][fA][#][mG][#][fA][#][3 × GalNac] |
| 6 | 1576 | [mG][#][fA][#][mC][fA][mA][fG][mU][fU][mC][fU][mC][fU][#][mG][#][fA][#][3 × GalNac] |
| 7 | 1577 | [mA][#][fA][#][mG][fU][mU][fC][mU][fC][mU][fG][mA][fG][#][mU][#][fA][#][3 × GalNac] |
| 8 | 1578 | [mG][#][fU][#][mU][fC][mU][fC][mU][fG][mA][fG][mU][fU][#][mC][#][fA][#][3 × GalNac] |
| 9 | 1579 | [mG][#][fU][#][mU][fA][mA][fG][mG][fA][mC][fA][mA][fG][#][mU][#][fA][#][3 × GalNac] |
| 10 | 1580 | [mC][#][fA][#][mA][fG][mU][fU][mC][fU][mC][fU][mG][fA][#][mG][#][fA][#][3 × GalNac] |
| 11 | 1581 | [mC][#][fC][#][mG][fU][mU][fA][mA][fG][mG][fA][mC][fA][#][mA][#][fA][#][3 × GalNac] |
| 12 | 1582 | [mA][#][fG][#][mA][fC][mC][fG][mC][fC][mA][fA][mG][fG][#][mA][#][fA][#][3 × GalNac] |
| 13 | 1583 | [mA][#][fG][#][mA][fC][mU][fA][mC][fU][mG][fG][mA][fG][#][mC][#][fA][#][3 × GalNac] |
| 14 | 1584 | [mG][#][fA][#][mG][fG][mC][fC][mG][fA][mG][fG][mA][fU][#][mG][#][fA][#][3 × GalNac] |

TABLE 2d-continued

| Nucleobase sequences and sugar-phosphate backbone modifications of the sense strands of 15 further exemplary constructs: | | |
|---|---|---|
| # | SEQ ID NO: | Sense strand modified |
| 15 | 1585 | [mA][#][fA][#][mG][fC][mA][fC][mG][fC][mC][fA][mC][fC][#][mA][#][fA][#][3 × GalNac] |

TABLE 3a

| Nucleobase sequences of the strands of 12 further exemplary constructs. | | |
|---|---|---|
| # | SEQ ID NO: | Strands unmodified |
| A277(15) | 792 | uuggauaggc agguggacuc accugccuau ccaa |
| A28(15) | 793 | ucaacaagga guacccgggg guacuccuug uuga |
| A277(14) | 794 | uuggauaggc agguggacua ccugccuauc caa |
| A28(14) | 795 | ucaacaagga guacccgggg uacuccuugu uga |
| A277(12-5) | 796 | uuggauaggc agguggacug ccuauccaa |
| A277(13-4) | 797 | uuggauaggc agguggacuu gccuauccaa |
| A28(14-4) | 798 | ucaacaagga guacccgggu acuccuuguu ga |
| A277(14)mF | 799 | uuggauaggc agguggacua ccugccuauc caa |
| A28(14)mF | 800 | ucaacaagga guacccgggg uacuccuugu uga |
| A277(12-5)mF | 801 | uuggauaggc agguggacug ccuauccaa |
| A277(13-4)mF | 802 | uuggauaggc agguggacuu gccuauccaa |
| A28(14-4)mF | 803 | ucaacaagga guacccgggu acuccuuguu ga |

Tables 3a to 3b below show nucleobase sequences and sugar-phosphate backbone modifications of 12 further exemplary constructs.

TABLE 3b

| Nucleobase sequences and sugar-phosphate backbone modifications of the strands of 12 further exemplary constructs: | | |
|---|---|---|
| # | SEQ ID NO: | Strands modified |
| A277(15) | 1586 | [mU][#][fU][#][mG][fG][mA][fU][mA][fG][mG][fC][mA][fG][mG][fU][mG][#][fG][#][mA][#][fC][#][mU][#][fC][mA][fC][mC][fU][mG][fC][mC][fU][mA][fU][mC][mC][#][mA][#][mA][#][3 × GalNAc] |
| A28(15) | 1587 | [mU][#][fC][#][mA][fA][mC][fA][mA][fG][mG][fA][mG][fU][mA][fC][mC][#][fC][#][mG][#][fG][#][mG][#][fG][mG][fU][mA][fC][mU][fC][mC][fU][mU][fG][mU][mU][#][mG][#][mA][#][3 × GalNAc] |
| A277(14) | 1588 | [mU][#][fU][#][mG][fG][mA][fU][mA][fG][mG][fC][mA][fG][mG][fU][#][mG][#][fG][#][mA][#][fC][#][mU][#][mA][fC][mC][fU][mG][fC][mC][fU][mA][fU][mC][mC][#][mA][#][mA][#][3 × GalNAc] |
| A28(14) | 1589 | [mU][#][fC][#][mA][fA][mC][fA][mA][fG][mG][fA][mG][fU][mA][fC][#][mC][#][fC][#][mG][#][fG][#][mG][#][mG][fU][mA][fC][mU][fC][mC][fU][mU][fG][mU][mU][#][mG][#][mA][#][3 × GalNAc] |
| A277(12-5) | 1590 | [mU][#][fU][#][mG][fG][mA][fU][mA][fG][mG][fC][mA][fG][#][mG][#][fU][mG][#][fG][#][mA][#][fC][fU][mG][fC][mC][fU][mA][fU][mC][mC][#][mA][#][mA][#][3 × GalNAc] |
| A277(13-4) | 1591 | [mU][#][fU][#][mG][fG][mA][fU][mA][fG][mG][fC][mA][fG][mG][#][fU][#][mG][#][fG][#][mA][#][fC][mU][fU][mG][fC][mC][fU][mA][fU][mC][mC][#][mA][#][mA][#][3 × GalNac] |
| A28(14-4) | 1592 | [mU][#][fC][#][mA][fA][mC][fA][mA][fG][mG][fA][mG][fU][mA][fC][#][mC][#][fC][#][mG][#][fG][#][mG][fU][mA][fC][mU][fC][mC][fU][mU][fG][mU][mU][#][mG][#][mA][#][3 × GalNAc] |
| A277(14)mF | 1593 | [mU][#][fU][#][mG][mG][mA][mU][mA][mG][mG][mC][mA][mG][mG][fU][#][mG][#][mG][#][mA][#][mC][#][mU][#][mA][fC][fC][fU][mG][mC][mC][mU][mA][mU][mC][mC][#][mA][#][mA][#][3 × GalNac] |
| A28(14)mF | 1594 | [mU][#][fC][#][mA][mA][mC][mA][mA][mG][mG][mA][mG][mU][mA][fC][#][mC][#][mC][#][mG][#][mG][#][mG][#][mG][fU][fA][fC][mU][mC][mC][mU][mU][mG][mU][mU][#][mG][#][mA][#][3 × GalNAc] |
| A277(12-5) mF | 1595 | [mU][#][fU][#][mG][mG][mA][mU][mA][mG][mG][mC][mA][mG][#][mG][#][fU][mG][#][mG][#][fA][#][fC][fU][mG][mC][mC][mU][mA][mU][mC][mC][#][mA][#][mA][#][3 × GalNAc] |
| A277(13-4) mF | 1596 | [mU][#][fU][#][mG][mG][mA][mU][mA][mG][mG][mC][mA][mG][mG][#][fU][#][mG][#][mG][#][mA][#][fC][fU][fU][mG][mC][mC][mU][mA][mU][mC][mC][#][mA][#][mA][#][3 × GalNAc] |

TABLE 3b-continued

| Nucleobase sequences and sugar-phosphate backbone modifications of the strands of 12 further exemplary constructs: | | |
|---|---|---|
| # | SEQ ID NO: | Strands modified |
| A28(14-4)mF | 1597 | [mU][#][fC][#][mA][mA][mC][mA][mA][mG][mG][mA][mG][mU][mA][fC][#][mC][#][mC][#][mG][#][mG][#][mG][fU][fA][fC][mU][mC][mC][mU][mU][mG][mU][mU][#][mG][#][mA][#][3 × GalNAc] |

It should also be noted that the scope of the compositions and methods described herein extends to sequences that correspond to those in the Tables above, and wherein the 5' nucleoside of the antisense (guide) strand (first region as defined in the items herein) can include any nucleobase that can be present in an RNA molecule, in other words can be any of adenine (A), uracil (U), guanine (G) or cytosine (C). Additionally, the scope of the present compositions and methods extends to sequences that correspond to those in Table 1a or Table 1 b, and wherein the 3' nucleoside of the sense (passenger) strand (second region as defined in the items herein) can include any nucleobase that can be present in an RNA molecule, in other words can be any of adenine (A), uracil (U), guanine (G) or cytosine (C), preferably however a nucleobase that is complementary to the 5' nucleobase of the antisense (guide) strand (first region as defined in the items herein).

While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the Examples described above may be combined with aspects of any of the other Examples described to form further Examples.

It will be understood that the above description of a preferred embodiment is given by way of example only and that various modifications may be made by those skilled in the art. What has been described above includes Examples of one or more embodiments. It is, of course, not possible to describe every conceivable modification and alteration of the above compounds, compositions or methods for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims.

EXAMPLES

The following Examples illustrate certain embodiments of the present disclosure and are not limiting. Moreover, where specific embodiments are provided, the generic application of those specific embodiments is contemplated. For example, disclosure of an oligonucleotide having a particular motif or modification patterns provides reasonable support for additional oligonucleotides having the same or similar motif or modification patterns.

The syntheses of the RNAi constructs as disclosed herein have been carried out using synthesis methods known to the person skilled in the art, such as synthesis methods disclosed in https://en.wikipedia.org/wiki/Oligonucleotide_synthesis {retrieved on 16 Feb. 2022}, wherein the methods disclosed on this website are incorporated by reference herein in their entirety. The only difference to the synthesis method disclosed in this reference is that GalNac phosphoramidite immobilized on a support is used in the synthesis method during the first synthesis step.

Example 1

Materials and Methods

Cell Culture:

HepG2 (ATCC cat. 85011430) cells were maintained by biweekly passing in EMEM supplemented with 10% FBS, 20 mM L-glutamine, 10 mM HEPES pH 7.2, 1 mM sodium pyruvate, 1×MEM non-essential amino acids, and 1×Pen/Strep (EMEM complete).

APOC3 Target identification and duplex preparation:

Targets to APOC3 were identified by bioinformatic analysis on human APOC3 mRNA sequence as given in RefSeq sequence ID NM_000040, wherein inter alia it has been taken into consideration that constructs as described herein should target APOC3 mRNA irrespective of splice variants and isoforms. 376 targets were selected for synthesis as asymmetric duplexes (14 nucleotide sense strand, 19 nucleotide antisense strand). Compounds were dissolved to 50 uM in molecular biology grade water and annealed by heating at 95 C for 5 minutes followed by gradual cooling to room temperature.

APOC3-Primary Screen:

On the day of transfection, HepG2 cells were collected by trypsinization, counted, and seeded in 96 well tissue culture treated plates at 10,000 cells per well in 50 uL complete EMEM with 20% FBS. Cells were allowed to rest for 4 hours before transfection with 2 pmoles of each respective APOC3 duplex in triplicate via RNAiMax (ThermoFisher). In brief, 8 pmoles of each duplex were diluted in 100 uL OptiMEM and mixed gently with 0.8 uL of RNAiMax in 100 uL OptiMEM to make 200 uL total complex. 50 uL of each RNAiMax complexed duplex was added to each respective triplicate well of HepG2 cells for a final mixture of 20 nM duplex in a volume of 100 uL, 50/50 EMEM/OptiMEM at 10% FBS.

72 hours post transfection, cells were harvested and RNA isolated using the PureLink Pro 96 total RNA Purification Kit (ThermoFisher, 12173011A) according to the manufacturer protocol. Harvested RNA was assayed for APOC3 expression via Taqman qPCR using the Luna Universal Probe One-Step RT-qPCR Kit (NEB, E3006). Two separate qPCR assays were performed for each sample using two separate APOC3 Taqman probe sets multiplexed with a common GAPDH VIC probe (ThermoFisher, 4326317E). Thermocycling and data acquisition was performed with an Applied Biosystems QuantStudio 3 Real-Time PCR System. Based on the results of the primary screen, a subset of 77 oligomeric compounds was selected which exhibit at least 70% target knockdown when assessed with either probe. These 77 compounds are defined by above items 3 and 4.

APOC3-Secondary Screen:

Based on data from the primary screen, a yet narrower set of the best performing 30 APOC3 duplexes were tested in dose curves. As before, HepG2 cells were collected by trypsinization and seeded in 96 well tissue culture plates at 10,000 cells per well in 50 uL complete EMEM with 20% FBS and allowed to rest for 4 hours. Transfection complexes were formed by gently mixing 36 pmoles of each duplex in 180 uL OptiMEM with 2.16 uL RNAiMax in 180 uL OptiMEM to make 360 uL total complex. A two fold dilution series was then performed with basal OptiMEM. 50 uL of each dilution was added to respective triplicates of HepG2 cells to make a final dilution series of 50 nM down to 0.32 nM in a volume of 100 uL, 50/50 EMEM/OptiMEM at 10% FBS.

72 hours post transfection, cells were harvested and RNA isolated using the PureLink Pro 96 total RNA Purification Kit (ThermoFisher, 12173011A) according to the manufacturer protocol. Harvested RNA was assayed for APOC3 expression via Taqman qPCR using the Luna Universal Probe One-Step RT-qPCR Kit (NEB, E3006). A single qPCR assay was performed for each sample using APOC3 Taqman probe set multiplexed with a common GAPDH VIC probe (ThermoFisher, 4326317E). Thermocycling and data acquisition was performed with an Applied Biosystems QuantStudio 3 Real-Time PCR System.

Example 2

Results

Table 4 below shows IC50 values (in nM) for the 30 constructs selected in accordance with the Examples.

| Sequence ID | % k/d at the highest conc. | IC50 |
|---|---|---|
| AP277 | 93.44 | 3.29 |
| AP337 | 93.10 | 4.10 |
| AP028 | 90.64 | 4.53 |
| AP343 | 93.10 | 4.70 |
| AP369 | 90.15 | 4.86 |
| AP366 | 95.63 | 5.56 |
| AP274 | 89.43 | 5.89 |
| AP367 | 88.85 | 5.99 |
| AP336 | 92.76 | 6.13 |
| AP332 | 90.23 | 6.35 |
| AP293 | 84.99 | 6.44 |
| AP373 | 89.76 | 6.46 |
| AP280 | 78.85 | 6.71 |
| AP221 | 92.66 | 6.84 |
| AP334 | 90.35 | 6.85 |
| AP286 | 83.77 | 6.89 |
| AP149 | 90.36 | 7.77 |
| AP193 | 91.30 | 7.83 |
| AP328 | 87.02 | 7.85 |
| AP175 | 94.58 | 8.28 |
| AP262 | 84.65 | 8.72 |
| AP254 | 90.79 | 9.11 |
| AP185 | 88.83 | 9.20 |
| AP328 | 88.99 | 9.44 |
| AP271 | 78.49 | 9.49 |
| AP137 | 86.09 | 9.79 |

-continued

| Sequence ID | % k/d at the highest conc. | IC50 |
|---|---|---|
| AP225 | 81.11 | 10.74 |
| AP167 | 84.77 | 11.13 |
| AP297 | 84.99 | 13.28 |
| AP191 | 84.23 | 14.27 |

The IC50 data in the single- to double-digit nanomolar range demonstrate outstanding performance of numerous constructs as described herein.

Example 3

Materials and Methods

Cell Culture:

Human primary hepatocytes (5 donor pooled—Sekisui XenoTech, HPCH05+) were thawed immediately prior to experimentation and cultured in 1×complete Williams medium (Gibco, A1217601) supplemented with Hepatocytes plating supplement pack (Gibco, CM3000). FBS concentration was modified from manufacture recipe to a final 2.5% (as opposed to 5%) for compound stability. 1×Complete WEM: 2.5% FBS, 1 μM Dexamethasone, Pen/Strep (100 U/mL/100 μg/mL), 4 μg/ml Human Insulin, 2 mM GlutaMAX, 15 mM HEPES, pH 7.4).

Hepatocytes were plated on Collagen I (rat tail) coated 96 well tissue culture plates (Gibco, A1142803).

APOC3 Compound Preparation:

Compounds were dissolved to 10 mg/mL in PBS and annealed by heating at 95 C for 5 minutes followed by rapid cooling on ice.

APOC3 Compound Transfections:

On the day of transfection, primary human hepatocytes were thawed in 45 mL of human OptiThaw (Sekisui Xenotech, K8000) and centrifuged down at 200 g for 5 minutes. Cells were resuspended in 2×complete WEM and counted. Cell were then plated in 50 uL of 2×complete WEM at 25,000 cells per well on 96 well type 1 rat tail Collagen plates and allowed to rest and attach for four hours before transfection.

Compounds were diluted further to 2 uM in basal WEM. A seven step, five fold dilution series was prepared in basal WEM from 2 uM to 0.000128 uM. 50 uL of each dilution was added to respective triplicates of the plated hepatocytes for a final dilution series of 1 uM down to 0.000064 uM in a volume of 100 uL 1×complete WEM.

72 hours post transfection, cells were harvested and RNA isolated using the PureLink Pro 96 total RNA Purification Kit (ThermoFisher, 12173011A) according to the manufacturer protocol. Harvested RNA was assayed for APOC3 expression via Taqman qPCR using the Luna Universal Probe One-Step RT-qPCR Kit (NEB, E3006). A single qPCR assay was performed for each sample using an APOC3 Taqman probe set (Hs00906501_g1-FAM) multiplexed with a common GAPDH VIC probe (ThermoFisher, 4326317E). Thermocycling and data acquisition was performed with an Applied Biosystems QuantStudio 3/5 Real-Time PCR System.

TABLE 5

| Constructs used as positive control | |
|---|---|
| A277(15)dup | 5' [mU][#][fU][#][mG][fG][mA][fU][mA][fG][mG][fC][mA][fG][mG][fU][mG][#][fG][#][mA][#][fC][#][rU] (SEQ ID NO: 1598)<br>5' [fC][#][mA][#][fC][mC][fU][mG][fC][mC][fU][mA][fU][mC][mC][#][mA][#][mA][#][3 × GalNAc] (SEQ ID NO: 1599) |
| A28(15)dup | 5' [mU][#][fC][#][mA][fA][mC][fA][mA][fG][mG][fA][mG][fU][mA][fC][mC][#][fC][#][mG][#][fG][#][rG] (SEQ ID NO: 1600)<br>5' [fG][#][mG][#][fU][mA][fC][mU][fC][mC][fU][mU][fG][mU][mU][#][mG][#][mA][#][3 × GalNAc] (SEQ ID NO: 1601) |
| P29-A28 | 5' [mU][#][fG][#][mC][fA][mA][fA][mA][fC][mA][fG][mG][fU][mC][fU][#][mA][#][fG][#][mA][#] [fA][#][rA][mG][#][fU][#][mA][fC][mU][fC][mC][fU][mU][fG][mU][mU][#][mG][#][mA][#][3 × galNAc] (SEQ ID NO: 1602)<br>5' [mU][#][fC][#][mA][fA][mC][fA][mA][fG][mG][fA][mG][fU][mA][fC][#][mC][#][fC][#][mG][#][fG][#] [rG][mA][#][fG][#][mA][fC][mC][fU][mG][fU][mU][fU][mU][mG][#][mC][#][mA][#][3 × GalNAc] (SEQ ID NO: 1603) |
| P29-A277 | 5' [mU][#][fG][#][mC][fA][mA][fA][mA][fC][mA][fG][mG][fU][mC][fU][#][mA][#][fG][#][mA][#][fA][#] [rA][mA][#][fC][#][mC][fU][mG][fC][mC][fU][mA][fU][mC][mC][#][mA][#][mA][#][3 × GalNac] (SEQ ID NO: 1604)<br>5' [mU][#][fU][#][mG][fG][mA][fU][mA][fG][mG][fC][mA][fG][mG][fU][#][mG][#][fG][#][mA][#] [fC][#][rU][mA][#][fG][#][mA][fC][mC][fU][mG][fU][mU][fU][mU][mG][#][mC][#][mA][#][3 × GalNAc] (SEQ ID NO: 1605) |
| TMPRSS6 | 5' vP[mA][fA][mC][fC][mA][fG][mA][fA][mG][fA][mA][fG][mC][fA][mG][fG][mU][fG][iN][fC][mU] [fG][fC][fU][mU][fC][mU][fU][mC][fU][mG][fG][mU][fU]#[3 × GalNAc] (SEQ ID NO: 1606) |

Note:
vP = vinyl-phosphonate;
iN = inverted with 2'OH

Results

As can be seen from FIG. 1*a*, several variations of both A28 and A277 structures demonstrated excellent activities.

Figure 1B:
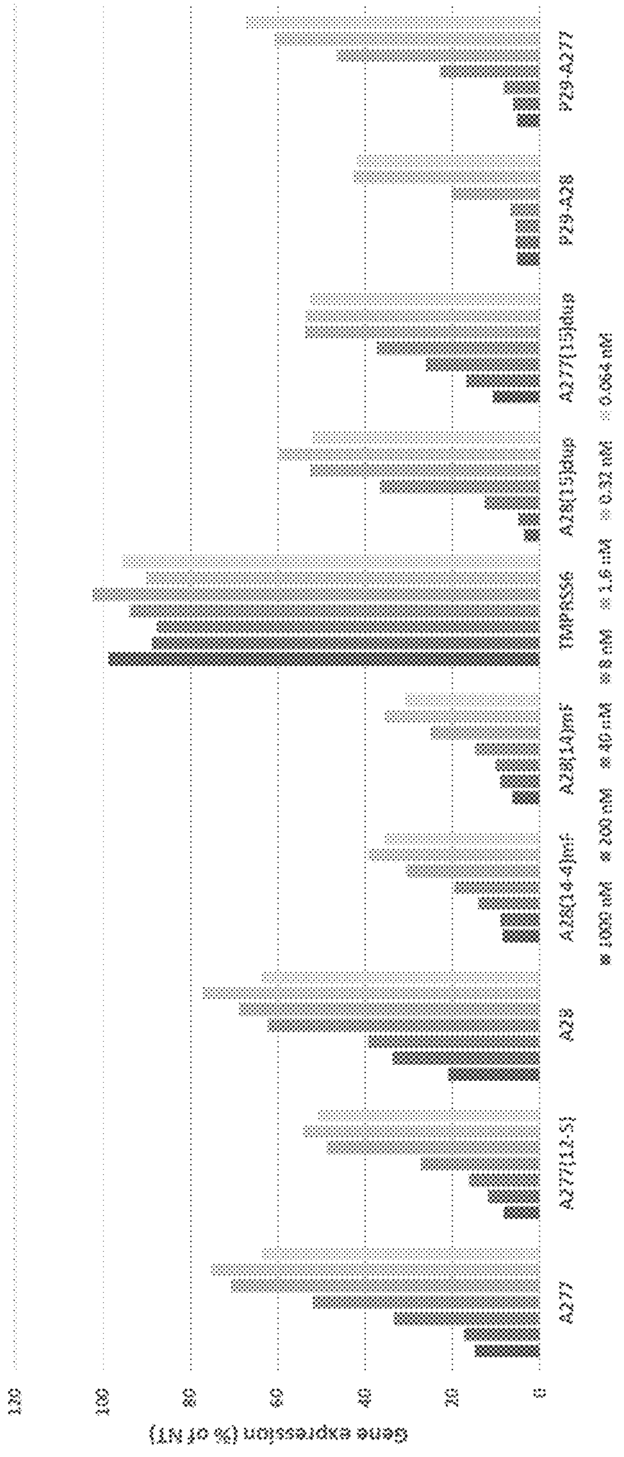
FIG. 1*b* shows dose curves of APOC3 leads for Humanized mouse study in primary human hepatocytes.
Figure 2:
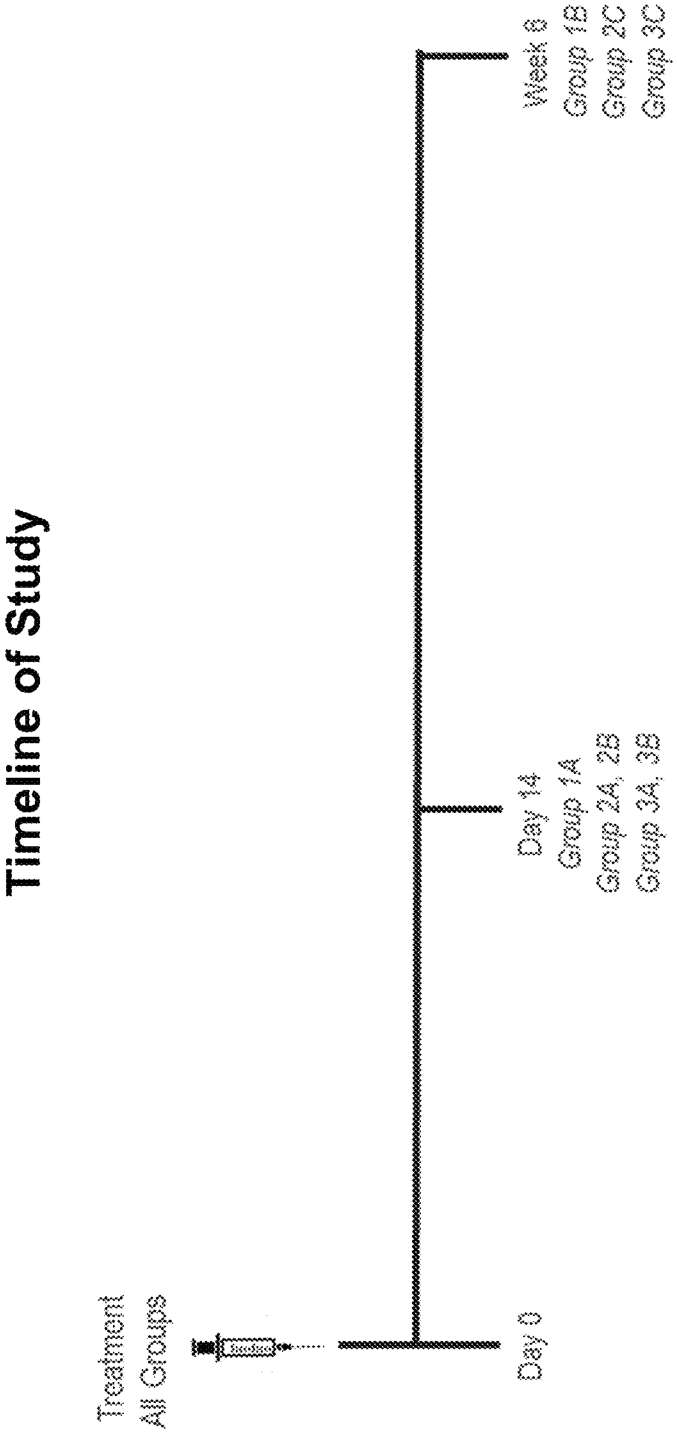
FIG. 2 shows a timeline including the time point of applying the dose to the mice and time points for taking samples.

As can be seen from FIG. 1*b*, all molecules produced excellent activities.

Example 4

Study Protocol

The following study protocol for the study entitled "mxRNA Leads for Candidate Screening Study in Male human liver-uPA-SCID mice, non-GLP" has been drafted before the animal experiments and studies have been completed and therefore uses the future tense. However, as said study has already been completely carried out, each usage of "future tense" should be considered as the "past tense" in the following description of the study protocol.

Study Objective(s)

The objective of this non-GLP study was to evaluate the dose and duration response effect of two selected mxRNA leads for candidate GalNAc-siRNA constructs targeting APOC3 using the human liver-uPA-SCID mice models. The compounds were administered subcutaneously and the mice survived for 14-days and 42-days.

Prior to necropsy, plasma and serum were collected. At necropsy, 3 liver biopsies (2 mm) per animal were preserved in separate vials in RNAlater, flash frozen, and stored at −80° C. Three more liver biopsies (2 mm) were taken, flash frozen in the same vial, and stored at −80° C.

Regulatory Compliance

This non-GLP study will not be conducted in accordance with the Food and Drug Administration's Good Laboratory Practice (GLP) regulations (21 CFR Part 58).

Animal Welfare Compliance

The procedures described and performed below will be conducted in accordance with the Guide for the Care and Use of Laboratory Animals, USDA *APHIS*, Animal Welfare Act and/or in accordance with the Standard Operating Procedures.

This protocol has been reviewed and approved by the Test Facility IACUC Committee.

Study Schedule

Acclimatization/Quarantine End Date: ≥5 days

Baseline Procedure Date: No baseline procedures Procedure Start Day 0 Date: Tentative: December Waiting on test material.

Necropsy Start: On Day 14- and 42-days post treatment.

In-Life Study Completion: 6 weeks post treatment

Preliminary Report: None required by Sponsor, Data only

Final Report Issued: None required

Test System Information

Animal Test

Common Name: Mouse

Breed/Class: Rodent—human liver-uPA-SCID mouse

Number of Animals (by gender): 36 Male, all naïve

Age Range: 14-19 weeks

Weight Range: Approx. 20 grams

The mice used in this study were human liver-uPA-SCID mice. About 80% of the hepatocytes of each mouse have been replaced by human hepatocytes. The skilled person is aware of ways of producing such mice; wherein at least some of these ways are shown and referenced in P. Meuleman and G. Leroux-Roels in Antiviral Res. 2008 December; 80(3):231-8 which is incorporated herein by reference in its entirety.

Acclimation Period:

Duration:

All animals will be acclimated for a minimum period of five (5) days prior to release by the Attending veterinarian, at which time the overall health of the animals will be evaluated. Animals which are not released from acclimation will be treated accordingly and further evaluation will be performed prior to release. All records from the acclimation period will remain in the study file.

Animal Identification Method and Location:

Animals will be assigned sequential numbers. The animals will be ear notched to permanently identify each animal. This method involves punching holes or notches in the ear pinna while anesthetized.

Alternatively, the animals may have a tattoo placed on their tail. A cage card will also be affixed to each animal cage denoting the animal number, gender, vendor, strain, study director, and study number Study Design Design Details This study will have one type of mice, 36 human liver-uPA-SCID mice. Animals will be grouped by treatment type, dosage, and survival period. Each animal will be treated by subcutaneous injection of test material. Groups 1A and 1B will have four animals receive a control dose of PBS. Groups 2A, 2B, 2C, 3A, 3B, and 3C will receive one dose (10 or 30 mg/kg) with four animals for each dose amount. All animals will be kept alive for 14 or 42 days. See study Table 6 below for details.

TABLE 6

Study Table

| Group | Number of human liver-uPA-SCID mice animals | Treatment Subcutaneous Injection Day 0 | Survival Days | Blood | Pre-Euthanasia and Necropsy |
|---|---|---|---|---|---|
| 1A | 4 | Control (PBS) | 14 | Plasma and | Pre-Euthanasia: |
| 1B | 4 | Control (PBS) | 42 | serum will | Plasma and serum |
| | | | | be | collection. |
| 2A | 4 | A28 mxRNA (10 mg/kg) | 14 | collected | Necropsy: |
| 2B | 4 | A28 mxRNA (30 mg/kg) | 14 | for all | 2 mm biopsy of left, |
| 2C | 4 | A28 mxRNA (10 mg/kg) | 42 | animals on | middle and right liver |
| 3A | 4 | A277 mxRNA (10 mg/kg) | 14 | necropsy | lobes in separate vials, |
| 3B | 4 | A277 mxRNA (30 mg/kg) | 14 | days 14 | in RNAlater for 15 min, |
| 3C | 4 | A277 mxRNA (10 mg/kg) | 42 | and 42. | flash freeze then |
| Spares | 4 | | | Send | stored at −80° C. |
| | | | | | |
| Total | 36 | | | Plasma and | 2 mm biopsy of left, |
| | | | | serum to | middle and right liver |
| | | | | Sponsor. | all in one vial, flash |
| | | | | | freeze then stored |
| | | | | | at −80° C. |
| | | | | | Rest of liver, flash |
| | | | | | freeze then stored |
| | | | | | at −80° C. |

Prior to necropsy, the animals will be deeply anesthetized and a terminal blood draw will be performed through the vena cava. The target blood volume to be collected per animal is as much blood as possible with a minimum of 1.2 mL which will be split equally between a serum and plasma separation tube. After separation (see section 14.10) the serum will be split equally in two separate vials and plasma also will be separated in two separate vials (see example below).

1.2 mL of blood=0.6 mL for serum and 0.6 mL for plasma separation tubes

Serum (0.3 mL after separation)=0.15 mL×2 vials

Plasma (0.3 mL after separation)=0.15 mL×2 vials.

Above serum and plasma samples will be labelled, flash frozen and stored at −80° C.

Additional blood collected over the minimum 1.2 mL volume will be placed in a serum separation tube, processed, serum transferred to a labelled vile, refrigerated at 4° C. for rodent lipid analysis.

Note: serum and plasma will be used to measure protein, caution should be taken to avoid hemolysis or clot formation.

At necropsy, three 2 mm biopsy punches will be taken from the left, middle and right liver lobes, placed in separate vials, soaked in RNAlater for 15 minutes, flash frozen and stored at −80° C. Another three 2 mm liver biopsies from the left, middle and right liver lobes will be placed into one vial, flash frozen and stored at −80° C. The rest of the liver will be flash frozen and stored in 10 mL conical tubes at −80° C.

Alteration of Study Design

Alterations of this protocol may be made as the study progresses. Changes (to the protocol) that have the potential to negatively impact the study or the safety of the study subjects would require IACUC approval.

Animal Inclusion and Exclusion Criteria

Any animals that are deemed unhealthy during veterinary pre-screen will be excluded from the study and replaced with a spare animal if available. For survival animals found dead or moribund after treatment may be replaced via study protocol amendment by a spare animal if available.

Animal Disposition

At the end of the study, the animals will be euthanized.

Route of Administration

Subcutaneous injection in the scruff. An injection volume of 200 uL.

Results

Figure 3:
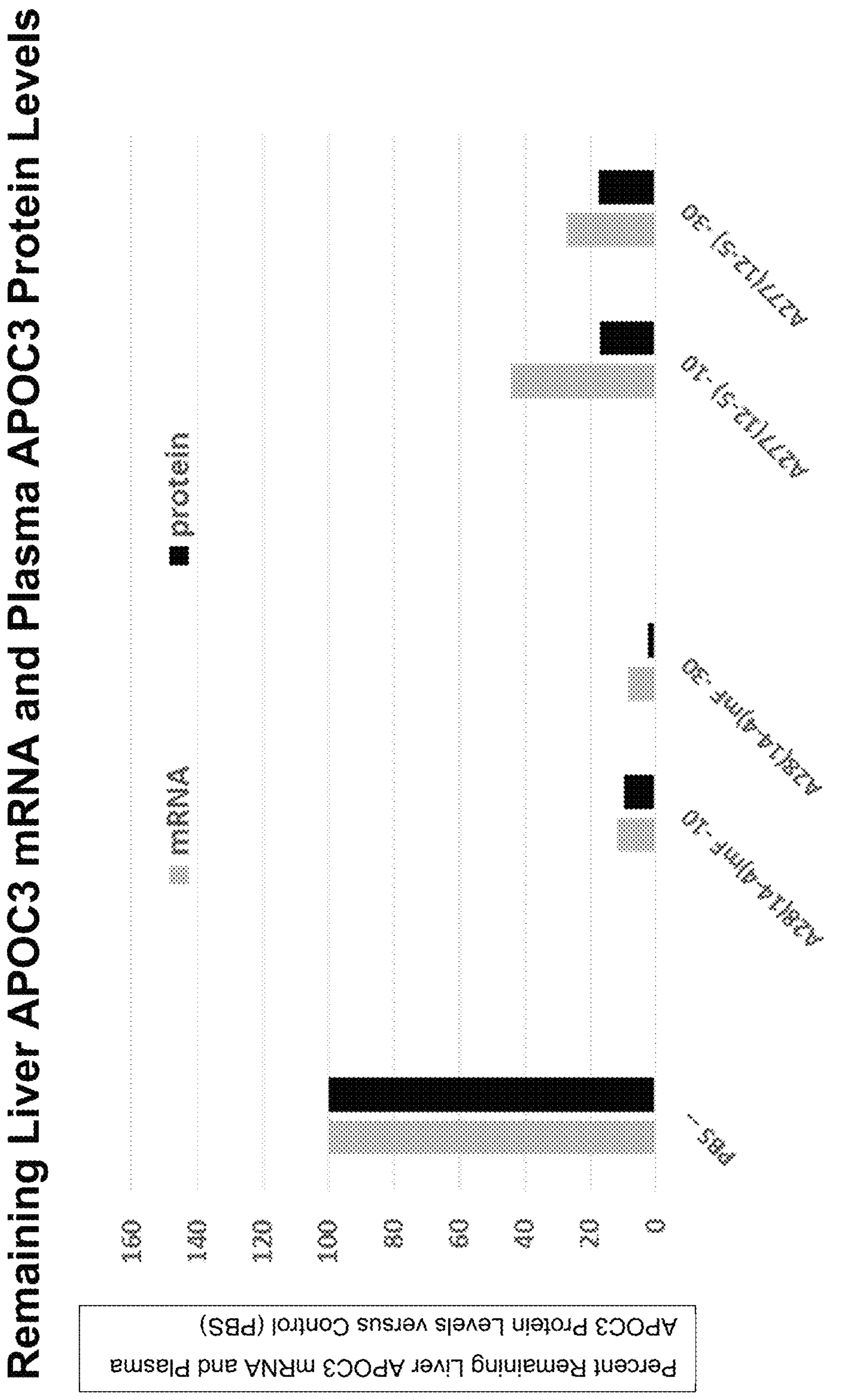
FIG. 3 shows remaining liver APOC3 mRNA and plasma APOC3 protein levels for the animals treated with APOC3-targeting mxRNA constructs as compared to the control animals.

FIG. 3 highlights the dose-response effect on the percent reduction of APOC3 mRNA in the liver tissues and APOC3 protein levels in the plasma of the animals treated with the different mxRNA constructs at Day 14 as compared to the control animals.

In addition, the following notes apply to FIG. 3:

A28(14-4)mF-10=A28(14-4)mF 10 mg/kg dose group

A28(14-4)mF-30=A28(14-4)mF 30 mg/kg dose group

A277(12-5)-10=A277(12-5) 10 mg/kg dose group

Figure 4:
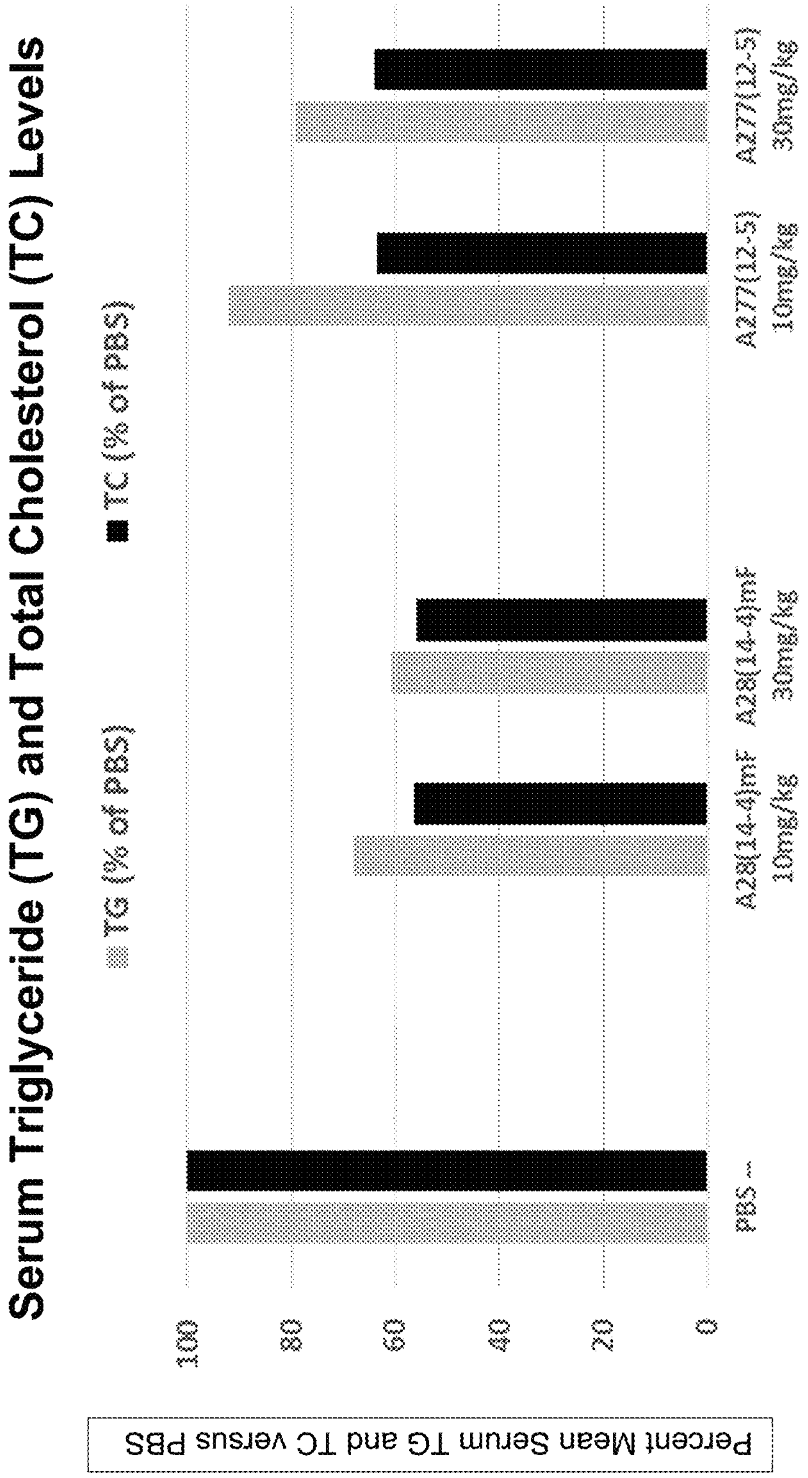
FIG. 4 shows serum triglycerides and total cholesterol in the serum of the animals treated with APOC3-targeting mxRNA constructs as compared to the control (PBS)

A277(12-5)-30=A277(12-5) 30 mg/kg dose group FIG. 4 highlights the dose-response effect on the mean percent reduction of Triglycerides and Total Cholesterol in the serum of the animals treated with the different APOC-3 targeting mxRNA constructs at Day 14 as compared to the control animals.

Figure 5A:
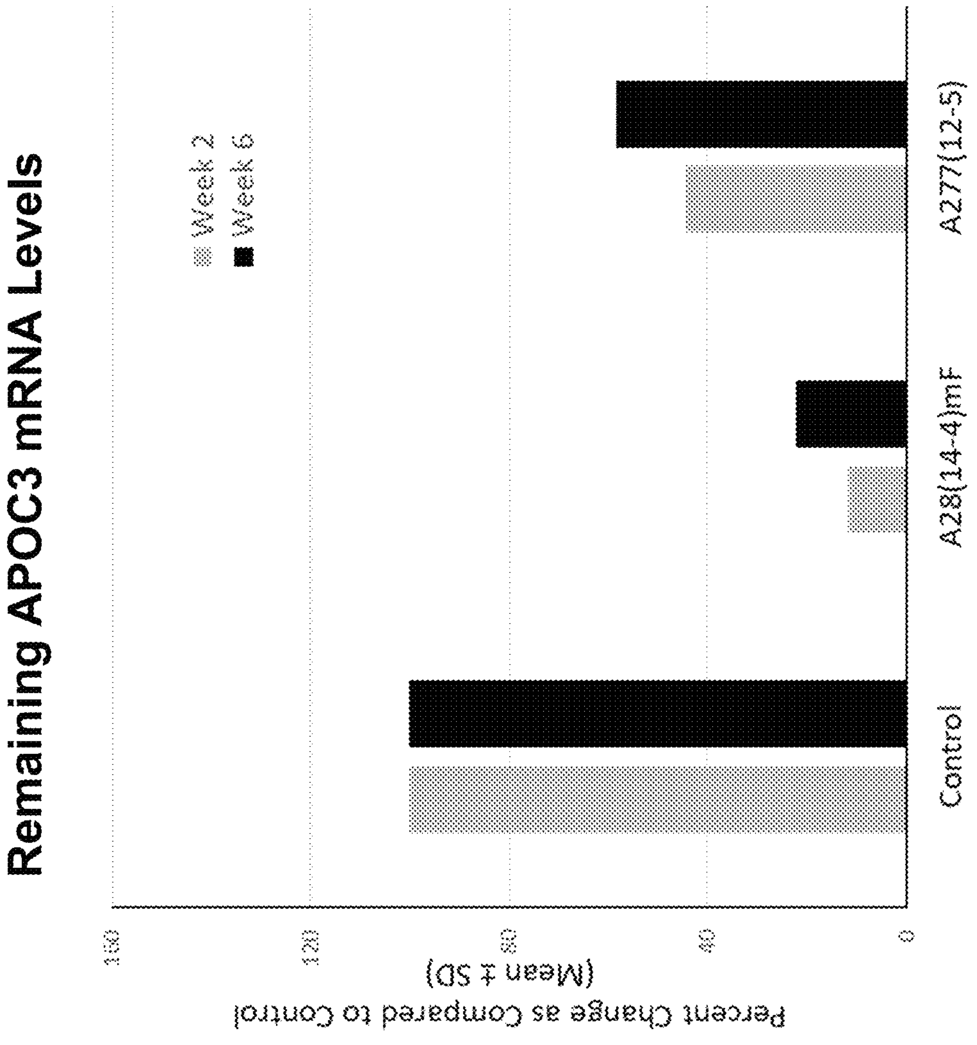
FIG. 5*a* shows a Mean Percent of remaining APOC3 mRNA in liver tissues in plasma measured using ELISA for the animals treated with APOC3-targeting mxRNA constructs (10 mg/kg) as compared to the control animals.
Figure 5B:
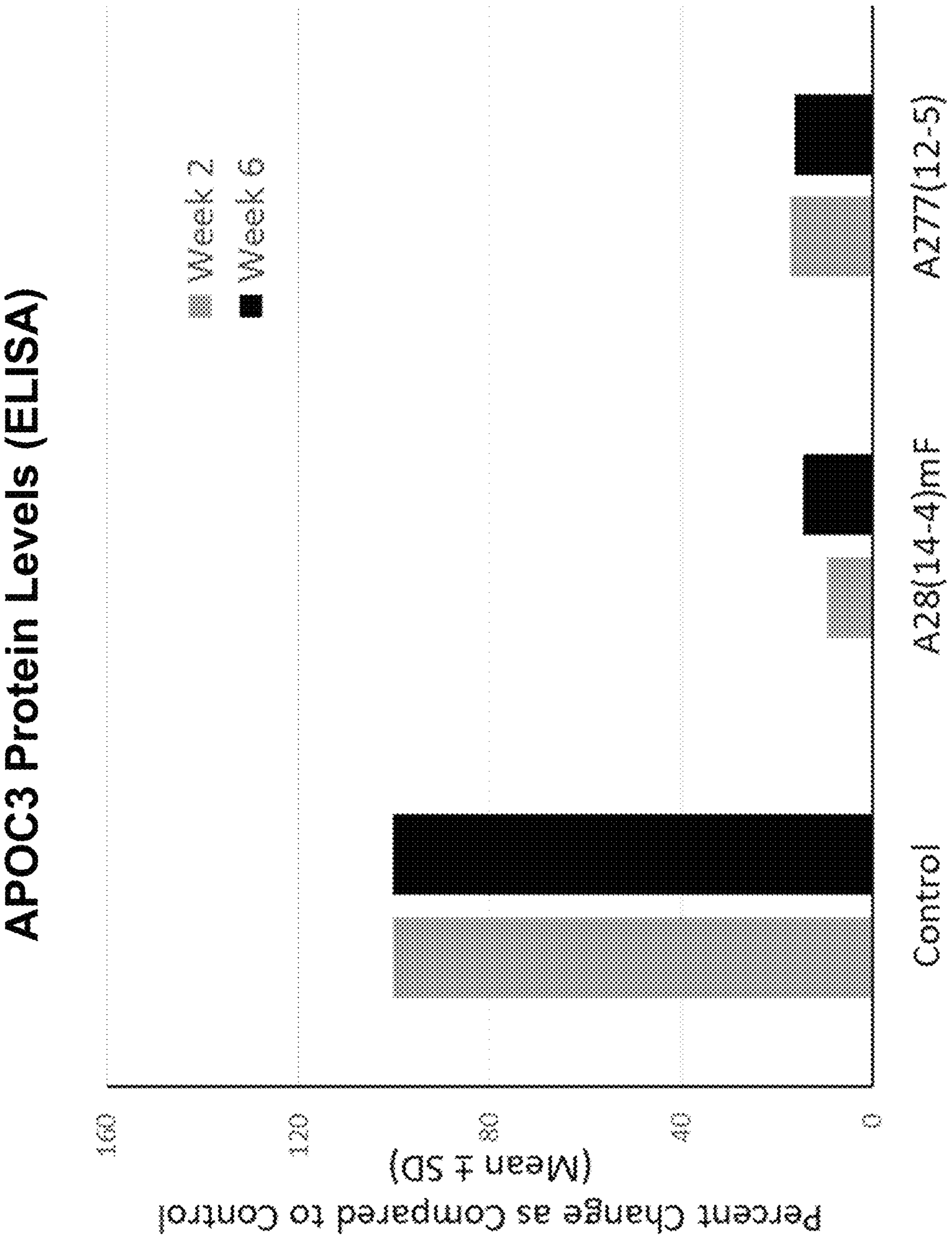
FIG. 5*b* shows APOC3 protein levels in plasma measured using ELISA for the animals treated with APOC3-targeting mxRNA constructs (10 mg/kg) as compared to the control animals.

FIGS. 5*a* and 5*b* highlight the duration effect on the mean percent reduction of APOC3 mRNA in liver tissues and APOC3 protein levels in the plasma of the animals treated with the different APOC3-targeting mxRNA (10 mg/kg) constructs at Day 14 (Week 2) and at Week 6 as compared to the control animals. Moreover, it is noted with respect to these Figures that an outlier from the A277(12-5) group is excluded.

Figure 6A:
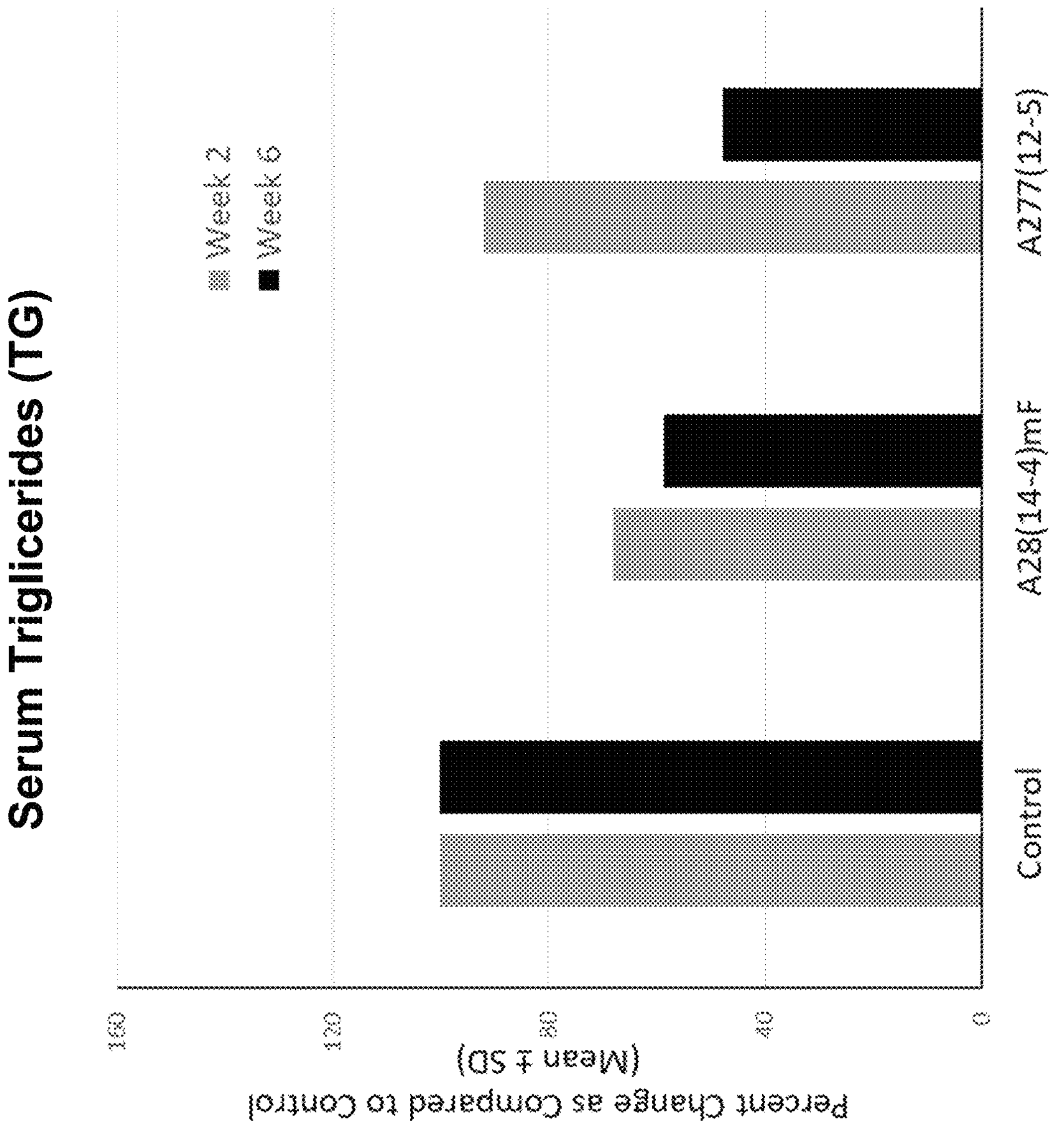
FIG. 6*a* shows the mean percent of triglycerides (TG) in the serum of the animals treated with APOC3 targeting mxRNA constructs as compared to the control animals at weeks 2 and 6.
Figure 6B:
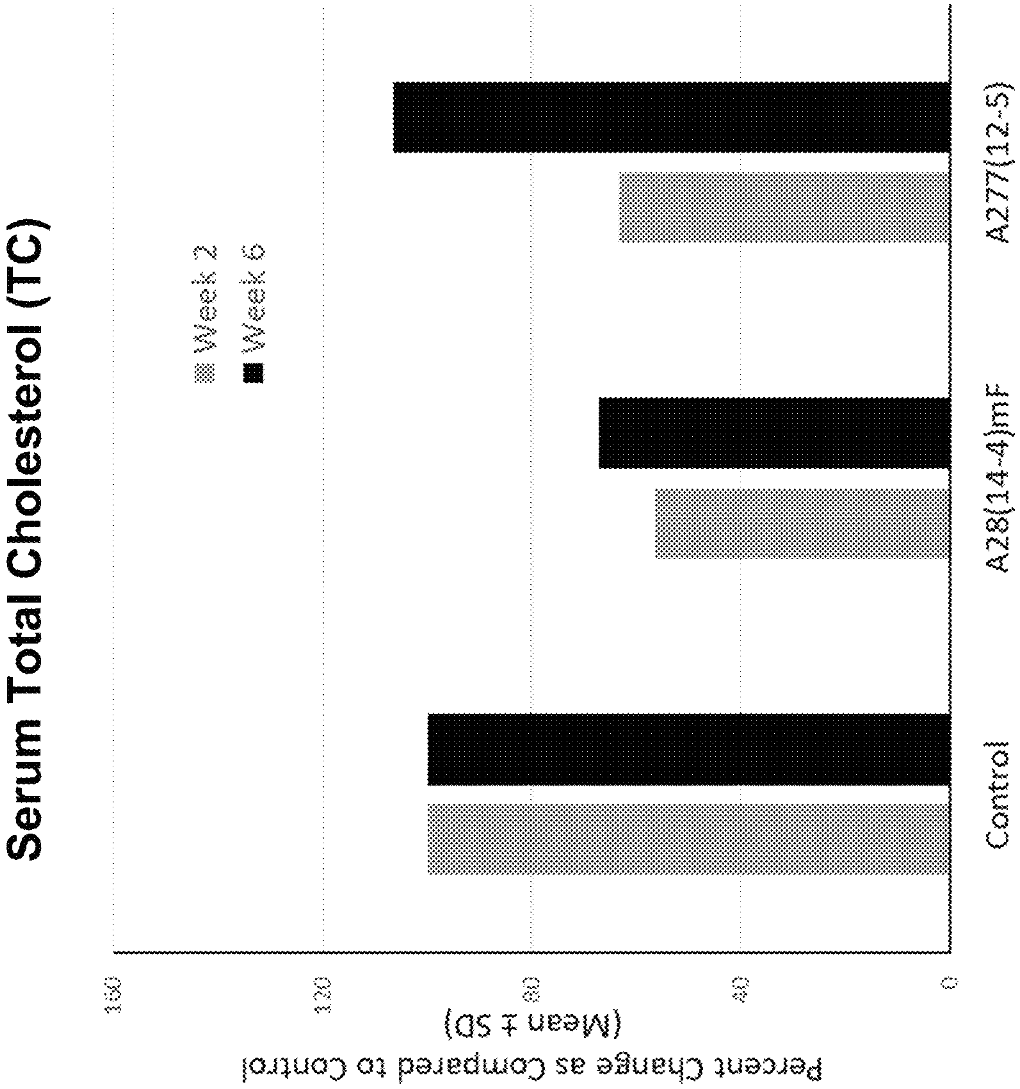
FIG. 6*b* shows the total cholesterol (TC) level in serum of animals treated with APOC3 targeting mxRNA constructs as compared to the control animals at weeks 2 and 6.

FIGS. 6*a* and 6*b* highlight the duration effect on the mean percent reduction of triglycerides (TGs) and total cholesterol (TC) in the serum of the animals treated with the different APOC3-targeting mxRNA (10 mg/kg) constructs at Day 14 (Week 2) and at Week 6 as compared to the control animals. With respect to these Figures it is noted, that an outlier from the A277(12-5) group is excluded.

Summary of Results

A28(14-4)mF APOC3-targeting mxRNA construct:

- 88% suppression of APOC3 mRNA as compared to control group at week 2 that was maintained at 78% on Week 6.
- 90% reduction in plasma APOC3 levels as compared to control group at week 6 that was sustained at 85% on Week 6.
- 32% reduction in serum triglycerides levels as compared to control group at week 2 that increased to 41% reduction on Week 6.
- 43% reduction in serum total cholesterol levels as compared to control group at week 2 that was maintained at 33% on Week 6.

A277(12-5) APOC3-targeting mxRNA construct:

- 56% suppression of APOC3 mRNA as compared to control group at week 2 that was maintained at 42% on Week 6.
- 83% reduction in plasma APOC3 levels as compared to control group at week 6 that was sustained at 84% on Week 6.
- 8% reduction in serum triglycerides levels as compared to control group at week 2 that increased to 52% reduction on Week 6.
- 36% reduction in serum total cholesterol levels as compared to control group at week 2 that was lost on Week 6.

CONCLUSIONS

Construct A28(14-4)mF produced outstanding activity, with 98% of the targeted protein downregulation at 2-week timepoint at 30 mg/kg dosing. Furthermore, construct A28 (14-4)mF sustained excellent (protein knockdown) activity at 10 mg/kg dosing both on week 2 and week 6.

Example 5

Figure 7:
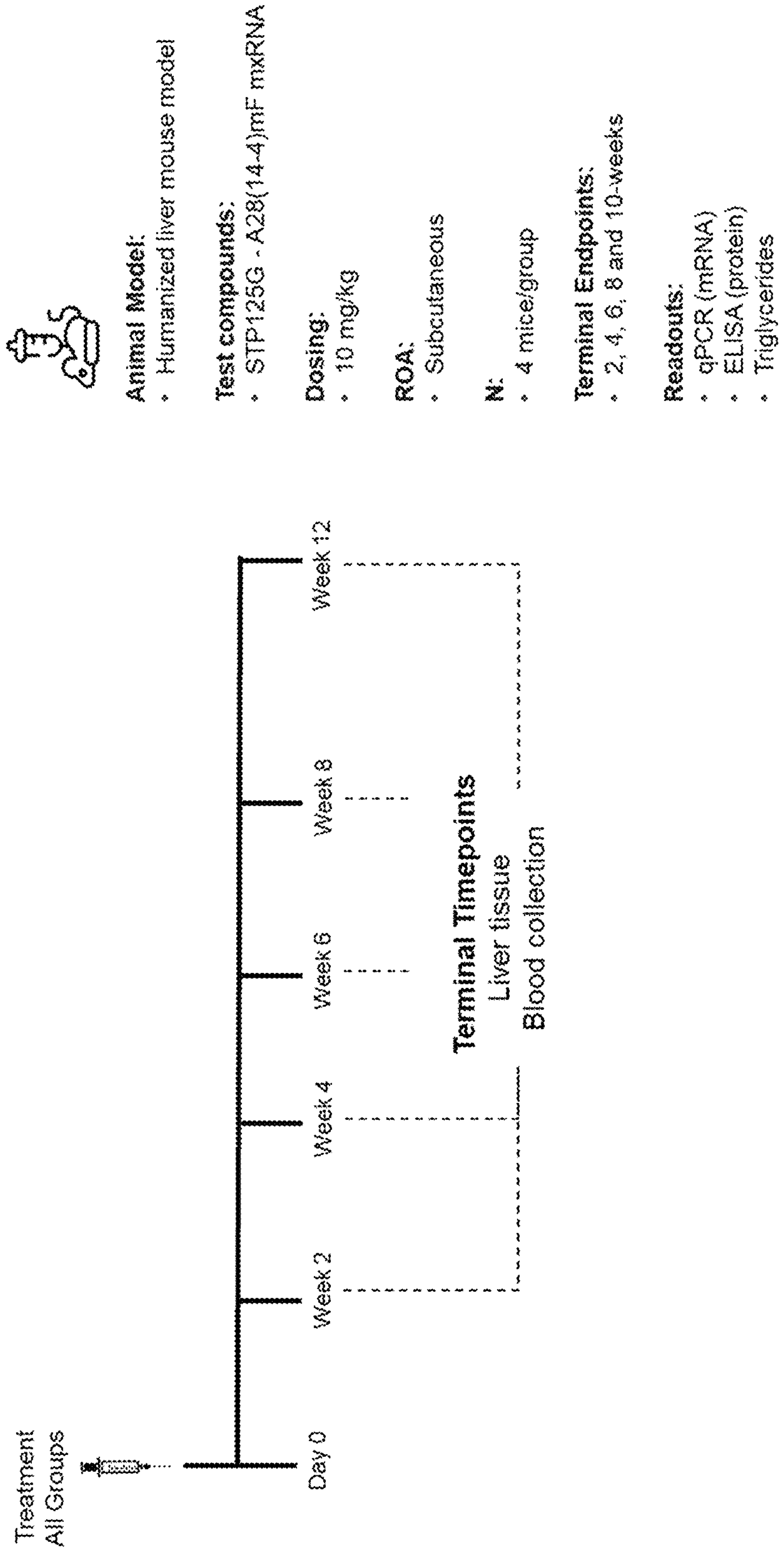
FIG. 7 prevents a schematic overview of the duration study performed with compound A28(14-4)mF (also designated STP125G) in mice with a humanized liver.
Figure 8A:
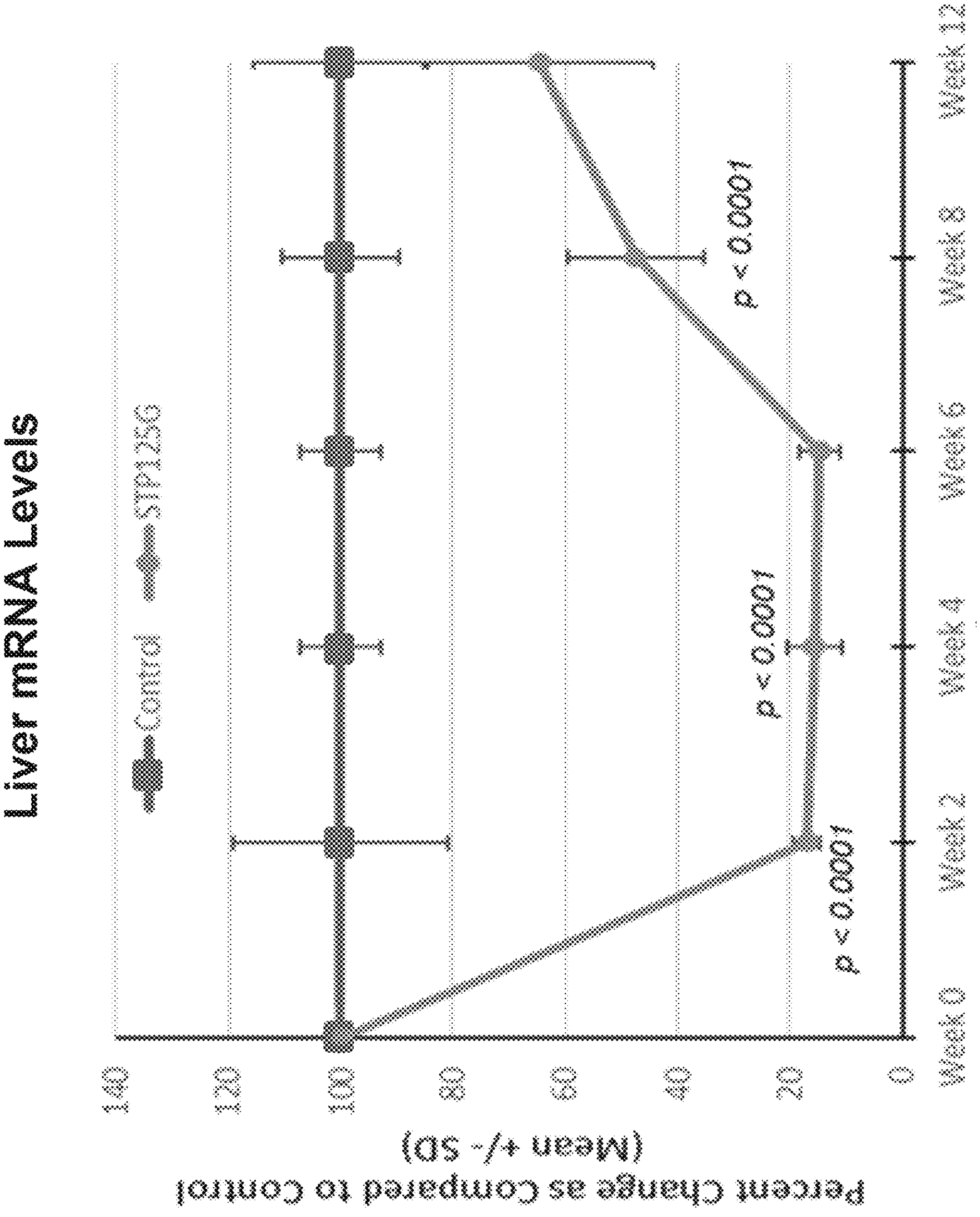
FIG. 8*a* shows APOC3 mRNA as a function of time as observed in the duration study between control and treatment groups.
Figure 8B:
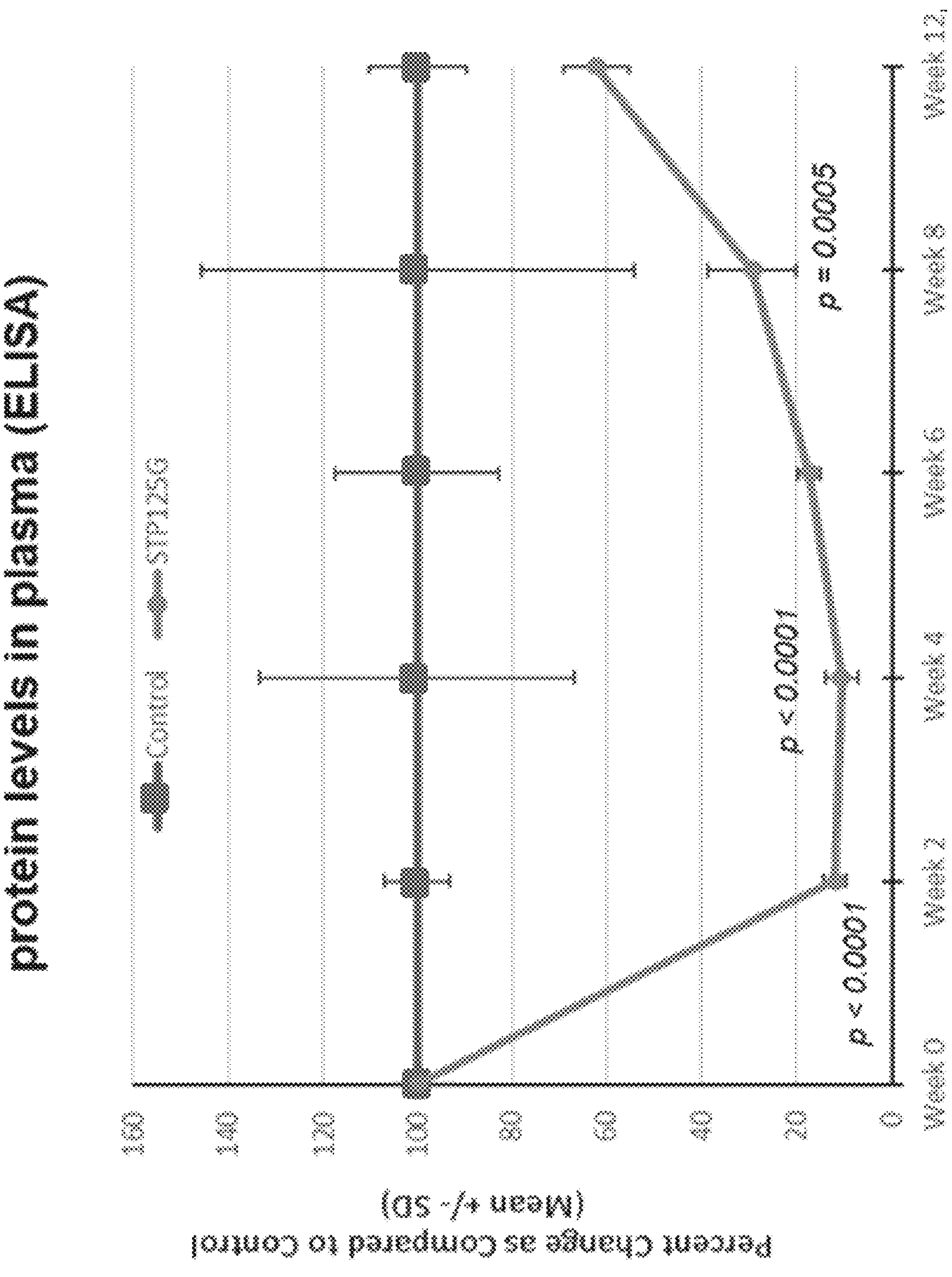
FIG. 8*b* shows APOC3 protein knockdown as a function of time as observed in the duration study between control and treatment groups.
Figure 9A:
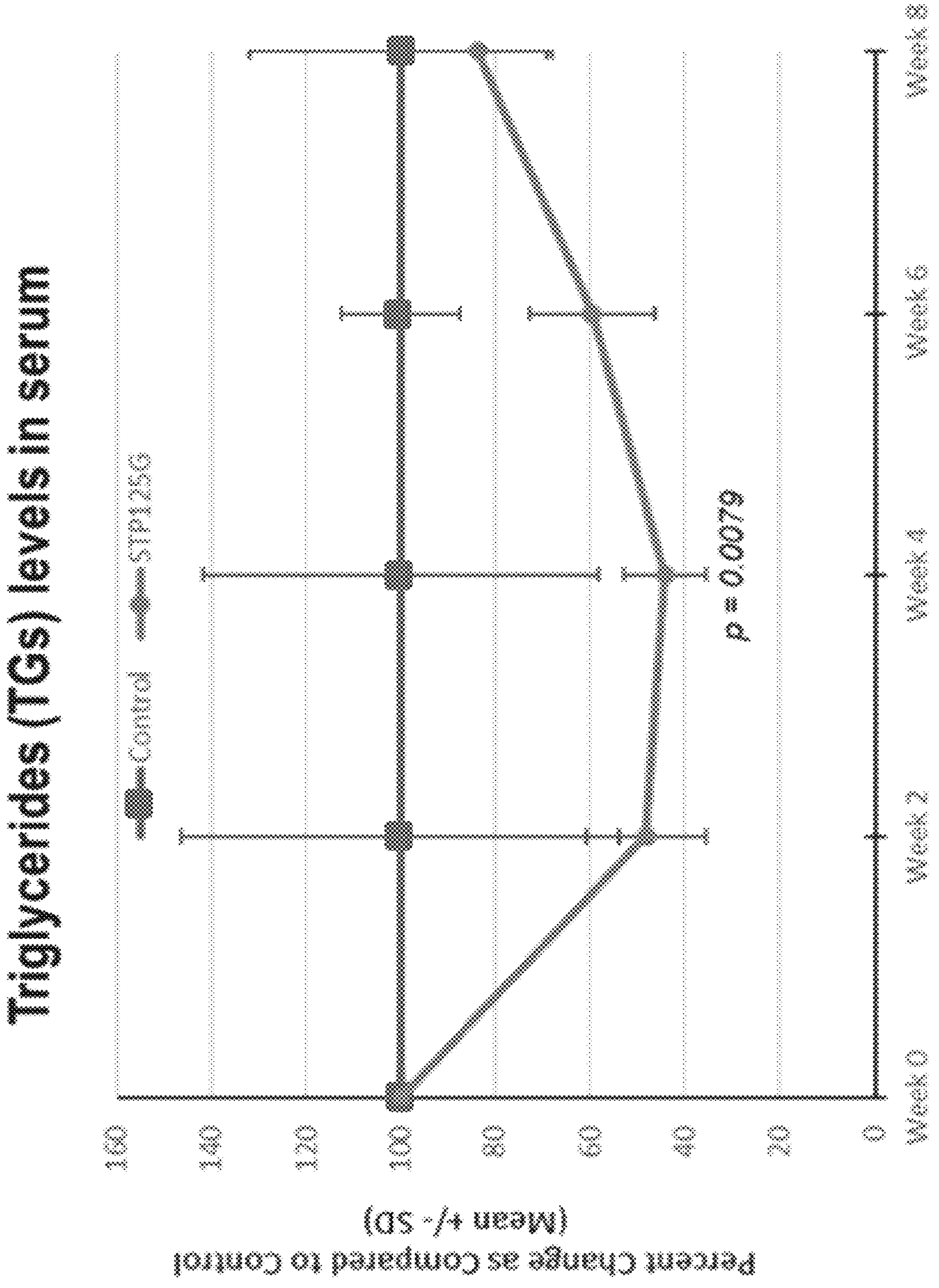
FIG. 9*a* show serum triglyceride levels as a function of time between control and treatment groups.
Figure 9B:
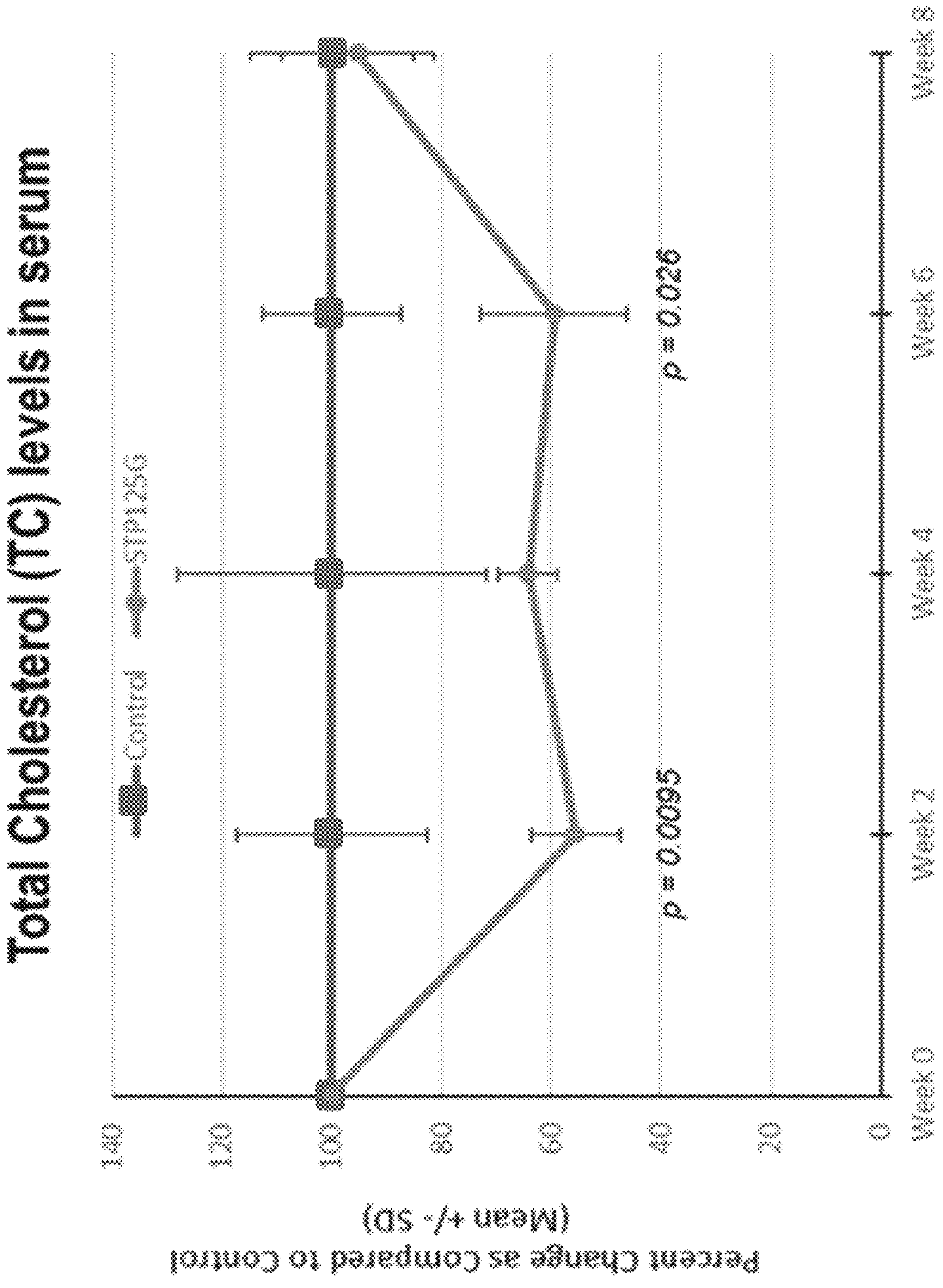
FIG. 9*b* show serum total cholesterol levels as a function of time between control and treatment groups.
Figure 10:
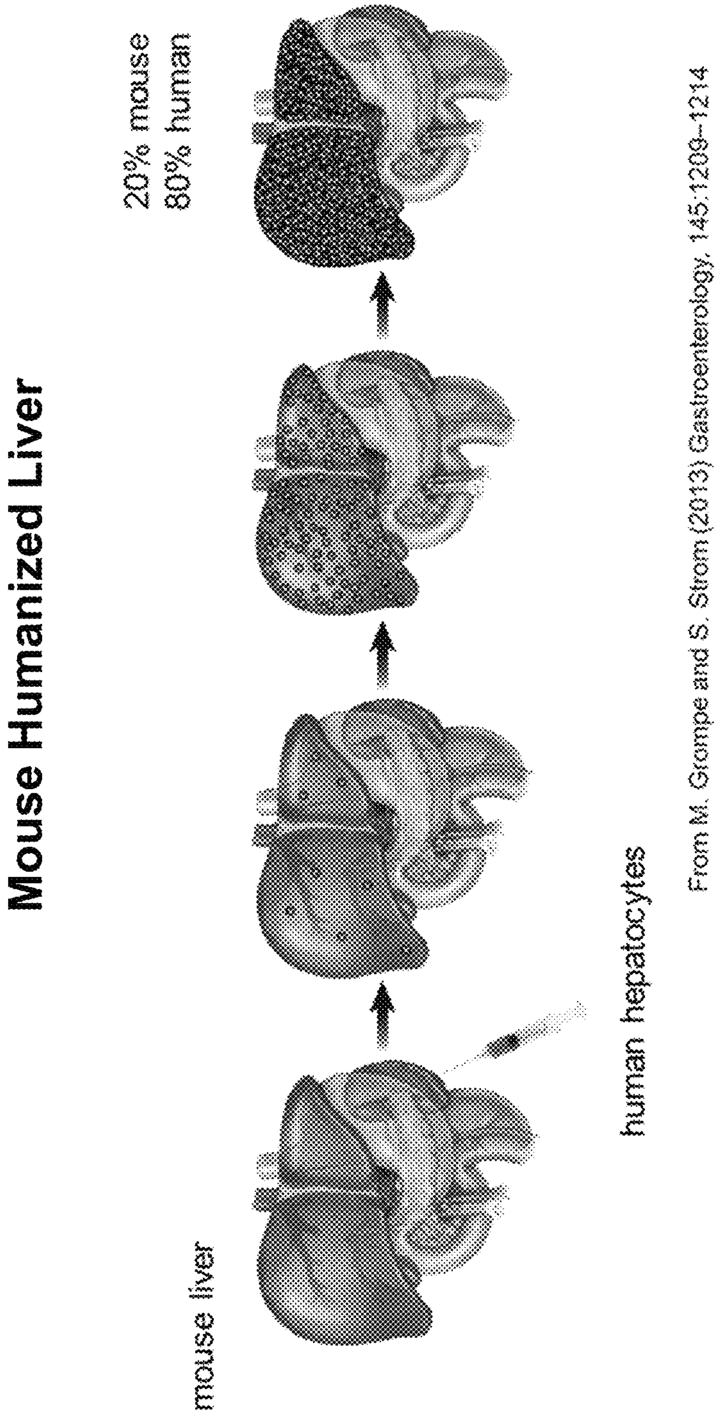
FIG. 10 illustrates the humanized liver of the mice used for the duration study.

Following the protocol described in detail in Example 4, the effects of compound A28(14-4)mF (also designated STP125G) have been observed over a longer period of time. See FIG. 7 for an overview of this extended study. The corresponding results are displayed in FIGS. 8*a* and 8*b* (APOC3 mRNA and protein knockdown, respectively), and FIGS. 9*a* and 9*b* (triglyceride and total cholesterol levels). Several Aspects are Notable:

- A single dose of 10 mg/kg is sufficient for knockdown of mRNA and protein for a period of six weeks with a rebound becoming slowly apparent toward the end of the study.
- Not only triglycerides (fat levels in blood primarily considered to be associated with APOC3) but also total cholesterol are downregulated.
- In the assessment of the latter findings, the properties of the mice used for the study must be considered. FIG. 10 shows that an estimated fraction of 20 to 25 percent of the cells of the humanized liver remain murine (mouse) cells. A28A(14-4)mF does not target murine APOC3. As a consequence, the non-silenced murine APOC3 contributes to the observed triglyceride and total cholesterol levels. Thus, the downregulation of these two blood fats in a purely human system is expected to exceed the results observed in this study.

The invention claimed is:

1. An siRNA compound that inhibits expression of APOC3, comprising a single strand of 33 or 34 nucleobases that is modified or unmodified, wherein said single strand comprises:

(i) a first nucleobase sequence directly linked to (ii) a second nucleobase sequence, wherein said first and second nucleobase sequences form a hairpin loop consisting of a duplex region of 14 or 15 base pairs, and a loop consisting of 4 or 5 nucleosides, wherein said first and second nucleobase sequences in unmodified form are, respectively, SEQ ID NOs: 23 and 423; 24 and 424; 28 and 428; 29 and 429; 31 and 431; 89 and 489; 90 and 490; 94 and 494; 117 and 517; 121 and 521; 128 and 528; 137 and 537; 138 and 538; 148 and 548; 149 and 549; 167 and 567; 171 and 571; 175 and 575; 185 and 585; 191 and 591; 193 and 593; 206 and 606; 209 and 609; 212 and 612; 213 and 613; 217 and 617; 218 and 618; 219 and 619; 220 and 620; 221 and 621; 223 and 623; 225 and 625; 254 and 654; 262 and 662; 271 and 671; 272 and 672; 274 and 674; 275 and 675; 276 and 676; 277 and 677; 278 and 678; 280 and 680; 281 and 681; 282 and 682; 283 and 683; 285 and 685; 286 and 686; 291 and 691; 293 and 693; 296 and 696; 297 and 697; 299 and 699; 300 and 700; 303 and 703; 324 and 724; 328 and 728; 331 and 731; 332 and 732; 334 and 734; 336 and 736; 337 and 737; 338 and 738; 339 and 739; 340 and 740; 341 and 741; 342 and 742; 343 and 743; 345 and 745; 346 and 746; 347 and 747; 366 and 766; 367 and 767; 369 and 769; 370 and 770; 368 and 768; 372 and 772; 373 and 773.

2. The compound according to claim 1, wherein said first nucleobase sequence and said second sequence are selected from: SEQ ID NOs: 28 and 428; 137 and 537; 149 and 549; 167 and 567; 175 and 575; 185 and 585; 191 and 591; 193 and 593; 221 and 621; 225 and 625; 254 and 654; 262 and 662; 271 and 671; 274 and 674; 277 and 677; 280 and 680; 286 and 686; 293 and 693; 297 and 697; 328 and 728; 332 and 732; 334 and 734; 336 and 736; 337 and 737; 343 and 743; 366 and 766; 367 and 767; 369 and 769; and 373 and 773.

3. The compound according to claim 2, wherein said first nucleobase sequence and said second nucleobase sequence are selected from the group consisting of: SEQ ID NOs: 28 and 428, 277 and 677, 336 and 736, 337 and 737, 366 and 766, 367 and 767, and 369 and 769.

4. The compound according to claim 1, further comprising one or more ligands, wherein said one or more ligands comprise one or more N-Acetyl-Galactosamine moieties.

5. The compound according to claim 1, wherein said single strand has a nucleobase sequence selected from the group consisting of SEQ ID NOs: 792-795 and SEQ ID NOs: 799-800.

6. The compound according to claim 5, wherein said single strand is modified and is selected from the group consisting of SEQ ID NOs: 1586-1589 and SEQ ID NOs: 1593-1594.

7. The compound according to claim 1, which comprises internucleoside linkages and wherein at least one internucleoside linkage is a modified internucleoside linkage wherein said modified internucleoside linkage optionally is a phosphorothioate or phosphorodithioate internucleoside linkage.

8. The compound according to claim 1, wherein at least one nucleoside comprises a modified sugar, wherein said modified sugar optionally is a 2'O-methyl or 2'-F modified sugar.

9. A pharmaceutical composition comprising a compound according to claim 1, and a physiologically acceptable excipient.

10. The pharmaceutical composition of claim 9, wherein said pharmaceutical composition further comprises one or more additional pharmaceutically active agents.

11. The pharmaceutical composition of claim 10, wherein said additional pharmaceutically active agent(s) is/are selected from the group consisting of: icosapent ethyl; an N-acetyl glucosamine-conjugated antisense oligonucleotide targeting ANGPTL3; statins; fibrates; ezetimibe; and a further oligomeric compound which is directed to a target different from APOC3, wherein said different target optionally is PCSK9.

12. A method of treating a disease or disorder comprising administering a compound according to claim 1 to an individual in need of treatment, wherein said disease or disorder is a disease or disorder requiring reduction of APOC3 expression levels.

13. An siRNA compound that inhibits expression of APOC3, comprising a single strand that is modified or unmodified, wherein the nucleobase sequence of said single strand consists of, in unmodified form, a nucleobase sequence selected from the group consisting of SEQ ID NOs: 796-798, and 801-803 and wherein the nucleobase sequence of said single strand consists of, in modified form, a nucleobase sequence selected from the group consisting of SEQ ID NOs: 1590-1592 and SEQ ID NOs: 1595-1597.

14. The compound according to claim 13, further comprising one or more ligands, wherein said one or more ligands comprise one or more N-Acetyl-Galactosamine moieties.

15. A pharmaceutical composition comprising a compound according to claim 13, and a physiologically acceptable excipient.

16. A pharmaceutical composition comprising a compound according to claim 14, and a physiologically acceptable excipient.

17. The pharmaceutical composition of claim 16, wherein said pharmaceutical composition further comprises one or more additional pharmaceutically active agents.

18. A method of treating a disease or disorder comprising administering a compound according to claim 13 to an individual in need of treatment, wherein said disease or disorder is a disease or disorder requiring reduction of APOC3 expression levels.

* * * * *

SEQUENCE LISTING

```
<160> NUMBER OF SEQ ID NOS: 1606

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

uucuagggau gaacugagc                                                   19


<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

ucucuaggga ugaacugag                                                   19
```

-continued

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 3
uccucuaggg augaacuga 19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 4
ugccucuagg gaugaacug 19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 5
uugccucuag ggaugaacu 19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 6
ucugccucua gggaugaac 19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 7
ugcugccucu agggaugaa 19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 8
uagcugccuc uagggauga 19

<210> SEQ ID NO 9

-continued

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 9
ugcagcugcc ucuagggau 19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 10
uagcagcugc cucuaggga 19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 11
ugagcagcug ccucuaggg 19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 12
uggagcagcu gccucuagg 19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 13
uuguuccugg agcagcugc 19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
ucuguuccug gagcagcug 19

<210> SEQ ID NO 15
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15

uccucuguuc cuggagcag                                                19


<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16

uaccucuguu ccuggagca                                                19


<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17

ucaccucugu uccuggagc                                                19


<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18

ugcaccucug uuccuggag                                                19


<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19

uggcaccucu guuccugga                                                19


<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20

uuggcaccuc uguuccugg                                                19


<210> SEQ ID NO 21
<211> LENGTH: 19
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 21
uauggcaccu cuguuccug 19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 22
ucauggcacc ucuguuccu 19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 23
uugcauggca ccucuguuc 19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
ucugcauggc accucuguu 19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
ugcugcaugg caccucugu 19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
uggcugcaug gcaccucug 19

<210> SEQ ID NO 27
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 27

ugggcugcau ggcaccucu                                                19


<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28

ucaacaagga guacccggg                                                19


<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29

uacaacaagg aguacccgg                                                19


<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30

uaacaacaag gaguacccg                                                19


<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31

ucaacaacaa ggaguaccc                                                19


<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32

ugcaacaaca aggaguacc                                                19


<210> SEQ ID NO 33
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
oligonucleotide

<400> SEQUENCE: 33
uggcaacaac aaggaguac 19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 34
ugggcaacaa caaggagua 19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
uagggcaaca acaaggagu 19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
ugagggcaac aacaaggag 19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 37
uggagggcaa caacaagga 19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 38
uaggagggca acaacaagg 19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
ucaggagggc aacaacaag 19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 40
uccaggaggg caacaacaa 19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 41
ugccaggagg gcaacaaca 19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 42
ucgccaggag ggcaacaac 19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 43
ugcgccagga gggcaacaa 19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44
uagcgccagg agggcaaca 19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide -continued

<400> SEQUENCE: 45
ugagcgccag gagggcaac 19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46
uggagcgcca ggagggcaa 19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
uaggagcgcc aggagggca 19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48
ugccaggagc gccaggagg 19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49
uagaggccag gagcgccag 19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50
ucagaggcca ggagcgcca 19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51
ugcagaggcc aggagcgcc 19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52
uggcagaggc caggagcgc 19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53
ugggcagagg ccaggagcg 19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54
uucgggcaga ggccaggag 19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 55
ucucgggcag aggccagga 19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 56
ugcucgggca gaggccagg 19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 57
uagcucgggc agaggccag 19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
uaagcucggg cagaggcca 19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59
ugaagcucgg gcagaggcc 19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 60
uugaagcucg ggcagaggc 19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 61
ucugaagcuc gggcagagg 19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
uucugaagcu cgggcagag 19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
ucucugaagc ucgggcaga 19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
uccucugaag cucgggcag 19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65
ugccucugaa gcucgggca 19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
uggccucuga agcucgggc 19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
ucggccucug aagcucggg 19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 68
uucggccucu gaagcucgg 19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 69
ucucggccuc ugaagcucg 19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uccucggccu cugaagcuc 19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uuccucggcc ucugaagcu 19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uauccucggc cucugaagc 19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ucauccucgg ccucugaag 19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ugcauccucg gccucugaa 19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uggcauccuc ggccucuga 19

-continued

```
<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76

uaggcauccu cggccucug                                                19


<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77

ugaggcaucc ucggccucu                                                19


<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78

uggaggcauc cucggccuc                                                19


<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79

ugggaggcau ccucggccu                                                19


<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80

uagggaggca uccucggcc                                                19


<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81

uaagggaggc auccucggc                                                19
```

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82
ugaagggagg cauccucgg 19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83
uagaagggag gcauccucg 19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84
ugagaaggga ggcauccuc 19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 85
uugagaaggg aggcauccu 19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 86
ucugagaagg gaggcaucc 19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 87
ugcugagaag ggaggcauc 19

<210> SEQ ID NO 88

<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uagcugagaa gggaggcau 19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uugaagcuga gaagggagg 19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uaugaagcug agaagggag 19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
ucaugaagcu gagaaggga 19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ugcaugaagc ugagaaggg 19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uugcaugaag cugagaagg 19

<210> SEQ ID NO 94
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 94
ucugcaugaa gcugagaag 19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 95
uccugcauga agcugagaa 19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 96
ucccugcaug aagcugaga 19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 97
uacccugcau gaagcugag 19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 98
uaacccugca ugaagcuga 19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 99
uuaacccugc augaagcug 19

<210> SEQ ID NO 100
<211> LENGTH: 19
<212> TYPE: RNA

-continued

<213> ORGANISM: Artificial Sequence
<220> FEATURE:
<223> OTHER INFORMATION: Description of Artificial Sequence: Synthetic
oligonucleotide

<400> SEQUENCE: 100
uguaacccug caugaagcu 19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 101
uuguaacccu gcaugaagc 19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 102
uauguaaccc ugcaugaag 19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 103
ucauguaacc cugcaugaa 19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 104
uucauguaac ccugcauga 19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105
uuucauguaa cccugcaug 19

<210> SEQ ID NO 106
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 106

ucuucaugua acccugcau                                                19


<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107

ugcuucaugu aacccugca                                                19


<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108

uugcuucaug uaacccugc                                                19


<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109

ugugcuucau guaacccug                                                19


<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110

ucgugcuuca uguaacccu                                                19


<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111

ugcgugcuuc auguaaccc                                                19


<210> SEQ ID NO 112
<211> LENGTH: 19
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 112
uggcgugcuu cauguaacc 19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 113
uuggcgugcu ucauguaac 19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 114
uguggcgugc uucauguaa 19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
ugguggcgug cuucaugua 19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
uugguggcgu gcuucaugu 19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
uuugguggcg ugcuucaug 19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 118 ucuuggugge gugcuucau 19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 119
uucuuggugg cgugcuuca 19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 120
ugucuuggug gcgugcuuc 19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 121
uggucuuggu ggcgugcuu 19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 122
ucggucuugg uggcgugcu 19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 123
ugcggucuug guggcgugc 19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 124
uggcggucuu gguggcgug 19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 125
uuggcggucu ugguggcgu 19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 126
uuuggcgguc uugguggcg 19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 127
ucuuggcggu cuugguggc 19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 128
uccuuggcgg ucuuggugg 19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 129
uuccuuggcg gucuuggug 19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 130
uauccuuggc ggucuuggu 19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 131
ucauccuugg cggucuugg 19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 132
ugcauccuug gcggucuug 19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 133
uugcauccuu ggcggucuu 19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 134
ugugcauccu uggcggucu 19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 135
uagugcaucc uuggcgguc 19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 136
ucagugcauc cuuggcggu 19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 137
uucagugcau ccuuggcgg 19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 138
ucucagugca uccuuggcg 19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 139
ugcucagugc auccuuggc 19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 140
uugcucagug cauccuugg 19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 141
ucugcucagu gcauccuug 19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 142
ugcugcucag ugcauccuu 19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 143
ucgcugcuca gugcauccu 19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 144
uacgcugcuc agugcaucc 19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 145
ucacgcugcu cagugcauc 19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 146
ugcacgcugc ucagugcau 19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 147
uugcacgcug cucagugca 19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 148
ucugcacgcu gcucagugc 19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uccugcacgc ugcucagug 19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
uuccugcacg cugcucagu 19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uacuccugca cgcugcuca 19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ugggacuccu gcacgcugc 19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uugggacucc ugcacgcug 19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ucugggacuc cugcacgcu 19

-continued

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
uccugggacu ccugcacgc 19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
uaccugggac uccugcacg 19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
ucaccuggga cuccugcac 19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
uccaccuggg acuccugca 19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 159
ugggccaccu gggacuccu 19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 160
uugggccacc ugggacucc 19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 161
uugcugggcc accugggac 19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 162
ucugcugggc caccuggga 19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 163
uggccugcug ggccaccug 19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 164
uccuggccug cugggccac 19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 165
uccaucgguc acccagccc 19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 166
ugccaucggu cacccagcc 19

<210> SEQ ID NO 167

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 167
uagccaucgg ucacccagc 19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 168
uaagccaucg gucacccag 19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 169
ugaagccauc ggucaccca 19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 170
uugaagccau cggucaccc 19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 171
ucugaagcca ucggucacc 19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 172
uacugaagcc aucggucac 19

<210> SEQ ID NO 173
<211> LENGTH: 19

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 173
uaacugaagc caucgguca 19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 174
ugaacugaag ccaucgguc 19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 175
uggaacugaa gccaucggu 19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 176
ugggaacuga agccaucgg 19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 177
uagggaacug aagccaucg 19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 178
ucagggaacu gaagccauc 19

<210> SEQ ID NO 179
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 179

uucagggaac ugaagccau                                              19


<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180

uuucagggaa cugaagcca                                              19


<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181

uuuucaggga acugaagcc                                              19


<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182

ucuuucaggg aacugaagc                                              19


<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183

uucuuucagg gaacugaag                                              19


<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184

ugucuuucag ggaacugaa                                              19


<210> SEQ ID NO 185
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 185
uagucuuuca gggaacuga 19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uuagucuuuc agggaacug 19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uguagucuuu cagggaacu 19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uaguagucuu ucagggaac 19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
ucaguagucu uucagggaa 19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uccaguaguc uuucaggga 19

<210> SEQ ID NO 191
<211> LENGTH: 19
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 191
uuccaguagu cuuucaggg 19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ucuccaguag ucuuucagg 19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
ugcuccagua gucuuucag 19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
uugcuccagu agucuuuca 19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ugugcuccag uagucuuuc 19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uggugcucca guagucuuu 19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 197
ucggugcucc aguagucuu 19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 198
uacggugcuc caguagucu 19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 199
uaacggugcu ccaguaguc 19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 200
uuaacggugc uccaguagu 19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 201
uuuaacggug cuccaguag 19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 202
ucuuaacggu gcuccagua 19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 203
uccuuaacgg ugcuccagu 19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 204
uuccuuaacg gugcuccag 19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 205
uguccuuaac ggugcucca 19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 206
uuguccuuaa cggugcucc 19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 207
uuuguccuua acggugcuc 19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 208
ucuuguccuu aacggugcu 19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 209
uacuuguccu uaacggugc 19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 210
uaacuugucc uuaacggug 19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 211
ugaacuuguc cuuaacggu 19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 212
uagaacuugu ccuuaacgg 19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 213
ugagaacuug uccuuaacg 19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 214
uagagaacuu guccuuaac 19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 215
ucagagaacu uguccuuaa 19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 216
uucagagaac uuguccuua 19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 217
ucucagagaa cuuguccuu 19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 218
uacucagaga acuuguccu 19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 219
uaacucagag aacuugucc 19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 220
ugaacucaga gaacuuguc 19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 221
ucagaacuca gagaacuug 19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 222
uccagaacuc agagaacuu 19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 223
ucccagaacu cagagaacu 19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 224
uucccagaac ucagagaac 19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 225
uaucccagaa cucagagaa 19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 226
uaaucccaga acucagaga 19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 227
uaaaucccag aacucagag 19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
ucaaauccca gaacucaga 19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uccaaauccc agaacucag 19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
uuccaaaucc cagaacuca 19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uguccaaauc ccagaacuc 19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
ugguccaaau cccagaacu 19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
uggguccaaa ucccagaac 19

```
<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234

uaggguccaa aucccagaa                                                    19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235

ucaggucca aaucccaga                                                     19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236

uucagggucc aaaucccag                                                    19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237

ugaccucagg guccaaauc                                                    19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238

uugaccucag gguccaaau                                                    19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239

ucugaccuca ggguccaaa                                                    19
```

-continued

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uucugaccuc aggguccaa                                                    19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ugucugaccu cagggucca                                                    19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uggucugacc ucagggucc                                                    19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uuggucugac cucaggguc                                                    19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uuuggucuga ccucagggu                                                    19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uguuggucug accucaggg                                                    19

<210> SEQ ID NO 246

-continued

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 246
uaguuggucu gaccucagg 19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 247
uaaguugguc ugaccucag 19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 248
ugaaguuggu cugaccuca 19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 249
uugaaguugg ucugaccuc 19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 250
ucugaaguug gucugaccu 19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 251
uggcugaagu uggucugac 19

<210> SEQ ID NO 252
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 252
ucggcugaag uuggucuga 19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 253
uacggcugaa guuggucug 19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 254
ucacggcuga aguuggucu 19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 255
uccacggcug aaguugguc 19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 256
ugccacggcu gaaguuggu 19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 257
ucagccacgg cugaaguug 19

<210> SEQ ID NO 258
<211> LENGTH: 19
<212> TYPE: RNA

-continued

<213> ORGANISM: Artificial Sequence
<220> FEATURE:
<223> OTHER INFORMATION: Description of Artificial Sequence: Synthetic oligonucleotide

<400> SEQUENCE: 258
ugcagccacg gcugaaguu 19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 259
uggcagccac ggcugaagu 19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 260
uaggcagcca cggcugaag 19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 261
ucaggcagcc acggcugaa 19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 262
uucucaggca gccacggcu 19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 263
ugucucaggc agccacggc 19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 264
uggucucagg cagccacgg 19

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 265
uaggucucag gcagccacg 19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 266
uugaggucuc aggcagcca 19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 267
uuugaggucu caggcagcc 19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 268
uauugagguc ucaggcagc 19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 269
uuauugaggu cucaggcag 19

<210> SEQ ID NO 270
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 270
uguauugagg ucucaggca 19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 271
ugguauugag gucucaggc 19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 272
uggguauuga ggucucagg 19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 273
uuaggcaggu ggacuuggg 19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 274
uauaggcagg uggacuugg 19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 275
ugauaggcag guggacuug 19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
uggauaggca gguggacuu 19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 277
uuggauaggc agguggacu 19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 278
uauggauagg cagguggac 19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 279
ugauggauag gcaggugga 19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 280
uggauggaua ggcaggugg 19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 281
uaggauggau aggcaggug 19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 282
ucaggaugga uaggcaggu 19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 283
ugcaggaugg auaggcagg 19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 284
ucgcaggaug gauaggcag 19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 285
uucgcaggau ggauaggca 19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 286
ucucgcagga uggauaggc 19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 287
ugcucgcagg auggauagg 19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 288
uagcucgcag gauggauag 19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 289
ugagcucgca ggauggaua 19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 290
uggagcucgc aggauggau 19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 291
uaggagcucg caggaugga 19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 292
uaaggagcuc gcaggaugg 19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 293
ucaaggagcu cgcaggaug 19

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 294
uccaaggagc ucgcaggau 19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 295
ucccaaggag cucgcagga 19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 296
uacccaagga gcucgcagg 19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 297
ugacccaagg agcucgcag 19

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 298
uggacccaag gagcucgca 19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 299
uaggacccaa ggagcucgc 19

<210> SEQ ID NO 300
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 300
ucaggaccca aggagcucg 19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 301
ugcaggaccc aaggagcuc 19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 302
uugcaggacc caaggagcu 19

<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 303
uuugcaggac ccaaggagc 19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 304
uauugcagga cccaaggag 19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 305
ugauugcagg acccaagga 19

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 306
uagauugcag gacccaagg 19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 307
ugagauugca ggacccaag 19

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 308
uggagauugc aggacccaa 19

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 309
uuggagauug caggaccca 19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 310
ucuggagauu gcaggaccc 19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 311
uccuggagau ugcaggacc 19

<210> SEQ ID NO 312
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 312
ucccuggaga uugcaggac 19

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 313
ugcccuggag auugcagga 19

<210> SEQ ID NO 314
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 314
uagcccugga gauugcagg 19

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 315
ucagcccugg agauugcag 19

<210> SEQ ID NO 316
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 316
ugcagcccug gagauugca 19

<210> SEQ ID NO 317
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 317
uggcagcccu ggagauugc 19

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
ugggcagccc uggagauug 19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uuuuaagcaa ccuacaggg 19

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
uuuuuaagca accuacagg 19

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
ucuuuuaagc aaccuacag 19

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uccuuuuaag caaccuaca 19

<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
ucccuuuuaa gcaaccuac 19

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uucccuuuua agcaaccua 19

<210> SEQ ID NO 325

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
ugucccuuuu aagcaaccu 19

<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
uacugucccu uuuaagcaa 19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327
uuacuguccc uuuuaagca 19

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328
uauacugucc cuuuuaagc 19

<210> SEQ ID NO 329
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 329
uaauacuguc ccuuuuaag 19

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 330
ugaauacugu cccuuuuaa 19

<210> SEQ ID NO 331
<211> LENGTH: 19

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
uagaauacug ucccuuuua 19

<210> SEQ ID NO 332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ugagaauacu gucccuuuu 19

<210> SEQ ID NO 333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uugagaauac ugucccuuu 19

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
ucugagaaua cugucccuu 19

<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
uacugagaau acugucccu 19

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ucacugagaa uacuguccc 19

<210> SEQ ID NO 337
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 337
ugcacugaga auacugucc 19

<210> SEQ ID NO 338
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 338
uagcacugag aauacuguc 19

<210> SEQ ID NO 339
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 339
ugagcacuga gaauacugu 19

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 340
uagagcacug agaauacug 19

<210> SEQ ID NO 341
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 341
ugagagcacu gagaauacu 19

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 342
uggagagcac ugagaauac 19

<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 343
uaggagagca cugagaaua 19

<210> SEQ ID NO 344
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 344
uuaggagagc acugagaau 19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 345
uguaggagag cacugagaa 19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 346
ugguaggaga gcacugaga 19

<210> SEQ ID NO 347
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 347
uggguaggag agcacugag 19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
uggccaggca ugagguggg 19

<210> SEQ ID NO 349
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 349
ugggccaggc augaggugg 19

<210> SEQ ID NO 350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
ugccagcaug ccuggaggg 19

<210> SEQ ID NO 351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uggccagcau gccuggagg 19

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uaggccagca ugccuggag 19

<210> SEQ ID NO 353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
ugaggccagc augccugga 19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uggaggccag caugccugg 19

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 355
ugggaggcca gcaugccug 19

<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 356
uugggaggcc agcaugccu 19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 357
uauugggagg ccagcaugc 19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 358
uuauugggag gccagcaug 19

<210> SEQ ID NO 359
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
uuuauuggga ggccagcau 19

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
uuuuauuggg aggccagca 19

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide -continued

<400> SEQUENCE: 361
ucuuuauugg gaggccagc 19

<210> SEQ ID NO 362
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 362
ugcuuuauug ggaggccag 19

<210> SEQ ID NO 363
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 363
uagcuuuauu gggaggcca 19

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 364
ucagcuuuau ugggaggcc 19

<210> SEQ ID NO 365
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 365
uccagcuuua uugggaggc 19

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 366
uuccagcuuu auugggagg 19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 367
uguccagcuu uauugggag 19

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 368
uuuguccagc uuuauuggg 19

<210> SEQ ID NO 369
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 369
ucuuguccag cuuuauugg 19

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 370
uucuugucca gcuuuauug 19

<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 371
uuucuugucc agcuuuauu 19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 372
ucuucuuguc cagcuuuau 19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 373
ugcuucuugu ccagcuuua 19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 374
ugcagcuucu uguccagcu 19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
uuagcagcuu cuuguccag 19

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
uauagcagcu ucuugucca 19

<210> SEQ ID NO 377
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
uaacucagag aacuugucc 19

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 378
uuguccuuaa cggugcucc 19

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 379
uaaucccaga acucagaga 19

<210> SEQ ID NO 380
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 380
uccuuggcgg ucuuggugg 19

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 381
ucugaagcca ucggucacc 19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 382
ucagagaacu uguccuuaa 19

<210> SEQ ID NO 383
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 383
uacucagaga acuuguccu 19

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 384
ugaacucaga gaacuuguc 19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 385
uacuuguccu uaacggugc 19

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
ucucagagaa cuuguccuu 19

<210> SEQ ID NO 387
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
uuuguccuua acggugcuc 19

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
uuccuuggcg gucuuggug 19

<210> SEQ ID NO 389
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 389
ugcuccagua gucuuucag 19

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
ucauccucgg ccucugaag 19

<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
uugguggcgu gcuucaugu 19

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392
uucuagggau gaacugagc 19

<210> SEQ ID NO 393
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393
ucucuaggga ugaacugag 19

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394
uccucuaggg augaacuga 19

<210> SEQ ID NO 395
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 395
ugccucuagg gaugaacug 19

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 396
uugccucuag ggaugaacu 19

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 397
ucugccucua gggaugaac 19

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 398
ugcugccucu agggaugaa 19

<210> SEQ ID NO 399
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 399
uagcugccuc uagggauga 19

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 400
ugcagcugcc ucuagggau 19

<210> SEQ ID NO 401
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 401
aguucauccc uagaa 15

<210> SEQ ID NO 402
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 402
guucaucccu agaga 15

<210> SEQ ID NO 403
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 403
uucaucccua gagga 15

<210> SEQ ID NO 404

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 404
ucaucccuag aggca 15

<210> SEQ ID NO 405
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 405
caucccuaga ggcaa 15

<210> SEQ ID NO 406
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406
aucccuagag gcaga 15

<210> SEQ ID NO 407
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407
ucccuagagg cagca 15

<210> SEQ ID NO 408
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408
cccuagaggc agcua 15

<210> SEQ ID NO 409
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409
cuagaggcag cugca 15

<210> SEQ ID NO 410
<211> LENGTH: 15

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410
uagaggcagc ugcua 15

<210> SEQ ID NO 411
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 411
agaggcagcu gcuca 15

<210> SEQ ID NO 412
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412
gaggcagcug cucca 15

<210> SEQ ID NO 413
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 413
cugcuccagg aacaa 15

<210> SEQ ID NO 414
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 414
ugcuccagga acaga 15

<210> SEQ ID NO 415
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 415
uccaggaaca gagga 15

<210> SEQ ID NO 416
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 416
ccaggaacag aggua 15

<210> SEQ ID NO 417
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 417
caggaacaga gguga 15

<210> SEQ ID NO 418
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418
aggaacagag gugca 15

<210> SEQ ID NO 419
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 419
ggaacagagg ugcca 15

<210> SEQ ID NO 420
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 420
gaacagaggu gccaa 15

<210> SEQ ID NO 421
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 421
aacagaggug ccaua 15

<210> SEQ ID NO 422
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 422
acagaggugc cauga 15

<210> SEQ ID NO 423
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 423
agaggugcca ugcaa 15

<210> SEQ ID NO 424
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 424
gaggugccau gcaga 15

<210> SEQ ID NO 425
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 425
aggugccaug cagca 15

<210> SEQ ID NO 426
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 426
ggugccaugc agcca 15

<210> SEQ ID NO 427
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 427
gugccaugca gccca 15

<210> SEQ ID NO 428
<211> LENGTH: 15
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 428
gguacuccuu guuga 15

<210> SEQ ID NO 429
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
guacuccuug uugua 15

<210> SEQ ID NO 430
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
uacuccuugu uguua 15

<210> SEQ ID NO 431
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
acuccuuguu guuga 15

<210> SEQ ID NO 432
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
cuccuuguug uugca 15

<210> SEQ ID NO 433
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uccuuguugu ugcca 15

<210> SEQ ID NO 434
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 434
ccuuguuguu gccca 15

<210> SEQ ID NO 435
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 435
cuuguuguug cccua 15

<210> SEQ ID NO 436
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 436
uuguuguugc ccuca 15

<210> SEQ ID NO 437
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 437
uguuguugcc cucca 15

<210> SEQ ID NO 438
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 438
guuguugccc uccua 15

<210> SEQ ID NO 439
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439
uuguugcccu ccuga 15

<210> SEQ ID NO 440
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440
uguugcccuc cugga 15

<210> SEQ ID NO 441
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 441
guugcccucc uggca 15

<210> SEQ ID NO 442
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 442
uugcccuccu ggcga 15

<210> SEQ ID NO 443
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 443
ugcccuccug gcgca 15

<210> SEQ ID NO 444
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 444
gcccuccugg cgcua 15

<210> SEQ ID NO 445
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 445
cccuccuggc gcuca 15

<210> SEQ ID NO 446
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 446
ccuccuggcg cucca 15

<210> SEQ ID NO 447
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 447
cuccuggcgc uccua 15

<210> SEQ ID NO 448
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 448
cuggcgcucc uggca 15

<210> SEQ ID NO 449
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 449
cgcuccuggc cucua 15

<210> SEQ ID NO 450
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 450
gcuccuggcc ucuga 15

<210> SEQ ID NO 451
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 451
cuccuggccu cugca 15

<210> SEQ ID NO 452
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 452

-continued uccuggccuc ugcca 15

<210> SEQ ID NO 453
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 453
ccuggccucu gccca 15

<210> SEQ ID NO 454
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 454
uggccucugc ccgaa 15

<210> SEQ ID NO 455
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 455
ggccucugcc cgaga 15

<210> SEQ ID NO 456
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 456
gccucugccc gagca 15

<210> SEQ ID NO 457
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 457
ccucugcccg agcua 15

<210> SEQ ID NO 458
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 458
cucugcccga gcuua 15

<210> SEQ ID NO 459
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 459
ucugcccgag cuuca 15

<210> SEQ ID NO 460
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 460
cugcccgagc uucaa 15

<210> SEQ ID NO 461
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 461
ugcccgagcu ucaga 15

<210> SEQ ID NO 462
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 462
gcccgagcuu cagaa 15

<210> SEQ ID NO 463
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 463
cccgagcuuc agaga 15

<210> SEQ ID NO 464
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 464
ccgagcuuca gagga 15

<210> SEQ ID NO 465
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
cgagcuucag aggca 15

<210> SEQ ID NO 466
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466
gagcuucaga ggcca 15

<210> SEQ ID NO 467
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
agcuucagag gccga 15

<210> SEQ ID NO 468
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468
gcuucagagg ccgaa 15

<210> SEQ ID NO 469
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
cuucagaggc cgaga 15

<210> SEQ ID NO 470
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 470
uucagaggcc gagga 15

-continued

<210> SEQ ID NO 471
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 471
ucagaggccg aggaa 15

<210> SEQ ID NO 472
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 472
cagaggccga ggaua 15

<210> SEQ ID NO 473
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 473
agaggccgag gauga 15

<210> SEQ ID NO 474
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 474
gaggccgagg augca 15

<210> SEQ ID NO 475
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 475
aggccgagga ugcca 15

<210> SEQ ID NO 476
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 476
ggccgaggau gccua 15

<210> SEQ ID NO 477
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477
gccgaggaug ccuca 15

<210> SEQ ID NO 478
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478
ccgaggaugc cucca 15

<210> SEQ ID NO 479
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479
cgaggaugcc uccca 15

<210> SEQ ID NO 480
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 480
gaggaugccu cccua 15

<210> SEQ ID NO 481
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 481
aggaugccuc ccuua 15

<210> SEQ ID NO 482
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 482
ggaugccucc cuuca 15

<210> SEQ ID NO 483

-continued

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 483
gaugccuccc uucua 15

<210> SEQ ID NO 484
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 484
augccucccu ucuca 15

<210> SEQ ID NO 485
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 485
ugccucccuu cucaa 15

<210> SEQ ID NO 486
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 486
gccucccuuc ucaga 15

<210> SEQ ID NO 487
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487
ccucccuucu cagca 15

<210> SEQ ID NO 488
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 488
cucccuucuc agcua 15

<210> SEQ ID NO 489
<211> LENGTH: 15

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 489
ccuucucagc uucaa 15

<210> SEQ ID NO 490
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 490
cuucucagcu ucaua 15

<210> SEQ ID NO 491
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 491
uucucagcuu cauga 15

<210> SEQ ID NO 492
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 492
ucucagcuuc augca 15

<210> SEQ ID NO 493
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 493
cucagcuuca ugcaa 15

<210> SEQ ID NO 494
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 494
ucagcuucau gcaga 15

<210> SEQ ID NO 495
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 495
cagcuucaug cagga 15

<210> SEQ ID NO 496
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 496
agcuucaugc aggga 15

<210> SEQ ID NO 497
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 497
gcuucaugca gggua 15

<210> SEQ ID NO 498
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 498
cuucaugcag gguua 15

<210> SEQ ID NO 499
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 499
uucaugcagg guuaa 15

<210> SEQ ID NO 500
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 500
ucaugcaggg uuaca 15

<210> SEQ ID NO 501
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 501
caugcagggu uacaa 15

<210> SEQ ID NO 502
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 502
augcaggguu acaua 15

<210> SEQ ID NO 503
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 503
ugcaggguua cauga 15

<210> SEQ ID NO 504
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 504
gcaggguuac augaa 15

<210> SEQ ID NO 505
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 505
caggguuaca ugaaa 15

<210> SEQ ID NO 506
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 506
aggguuacau gaaga 15

<210> SEQ ID NO 507
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 507
ggguuacaug aagca 15

<210> SEQ ID NO 508
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 508
gguuacauga agcaa 15

<210> SEQ ID NO 509
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 509
guuacaugaa gcaca 15

<210> SEQ ID NO 510
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 510
uuacaugaag cacga 15

<210> SEQ ID NO 511
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 511
uacaugaagc acgca 15

<210> SEQ ID NO 512
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 512
acaugaagca cgcca 15

<210> SEQ ID NO 513
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 513
caugaagcac gccaa 15

<210> SEQ ID NO 514
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 514
augaagcacg ccaca 15

<210> SEQ ID NO 515
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 515
ugaagcacgc cacca 15

<210> SEQ ID NO 516
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 516
gaagcacgcc accaa 15

<210> SEQ ID NO 517
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 517
aagcacgcca ccaaa 15

<210> SEQ ID NO 518
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 518
agcacgccac caaga 15

<210> SEQ ID NO 519
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 519
gcacgccacc aagaa 15

<210> SEQ ID NO 520
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 520
cacgccacca agaca 15

<210> SEQ ID NO 521
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 521
acgccaccaa gacca 15

<210> SEQ ID NO 522
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 522
cgccaccaag accga 15

<210> SEQ ID NO 523
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 523
gccaccaaga ccgca 15

<210> SEQ ID NO 524
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 524
ccaccaagac cgcca 15

<210> SEQ ID NO 525
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 525
caccaagacc gccaa 15

<210> SEQ ID NO 526
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 526
accaagaccg ccaaa 15

<210> SEQ ID NO 527
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 527
ccaagaccgc caaga 15

<210> SEQ ID NO 528
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 528
caagaccgcc aagga 15

<210> SEQ ID NO 529
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 529
aagaccgcca aggaa 15

<210> SEQ ID NO 530
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 530
agaccgccaa ggaua 15

<210> SEQ ID NO 531
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 531
gaccgccaag gauga 15

<210> SEQ ID NO 532
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 532
accgccaagg augca 15

<210> SEQ ID NO 533
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 533
ccgccaagga ugcaa 15

<210> SEQ ID NO 534
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 534
cgccaaggau gcaca 15

<210> SEQ ID NO 535
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 535
gccaaggaug cacua 15

<210> SEQ ID NO 536
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 536
ccaaggaugc acuga 15

<210> SEQ ID NO 537
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 537
caaggaugca cugaa 15

<210> SEQ ID NO 538
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 538
aaggaugcac ugaga 15

<210> SEQ ID NO 539
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 539
aggaugcacu gagca 15

<210> SEQ ID NO 540
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 540
ggaugcacug agcaa 15

<210> SEQ ID NO 541
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 541
gaugcacuga gcaga 15

<210> SEQ ID NO 542
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 542
augcacugag cagca 15

<210> SEQ ID NO 543
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 543
ugcacugagc agcga 15

<210> SEQ ID NO 544
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 544
gcacugagca gcgua 15

<210> SEQ ID NO 545
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 545
cacugagcag cguga 15

<210> SEQ ID NO 546
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 546
acugagcagc gugca 15

<210> SEQ ID NO 547
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 547
cugagcagcg ugcaa 15

<210> SEQ ID NO 548
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 548
ugagcagcgu gcaga 15

<210> SEQ ID NO 549
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 549
gagcagcgug cagga 15

<210> SEQ ID NO 550
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 550
agcagcgugc aggaa 15

<210> SEQ ID NO 551
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 551
cagcgugcag gagua 15

<210> SEQ ID NO 552
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 552
cgugcaggag uccca 15

<210> SEQ ID NO 553
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 553
gugcaggagu cccaa 15

<210> SEQ ID NO 554
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 554
ugcaggaguc ccaga 15

<210> SEQ ID NO 555
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 555
gcaggagucc cagga 15

<210> SEQ ID NO 556
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 556
caggaguccc aggua 15

<210> SEQ ID NO 557
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 557
aggaguccca gguga 15

<210> SEQ ID NO 558
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 558
ggagucccag gugga 15

<210> SEQ ID NO 559
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 559
gucccaggug gccca 15

<210> SEQ ID NO 560
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 560
ucccaggugg cccaa 15

<210> SEQ ID NO 561
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 561
cagguggccc agcaa 15

<210> SEQ ID NO 562

<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562
agguggccca gcaga 15

<210> SEQ ID NO 563
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563
uggcccagca ggcca 15

<210> SEQ ID NO 564
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
cccagcaggc cagga 15

<210> SEQ ID NO 565
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565
ugggugaccg augga 15

<210> SEQ ID NO 566
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 566
gggugaccga uggca 15

<210> SEQ ID NO 567
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 567
ggugaccgau ggcua 15

<210> SEQ ID NO 568
<211> LENGTH: 15

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 568
gugaccgaug gcuua 15

<210> SEQ ID NO 569
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 569
ugaccgaugg cuuca 15

<210> SEQ ID NO 570
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 570
gaccgauggc uucaa 15

<210> SEQ ID NO 571
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 571
accgauggcu ucaga 15

<210> SEQ ID NO 572
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 572
ccgauggcuu cagua 15

<210> SEQ ID NO 573
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 573
cgauggcuuc aguua 15

<210> SEQ ID NO 574
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 574
gauggcuuca guuca 15

<210> SEQ ID NO 575
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 575
auggcuucag uucca 15

<210> SEQ ID NO 576
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 576
uggcuucagu uccca 15

<210> SEQ ID NO 577
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 577
ggcuucaguu cccua 15

<210> SEQ ID NO 578
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 578
gcuucaguuc ccuga 15

<210> SEQ ID NO 579
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 579
cuucaguucc cugaa 15

<210> SEQ ID NO 580
<211> LENGTH: 15
<212> TYPE: RNA
<213> ORGANISM: Artificial Sequence -continued
<220> FEATURE:
<223> OTHER INFORMATION: Description of Artificial Sequence: Synthetic
oligonucleotide

<400> SEQUENCE: 580
uucaguuccc ugaaa 15

<210> SEQ ID NO 581
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 581
ucaguucccu gaaaa 15

<210> SEQ ID NO 582
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 582
caguucccug aaaga 15

<210> SEQ ID NO 583
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 583
aguucccuga aagaa 15

<210> SEQ ID NO 584
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 584
guucccugaa agaca 15

<210> SEQ ID NO 585
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 585
uucccugaaa gacua 15

<210> SEQ ID NO 586
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 586
ucccugaaag acuaa 15

<210> SEQ ID NO 587
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 587
cccugaaaga cuaca 15

<210> SEQ ID NO 588
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 588
ccugaaagac uacua 15

<210> SEQ ID NO 589
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 589
cugaaagacu acuga 15

<210> SEQ ID NO 590
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 590
ugaaagacua cugga 15

<210> SEQ ID NO 591
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 591
gaaagacuac uggaa 15

<210> SEQ ID NO 592
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 592
aaagacuacu ggaga 15

<210> SEQ ID NO 593
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 593
aagacuacug gagca 15

<210> SEQ ID NO 594
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 594
agacuacugg agcaa 15

<210> SEQ ID NO 595
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 595
gacuacugga gcaca 15

<210> SEQ ID NO 596
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 596
acuacuggag cacca 15

<210> SEQ ID NO 597
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 597
cuacuggagc accga 15

<210> SEQ ID NO 598
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 598
uacuggagca ccgua 15

<210> SEQ ID NO 599
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 599
acuggagcac cguua 15

<210> SEQ ID NO 600
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 600
cuggagcacc guuaa 15

<210> SEQ ID NO 601
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 601
uggagcaccg uuaaa 15

<210> SEQ ID NO 602
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 602
ggagcaccgu uaaga 15

<210> SEQ ID NO 603
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 603
gagcaccguu aagga 15

<210> SEQ ID NO 604
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 604
agcaccguua aggaa 15

<210> SEQ ID NO 605
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 605
gcaccguuaa ggaca 15

<210> SEQ ID NO 606
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 606
caccguuaag gacaa 15

<210> SEQ ID NO 607
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 607
accguuaagg acaaa 15

<210> SEQ ID NO 608
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 608
ccguuaagga caaga 15

<210> SEQ ID NO 609
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 609
cguuaaggac aagua 15

<210> SEQ ID NO 610
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 610
guuaaggaca aguua 15

<210> SEQ ID NO 611
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 611
uuaaggacaa guuca 15

<210> SEQ ID NO 612
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 612
uaaggacaag uucua 15

<210> SEQ ID NO 613
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 613
aaggacaagu ucuca 15

<210> SEQ ID NO 614
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 614
aggacaaguu cucua 15

<210> SEQ ID NO 615
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 615
ggacaaguuc ucuga 15

<210> SEQ ID NO 616
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 616
gacaaguucu cugaa 15

<210> SEQ ID NO 617
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 617
acaaguucuc ugaga 15

<210> SEQ ID NO 618
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 618
caaguucucu gagua 15

<210> SEQ ID NO 619
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 619
aaguucucug aguua 15

<210> SEQ ID NO 620
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 620
aguucucuga guuca 15

<210> SEQ ID NO 621
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 621
uucucugagu ucuga 15

<210> SEQ ID NO 622
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 622
ucucugaguu cugga 15

<210> SEQ ID NO 623
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 623
cucugaguuc uggga 15

<210> SEQ ID NO 624
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 624
ucugaguucu gggaa 15

<210> SEQ ID NO 625
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 625
cugaguucug ggaua 15

<210> SEQ ID NO 626
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 626
ugaguucugg gauua 15

<210> SEQ ID NO 627
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 627
gaguucuggg auuua 15

<210> SEQ ID NO 628
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 628
aguucuggga uuuga 15

<210> SEQ ID NO 629
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 629
guucugggau uugga 15

<210> SEQ ID NO 630
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 630
uucugggauu uggaa 15

<210> SEQ ID NO 631
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 631
ucugggauuu ggaca 15

<210> SEQ ID NO 632
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 632
cugggauuug gacca 15

<210> SEQ ID NO 633
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 633
ugggauuugg accca 15

<210> SEQ ID NO 634
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 634
gggauuugga cccua 15

<210> SEQ ID NO 635
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 635
ggauuuggac ccuga 15

<210> SEQ ID NO 636
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 636
gauuuggacc cugaa 15

<210> SEQ ID NO 637
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 637
uggacccuga gguca 15

<210> SEQ ID NO 638
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 638
ggacccugag gucaa 15

<210> SEQ ID NO 639
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 639
gacccugagg ucaga 15

<210> SEQ ID NO 640
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 640
acccugaggu cagaa 15

<210> SEQ ID NO 641

-continued

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 641
cccugagguc agaca 15

<210> SEQ ID NO 642
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 642
ccugagguca gacca 15

<210> SEQ ID NO 643
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 643
cugaggucag accaa 15

<210> SEQ ID NO 644
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 644
ugaggucaga ccaaa 15

<210> SEQ ID NO 645
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 645
gaggucagac caaca 15

<210> SEQ ID NO 646
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 646
aggucagacc aacua 15

<210> SEQ ID NO 647
<211> LENGTH: 15

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647

ggucagacca acuua                                                    15


<210> SEQ ID NO 648
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648

gucagaccaa cuuca                                                    15


<210> SEQ ID NO 649
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649

ucagaccaac uucaa                                                    15


<210> SEQ ID NO 650
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650

cagaccaacu ucaga                                                    15


<210> SEQ ID NO 651
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651

gaccaacuuc agcca                                                    15


<210> SEQ ID NO 652
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652

accaacuuca gccga                                                    15


<210> SEQ ID NO 653
<211> LENGTH: 15
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 653
ccaacuucag ccgua 15

<210> SEQ ID NO 654
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 654
caacuucagc cguga 15

<210> SEQ ID NO 655
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 655
aacuucagcc gugga 15

<210> SEQ ID NO 656
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 656
acuucagccg uggca 15

<210> SEQ ID NO 657
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 657
uucagccgug gcuga 15

<210> SEQ ID NO 658
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 658
ucagccgugg cugca 15

<210> SEQ ID NO 659
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
cagccguggc ugcca 15

<210> SEQ ID NO 660
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
agccguggcu gccua 15

<210> SEQ ID NO 661
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
gccguggcug ccuga 15

<210> SEQ ID NO 662
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
guggcugccu gagaa 15

<210> SEQ ID NO 663
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
uggcugccug agaca 15

<210> SEQ ID NO 664
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
ggcugccuga gacca 15

<210> SEQ ID NO 665
<211> LENGTH: 15
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 665
gcugccugag accua                                                        15

<210> SEQ ID NO 666
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
ugccugagac cucaa                                                        15

<210> SEQ ID NO 667
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
gccugagacc ucaaa                                                        15

<210> SEQ ID NO 668
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
ccugagaccu caaua                                                        15

<210> SEQ ID NO 669
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
cugagaccuc aauaa                                                        15

<210> SEQ ID NO 670
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
ugagaccuca auaca                                                        15

<210> SEQ ID NO 671
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 671
gagaccucaa uacca 15

<210> SEQ ID NO 672
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 672
agaccucaau accca 15

<210> SEQ ID NO 673
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 673
aguccaccug ccuaa 15

<210> SEQ ID NO 674
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 674
guccaccugc cuaua 15

<210> SEQ ID NO 675
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 675
uccaccugcc uauca 15

<210> SEQ ID NO 676
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 676
ccaccugccu aucca 15

<210> SEQ ID NO 677
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 677
caccugccua uccaa 15

<210> SEQ ID NO 678
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 678
accugccuau ccaua 15

<210> SEQ ID NO 679
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 679
ccugccuauc cauca 15

<210> SEQ ID NO 680
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 680
cugccuaucc aucca 15

<210> SEQ ID NO 681
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 681
ugccuaucca uccua 15

<210> SEQ ID NO 682
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 682
gccuauccau ccuga 15

<210> SEQ ID NO 683
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 683
ccuauccauc cugca 15

<210> SEQ ID NO 684
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 684
cuauccaucc ugcga 15

<210> SEQ ID NO 685
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 685
uauccauccu gcgaa 15

<210> SEQ ID NO 686
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 686
auccauccug cgaga 15

<210> SEQ ID NO 687
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 687
uccauccugc gagca 15

<210> SEQ ID NO 688
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 688
ccauccugcg agcua 15

<210> SEQ ID NO 689
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 689
cauccugcga gcuca 15

<210> SEQ ID NO 690
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 690
auccugcgag cucca 15

<210> SEQ ID NO 691
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 691
uccugcgagc uccua 15

<210> SEQ ID NO 692
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 692
ccugcgagcu ccuua 15

<210> SEQ ID NO 693
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 693
cugcgagcuc cuuga 15

<210> SEQ ID NO 694
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 694
ugcgagcucc uugga 15

<210> SEQ ID NO 695
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 695
gcgagcuccu uggga                                                    15

<210> SEQ ID NO 696
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
cgagcuccuu gggua                                                    15

<210> SEQ ID NO 697
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
gagcuccuug gguca                                                    15

<210> SEQ ID NO 698
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
agcuccuugg gucca                                                    15

<210> SEQ ID NO 699
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
gcuccuuggg uccua                                                    15

<210> SEQ ID NO 700
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
cuccuugggu ccuga                                                    15

<210> SEQ ID NO 701
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
uccuuggguc cugca                                                    15

<210> SEQ ID NO 702
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 702
ccuugggucc ugcaa 15

<210> SEQ ID NO 703
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 703
cuuggguccu gcaaa 15

<210> SEQ ID NO 704
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 704
uuggguccug caaua 15

<210> SEQ ID NO 705
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 705
uggguccugc aauca 15

<210> SEQ ID NO 706
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 706
ggguccugca aucua 15

<210> SEQ ID NO 707
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 707
gguccugcaa ucuca 15

<210> SEQ ID NO 708
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 708
guccugcaau cucca 15

<210> SEQ ID NO 709
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 709
uccugcaauc uccaa 15

<210> SEQ ID NO 710
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 710
ccugcaaucu ccaga 15

<210> SEQ ID NO 711
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 711
cugcaaucuc cagga 15

<210> SEQ ID NO 712
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 712
ugcaaucucc aggga 15

<210> SEQ ID NO 713
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 713
gcaaucucca gggca 15

<210> SEQ ID NO 714
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 714
caaucuccag ggcua 15

<210> SEQ ID NO 715
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 715
aaucuccagg gcuga 15

<210> SEQ ID NO 716
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 716
aucuccaggg cugca 15

<210> SEQ ID NO 717
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 717
ucuccagggc ugcca 15

<210> SEQ ID NO 718
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 718
cuccagggcu gccca 15

<210> SEQ ID NO 719
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 719
guagguugcu uaaaa 15

<210> SEQ ID NO 720

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
uagguugcuu aaaaa 15

<210> SEQ ID NO 721
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 721
agguugcuua aaaga 15

<210> SEQ ID NO 722
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 722
gguugcuuaa aagga 15

<210> SEQ ID NO 723
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 723
guugcuuaaa aggga 15

<210> SEQ ID NO 724
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 724
uugcuuaaaa gggaa 15

<210> SEQ ID NO 725
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 725
ugcuuaaaag ggaca 15

<210> SEQ ID NO 726
<211> LENGTH: 15

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 726
uuaaaaggga cagua 15

<210> SEQ ID NO 727
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 727
uaaaagggac aguaa 15

<210> SEQ ID NO 728
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 728
aaaagggaca guaua 15

<210> SEQ ID NO 729
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 729
aaagggacag uauua 15

<210> SEQ ID NO 730
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 730
aagggacagu auuca 15

<210> SEQ ID NO 731
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 731
agggacagua uucua 15

<210> SEQ ID NO 732
<211> LENGTH: 15
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 732
gggacaguau ucuca 15

<210> SEQ ID NO 733
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 733
ggacaguauu cucaa 15

<210> SEQ ID NO 734
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 734
gacaguauuc ucaga 15

<210> SEQ ID NO 735
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 735
acaguauucu cagua 15

<210> SEQ ID NO 736
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 736
caguauucuc aguga 15

<210> SEQ ID NO 737
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 737
aguauucuca gugca 15

<210> SEQ ID NO 738
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
guauucucag ugcua 15

<210> SEQ ID NO 739
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
uauucucagu gcuca 15

<210> SEQ ID NO 740
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
auucucagug cucua 15

<210> SEQ ID NO 741
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
uucucagugc ucuca 15

<210> SEQ ID NO 742
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
ucucagugcu cucca 15

<210> SEQ ID NO 743
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
cucagugcuc uccua 15

<210> SEQ ID NO 744
<211> LENGTH: 15
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 744
ucagugcucu ccuaa 15

<210> SEQ ID NO 745
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
cagugcucuc cuaca 15

<210> SEQ ID NO 746
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
agugcucucc uacca 15

<210> SEQ ID NO 747
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
gugcucuccu accca 15

<210> SEQ ID NO 748
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
ccucaugccu ggcca 15

<210> SEQ ID NO 749
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
cucaugccug gccca 15

<210> SEQ ID NO 750
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 750
ccaggcaugc uggca 15

<210> SEQ ID NO 751
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 751
caggcaugcu ggcca 15

<210> SEQ ID NO 752
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 752
aggcaugcug gccua 15

<210> SEQ ID NO 753
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 753
ggcaugcugg ccuca 15

<210> SEQ ID NO 754
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 754
gcaugcuggc cucca 15

<210> SEQ ID NO 755
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 755
caugcuggcc uccca 15

<210> SEQ ID NO 756
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 756
augcuggccu cccaa 15

<210> SEQ ID NO 757
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 757
gcuggccucc caaua 15

<210> SEQ ID NO 758
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758
cuggccuccc aauaa 15

<210> SEQ ID NO 759
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759
uggccuccca auaaa 15

<210> SEQ ID NO 760
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760
ggccucccaa uaaaa 15

<210> SEQ ID NO 761
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 761
gccucccaau aaaga 15

<210> SEQ ID NO 762
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 762
ccucccaaua aagca 15

<210> SEQ ID NO 763
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 763
cucccaauaa agcua 15

<210> SEQ ID NO 764
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 764
ucccaauaaa gcuga 15

<210> SEQ ID NO 765
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 765
cccaauaaag cugga 15

<210> SEQ ID NO 766
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 766
ccaauaaagc uggaa 15

<210> SEQ ID NO 767
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 767
caauaaagcu ggaca 15

<210> SEQ ID NO 768
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 768
auaaagcugg acaaa 15

<210> SEQ ID NO 769
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 769
uaaagcugga caaga 15

<210> SEQ ID NO 770
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 770
aaagcuggac aagaa 15

<210> SEQ ID NO 771
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 771
aagcuggaca agaaa 15

<210> SEQ ID NO 772
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 772
agcuggacaa gaaga 15

<210> SEQ ID NO 773
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 773
gcuggacaag aagca 15

<210> SEQ ID NO 774
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 774
ggacaagaag cugca 15

<210> SEQ ID NO 775
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 775
acaagaagcu gcuaa 15

<210> SEQ ID NO 776
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 776
caagaagcug cuaua 15

<210> SEQ ID NO 777
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 777
aguucucuga guua 14

<210> SEQ ID NO 778
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 778
accguuaagg acaa 14

<210> SEQ ID NO 779
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 779
gaguucuggg auua 14

<210> SEQ ID NO 780
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 780
aagaccgcca agga 14

<210> SEQ ID NO 781
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 781
ccgauggcuu caga 14

<210> SEQ ID NO 782
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 782
gacaaguucu cuga 14

<210> SEQ ID NO 783
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 783
aaguucucug agua 14

<210> SEQ ID NO 784
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 784
guucucugag uuca 14

<210> SEQ ID NO 785
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 785
guuaaggaca agua 14

<210> SEQ ID NO 786
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 786
caaguucucu gaga 14

<210> SEQ ID NO 787
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 787
ccguuaagga caaa 14

<210> SEQ ID NO 788
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 788
agaccgccaa ggaa 14

<210> SEQ ID NO 789
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 789
agacuacugg agca 14

<210> SEQ ID NO 790
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 790
gaggccgagg auga 14

<210> SEQ ID NO 791
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 791
aagcacgcca ccaa 14

<210> SEQ ID NO 792
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(15)

<400> SEQUENCE: 792
uuggauaggc agguggacuc accugccuau ccaa 34

<210> SEQ ID NO 793
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A28(15)

<400> SEQUENCE: 793
ucaacaagga guacccgggg guacuccuug uuga 34

<210> SEQ ID NO 794
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(14)

<400> SEQUENCE: 794
uuggauaggc agguggacua ccugccuauc caa 33

<210> SEQ ID NO 795
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A28(14)

<400> SEQUENCE: 795
ucaacaagga guacccgggg uacuccuugu uga 33

<210> SEQ ID NO 796
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(12-5)

<400> SEQUENCE: 796
uuggauaggc agguggacug ccuauccaa 29

<210> SEQ ID NO 797
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(13-4)

<400> SEQUENCE: 797
uuggauaggc agguggacuu gccuauccaa 30

<210> SEQ ID NO 798
<211> LENGTH: 32

<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A28(14-4)

<400> SEQUENCE: 798
ucaacaagga guacccgggu acuccuuguu ga 32

<210> SEQ ID NO 799
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(14)mF

<400> SEQUENCE: 799
uuggauaggc agguggacua ccugccuauc caa 33

<210> SEQ ID NO 800
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A28(14)mF

<400> SEQUENCE: 800
ucaacaagga guacccgggg uacuccuugu uga 33

<210> SEQ ID NO 801
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(12-5)mF

<400> SEQUENCE: 801
uuggauaggc agguggacug ccuauccaa 29

<210> SEQ ID NO 802
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A277(13-4)mF

<400> SEQUENCE: 802
uuggauaggc agguggacuu gccuauccaa 30

<210> SEQ ID NO 803
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: A28(14-4)mF

<400> SEQUENCE: 803
ucaacaagga guacccgggu acuccuuguu ga 32

<210> SEQ ID NO 804
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 804
uucuagggau gaacugagc 19

<210> SEQ ID NO 805
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 805
ucucuaggga ugaacugag 19

<210> SEQ ID NO 806
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 806
uccucuaggg augaacuga 19

<210> SEQ ID NO 807
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 807
ugccucuagg gaugaacug 19

<210> SEQ ID NO 808
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 808
uugccucuag ggaugaacu 19

<210> SEQ ID NO 809
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 809
ucugccucua gggaugaac 19

<210> SEQ ID NO 810
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 810
ugcugccucu agggaugaa 19

<210> SEQ ID NO 811
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 811
uagcugccuc uagggauga 19

<210> SEQ ID NO 812
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 812
ugcagcugcc ucuagggau 19

<210> SEQ ID NO 813
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 813
uagcagcugc cucuaggga 19

<210> SEQ ID NO 814
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 814
ugagcagcug ccucuaggg 19

<210> SEQ ID NO 815
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 815
uggagcagcu gccucuagg 19

<210> SEQ ID NO 816
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 816
uuguuccugg agcagcugc 19

<210> SEQ ID NO 817
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 817
ucuguuccug gagcagcug 19

<210> SEQ ID NO 818
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 818
uccucuguuc cuggagcag 19

<210> SEQ ID NO 819
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 819
uaccucuguu ccuggagca 19

<210> SEQ ID NO 820
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 820
ucaccucugu uccuggagc 19

<210> SEQ ID NO 821
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 821
ugcaccucug uuccuggag 19

<210> SEQ ID NO 822
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 822
uggcaccucu guuccugga 19

<210> SEQ ID NO 823
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 823
uuggcaccuc uguuccugg 19

<210> SEQ ID NO 824
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 824
uauggcaccu cuguuccug 19

<210> SEQ ID NO 825
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 825
ucauggcacc ucuguuccu 19

<210> SEQ ID NO 826
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 826
uugcauggca ccucuguuc 19

<210> SEQ ID NO 827
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 827
ucugcauggc accucuguu 19

<210> SEQ ID NO 828
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 828
ugcugcaugg caccucugu 19

<210> SEQ ID NO 829
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 829
uggcugcaug gcaccucug 19

<210> SEQ ID NO 830
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 830
ugggcugcau ggcaccucu 19

<210> SEQ ID NO 831
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 831
ucaacaagga guacccggg 19

<210> SEQ ID NO 832
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 832
uacaacaagg aguacccgg 19

<210> SEQ ID NO 833
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 833
uaacaacaag gaguacccg 19

<210> SEQ ID NO 834
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 834
ucaacaacaa ggaguaccc 19

<210> SEQ ID NO 835
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 835
ugcaacaaca aggaguacc 19

<210> SEQ ID NO 836
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 836
uggcaacaac aaggaguac 19

<210> SEQ ID NO 837
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 837
ugggcaacaa caaggagua 19

<210> SEQ ID NO 838
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 838
uagggcaaca acaaggagu 19

<210> SEQ ID NO 839
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 839
ugagggcaac aacaaggag 19

<210> SEQ ID NO 840
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 840
uggagggcaa caacaagga 19

<210> SEQ ID NO 841
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 841
uaggagggca acaacaagg 19

<210> SEQ ID NO 842
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 842
ucaggagggc aacaacaag 19

<210> SEQ ID NO 843
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 843
uccaggaggg caacaacaa 19

<210> SEQ ID NO 844
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 844
ugccaggagg gcaacaaca 19

<210> SEQ ID NO 845
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 845
ucgccaggag ggcaacaac 19

<210> SEQ ID NO 846
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 846
ugcgccagga gggcaacaa 19

<210> SEQ ID NO 847
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 847
uagcgccagg agggcaaca 19

<210> SEQ ID NO 848
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 848
ugagcgccag gagggcaac 19

<210> SEQ ID NO 849
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 849
uggagcgcca ggagggcaa 19

<210> SEQ ID NO 850
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 850
uaggagcgcc aggagggca 19

<210> SEQ ID NO 851
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 851
ugccaggagc gccaggagg 19

<210> SEQ ID NO 852
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 852
uagaggccag gagcgccag 19

<210> SEQ ID NO 853
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 853
ucagaggcca ggagcgcca 19

<210> SEQ ID NO 854
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 854
ugcagaggcc aggagcgcc 19

<210> SEQ ID NO 855
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 855
uggcagaggc caggagcgc 19

<210> SEQ ID NO 856
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 856
ugggcagagg ccaggagcg 19

<210> SEQ ID NO 857
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 857
uucgggcaga ggccaggag 19

<210> SEQ ID NO 858
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 858
ucucgggcag aggccagga 19

<210> SEQ ID NO 859
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 859
ugcucgggca gaggccagg 19

<210> SEQ ID NO 860
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 860
uagcucgggc agaggccag 19

<210> SEQ ID NO 861
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 861
uaagcucggg cagaggcca 19

<210> SEQ ID NO 862
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 862
ugaagcucgg gcagaggcc 19

<210> SEQ ID NO 863
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 863
uugaagcucg ggcagaggc 19

<210> SEQ ID NO 864

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 864
ucugaagcuc gggcagagg 19

<210> SEQ ID NO 865
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 865
uucugaagcu cgggcagag 19

<210> SEQ ID NO 866
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 866
ucucugaagc ucgggcaga 19

<210> SEQ ID NO 867
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 867
uccucugaag cucgggcag 19

<210> SEQ ID NO 868
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 868
ugccucugaa gcucgggca 19

<210> SEQ ID NO 869
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 869
uggccucuga agcucgggc 19

<210> SEQ ID NO 870
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 870
ucggccucug aagcucggg 19

<210> SEQ ID NO 871
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 871
uucggccucu gaagcucgg 19

<210> SEQ ID NO 872
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 872
ucucggccuc ugaagcucg 19

<210> SEQ ID NO 873
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 873
uccucggccu cugaagcuc 19

<210> SEQ ID NO 874
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 874
uuccucggcc ucugaagcu 19

<210> SEQ ID NO 875
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 875
uauccucggc cucugaagc 19

<210> SEQ ID NO 876
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 876

ucauccucgg ccucugaag                                                19


<210> SEQ ID NO 877
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877

ugcauccucg gccucugaa                                                19


<210> SEQ ID NO 878
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878

uggcauccuc ggccucuga                                                19


<210> SEQ ID NO 879
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879

uaggcauccu cggccucug                                                19


<210> SEQ ID NO 880
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 880

ugaggcaucc ucggccucu                                                19


<210> SEQ ID NO 881
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 881

uggaggcauc cucggccuc                                                19


<210> SEQ ID NO 882
<211> LENGTH: 19
<212> TYPE: RNA
<213> ORGANISM: Artificial Sequence
```

<220> FEATURE:
<223> OTHER INFORMATION: Description of Artificial Sequence: Synthetic
oligonucleotide

<400> SEQUENCE: 882
ugggaggcau ccucggccu 19

<210> SEQ ID NO 883
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 883
uagggaggca uccucggcc 19

<210> SEQ ID NO 884
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 884
uaagggaggc auccucggc 19

<210> SEQ ID NO 885
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 885
ugaagggagg cauccucgg 19

<210> SEQ ID NO 886
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 886
uagaagggag gcauccucg 19

<210> SEQ ID NO 887
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 887
ugagaaggga ggcauccuc 19

<210> SEQ ID NO 888
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 888
uugagaaggg aggcauccu 19

<210> SEQ ID NO 889
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 889
ucugagaagg gaggcaucc 19

<210> SEQ ID NO 890
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 890
ugcugagaag ggaggcauc 19

<210> SEQ ID NO 891
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 891
uagcugagaa gggaggcau 19

<210> SEQ ID NO 892
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 892
uugaagcuga gaagggagg 19

<210> SEQ ID NO 893
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 893
uaugaagcug agaagggag 19

<210> SEQ ID NO 894
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 894
ucaugaagcu gagaaggga 19

<210> SEQ ID NO 895
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 895
ugcaugaagc ugagaaggg 19

<210> SEQ ID NO 896
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 896
uugcaugaag cugagaagg 19

<210> SEQ ID NO 897
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 897
ucugcaugaa gcugagaag 19

<210> SEQ ID NO 898
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 898
uccugcauga agcugagaa 19

<210> SEQ ID NO 899
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 899
ucccugcaug aagcugaga 19

<210> SEQ ID NO 900
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 900
uacccugcau gaagcugag 19

<210> SEQ ID NO 901
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 901
uaacccugca ugaagcuga 19

<210> SEQ ID NO 902
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 902
uuaacccugc augaagcug 19

<210> SEQ ID NO 903
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 903
uguaacccug caugaagcu 19

<210> SEQ ID NO 904
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 904
uuguaacccu gcaugaagc 19

<210> SEQ ID NO 905
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 905
uauguaaccc ugcaugaag 19

<210> SEQ ID NO 906
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 906
ucauguaacc cugcaugaa 19

<210> SEQ ID NO 907
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 907
uucauguaac ccugcauga 19

<210> SEQ ID NO 908
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 908
uuucauguaa cccugcaug 19

<210> SEQ ID NO 909
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 909
ucuucaugua acccugcau 19

<210> SEQ ID NO 910
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 910
ugcuucaugu aacccugca 19

<210> SEQ ID NO 911
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 911
uugcuucaug uaacccugc 19

<210> SEQ ID NO 912
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 912
ugugcuucau guaacccug 19

<210> SEQ ID NO 913
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 913
ucgugcuuca uguaacccu 19

<210> SEQ ID NO 914
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 914
ugcgugcuuc auguaaccc 19

<210> SEQ ID NO 915
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 915
uggcgugcuu cauguaacc 19

<210> SEQ ID NO 916
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 916
uuggcgugcu ucauguaac 19

<210> SEQ ID NO 917
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 917
uguggcgugc uucauguaa 19

<210> SEQ ID NO 918
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 918

-continued

```
uggugggcgug cuucaugua                                                 19


<210> SEQ ID NO 919
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 919

uugguggcgu gcuucaugu                                                  19


<210> SEQ ID NO 920
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 920

uuugguggcg ugcuucaug                                                  19


<210> SEQ ID NO 921
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 921

ucuugguggc gugcuucau                                                  19


<210> SEQ ID NO 922
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 922

uucuuggugg cgugcuuca                                                  19


<210> SEQ ID NO 923
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923

ugucuuggug gcgugcuuc                                                  19


<210> SEQ ID NO 924
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924

uggucuuggu ggcgugcuu                                                  19
```

<210> SEQ ID NO 925
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 925
ucggucuugg uggcgugcu 19

<210> SEQ ID NO 926
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 926
ugcggucuug guggcgugc 19

<210> SEQ ID NO 927
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 927
uggcggucuu gguggcgug 19

<210> SEQ ID NO 928
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 928
uuggcggucu ugguggcgu 19

<210> SEQ ID NO 929
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 929
uuuggcgguc uugguggcg 19

<210> SEQ ID NO 930
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 930
ucuuggcggu cuugguggc 19

<210> SEQ ID NO 931
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 931
uccuuggcgg ucuuggugg 19

<210> SEQ ID NO 932
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 932
uuccuuggcg gucuuggug 19

<210> SEQ ID NO 933
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 933
uauccuuggc ggucuuggu 19

<210> SEQ ID NO 934
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 934
ucauccuugg cggucuugg 19

<210> SEQ ID NO 935
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 935
ugcauccuug gcggucuug 19

<210> SEQ ID NO 936
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 936
uugcauccuu ggcggucuu 19

<210> SEQ ID NO 937
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 937
ugugcauccu uggcggucu 19

<210> SEQ ID NO 938
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 938
uagugcaucc uuggcgguc 19

<210> SEQ ID NO 939
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 939
ucagugcauc cuuggcggu 19

<210> SEQ ID NO 940
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 940
uucagugcau ccuuggcgg 19

<210> SEQ ID NO 941
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 941
ucucagugca uccuuggcg 19

<210> SEQ ID NO 942
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 942
ugcucagugc auccuuggc 19

<210> SEQ ID NO 943

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 943
uugcucagug cauccuugg 19

<210> SEQ ID NO 944
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 944
ucugcucagu gcauccuug 19

<210> SEQ ID NO 945
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 945
ugcugcucag ugcauccuu 19

<210> SEQ ID NO 946
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 946
ucgcugcuca gugcauccu 19

<210> SEQ ID NO 947
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 947
uacgcugcuc agugcaucc 19

<210> SEQ ID NO 948
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 948
ucacgcugcu cagugcauc 19

<210> SEQ ID NO 949
<211> LENGTH: 19

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 949
ugcacgcugc ucagugcau 19

<210> SEQ ID NO 950
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 950
uugcacgcug cucagugca 19

<210> SEQ ID NO 951
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 951
ucugcacgcu gcucagugc 19

<210> SEQ ID NO 952
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 952
uccugcacgc ugcucagug 19

<210> SEQ ID NO 953
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 953
uuccugcacg cugcucagu 19

<210> SEQ ID NO 954
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 954
uacuccugca cgcugcuca 19

<210> SEQ ID NO 955
<211> LENGTH: 19
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 955
ugggacuccu gcacgcugc 19

<210> SEQ ID NO 956
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 956
uugggacucc ugcacgcug 19

<210> SEQ ID NO 957
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 957
ucugggacuc cugcacgcu 19

<210> SEQ ID NO 958
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 958
uccugggacu ccugcacgc 19

<210> SEQ ID NO 959
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 959
uaccugggac uccugcacg 19

<210> SEQ ID NO 960
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 960
ucaccuggga cuccugcac 19

<210> SEQ ID NO 961
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 961
uccaccuggg acuccugca 19

<210> SEQ ID NO 962
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 962
ugggccaccu gggacuccu 19

<210> SEQ ID NO 963
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 963
uugggccacc ugggacucc 19

<210> SEQ ID NO 964
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 964
uugcugggcc accugggac 19

<210> SEQ ID NO 965
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 965
ucugcugggc caccuggga 19

<210> SEQ ID NO 966
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 966
uggccugcug ggccaccug 19

<210> SEQ ID NO 967
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 967
uccuggccug cugggccac 19

<210> SEQ ID NO 968
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
uccaucgguc acccagccc 19

<210> SEQ ID NO 969
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
ugccaucggu cacccagcc 19

<210> SEQ ID NO 970
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
uagccaucgg ucacccagc 19

<210> SEQ ID NO 971
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 971
uaagccaucg gucacccag 19

<210> SEQ ID NO 972
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
ugaagccauc ggucaccca 19

<210> SEQ ID NO 973
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 973
uugaagccau cggucaccc 19

<210> SEQ ID NO 974
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 974
ucugaagcca ucggucacc 19

<210> SEQ ID NO 975
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 975
uacugaagcc aucggucac 19

<210> SEQ ID NO 976
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 976
uaacugaagc caucgguca 19

<210> SEQ ID NO 977
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 977
ugaacugaag ccaucgguc 19

<210> SEQ ID NO 978
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 978
uggaacugaa gccaucggu 19

<210> SEQ ID NO 979
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 979
ugggaacuga agccaucgg 19

<210> SEQ ID NO 980
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 980
uagggaacug aagccaucg 19

<210> SEQ ID NO 981
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 981
ucagggaacu gaagccauc 19

<210> SEQ ID NO 982
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 982
uucagggaac ugaagccau 19

<210> SEQ ID NO 983
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 983
uuucagggaa cugaagcca 19

<210> SEQ ID NO 984
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 984
uuuucaggga acugaagcc 19

<210> SEQ ID NO 985
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 985
ucuuucaggg aacugaagc 19

<210> SEQ ID NO 986
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 986
uucuuucagg gaacugaag 19

<210> SEQ ID NO 987
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 987
ugucuuucag ggaacugaa 19

<210> SEQ ID NO 988
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 988
uagucuuuca gggaacuga 19

<210> SEQ ID NO 989
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 989
uuagucuuuc agggaacug 19

<210> SEQ ID NO 990
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 990
uguagucuuu cagggaacu 19

<210> SEQ ID NO 991
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 991
uaguagucuu ucagggaac 19

<210> SEQ ID NO 992
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 992
ucaguagucu uucagggaa 19

<210> SEQ ID NO 993
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 993
uccaguaguc uuucaggga 19

<210> SEQ ID NO 994
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 994
uuccaguagu cuuucaggg 19

<210> SEQ ID NO 995
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 995
ucuccaguag ucuuucagg 19

<210> SEQ ID NO 996
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 996
ugcuccagua gucuuucag 19

<210> SEQ ID NO 997
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 997

-continued uugcuccagu agucuuuca 19

<210> SEQ ID NO 998
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998
ugugcuccag uagucuuuc 19

<210> SEQ ID NO 999
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999
uggugcucca guagucuuu 19

<210> SEQ ID NO 1000
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1000
ucggugcucc aguagucuu 19

<210> SEQ ID NO 1001
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001
uacggugcuc caguagucu 19

<210> SEQ ID NO 1002
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1002
uaacggugcu ccaguaguc 19

<210> SEQ ID NO 1003
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1003
uuaacggugc uccaguagu 19

<210> SEQ ID NO 1004
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1004
uuuaacggug cuccaguag 19

<210> SEQ ID NO 1005
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1005
ucuuaacggu gcuccagua 19

<210> SEQ ID NO 1006
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1006
uccuuaacgg ugcuccagu 19

<210> SEQ ID NO 1007
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1007
uuccuuaacg gugcuccag 19

<210> SEQ ID NO 1008
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1008
uguccuuaac ggugcucca 19

<210> SEQ ID NO 1009
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1009
uuguccuuaa cggugcucc 19

<210> SEQ ID NO 1010
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1010
uuuguccuua acggugcuc 19

<210> SEQ ID NO 1011
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
ucuuguccuu aacggugcu 19

<210> SEQ ID NO 1012
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
uacuuguccu uaacggugc 19

<210> SEQ ID NO 1013
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1013
uaacuugucc uuaacggug 19

<210> SEQ ID NO 1014
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
ugaacuuguc cuuaacggu 19

<210> SEQ ID NO 1015
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
uagaacuugu ccuuaacgg 19

<210> SEQ ID NO 1016
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1016
ugagaacuug uccuuaacg 19

<210> SEQ ID NO 1017
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1017
uagagaacuu guccuuaac 19

<210> SEQ ID NO 1018
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1018
ucagagaacu uguccuuaa 19

<210> SEQ ID NO 1019
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1019
uucagagaac uuguccuua 19

<210> SEQ ID NO 1020
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1020
ucucagagaa cuuguccuu 19

<210> SEQ ID NO 1021
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1021
uacucagaga acuuguccu 19

<210> SEQ ID NO 1022

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1022
uaacucagag aacuugucc 19

<210> SEQ ID NO 1023
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1023
ugaacucaga gaacuuguc 19

<210> SEQ ID NO 1024
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1024
ucagaacuca gagaacuug 19

<210> SEQ ID NO 1025
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1025
uccagaacuc agagaacuu 19

<210> SEQ ID NO 1026
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1026
ucccagaacu cagagaacu 19

<210> SEQ ID NO 1027
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1027
uucccagaac ucagagaac 19

<210> SEQ ID NO 1028
<211> LENGTH: 19

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1028
uaucccagaa cucagagaa 19

<210> SEQ ID NO 1029
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1029
uaaucccaga acucagaga 19

<210> SEQ ID NO 1030
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1030
uaaaucccag aacucagag 19

<210> SEQ ID NO 1031
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1031
ucaaauccca gaacucaga 19

<210> SEQ ID NO 1032
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1032
uccaaauccc agaacucag 19

<210> SEQ ID NO 1033
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1033
uuccaaaucc cagaacuca 19

<210> SEQ ID NO 1034
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1034
uguccaaauc ccagaacuc 19

<210> SEQ ID NO 1035
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1035
ugguccaaau cccagaacu 19

<210> SEQ ID NO 1036
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1036
uggguccaaa ucccagaac 19

<210> SEQ ID NO 1037
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1037
uaggguccaa aucccagaa 19

<210> SEQ ID NO 1038
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1038
ucagggucca aaucccaga 19

<210> SEQ ID NO 1039
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1039
uucagggucc aaaucccag 19

<210> SEQ ID NO 1040
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1040
ugaccucagg guccaaauc 19

<210> SEQ ID NO 1041
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1041
uugaccucag gguccaaau 19

<210> SEQ ID NO 1042
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1042
ucugaccuca ggguccaaa 19

<210> SEQ ID NO 1043
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1043
uucugaccuc aggguccaa 19

<210> SEQ ID NO 1044
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1044
ugucugaccu cagggucca 19

<210> SEQ ID NO 1045
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1045
uggucugacc ucaggucc 19

<210> SEQ ID NO 1046
<211> LENGTH: 19
<212> TYPE: RNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 1046

uuggucugac cucaggguc                                                          19

<210> SEQ ID NO 1047
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047

uuuggucuga ccucagggu                                                          19

<210> SEQ ID NO 1048
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1048

uguuggucug accucaggg                                                          19

<210> SEQ ID NO 1049
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1049

uaguuggucu gaccucagg                                                          19

<210> SEQ ID NO 1050
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1050

uaaguugguc ugaccucag                                                          19

<210> SEQ ID NO 1051
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1051

ugaaguuggu cugaccuca                                                          19

<210> SEQ ID NO 1052
<211> LENGTH: 19
<212> TYPE: RNA
<213> ORGANISM: Artificial Sequence
<220> FEATURE:
<223> OTHER INFORMATION: Description of Artificial Sequence: Synthetic
```

oligonucleotide

<400> SEQUENCE: 1052
uugaaguugg ucugaccuc 19

<210> SEQ ID NO 1053
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1053
ucugaaguug gucugaccu 19

<210> SEQ ID NO 1054
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1054
uggcugaagu uggucugac 19

<210> SEQ ID NO 1055
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1055
ucggcugaag uuggucuga 19

<210> SEQ ID NO 1056
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1056
uacggcugaa guuggucug 19

<210> SEQ ID NO 1057
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1057
ucacggcuga aguuggucu 19

<210> SEQ ID NO 1058
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1058
uccacggcug aaguugguc 19

<210> SEQ ID NO 1059
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1059
ugccacggcu gaaguuggu 19

<210> SEQ ID NO 1060
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1060
ucagccacgg cugaaguug 19

<210> SEQ ID NO 1061
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1061
ugcagccacg gcugaaguu 19

<210> SEQ ID NO 1062
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1062
uggcagccac ggcugaagu 19

<210> SEQ ID NO 1063
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1063
uaggcagcca cggcugaag 19

<210> SEQ ID NO 1064
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1064
ucaggcagcc acggcugaa 19

<210> SEQ ID NO 1065
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1065
uucucaggca gccacggcu 19

<210> SEQ ID NO 1066
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1066
ugucucaggc agccacggc 19

<210> SEQ ID NO 1067
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1067
uggucucagg cagccacgg 19

<210> SEQ ID NO 1068
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1068
uaggucucag gcagccacg 19

<210> SEQ ID NO 1069
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1069
uugaggucuc aggcagcca 19

<210> SEQ ID NO 1070
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1070
uuugaggucu caggcagcc 19

<210> SEQ ID NO 1071
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1071
uauugagguc ucaggcagc 19

<210> SEQ ID NO 1072
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1072
uuauugaggu cucaggcag 19

<210> SEQ ID NO 1073
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1073
uguauugagg ucucaggca 19

<210> SEQ ID NO 1074
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1074
ugguauugag gucucaggc 19

<210> SEQ ID NO 1075
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1075
uggguauuga ggucucagg 19

<210> SEQ ID NO 1076
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1076
uuaggcaggu ggacuuggg 19

<210> SEQ ID NO 1077
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077
uauaggcagg uggacuugg 19

<210> SEQ ID NO 1078
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
ugauaggcag guggacuug 19

<210> SEQ ID NO 1079
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
uggauaggca gguggacuu 19

<210> SEQ ID NO 1080
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080
uuggauaggc agguggacu 19

<210> SEQ ID NO 1081
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081
uauggauagg cagguggac 19

<210> SEQ ID NO 1082
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082
ugauggauag gcaggugga 19

<210> SEQ ID NO 1083
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1083
uggauggaua ggcaggugg 19

<210> SEQ ID NO 1084
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1084
uaggauggau aggcaggug 19

<210> SEQ ID NO 1085
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1085
ucaggaugga uaggcaggu 19

<210> SEQ ID NO 1086
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086
ugcaggaugg auaggcagg 19

<210> SEQ ID NO 1087
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1087
ucgcaggaug gauaggcag 19

<210> SEQ ID NO 1088
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1088
uucgcaggau ggauaggca 19

<210> SEQ ID NO 1089
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1089
ucucgcagga uggauaggc 19

<210> SEQ ID NO 1090
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1090
ugcucgcagg auggauagg 19

<210> SEQ ID NO 1091
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1091
uagcucgcag gauggauag 19

<210> SEQ ID NO 1092
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1092
ugagcucgca ggauggaua 19

<210> SEQ ID NO 1093
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1093
uggagcucgc aggauggau 19

<210> SEQ ID NO 1094
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1094
uaggagcucg caggaugga 19

<210> SEQ ID NO 1095
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1095
uaaggagcuc gcaggaugg 19

<210> SEQ ID NO 1096
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1096
ucaaggagcu cgcaggaug 19

<210> SEQ ID NO 1097
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1097
uccaaggagc ucgcaggau 19

<210> SEQ ID NO 1098
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1098
ucccaaggag cucgcagga 19

<210> SEQ ID NO 1099
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1099
uacccaagga gcucgcagg 19

<210> SEQ ID NO 1100
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1100
ugacccaagg agcucgcag 19

<210> SEQ ID NO 1101

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1101
uggacccaag gagcucgca 19

<210> SEQ ID NO 1102
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1102
uaggacccaa ggagcucgc 19

<210> SEQ ID NO 1103
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1103
ucaggaccca aggagcucg 19

<210> SEQ ID NO 1104
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1104
ugcaggaccc aaggagcuc 19

<210> SEQ ID NO 1105
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105
uugcaggacc caaggagcu 19

<210> SEQ ID NO 1106
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106
uuugcaggac ccaaggagc 19

<210> SEQ ID NO 1107
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1107
uauugcagga cccaaggag 19

<210> SEQ ID NO 1108
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1108
ugauugcagg acccaagga 19

<210> SEQ ID NO 1109
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1109
uagauugcag gacccaagg 19

<210> SEQ ID NO 1110
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1110
ugagauugca ggacccaag 19

<210> SEQ ID NO 1111
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1111
uggagauugc aggacccaa 19

<210> SEQ ID NO 1112
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1112
uuggagauug caggaccca 19

<210> SEQ ID NO 1113
<211> LENGTH: 19
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1113
ucuggagauu gcaggaccc 19

<210> SEQ ID NO 1114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1114
uccuggagau ugcaggacc 19

<210> SEQ ID NO 1115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1115
ucccuggaga uugcaggac 19

<210> SEQ ID NO 1116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1116
ugcccuggag auugcagga 19

<210> SEQ ID NO 1117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1117
uagcccugga gauugcagg 19

<210> SEQ ID NO 1118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1118
ucagcccugg agauugcag 19

<210> SEQ ID NO 1119
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1119
ugcagcccug gagauugca 19

<210> SEQ ID NO 1120
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1120
uggcagcccu ggagauugc 19

<210> SEQ ID NO 1121
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1121
ugggcagccc uggagauug 19

<210> SEQ ID NO 1122
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1122
uuuuaagcaa ccuacaggg 19

<210> SEQ ID NO 1123
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1123
uuuuuaagca accuacagg 19

<210> SEQ ID NO 1124
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1124
ucuuuuaagc aaccuacag 19

<210> SEQ ID NO 1125
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1125
uccuuuuaag caaccuaca 19

<210> SEQ ID NO 1126
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1126
ucccuuuuaa gcaaccuac 19

<210> SEQ ID NO 1127
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1127
uucccuuuua agcaaccua 19

<210> SEQ ID NO 1128
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1128
ugucccuuuu aagcaaccu 19

<210> SEQ ID NO 1129
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1129
uacugucccu uuuaagcaa 19

<210> SEQ ID NO 1130
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130
uuacuguccc uuuuaagca 19

<210> SEQ ID NO 1131
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1131
uauacugucc cuuuuaagc 19

<210> SEQ ID NO 1132
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1132
uaauacuguc ccuuuuaag 19

<210> SEQ ID NO 1133
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1133
ugaauacugu cccuuuuaa 19

<210> SEQ ID NO 1134
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1134
uagaauacug ucccuuuua 19

<210> SEQ ID NO 1135
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1135
ugagaauacu gucccuuuu 19

<210> SEQ ID NO 1136
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1136
uugagaauac ugucccuuu 19

<210> SEQ ID NO 1137
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1137
ucugagaaua cugucccuu 19

<210> SEQ ID NO 1138
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1138
uacugagaau acugucccu 19

<210> SEQ ID NO 1139
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1139
ucacugagaa uacuguccc 19

<210> SEQ ID NO 1140
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140
ugcacugaga auacugucc 19

<210> SEQ ID NO 1141
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1141
uagcacugag aauacuguc 19

<210> SEQ ID NO 1142
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1142
ugagcacuga gaauacugu 19

<210> SEQ ID NO 1143
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1143
uagagcacug agaauacug 19

<210> SEQ ID NO 1144
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1144
ugagagcacu gagaauacu 19

<210> SEQ ID NO 1145
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1145
uggagagcac ugagaauac 19

<210> SEQ ID NO 1146
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1146
uaggagagca cugagaaua 19

<210> SEQ ID NO 1147
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1147
uuaggagagc acugagaau 19

<210> SEQ ID NO 1148
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1148
uguaggagag cacugagaa 19

<210> SEQ ID NO 1149
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1149
ugguaggaga gcacugaga 19

<210> SEQ ID NO 1150
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1150
uggguaggag agcacugag 19

<210> SEQ ID NO 1151
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1151
uggccaggca ugagguggg 19

<210> SEQ ID NO 1152
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1152
ugggccaggc augaggugg 19

<210> SEQ ID NO 1153
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1153
ugccagcaug ccuggaggg 19

<210> SEQ ID NO 1154
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1154
uggccagcau gccuggagg 19

<210> SEQ ID NO 1155
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1155
uaggccagca ugccuggag 19

<210> SEQ ID NO 1156
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1156
ugaggccagc augccugga 19

<210> SEQ ID NO 1157
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1157
uggaggccag caugccugg 19

<210> SEQ ID NO 1158
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1158
ugggaggcca gcaugccug 19

<210> SEQ ID NO 1159
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1159
uugggaggcc agcaugccu 19

<210> SEQ ID NO 1160
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1160
uauugggagg ccagcaugc 19

<210> SEQ ID NO 1161
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1161
uuauugggag gccagcaug 19

<210> SEQ ID NO 1162
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1162
uuuauuggga ggccagcau 19

<210> SEQ ID NO 1163
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1163
uuuuauuggg aggccagca 19

<210> SEQ ID NO 1164
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1164
ucuuuauugg gaggccagc 19

<210> SEQ ID NO 1165
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1165
ugcuuuauug ggaggccag 19

<210> SEQ ID NO 1166
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1166
uagcuuuauu gggaggcca 19

<210> SEQ ID NO 1167
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1167
ucagcuuuau ugggaggcc 19

<210> SEQ ID NO 1168
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1168
uccagcuuua uugggaggc 19

<210> SEQ ID NO 1169
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1169
uuccagcuuu auugggagg 19

<210> SEQ ID NO 1170
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1170
uguccagcuu uauugggag 19

<210> SEQ ID NO 1171
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1171
uuuguccagc uuuauuggg 19

<210> SEQ ID NO 1172
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1172
ucuuguccag cuuuauugg 19

<210> SEQ ID NO 1173
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1173
uucuugucca gcuuuauug 19

<210> SEQ ID NO 1174
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1174
uuucuugucc agcuuuauu 19

<210> SEQ ID NO 1175
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1175
ucuucuuguc cagcuuuau 19

<210> SEQ ID NO 1176
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1176
ugcuucuugu ccagcuuua 19

<210> SEQ ID NO 1177
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1177
ugcagcuucu uguccagcu 19

<210> SEQ ID NO 1178
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1178
uuagcagcuu cuuguccag 19

<210> SEQ ID NO 1179
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1179
uauagcagcu ucuugucca 19

<210> SEQ ID NO 1180

<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1180
aguucauccc uagaa 15

<210> SEQ ID NO 1181
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1181
guucaucccu agaga 15

<210> SEQ ID NO 1182
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1182
uucaucccua gagga 15

<210> SEQ ID NO 1183
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1183
ucaucccuag aggca 15

<210> SEQ ID NO 1184
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1184
caucccuaga ggcaa 15

<210> SEQ ID NO 1185
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1185
aucccuagag gcaga 15

<210> SEQ ID NO 1186
<211> LENGTH: 15

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1186
ucccuagagg cagca 15

<210> SEQ ID NO 1187
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1187
cccuagaggc agcua 15

<210> SEQ ID NO 1188
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1188
cuagaggcag cugca 15

<210> SEQ ID NO 1189
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1189
uagaggcagc ugcua 15

<210> SEQ ID NO 1190
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1190
agaggcagcu gcuca 15

<210> SEQ ID NO 1191
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1191
gaggcagcug cucca 15

<210> SEQ ID NO 1192
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1192
cugcuccagg aacaa 15

<210> SEQ ID NO 1193
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1193
ugcuccagga acaga 15

<210> SEQ ID NO 1194
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1194
uccaggaaca gagga 15

<210> SEQ ID NO 1195
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1195
ccaggaacag aggua 15

<210> SEQ ID NO 1196
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1196
caggaacaga gguga 15

<210> SEQ ID NO 1197
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1197
aggaacagag gugca 15

<210> SEQ ID NO 1198
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1198
ggaacagagg ugcca 15

<210> SEQ ID NO 1199
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1199
gaacagaggu gccaa 15

<210> SEQ ID NO 1200
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1200
aacagaggug ccaua 15

<210> SEQ ID NO 1201
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1201
acagaggugc cauga 15

<210> SEQ ID NO 1202
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1202
agaggugcca ugcaa 15

<210> SEQ ID NO 1203
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1203
gaggugccau gcaga 15

<210> SEQ ID NO 1204
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1204
aggugccaug cagca 15

<210> SEQ ID NO 1205
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1205
ggugccaugc agcca 15

<210> SEQ ID NO 1206
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1206
gugccaugca gccca 15

<210> SEQ ID NO 1207
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1207
gguacuccuu guuga 15

<210> SEQ ID NO 1208
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1208
guacuccuug uugua 15

<210> SEQ ID NO 1209
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1209
uacuccuugu uguua 15

<210> SEQ ID NO 1210
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1210
acuccuuguu guuga 15

<210> SEQ ID NO 1211
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1211
cuccuuguug uugca 15

<210> SEQ ID NO 1212
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1212
uccuuguugu ugcca 15

<210> SEQ ID NO 1213
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1213
ccuuguuguu gccca 15

<210> SEQ ID NO 1214
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1214
cuuguuguug cccua 15

<210> SEQ ID NO 1215
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1215
uuguuguugc ccuca 15

<210> SEQ ID NO 1216
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1216
uguuguugcc cucca 15

<210> SEQ ID NO 1217
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1217
guuguugccc uccua 15

<210> SEQ ID NO 1218
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1218
uuguugcccu ccuga 15

<210> SEQ ID NO 1219
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1219
uguugcccuc cugga 15

<210> SEQ ID NO 1220
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1220
guugcccucc uggca 15

<210> SEQ ID NO 1221
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1221
uugcccuccu ggcga 15

<210> SEQ ID NO 1222
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1222
ugcccuccug gcgca 15

<210> SEQ ID NO 1223
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1223
gcccuccugg cgcua 15

<210> SEQ ID NO 1224
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1224
cccuccuggc gcuca 15

<210> SEQ ID NO 1225
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1225
ccuccuggcg cucca 15

<210> SEQ ID NO 1226
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1226
cuccuggcgc uccua 15

<210> SEQ ID NO 1227
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1227
cuggcgcucc uggca 15

<210> SEQ ID NO 1228
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1228
cgcuccuggc cucua 15

<210> SEQ ID NO 1229
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1229
gcuccuggcc ucuga 15

<210> SEQ ID NO 1230
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1230
cuccuggccu cugca 15

<210> SEQ ID NO 1231
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1231
uccuggccuc ugcca 15

<210> SEQ ID NO 1232
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1232
ccuggccucu gccca 15

<210> SEQ ID NO 1233
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1233
uggccucugc ccgaa 15

<210> SEQ ID NO 1234
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1234

-continued ggccucugcc cgaga 15

<210> SEQ ID NO 1235
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1235
gccucugccc gagca 15

<210> SEQ ID NO 1236
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1236
ccucugcccg agcua 15

<210> SEQ ID NO 1237
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1237
cucugcccga gcuua 15

<210> SEQ ID NO 1238
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
ucugcccgag cuuca 15

<210> SEQ ID NO 1239
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
cugcccgagc uucaa 15

<210> SEQ ID NO 1240
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
ugcccgagcu ucaga 15

<210> SEQ ID NO 1241
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1241
gcccgagcuu cagaa 15

<210> SEQ ID NO 1242
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1242
cccgagcuuc agaga 15

<210> SEQ ID NO 1243
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1243
ccgagcuuca gagga 15

<210> SEQ ID NO 1244
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1244
cgagcuucag aggca 15

<210> SEQ ID NO 1245
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1245
gagcuucaga ggcca 15

<210> SEQ ID NO 1246
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1246
agcuucagag gccga 15

<210> SEQ ID NO 1247
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1247
gcuucagagg ccgaa 15

<210> SEQ ID NO 1248
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1248
cuucagaggc cgaga 15

<210> SEQ ID NO 1249
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1249
uucagaggcc gagga 15

<210> SEQ ID NO 1250
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1250
ucagaggccg aggaa 15

<210> SEQ ID NO 1251
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1251
cagaggccga ggaua 15

<210> SEQ ID NO 1252
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1252
agaggccgag gauga 15

-continued

<210> SEQ ID NO 1253
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1253
gaggccgagg augca 15

<210> SEQ ID NO 1254
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1254
aggccgagga ugcca 15

<210> SEQ ID NO 1255
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1255
ggccgaggau gccua 15

<210> SEQ ID NO 1256
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1256
gccgaggaug ccuca 15

<210> SEQ ID NO 1257
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1257
ccgaggaugc cucca 15

<210> SEQ ID NO 1258
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1258
cgaggaugcc uccca 15

<210> SEQ ID NO 1259

<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1259
gaggaugccu cccua 15

<210> SEQ ID NO 1260
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1260
aggaugccuc ccuua 15

<210> SEQ ID NO 1261
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1261
ggaugccucc cuuca 15

<210> SEQ ID NO 1262
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1262
gaugccuccc uucua 15

<210> SEQ ID NO 1263
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1263
augccucccu ucuca 15

<210> SEQ ID NO 1264
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1264
ugccucccuu cucaa 15

<210> SEQ ID NO 1265
<211> LENGTH: 15

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1265
gccucccuuc ucaga 15

<210> SEQ ID NO 1266
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1266
ccucccuucu cagca 15

<210> SEQ ID NO 1267
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1267
cucccuucuc agcua 15

<210> SEQ ID NO 1268
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1268
ccuucucagc uucaa 15

<210> SEQ ID NO 1269
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1269
cuucucagcu ucaua 15

<210> SEQ ID NO 1270
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1270
uucucagcuu cauga 15

<210> SEQ ID NO 1271
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1271
ucucagcuuc augca 15

<210> SEQ ID NO 1272
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1272
cucagcuuca ugcaa 15

<210> SEQ ID NO 1273
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1273
ucagcuucau gcaga 15

<210> SEQ ID NO 1274
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1274
cagcuucaug cagga 15

<210> SEQ ID NO 1275
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1275
agcuucaugc aggga 15

<210> SEQ ID NO 1276
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1276
gcuucaugca gggua 15

<210> SEQ ID NO 1277
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1277
cuucaugcag gguua 15

<210> SEQ ID NO 1278
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1278
uucaugcagg guuaa 15

<210> SEQ ID NO 1279
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1279
ucaugcaggg uuaca 15

<210> SEQ ID NO 1280
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1280
caugcagggu uacaa 15

<210> SEQ ID NO 1281
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1281
augcaggguu acaua 15

<210> SEQ ID NO 1282
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1282
ugcaggguua cauga 15

<210> SEQ ID NO 1283
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1283
gcaggguuac augaa 15

<210> SEQ ID NO 1284
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1284
caggguuaca ugaaa 15

<210> SEQ ID NO 1285
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1285
aggguuacau gaaga 15

<210> SEQ ID NO 1286
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1286
ggguuacaug aagca 15

<210> SEQ ID NO 1287
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1287
gguuacauga agcaa 15

<210> SEQ ID NO 1288
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1288
guuacaugaa gcaca 15

<210> SEQ ID NO 1289
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1289
uuacaugaag cacga 15

<210> SEQ ID NO 1290
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1290
uacaugaagc acgca 15

<210> SEQ ID NO 1291
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1291
acaugaagca cgcca 15

<210> SEQ ID NO 1292
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1292
caugaagcac gccaa 15

<210> SEQ ID NO 1293
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1293
augaagcacg ccaca 15

<210> SEQ ID NO 1294
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1294
ugaagcacgc cacca 15

<210> SEQ ID NO 1295
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1295
gaagcacgcc accaa 15

<210> SEQ ID NO 1296
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1296
aagcacgcca ccaaa 15

<210> SEQ ID NO 1297
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1297
agcacgccac caaga 15

<210> SEQ ID NO 1298
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1298
gcacgccacc aagaa 15

<210> SEQ ID NO 1299
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1299
cacgccacca agaca 15

<210> SEQ ID NO 1300
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1300
acgccaccaa gacca 15

<210> SEQ ID NO 1301
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1301
cgccaccaag accga 15

<210> SEQ ID NO 1302
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1302
gccaccaaga ccgca 15

<210> SEQ ID NO 1303
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1303
ccaccaagac cgcca 15

<210> SEQ ID NO 1304
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1304
caccaagacc gccaa 15

<210> SEQ ID NO 1305
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1305
accaagaccg ccaaa 15

<210> SEQ ID NO 1306
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1306
ccaagaccgc caaga 15

<210> SEQ ID NO 1307
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1307
caagaccgcc aagga 15

<210> SEQ ID NO 1308
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1308
aagaccgcca aggaa 15

<210> SEQ ID NO 1309
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1309
agaccgccaa ggaua 15

<210> SEQ ID NO 1310
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1310
gaccgccaag gauga 15

<210> SEQ ID NO 1311
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1311
accgccaagg augca 15

<210> SEQ ID NO 1312
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1312
ccgccaagga ugcaa 15

<210> SEQ ID NO 1313
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1313
cgccaaggau gcaca 15

<210> SEQ ID NO 1314
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1314
gccaaggaug cacua 15

<210> SEQ ID NO 1315
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1315
ccaaggaugc acuga 15

<210> SEQ ID NO 1316
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1316
caaggaugca cugaa 15

<210> SEQ ID NO 1317
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1317
aaggaugcac ugaga 15

<210> SEQ ID NO 1318
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1318
aggaugcacu gagca 15

<210> SEQ ID NO 1319
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1319
ggaugcacug agcaa 15

<210> SEQ ID NO 1320
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1320
gaugcacuga gcaga 15

<210> SEQ ID NO 1321
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1321
augcacugag cagca 15

<210> SEQ ID NO 1322
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1322
ugcacugagc agcga 15

<210> SEQ ID NO 1323
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1323
gcacugagca gcgua 15

<210> SEQ ID NO 1324
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1324
cacugagcag cguga 15

<210> SEQ ID NO 1325
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1325
acugagcagc gugca 15

<210> SEQ ID NO 1326
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1326
cugagcagcg ugcaa 15

<210> SEQ ID NO 1327
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1327
ugagcagcgu gcaga 15

<210> SEQ ID NO 1328
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1328
gagcagcgug cagga 15

<210> SEQ ID NO 1329
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1329
agcagcgugc aggaa 15

<210> SEQ ID NO 1330
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1330
cagcgugcag gagua 15

<210> SEQ ID NO 1331
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1331
cgugcaggag uccca 15

<210> SEQ ID NO 1332
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1332
gugcaggagu cccaa 15

<210> SEQ ID NO 1333
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1333
ugcaggaguc ccaga 15

<210> SEQ ID NO 1334
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1334
gcaggagucc cagga 15

<210> SEQ ID NO 1335
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1335
caggaguccc aggua 15

<210> SEQ ID NO 1336
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1336
aggaguccca gguga 15

<210> SEQ ID NO 1337
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1337
ggagucccag gugga 15

<210> SEQ ID NO 1338

-continued

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1338
gucccaggug gccca 15

<210> SEQ ID NO 1339
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1339
ucccaggugg cccaa 15

<210> SEQ ID NO 1340
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1340
cagguggccc agcaa 15

<210> SEQ ID NO 1341
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1341
agguggccca gcaga 15

<210> SEQ ID NO 1342
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1342
uggcccagca ggcca 15

<210> SEQ ID NO 1343
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1343
cccagcaggc cagga 15

<210> SEQ ID NO 1344
<211> LENGTH: 15

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1344
ugggugaccg augga 15

<210> SEQ ID NO 1345
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1345
gggugaccga uggca 15

<210> SEQ ID NO 1346
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1346
ggugaccgau ggcua 15

<210> SEQ ID NO 1347
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1347
gugaccgaug gcuua 15

<210> SEQ ID NO 1348
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1348
ugaccgaugg cuuca 15

<210> SEQ ID NO 1349
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1349
gaccgauggc uucaa 15

<210> SEQ ID NO 1350
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1350
accgauggcu ucaga 15

<210> SEQ ID NO 1351
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1351
ccgauggcuu cagua 15

<210> SEQ ID NO 1352
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1352
cgauggcuuc aguua 15

<210> SEQ ID NO 1353
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1353
gauggcuuca guuca 15

<210> SEQ ID NO 1354
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1354
auggcuucag uucca 15

<210> SEQ ID NO 1355
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1355
uggcuucagu uccca 15

<210> SEQ ID NO 1356
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1356
ggcuucaguu cccua 15

<210> SEQ ID NO 1357
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1357
gcuucaguuc ccuga 15

<210> SEQ ID NO 1358
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1358
cuucaguucc cugaa 15

<210> SEQ ID NO 1359
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1359
uucaguuccc ugaaa 15

<210> SEQ ID NO 1360
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1360
ucaguucccu gaaaa 15

<210> SEQ ID NO 1361
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1361
caguucccug aaaga 15

<210> SEQ ID NO 1362
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1362
aguucccuga aagaa 15

<210> SEQ ID NO 1363
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1363
guucccugaa agaca 15

<210> SEQ ID NO 1364
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1364
uucccugaaa gacua 15

<210> SEQ ID NO 1365
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1365
ucccugaaag acuaa 15

<210> SEQ ID NO 1366
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1366
cccugaaaga cuaca 15

<210> SEQ ID NO 1367
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1367
ccugaaagac uacua 15

<210> SEQ ID NO 1368
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1368
cugaaagacu acuga 15

<210> SEQ ID NO 1369
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1369
ugaaagacua cugga 15

<210> SEQ ID NO 1370
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1370
gaaagacuac uggaa 15

<210> SEQ ID NO 1371
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1371
aaagacuacu ggaga 15

<210> SEQ ID NO 1372
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1372
aagacuacug gagca 15

<210> SEQ ID NO 1373
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1373
agacuacugg agcaa 15

<210> SEQ ID NO 1374
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1374
gacuacugga gcaca 15

<210> SEQ ID NO 1375
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1375
acuacuggag cacca 15

<210> SEQ ID NO 1376
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1376
cuacuggagc accga 15

<210> SEQ ID NO 1377
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1377
uacuggagca ccgua 15

<210> SEQ ID NO 1378
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1378
acuggagcac cguua 15

<210> SEQ ID NO 1379
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1379
cuggagcacc guuaa 15

<210> SEQ ID NO 1380
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1380
uggagcaccg uuaaa 15

<210> SEQ ID NO 1381
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1381
ggagcaccgu uaaga 15

<210> SEQ ID NO 1382
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1382
gagcaccguu aagga 15

<210> SEQ ID NO 1383
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1383
agcaccguua aggaa 15

<210> SEQ ID NO 1384
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1384
gcaccguuaa ggaca 15

<210> SEQ ID NO 1385
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1385
caccguuaag gacaa 15

<210> SEQ ID NO 1386
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1386
accguuaagg acaaa 15

<210> SEQ ID NO 1387
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1387
ccguuaagga caaga 15

<210> SEQ ID NO 1388
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1388
cguuaaggac aagua 15

<210> SEQ ID NO 1389
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1389
guuaaggaca aguua 15

<210> SEQ ID NO 1390
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1390
uuaaggacaa guuca 15

<210> SEQ ID NO 1391
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1391
uaaggacaag uucua 15

<210> SEQ ID NO 1392
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1392
aaggacaagu ucuca 15

<210> SEQ ID NO 1393
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1393
aggacaaguu cucua 15

<210> SEQ ID NO 1394
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1394
ggacaaguuc ucuga 15

<210> SEQ ID NO 1395
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1395
gacaaguucu cugaa 15

<210> SEQ ID NO 1396
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1396
acaaguucuc ugaga 15

<210> SEQ ID NO 1397
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1397
caaguucucu gagua 15

<210> SEQ ID NO 1398
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1398
aaguucucug aguua 15

<210> SEQ ID NO 1399
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1399
aguucucuga guuca 15

<210> SEQ ID NO 1400
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1400
uucucugagu ucuga 15

<210> SEQ ID NO 1401
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1401
ucucugaguu cugga 15

<210> SEQ ID NO 1402
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1402
cucugaguuc uggga 15

<210> SEQ ID NO 1403
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1403
ucugaguucu gggaa 15

<210> SEQ ID NO 1404
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1404
cugaguucug ggaua 15

<210> SEQ ID NO 1405
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1405
ugaguucugg gauua 15

<210> SEQ ID NO 1406
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1406
gaguucuggg auuua 15

<210> SEQ ID NO 1407
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1407
aguucuggga uuuga 15

<210> SEQ ID NO 1408
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1408
guucugggau uugga 15

<210> SEQ ID NO 1409
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1409
uucugggauu uggaa 15

<210> SEQ ID NO 1410
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1410
ucugggauuu ggaca 15

<210> SEQ ID NO 1411
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1411
cugggauuug gacca 15

<210> SEQ ID NO 1412
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1412
ugggauuugg accca 15

<210> SEQ ID NO 1413
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1413
gggauuugga cccua 15

<210> SEQ ID NO 1414
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1414
ggauuuggac ccuga 15

<210> SEQ ID NO 1415
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1415
gauuuggacc cugaa 15

<210> SEQ ID NO 1416
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1416
uggacccuga gguca 15

<210> SEQ ID NO 1417

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1417
ggacccugag gucaa 15

<210> SEQ ID NO 1418
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1418
gacccugagg ucaga 15

<210> SEQ ID NO 1419
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1419
acccugaggu cagaa 15

<210> SEQ ID NO 1420
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1420
cccugagguc agaca 15

<210> SEQ ID NO 1421
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1421
ccugagguca gacca 15

<210> SEQ ID NO 1422
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1422
cugaggucag accaa 15

<210> SEQ ID NO 1423
<211> LENGTH: 15

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1423
ugaggucaga ccaaa 15

<210> SEQ ID NO 1424
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1424
gaggucagac caaca 15

<210> SEQ ID NO 1425
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1425
aggucagacc aacua 15

<210> SEQ ID NO 1426
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1426
ggucagacca acuua 15

<210> SEQ ID NO 1427
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1427
gucagaccaa cuuca 15

<210> SEQ ID NO 1428
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1428
ucagaccaac uucaa 15

<210> SEQ ID NO 1429
<211> LENGTH: 15
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1429
cagaccaacu ucaga 15

<210> SEQ ID NO 1430
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1430
gaccaacuuc agcca 15

<210> SEQ ID NO 1431
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1431
accaacuuca gccga 15

<210> SEQ ID NO 1432
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1432
ccaacuucag ccgua 15

<210> SEQ ID NO 1433
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1433
caacuucagc cguga 15

<210> SEQ ID NO 1434
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1434
aacuucagcc gugga 15

<210> SEQ ID NO 1435
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1435
acuucagccg uggca 15

<210> SEQ ID NO 1436
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1436
uucagccgug gcuga 15

<210> SEQ ID NO 1437
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1437
ucagccgugg cugca 15

<210> SEQ ID NO 1438
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1438
cagccguggc ugcca 15

<210> SEQ ID NO 1439
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1439
agccguggcu gccua 15

<210> SEQ ID NO 1440
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1440
gccguggcug ccuga 15

<210> SEQ ID NO 1441
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1441
guggcugccu gagaa 15

<210> SEQ ID NO 1442
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1442
uggcugccug agaca 15

<210> SEQ ID NO 1443
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1443
ggcugccuga gacca 15

<210> SEQ ID NO 1444
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1444
gcugccugag accua 15

<210> SEQ ID NO 1445
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1445
ugccugagac cucaa 15

<210> SEQ ID NO 1446
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1446
gccugagacc ucaaa 15

<210> SEQ ID NO 1447
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1447
ccugagaccu caaua 15

<210> SEQ ID NO 1448
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1448
cugagaccuc aauaa 15

<210> SEQ ID NO 1449
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1449
ugagaccuca auaca 15

<210> SEQ ID NO 1450
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1450
gagaccucaa uacca 15

<210> SEQ ID NO 1451
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1451
agaccucaau accca 15

<210> SEQ ID NO 1452
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1452
aguccaccug ccuaa 15

<210> SEQ ID NO 1453
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1453
guccaccugc cuaua 15

<210> SEQ ID NO 1454
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1454
uccaccugcc uauca 15

<210> SEQ ID NO 1455
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1455
ccaccugccu aucca 15

<210> SEQ ID NO 1456
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1456
caccugccua uccaa 15

<210> SEQ ID NO 1457
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1457
accugccuau ccaua 15

<210> SEQ ID NO 1458
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1458
ccugccuauc cauca 15

<210> SEQ ID NO 1459
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1459
cugccuaucc aucca 15

<210> SEQ ID NO 1460
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1460
ugccuaucca uccua 15

<210> SEQ ID NO 1461
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1461
gccuauccau ccuga 15

<210> SEQ ID NO 1462
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1462
ccuauccauc cugca 15

<210> SEQ ID NO 1463
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1463
cuauccaucc ugcga 15

<210> SEQ ID NO 1464
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1464
uauccauccu gcgaa 15

<210> SEQ ID NO 1465
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1465
auccauccug cgaga 15

<210> SEQ ID NO 1466
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1466
uccauccugc gagca 15

<210> SEQ ID NO 1467
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1467
ccauccugcg agcua 15

<210> SEQ ID NO 1468
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1468
cauccugcga gcuca 15

<210> SEQ ID NO 1469
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1469
auccugcgag cucca 15

<210> SEQ ID NO 1470
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1470
uccugcgagc uccua 15

<210> SEQ ID NO 1471
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1471
ccugcgagcu ccuua 15

<210> SEQ ID NO 1472
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1472
cugcgagcuc cuuga 15

<210> SEQ ID NO 1473
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1473
ugcgagcucc uugga 15

<210> SEQ ID NO 1474
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1474
gcgagcuccu uggga 15

<210> SEQ ID NO 1475
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1475
cgagcuccuu gggua 15

<210> SEQ ID NO 1476
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1476
gagcuccuug gguca 15

<210> SEQ ID NO 1477
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1477
agcuccuugg gucca 15

```
<210> SEQ ID NO 1478
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1478

gcuccuuggg uccua                                                      15

<210> SEQ ID NO 1479
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1479

cuccuugggu ccuga                                                      15

<210> SEQ ID NO 1480
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1480

uccuuggguc cugca                                                      15

<210> SEQ ID NO 1481
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1481

ccuugggucc ugcaa                                                      15

<210> SEQ ID NO 1482
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1482

cuuggguccu gcaaa                                                      15

<210> SEQ ID NO 1483
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1483

uuggguccug caaua                                                      15
```

<210> SEQ ID NO 1484
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1484
uggguccugc aauca 15

<210> SEQ ID NO 1485
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1485
ggguccugca aucua 15

<210> SEQ ID NO 1486
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1486
gguccugcaa ucuca 15

<210> SEQ ID NO 1487
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1487
guccugcaau cucca 15

<210> SEQ ID NO 1488
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1488
uccugcaauc uccaa 15

<210> SEQ ID NO 1489
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1489
ccugcaaucu ccaga 15

<210> SEQ ID NO 1490
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1490
cugcaaucuc cagga 15

<210> SEQ ID NO 1491
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1491
ugcaaucucc aggga 15

<210> SEQ ID NO 1492
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1492
gcaaucucca gggca 15

<210> SEQ ID NO 1493
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1493
caaucuccag ggcua 15

<210> SEQ ID NO 1494
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1494
aaucuccagg gcuga 15

<210> SEQ ID NO 1495
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1495
aucuccaggg cugca 15

<210> SEQ ID NO 1496

<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1496
ucuccagggc ugcca 15

<210> SEQ ID NO 1497
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1497
cuccagggcu gccca 15

<210> SEQ ID NO 1498
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1498
guagguugcu uaaaa 15

<210> SEQ ID NO 1499
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1499
uagguugcuu aaaaa 15

<210> SEQ ID NO 1500
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1500
agguugcuua aaaga 15

<210> SEQ ID NO 1501
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1501
gguugcuuaa aagga 15

<210> SEQ ID NO 1502
<211> LENGTH: 15

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1502
guugcuuaaa aggga 15

<210> SEQ ID NO 1503
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1503
uugcuuaaaa gggaa 15

<210> SEQ ID NO 1504
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1504
ugcuuaaaag ggaca 15

<210> SEQ ID NO 1505
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1505
uuaaaaggga cagua 15

<210> SEQ ID NO 1506
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1506
uaaaagggac aguaa 15

<210> SEQ ID NO 1507
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1507
aaaagggaca guaua 15

<210> SEQ ID NO 1508
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1508
aaagggacag uauua 15

<210> SEQ ID NO 1509
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1509
aagggacagu auuca 15

<210> SEQ ID NO 1510
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1510
agggacagua uucua 15

<210> SEQ ID NO 1511
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1511
gggacaguau ucuca 15

<210> SEQ ID NO 1512
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1512
ggacaguauu cucaa 15

<210> SEQ ID NO 1513
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1513
gacaguauuc ucaga 15

<210> SEQ ID NO 1514
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1514
acaguauucu cagua 15

<210> SEQ ID NO 1515
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1515
caguauucuc aguga 15

<210> SEQ ID NO 1516
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1516
aguauucuca gugca 15

<210> SEQ ID NO 1517
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1517
guauucucag ugcua 15

<210> SEQ ID NO 1518
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1518
uauucucagu gcuca 15

<210> SEQ ID NO 1519
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1519
auucucagug cucua 15

<210> SEQ ID NO 1520
<211> LENGTH: 15
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1520
uucucagugc ucuca 15

<210> SEQ ID NO 1521
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1521
ucucagugcu cucca 15

<210> SEQ ID NO 1522
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1522
cucagugcuc uccua 15

<210> SEQ ID NO 1523
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1523
ucagugcucu ccuaa 15

<210> SEQ ID NO 1524
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1524
cagugcucuc cuaca 15

<210> SEQ ID NO 1525
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1525
agugcucucc uacca 15

<210> SEQ ID NO 1526
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1526
gugcucuccu accca 15

<210> SEQ ID NO 1527
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1527
ccucaugccu ggcca 15

<210> SEQ ID NO 1528
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1528
cucaugccug gccca 15

<210> SEQ ID NO 1529
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1529
ccaggcaugc uggca 15

<210> SEQ ID NO 1530
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1530
caggcaugcu ggcca 15

<210> SEQ ID NO 1531
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1531
aggcaugcug gccua 15

<210> SEQ ID NO 1532
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1532
ggcaugcugg ccuca 15

<210> SEQ ID NO 1533
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1533
gcaugcuggc cucca 15

<210> SEQ ID NO 1534
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1534
caugcuggcc uccca 15

<210> SEQ ID NO 1535
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1535
augcuggccu cccaa 15

<210> SEQ ID NO 1536
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1536
gcuggccucc caaua 15

<210> SEQ ID NO 1537
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1537
cuggccuccc aauaa 15

<210> SEQ ID NO 1538
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1538
uggccuccca auaaa 15

<210> SEQ ID NO 1539
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1539
ggccucccaa uaaaa 15

<210> SEQ ID NO 1540
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1540
gccucccaau aaaga 15

<210> SEQ ID NO 1541
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1541
ccucccaaua aagca 15

<210> SEQ ID NO 1542
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1542
cucccaauaa agcua 15

<210> SEQ ID NO 1543
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1543
ucccaauaaa gcuga 15

<210> SEQ ID NO 1544
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1544
cccaauaaag cugga 15

<210> SEQ ID NO 1545
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1545
ccaauaaagc uggaa 15

<210> SEQ ID NO 1546
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1546
caauaaagcu ggaca 15

<210> SEQ ID NO 1547
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1547
auaaagcugg acaaa 15

<210> SEQ ID NO 1548
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1548
uaaagcugga caaga 15

<210> SEQ ID NO 1549
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1549
aaagcuggac aagaa 15

<210> SEQ ID NO 1550
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1550
aagcuggaca agaaa 15

<210> SEQ ID NO 1551
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1551
agcuggacaa gaaga 15

<210> SEQ ID NO 1552
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1552
gcuggacaag aagca 15

<210> SEQ ID NO 1553
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1553
ggacaagaag cugca 15

<210> SEQ ID NO 1554
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1554
acaagaagcu gcuaa 15

<210> SEQ ID NO 1555
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1555
caagaagcug cuaua 15

<210> SEQ ID NO 1556
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1556
uaacucagag aacuugucc 19

<210> SEQ ID NO 1557
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1557
uuguccuuaa cggugcucc 19

<210> SEQ ID NO 1558
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1558
uaaucccaga acucagaga 19

<210> SEQ ID NO 1559
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1559
uccuuggcgg ucuuggugg 19

<210> SEQ ID NO 1560
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1560
ucugaagcca ucggucacc 19

<210> SEQ ID NO 1561
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1561
ucagagaacu uguccuuaa 19

<210> SEQ ID NO 1562
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1562
uacucagaga acuuguccu 19

<210> SEQ ID NO 1563
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1563
ugaacucaga gaacuuguc 19

<210> SEQ ID NO 1564
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1564
uacuuguccu uaacggugc 19

<210> SEQ ID NO 1565
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1565
ucucagagaa cuuguccuu 19

<210> SEQ ID NO 1566
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1566
uuuguccuua acggugcuc 19

<210> SEQ ID NO 1567
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1567
uuccuuggcg gucuuggug 19

<210> SEQ ID NO 1568
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1568
ugcuccagua gucuuucag 19

<210> SEQ ID NO 1569
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1569
ucauccucgg ccucugaag 19

<210> SEQ ID NO 1570
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1570
uugguggcgu gcuucaugu 19

<210> SEQ ID NO 1571
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1571
aguucucuga guua 14

<210> SEQ ID NO 1572
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1572
accguuaagg acaa 14

<210> SEQ ID NO 1573
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1573
gaguucuggg auua 14

<210> SEQ ID NO 1574
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1574
aagaccgcca agga 14

<210> SEQ ID NO 1575

<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1575
ccgauggcuu caga 14

<210> SEQ ID NO 1576
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1576
gacaaguucu cuga 14

<210> SEQ ID NO 1577
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1577
aaguucucug agua 14

<210> SEQ ID NO 1578
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1578
guucucugag uuca 14

<210> SEQ ID NO 1579
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1579
guuaaggaca agua 14

<210> SEQ ID NO 1580
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1580
caaguucucu gaga 14

<210> SEQ ID NO 1581
<211> LENGTH: 14

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1581
ccguuaagga caaa 14

<210> SEQ ID NO 1582
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1582
agaccgccaa ggaa 14

<210> SEQ ID NO 1583
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1583
agacuacugg agca 14

<210> SEQ ID NO 1584
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1584
gaggccgagg auga 14

<210> SEQ ID NO 1585
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1585
aagcacgcca ccaa 14

<210> SEQ ID NO 1586
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1586
uuggauaggc agguggacuc accugccuau ccaa 34

<210> SEQ ID NO 1587
<211> LENGTH: 34
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1587
ucaacaagga guacccgggg guacuccuug uuga 34

<210> SEQ ID NO 1588
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1588
uuggauaggc agguggacua ccugccuauc caa 33

<210> SEQ ID NO 1589
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1589
ucaacaagga guacccgggg uacuccuugu uga 33

<210> SEQ ID NO 1590
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1590
uuggauaggc agguggacug ccuauccaa 29

<210> SEQ ID NO 1591
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1591
uuggauaggc agguggacuu gccuauccaa 30

<210> SEQ ID NO 1592
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1592
ucaacaagga guacccgggu acuccuuguu ga 32

<210> SEQ ID NO 1593
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1593
uuggauaggc agguggacua ccugccuauc caa 33

<210> SEQ ID NO 1594
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1594
ucaacaagga guacccgggg uacuccuugu uga 33

<210> SEQ ID NO 1595
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1595
uuggauaggc agguggacug ccuauccaa 29

<210> SEQ ID NO 1596
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1596
uuggauaggc agguggacuu gccuauccaa 30

<210> SEQ ID NO 1597
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1597
ucaacaagga guacccgggu acuccuuguu ga 32

<210> SEQ ID NO 1598
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1598
uuggauaggc agguggacu 19

<210> SEQ ID NO 1599
<211> LENGTH: 15
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1599
caccugccua uccaa 15

<210> SEQ ID NO 1600
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1600
ucaacaagga guacccggg 19

<210> SEQ ID NO 1601
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1601
gguacuccuu guuga 15

<210> SEQ ID NO 1602
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1602
ugcaaaacag gucuagaaag uacuccuugu uga 33

<210> SEQ ID NO 1603
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1603
ucaacaagga guacccggga gaccuguuuu gca 33

<210> SEQ ID NO 1604
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1604
ugcaaaacag gucuagaaaa ccugccuauc caa 33

<210> SEQ ID NO 1605
<211> LENGTH: 33
<212> TYPE: RNA
<213> ORGANISM: Artificial Sequence
<220> FEATURE:
<223> OTHER INFORMATION: Description of Artificial Sequence: Synthetic -continued

```
      oligonucleotide

<400> SEQUENCE: 1605

uuggauaggc agguggacua gaccuguuuu gca                              33


<210> SEQ ID NO 1606
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a, c, u, g, unknown or other

<400> SEQUENCE: 1606

aaccagaaga agcaggugnc ugcuucuucu gguu                             34
```